(12) United States Patent
Skog et al.

(10) Patent No.: US 10,465,183 B2
(45) Date of Patent: Nov. 5, 2019

(54) METHODS FOR ISOLATING MICROVESICLES AND EXTRACTING NUCLEIC ACIDS FROM BIOLOGICAL SAMPLES

(71) Applicant: Exosome Diagnostics, Inc., Cambridge, MA (US)

(72) Inventors: Johan Karl Olov Skog, Cambridge, MA (US); Daniel Enderle, Martinsried (DE); Aparna Ramachandran, Iselin, NJ (US); Haoheng Yan, Hastings on Hudson, NY (US); Emily Berghoff, Cambridge, MA (US); Tai-Fen Wei, Cambridge, MA (US); Mikkel Noerholm, Gauting (DE)

(73) Assignee: Exosome Diagnostics, Inc., Waltham, MA (US)

( * ) Notice: Subject to any disclaimer, the term of this patent is extended or adjusted under 35 U.S.C. 154(b) by 175 days.

(21) Appl. No.: 15/325,021

(22) PCT Filed: Jul. 9, 2015

(86) PCT No.: PCT/US2015/039760
§ 371 (c)(1),
(2) Date: Jan. 9, 2017

(87) PCT Pub. No.: WO2016/007755
PCT Pub. Date: Jan. 14, 2016

(65) Prior Publication Data
US 2017/0198280 A1    Jul. 13, 2017

Related U.S. Application Data

(60) Provisional application No. 62/022,538, filed on Jul. 9, 2014, provisional application No. 62/079,763, filed on Nov. 14, 2014, provisional application No. 62/166,890, filed on May 27, 2015.

(51) Int. Cl.
*C12N 15/10*        (2006.01)

(52) U.S. Cl.
CPC .................. *C12N 15/1006* (2013.01)

(58) Field of Classification Search
CPC .......... C12Q 1/6806; C12N 15/1006
See application file for complete search history.

(56) References Cited

U.S. PATENT DOCUMENTS

| 4,935,342 | A | 6/1990 | Seligson et al. |
| 5,438,128 | A | 8/1995 | Nieuwkerk et al. |
| 5,639,606 | A | 6/1997 | Willey |
| 6,812,023 | B1 | 11/2004 | Lamparski et al. |
| 6,899,863 | B1 | 5/2005 | Dhellin et al. |
| 7,198,923 | B1 | 4/2007 | Abrignani et al. |
| 2014/0093880 | A1 | 4/2014 | Kim et al. |
| 2015/0353920 | A1 | 12/2015 | Enderle et al. |

FOREIGN PATENT DOCUMENTS

| WO | WO 2009/100029 A1 | 8/2009 |
| WO | WO 2010/065765 A2 | 6/2010 |
| WO | WO 2010/141862 A2 | 9/2010 |
| WO | WO 2011/151428 A1 | 12/2011 |
| WO | WO 2012/006476 A2 | 1/2012 |
| WO | WO 2012/064993 A1 | 5/2012 |
| WO | WO 2012/087241 A1 | 6/2012 |
| WO | WO 2012/155014 A1 | 11/2012 |
| WO | WO 2012/174282 A2 | 12/2012 |
| WO | WO 2014/036391 A1 | 6/2014 |
| WO | WO 2014/107571 A1 | 7/2014 |
| WO | WO 2016/007755 A1 | 1/2016 |

OTHER PUBLICATIONS

Qiagen miRNeasy Mini Kit, For purification of microRNA and total RNA from tissues and cells, from Qiagen.com website, product details, 2013, pp. 1-3.*
Al-Nedawi, et al., "Intercellular transfer of the oncogenic receptor EGFRvIII by microvesicles derived from tumour cells." Nat Cell Biol. (2008); 10(5): 619-624.
Balzar, et al., "The biology of the 17-1A antigen (Ep-CAM)." J Mol Med. (1999); 77(10): 699-712.
Cheruvanky, et al., "Rapid isolation of urinary exosomal biomarkers using a nanomembrane ultrafiltration concentrator." Am J Physiol Renal Physiol. (2007); 292: F1657-F1661.
Enderle et al., "Characterization of RNA from Exosomes and other Extracellular Vesicles Isolated by a Novel Spin Column-Based Method", PLOS One; Aug. 28, 2015, pp. 1-19; vol. No. 8, United States.
Extended European Search Report for European Application No. 14735397.3 dated Feb. 22, 2017, 7 pages.
Extended European Search Report for European Application No. 15818561.1 dated Nov. 7, 2017, 9 pages.
Hahn, "Molecular biology of double-minute chromosomes." BioEssays (1993); 15(7): 477-484.

(Continued)

*Primary Examiner* — David C Thomas

(74) *Attorney, Agent, or Firm* — Cooley LLP; Ivor R. Elrifi; Matthew Pavao

(57) ABSTRACT

The invention provides novel methods and kits for isolating nucleic acids from biological samples, including cell-free DNA and/or cell-free DNA and nucleic acids including at least RNA from microvesicles, and for extracting nucleic acids from the microvesicles and/or from the biological samples.

13 Claims, 228 Drawing Sheets

(56) References Cited

OTHER PUBLICATIONS

International Preliminary Report on Patentability for International Application No. PCT/US2015/039760 dated Jan. 10, 2017, 6 pages.
International Preliminary Report on Patentability for International Application No. PCT/US2014/010173 dated Jul. 7, 2015, 8 pages.
International Search Report for International Application No. PCT/US2015/039760 dated Oct. 8, 2015, 2 pages.
International Search Report for International Application No. PCT/US2014/010173 dated May 7, 2014, 3 pages.
Miranda, et al., "Nucleic acids within urinary exosomes/microvesicles are potential biomarkers for renal disease." Kidney International (2010); 78(2): 191-199.
Nilsson, et al., "Prostate cancer-derived urine exosomes: A novel approach to biomarkers for prostate cancer." British Journal of Cancer (2009); 100: 1603-1607.
Raj, et al., "Urinary Exosomes for Protein Biomarker Research: Human Diseases and Protein Functions." Edited by Tsa Kwong Man, published on line, Mass Spectrometry and Proteomics, Institute of Protein Biochemistry-CNR, Naples, Feb. 10, 2012, pp. 49-64.
Raposo, et al., "B lymphocytes secrete antigen-presenting vesicles." Journal of Experimental Medicine (1996); 183: 1161-1172.
Skog, et al., "Glioblastoma microvesicles transport RNA and proteins that promote tumour growth and provide diagnostic biomarkers." Nature Cell Biology (2008); 10(12): 1470-1476.
Taylor and Gercel-Taylor, "MicroRNA signatures of tumor-derived exosomes as diagnostic biomarkers of ovarian cancer." Gynecol Oncol. (2008); 110: 13-21.
Went, et al., "Frequent EpCam protein expression in human carcinomas." Hum Pathol. (2004); 35: 122-128.
Written Opinion for International Application No. PCT/US2015/039760 dated Oct. 8, 2015, 5 pages.
Written Opinion for International Application No. PCT/US2014/010173 dated May 7, 2014, 7 pages.
Extended European Search Report for European Application No. 18199291.8, dated Feb. 28, 2019, 7 pages.

\* cited by examiner

*One combined workflow instead of two separate ones*

- Bind cfDNA & MVs to membrane filter & wash
- QIAzol on-membrane lysis; release of RNA/DNA
- Combined RNA + DNA protocol
  - Phenol/Chloroform extraction w/PLG tubes
  - Ethanol conditioning
  - Bind to silica column and wash
  - Elute
  - cDNA synthesis
  - qPCR or UDS Figure

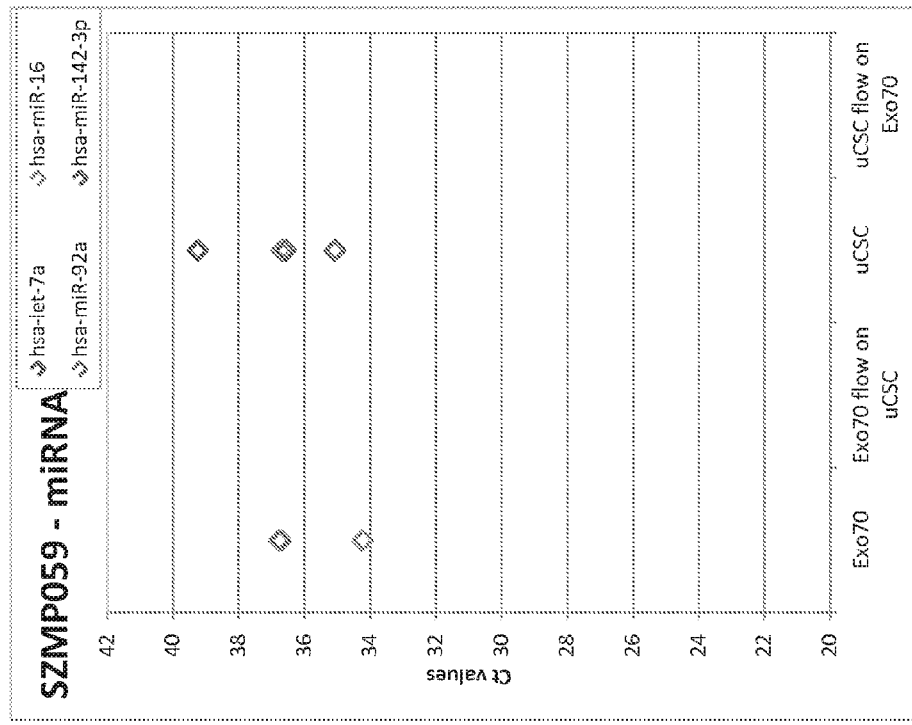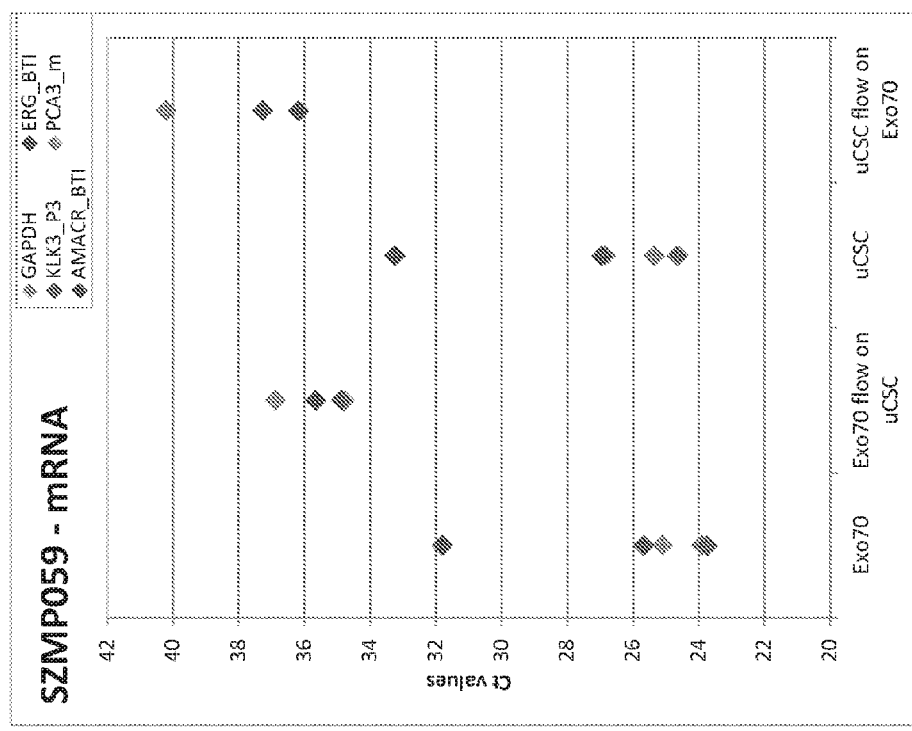
Figure 12

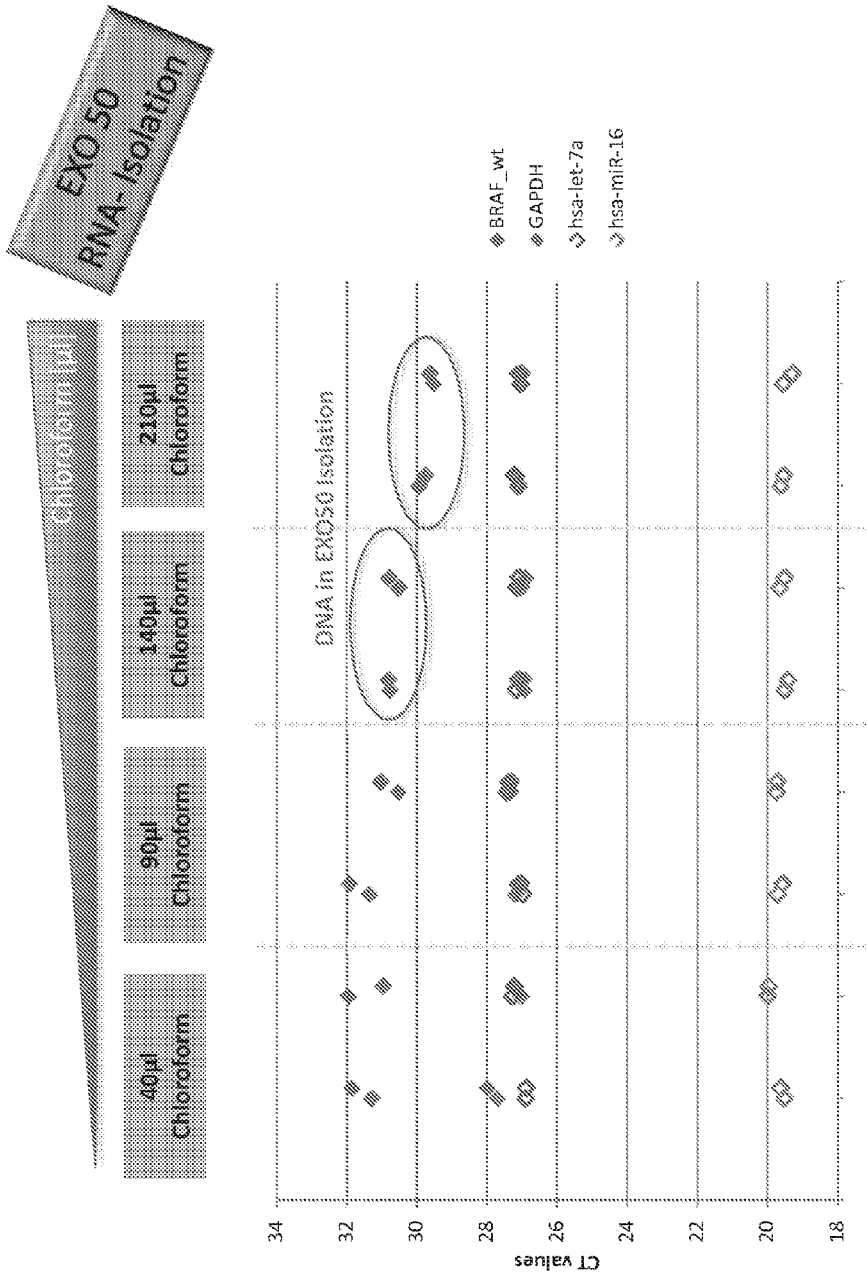

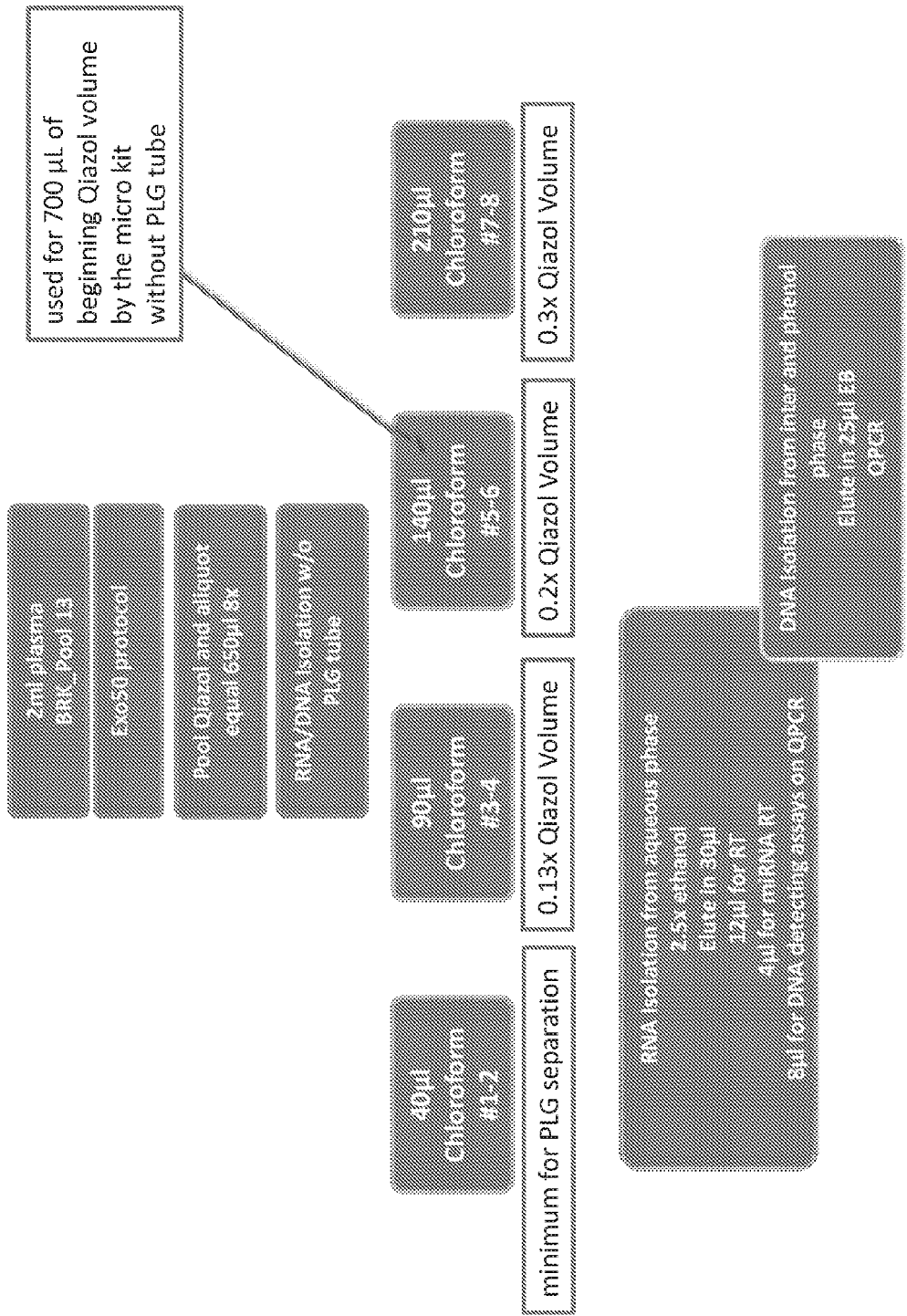

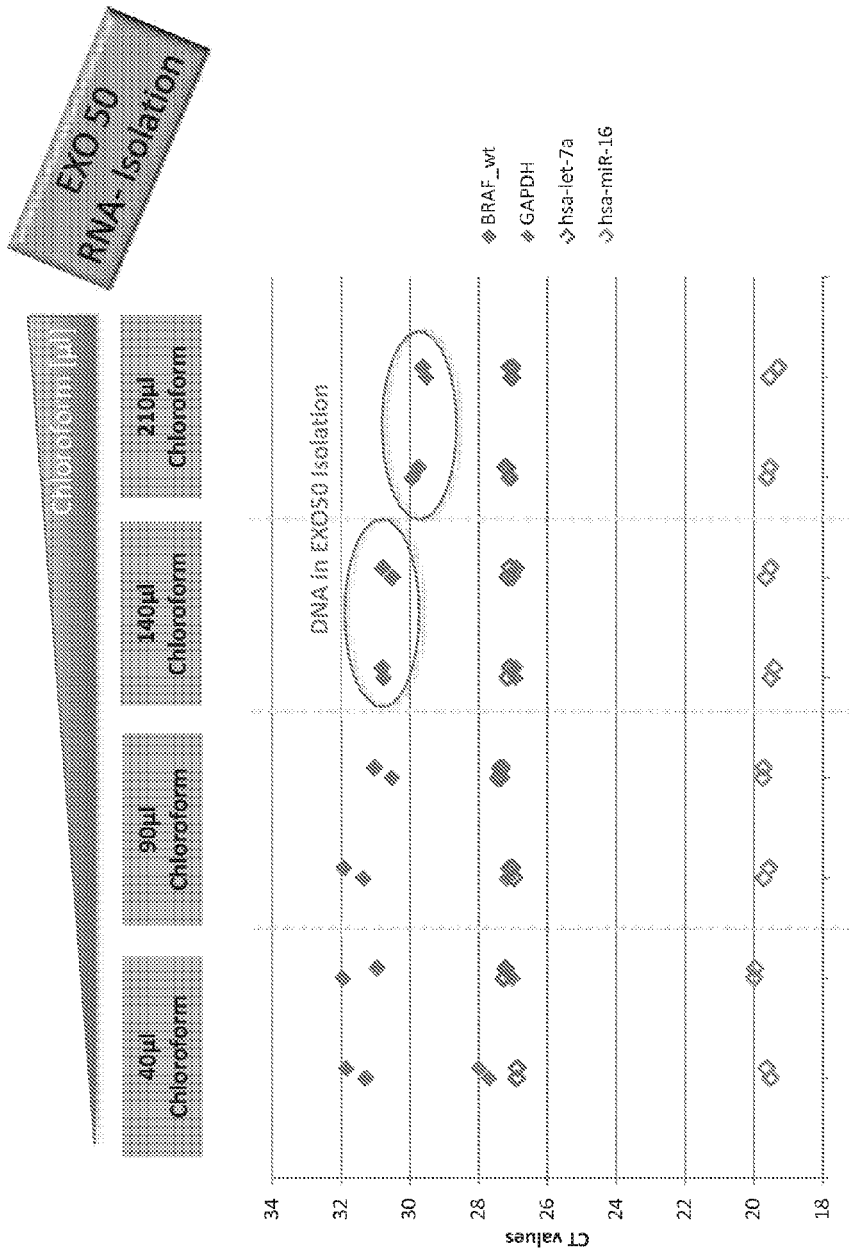

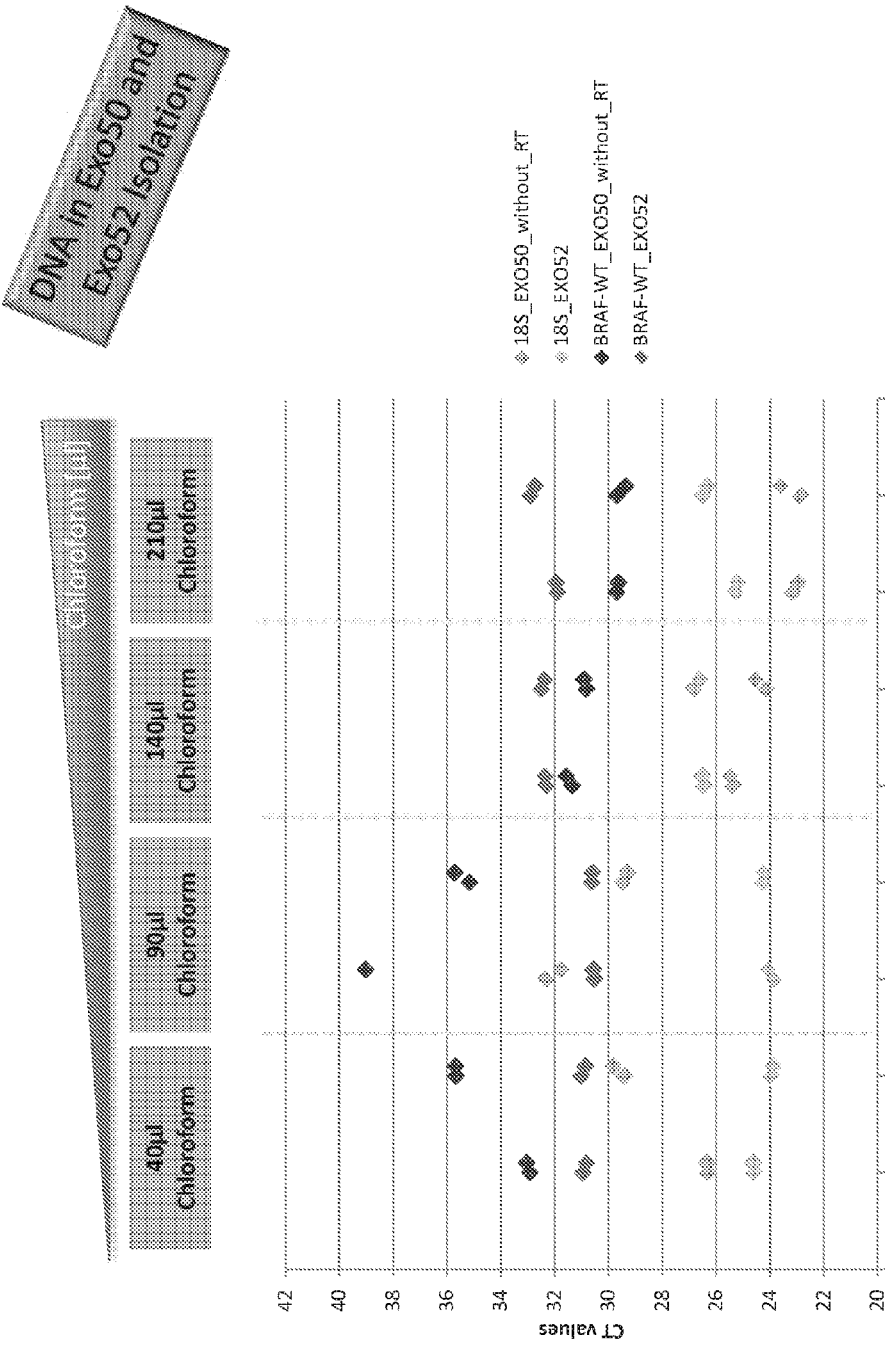

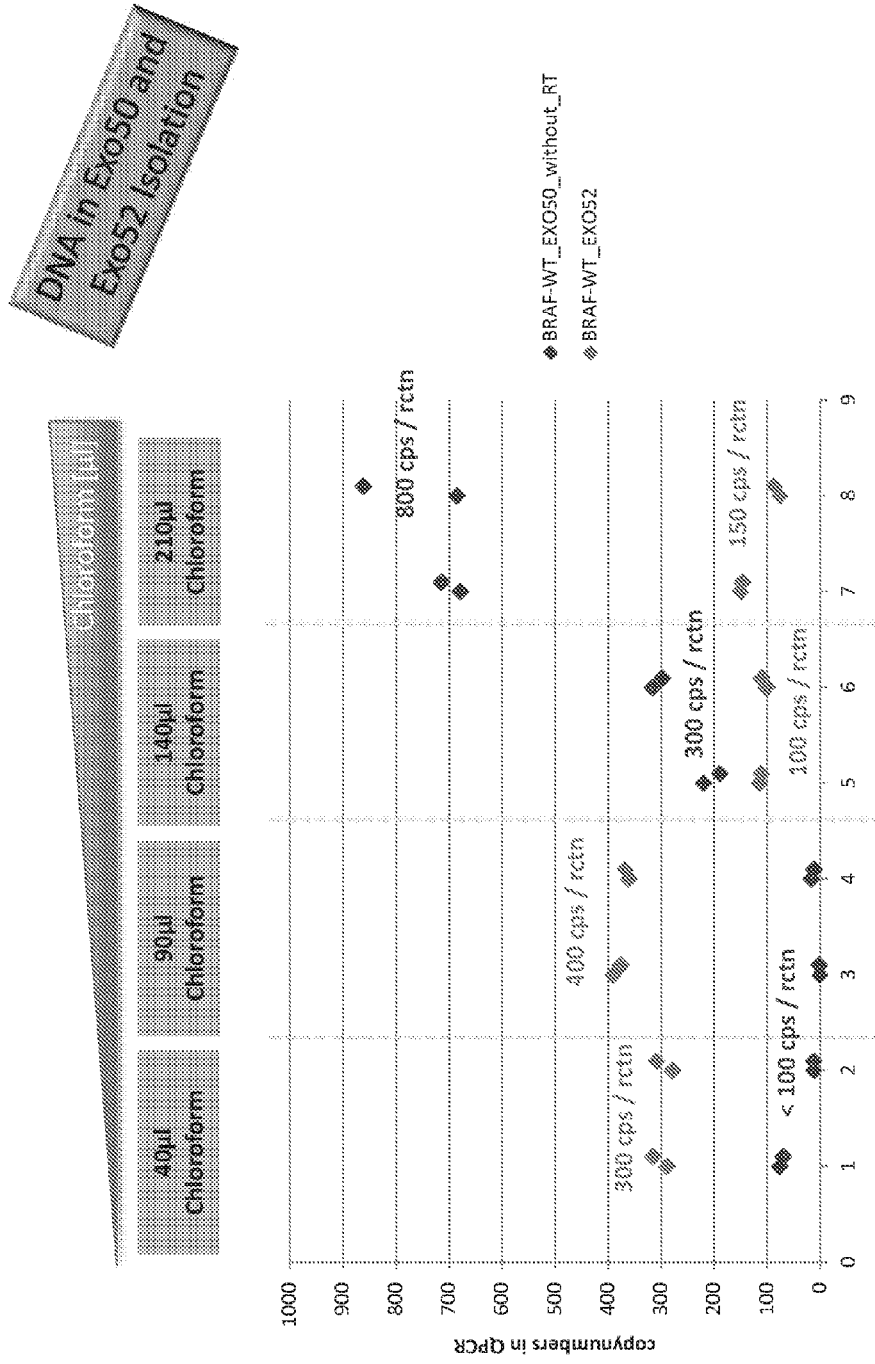

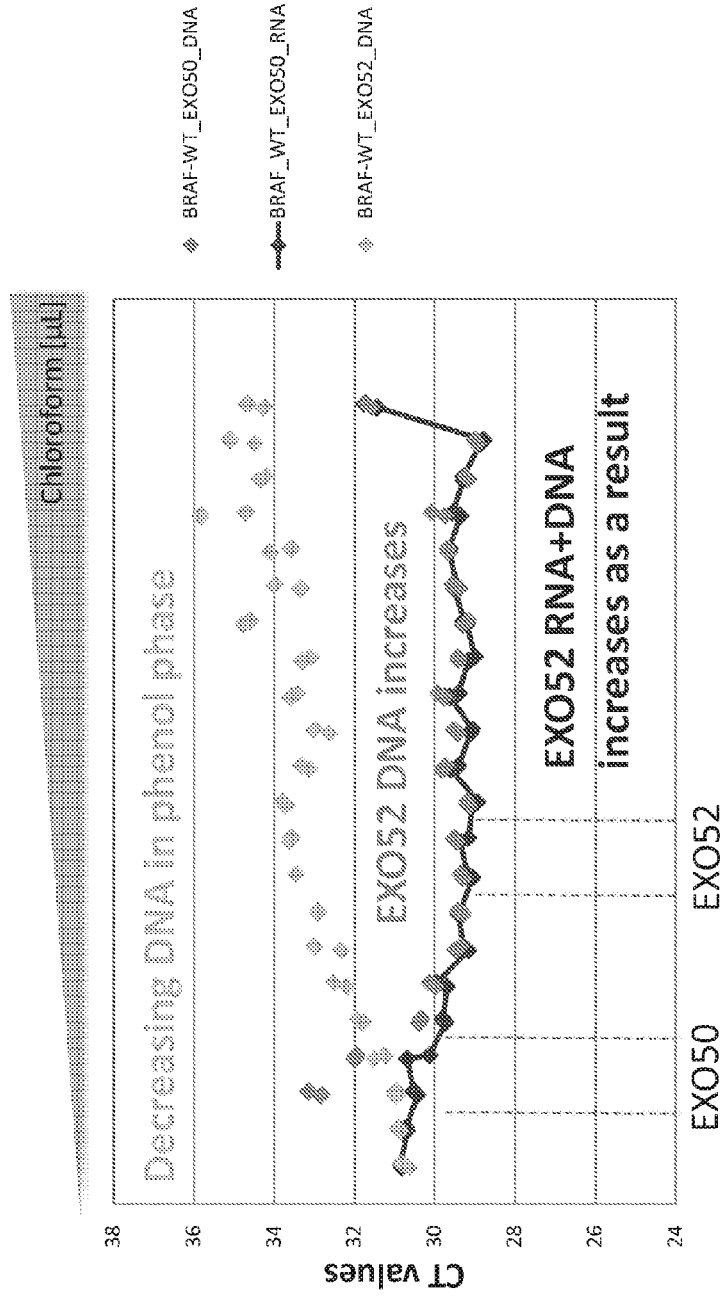

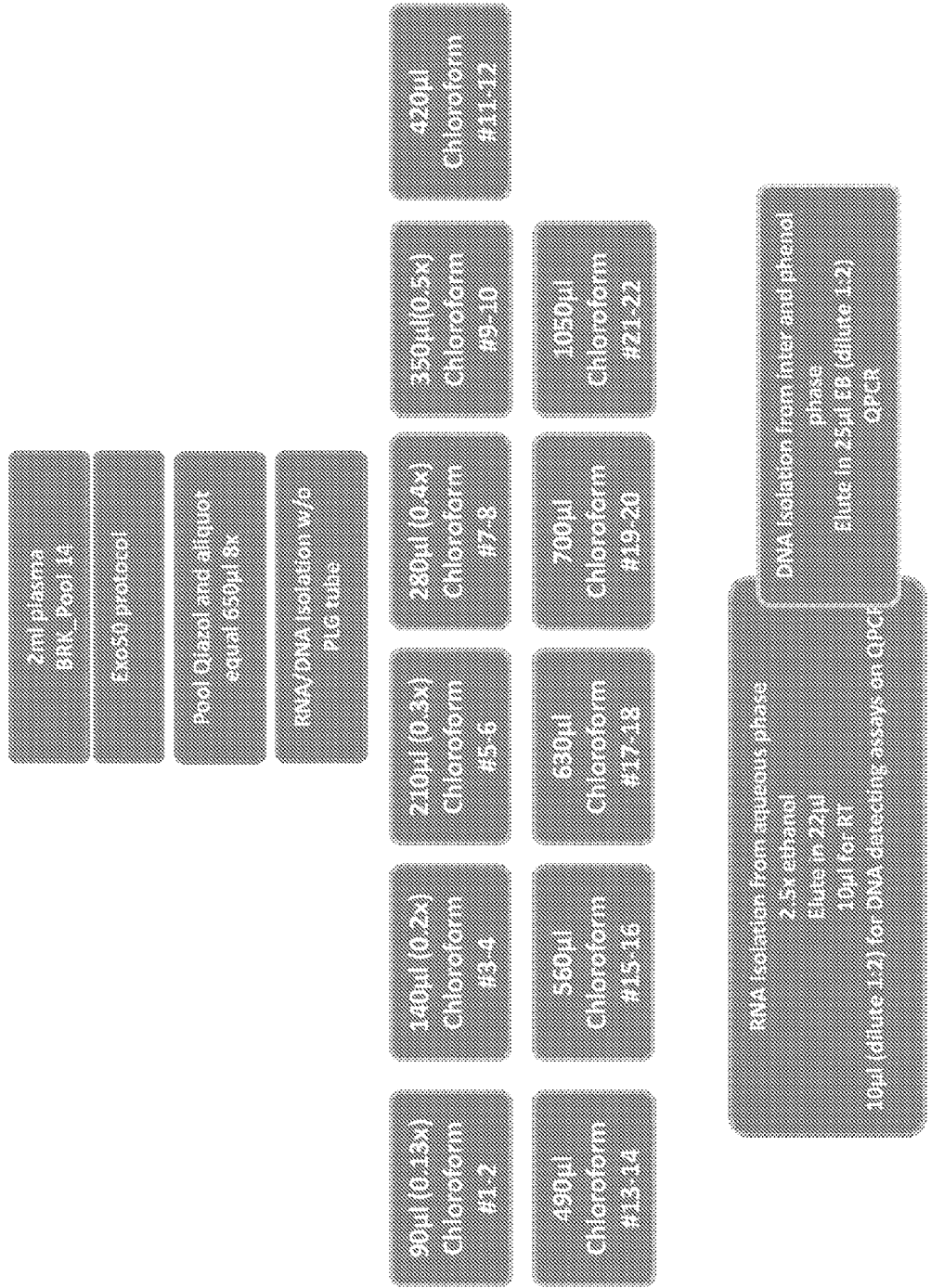

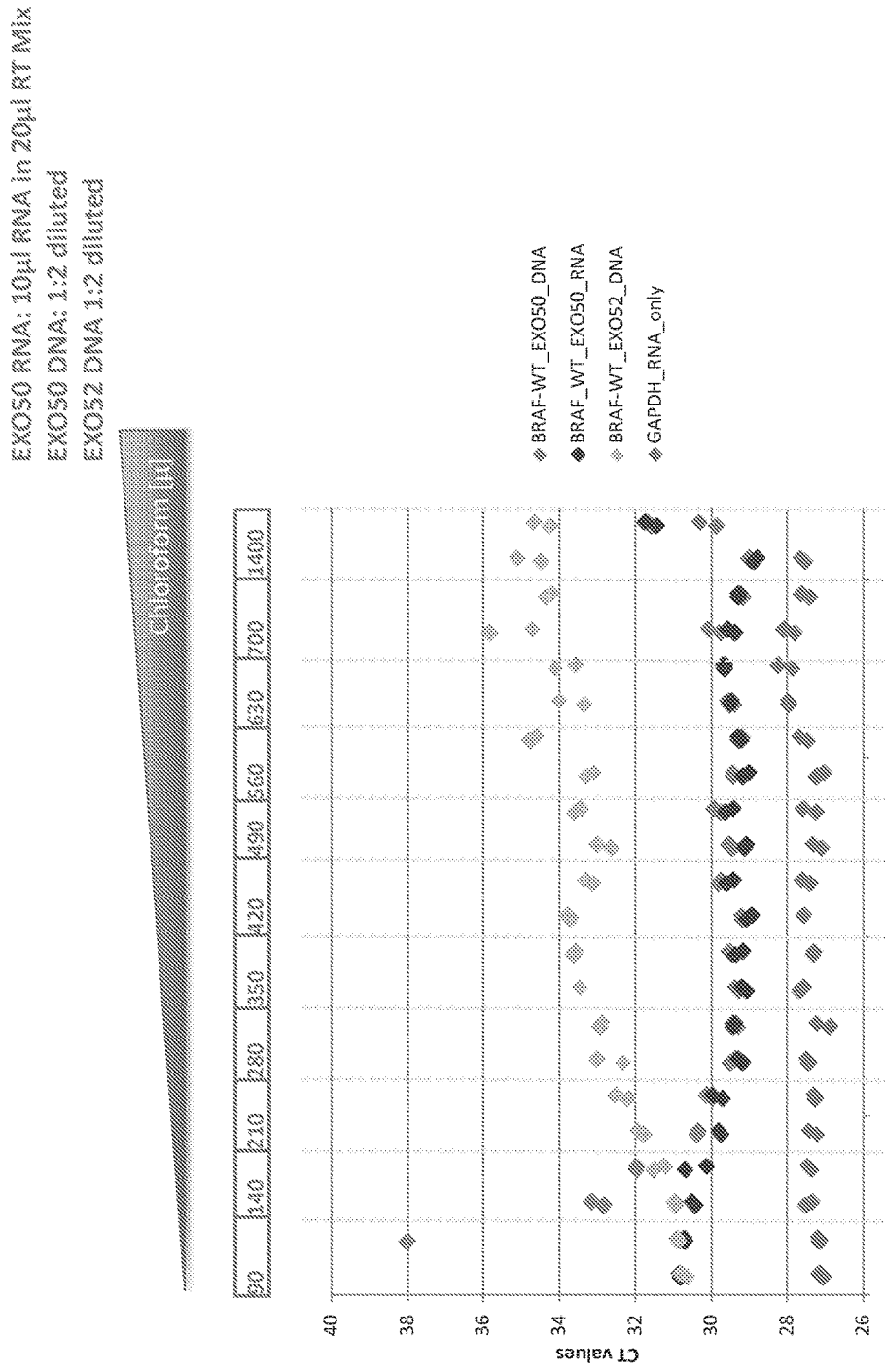

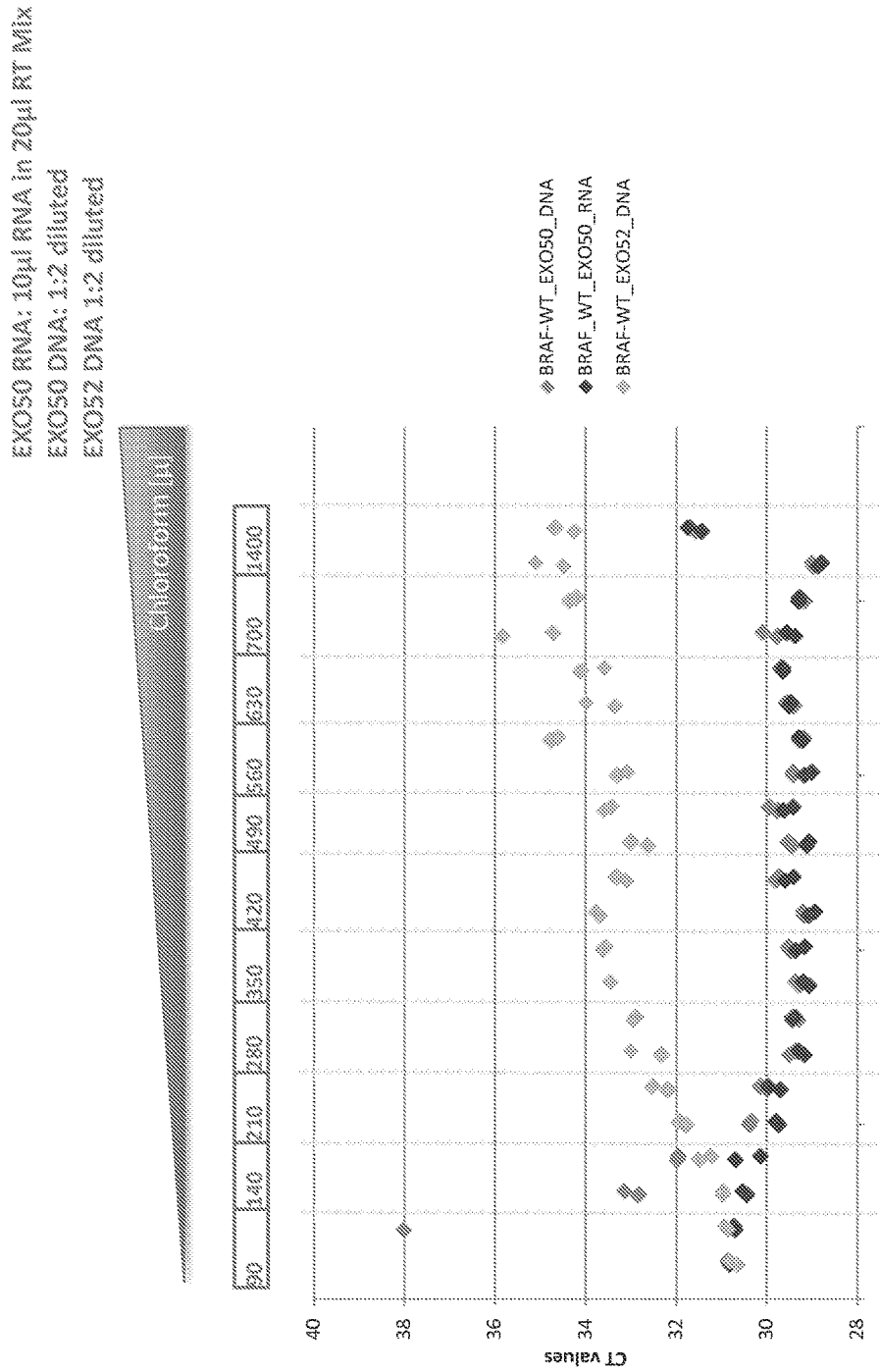

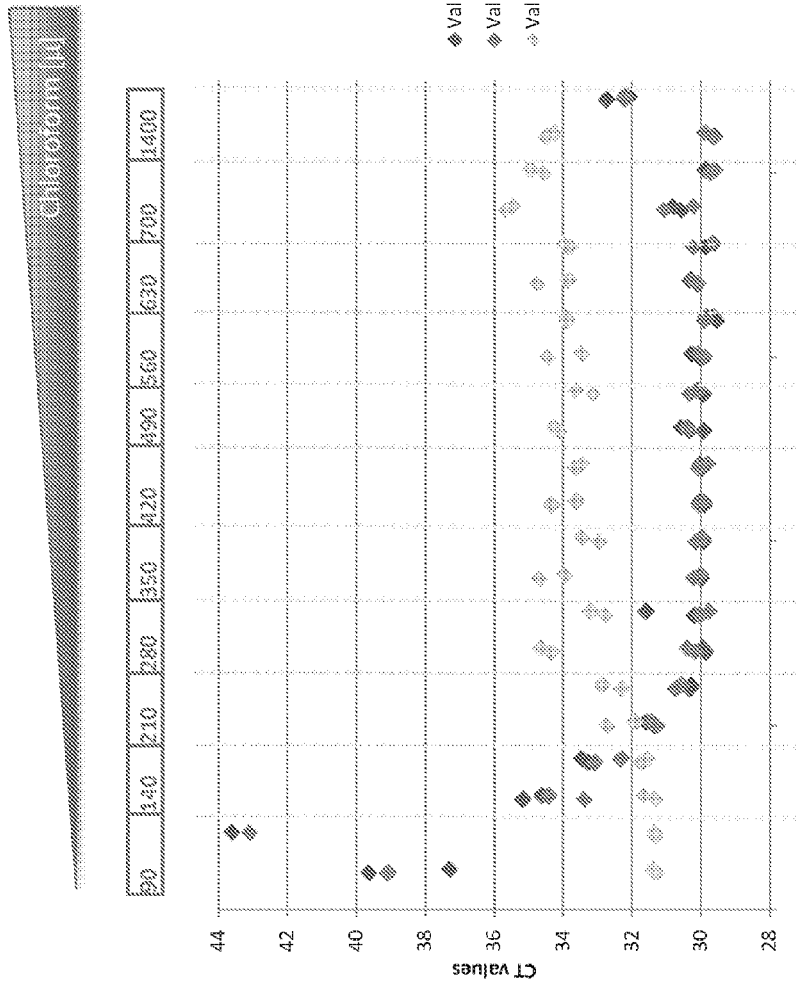

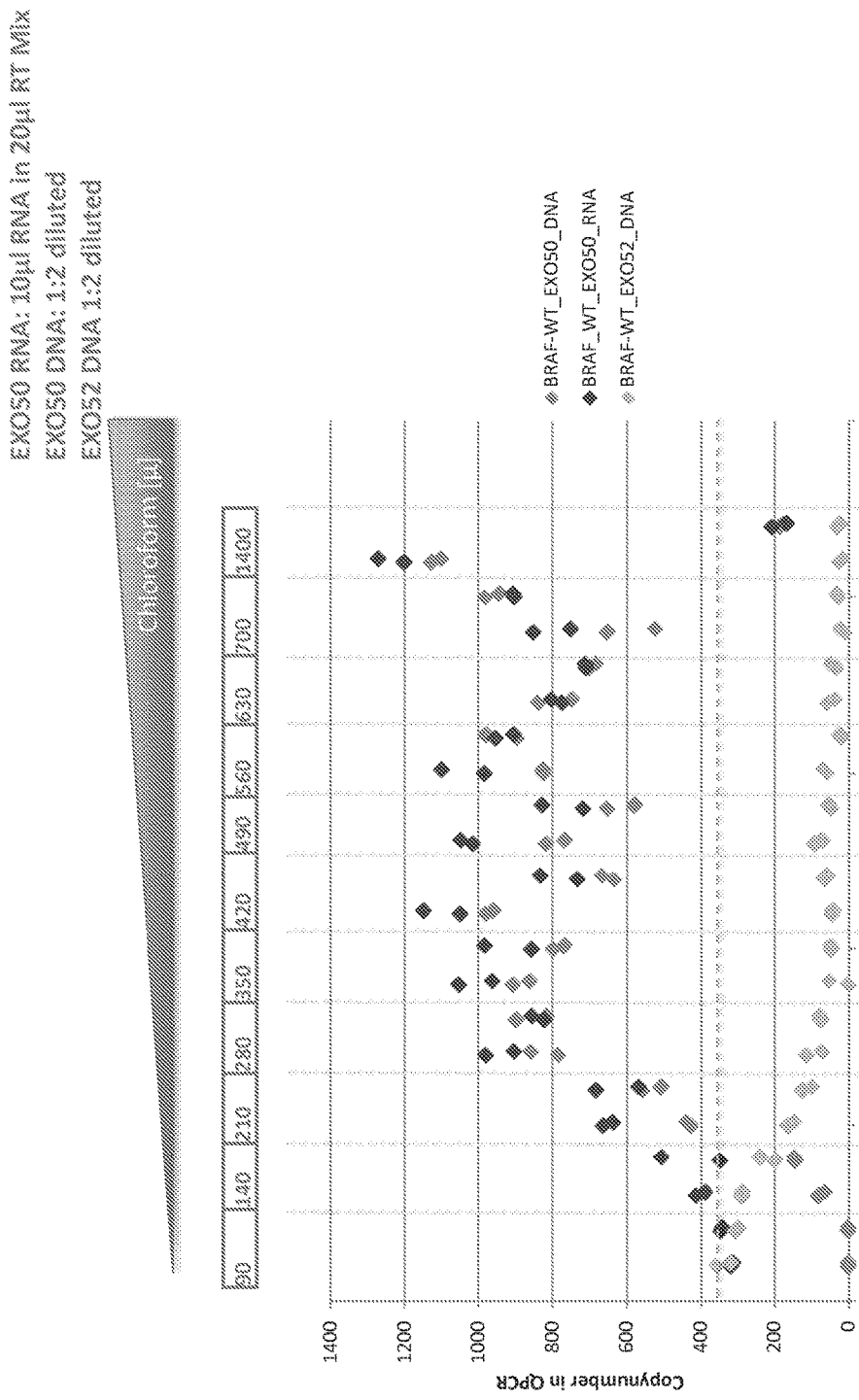

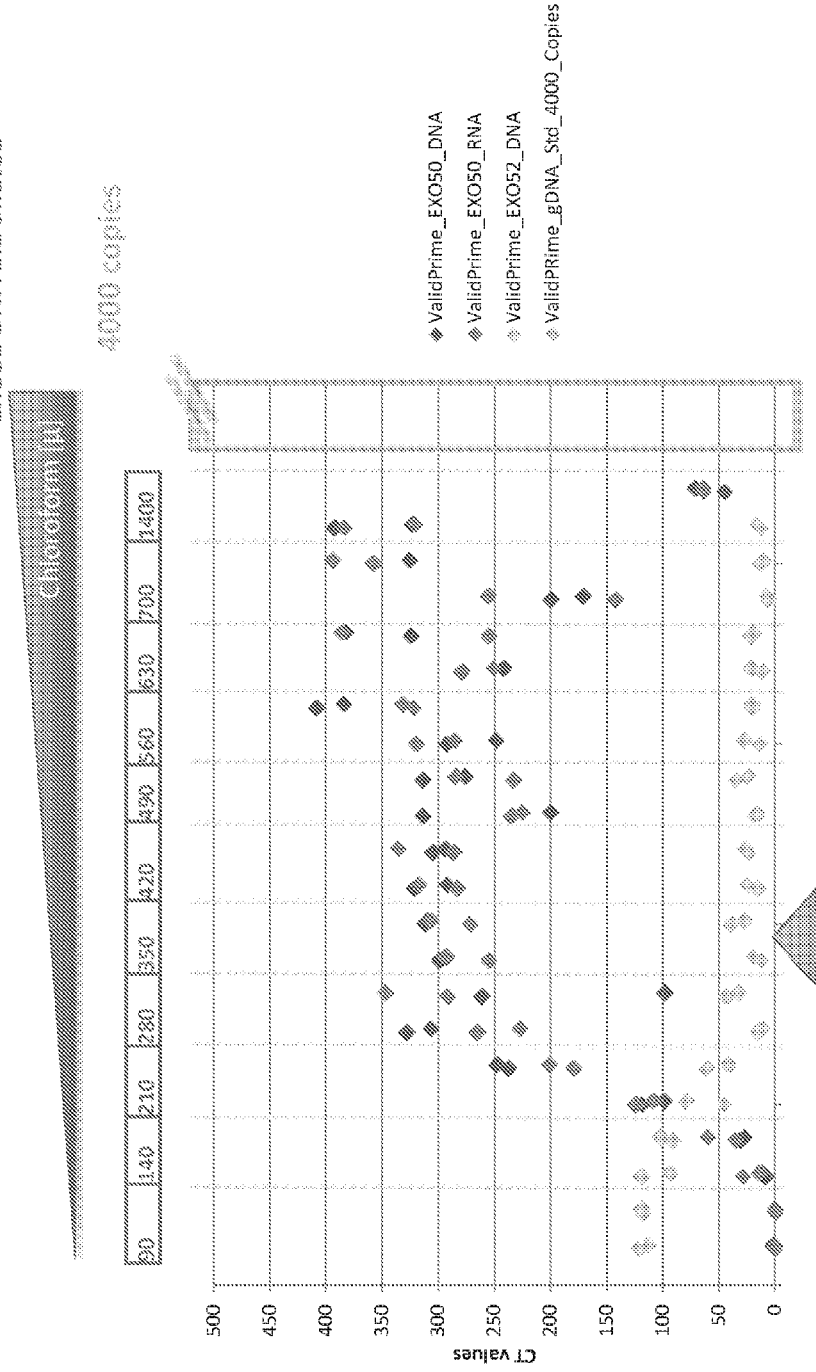

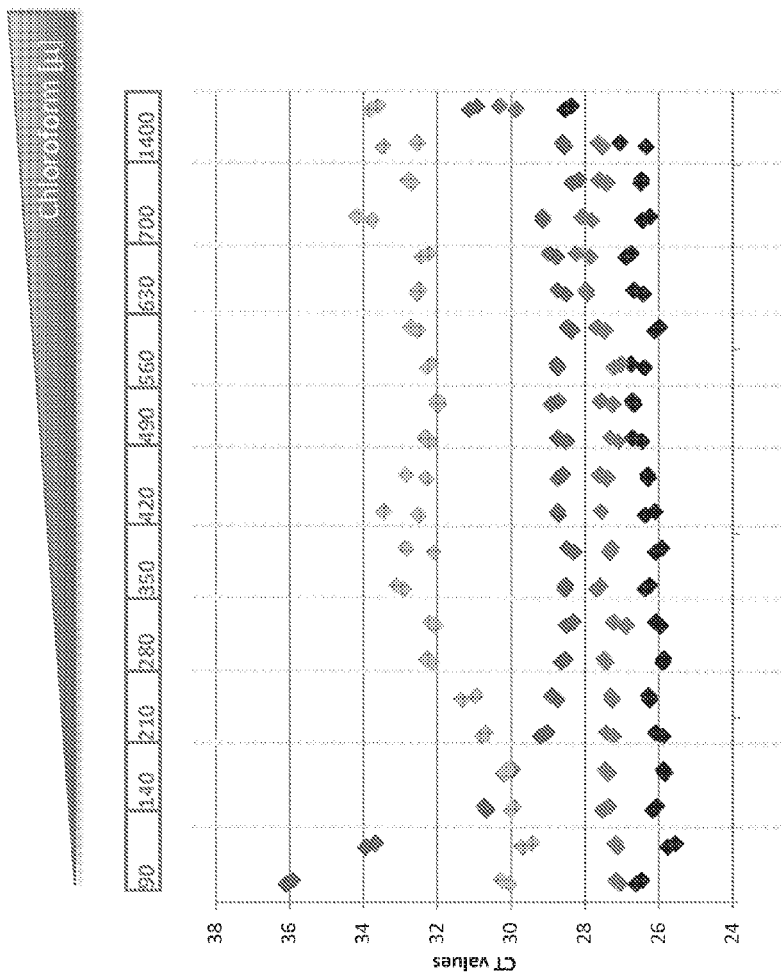

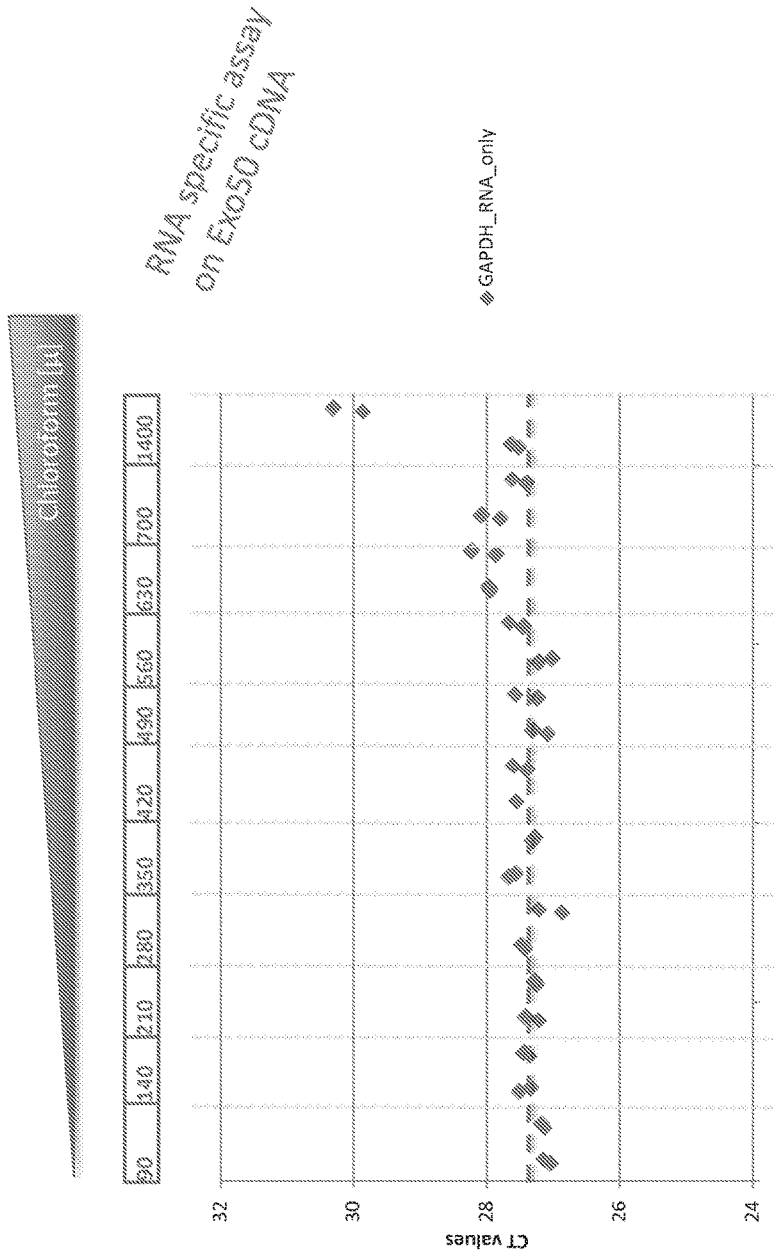

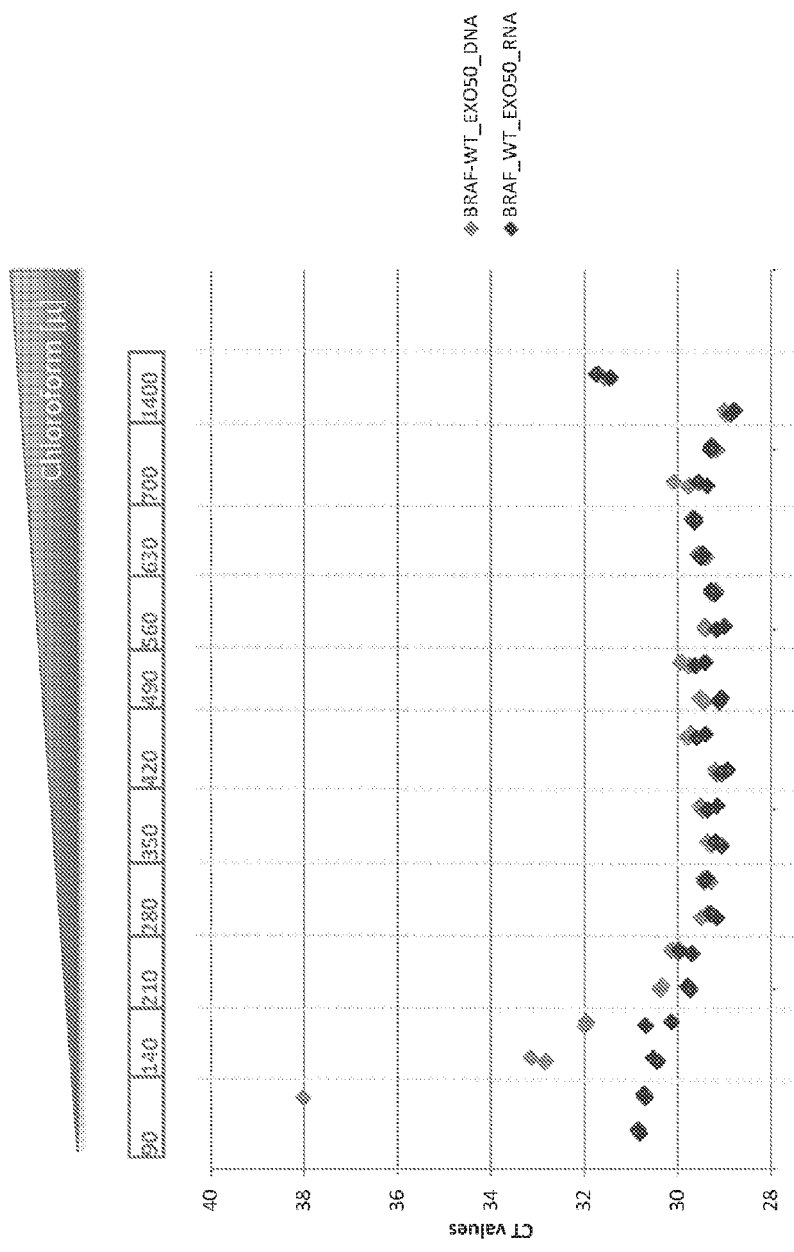

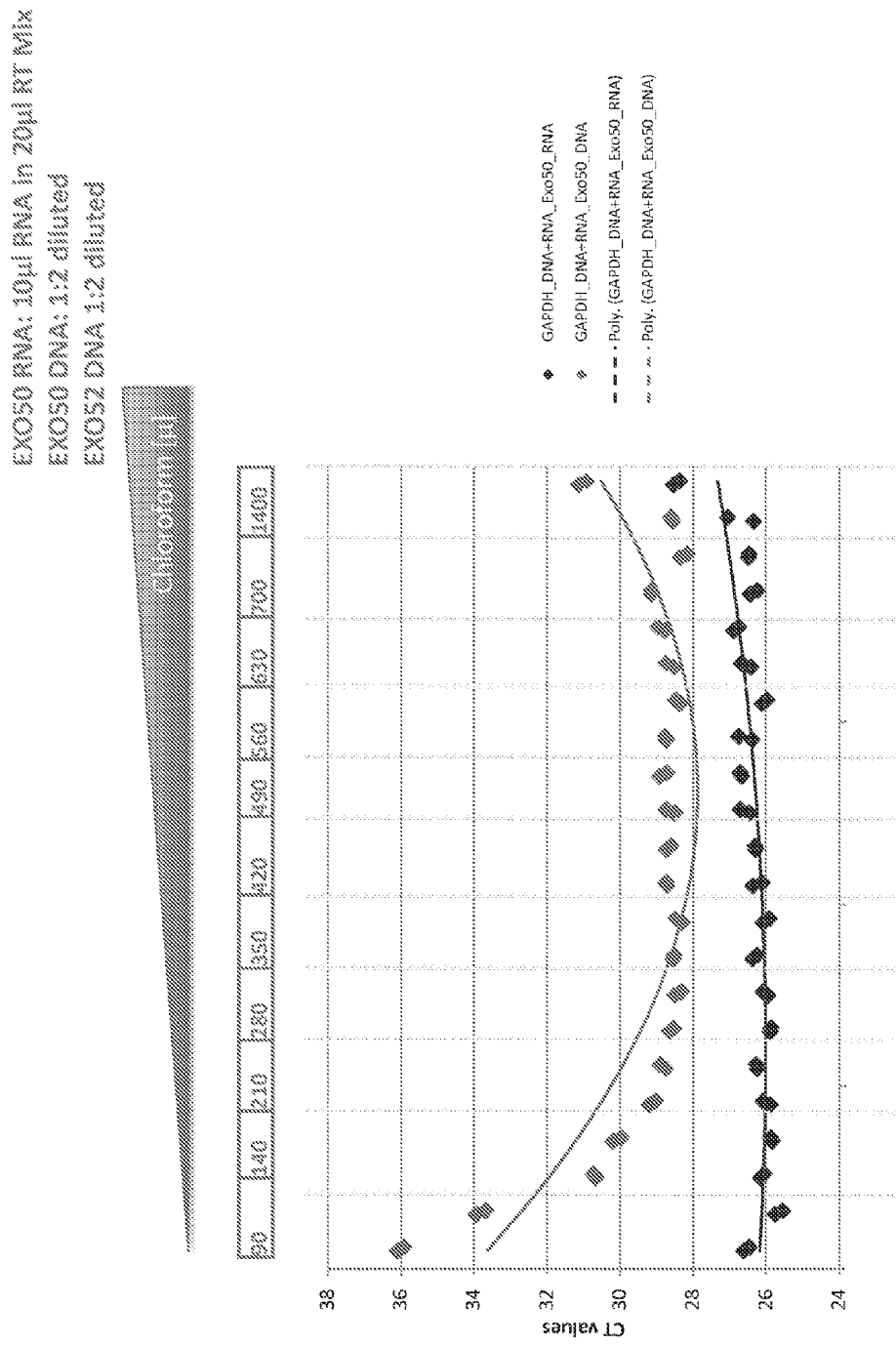

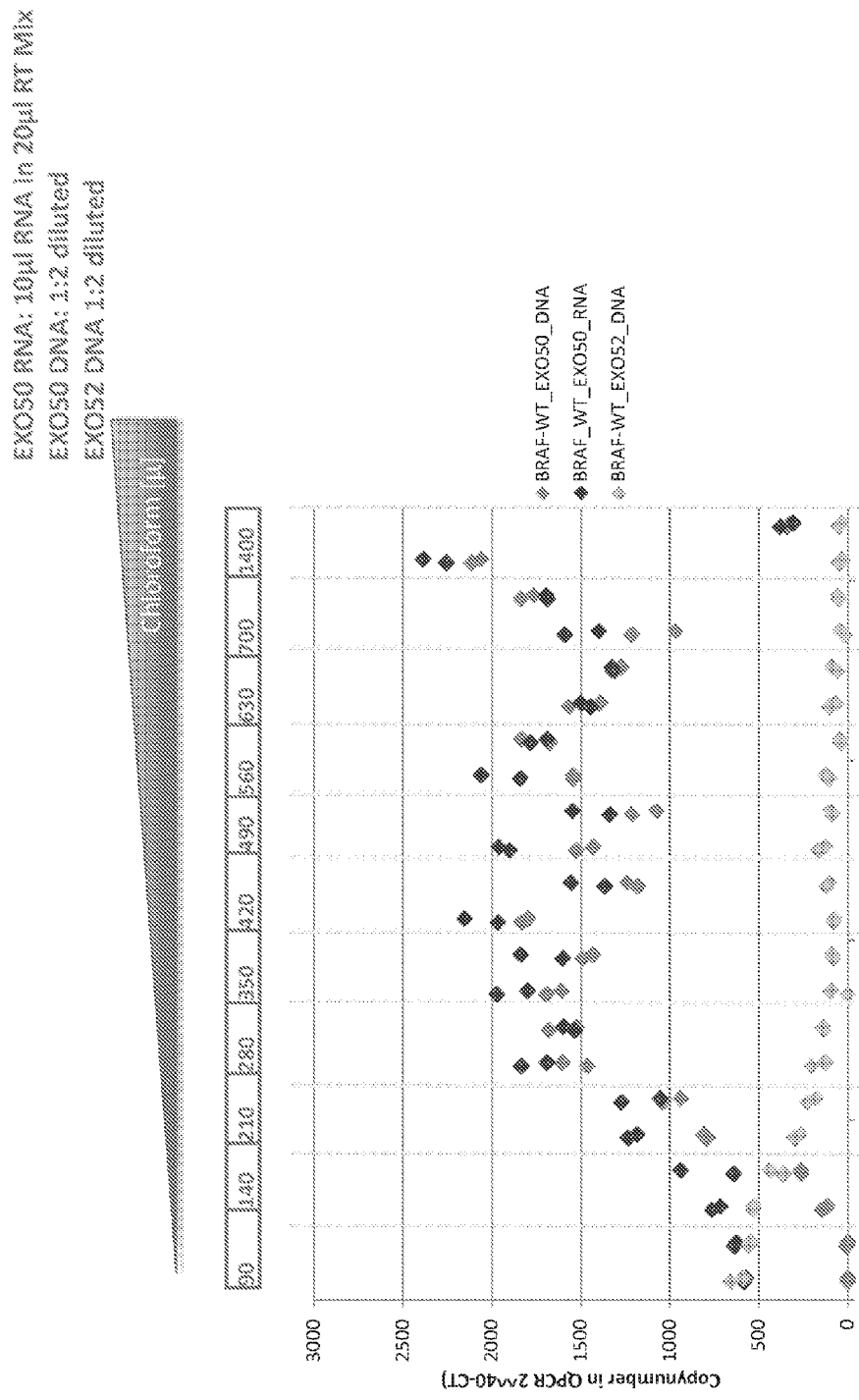

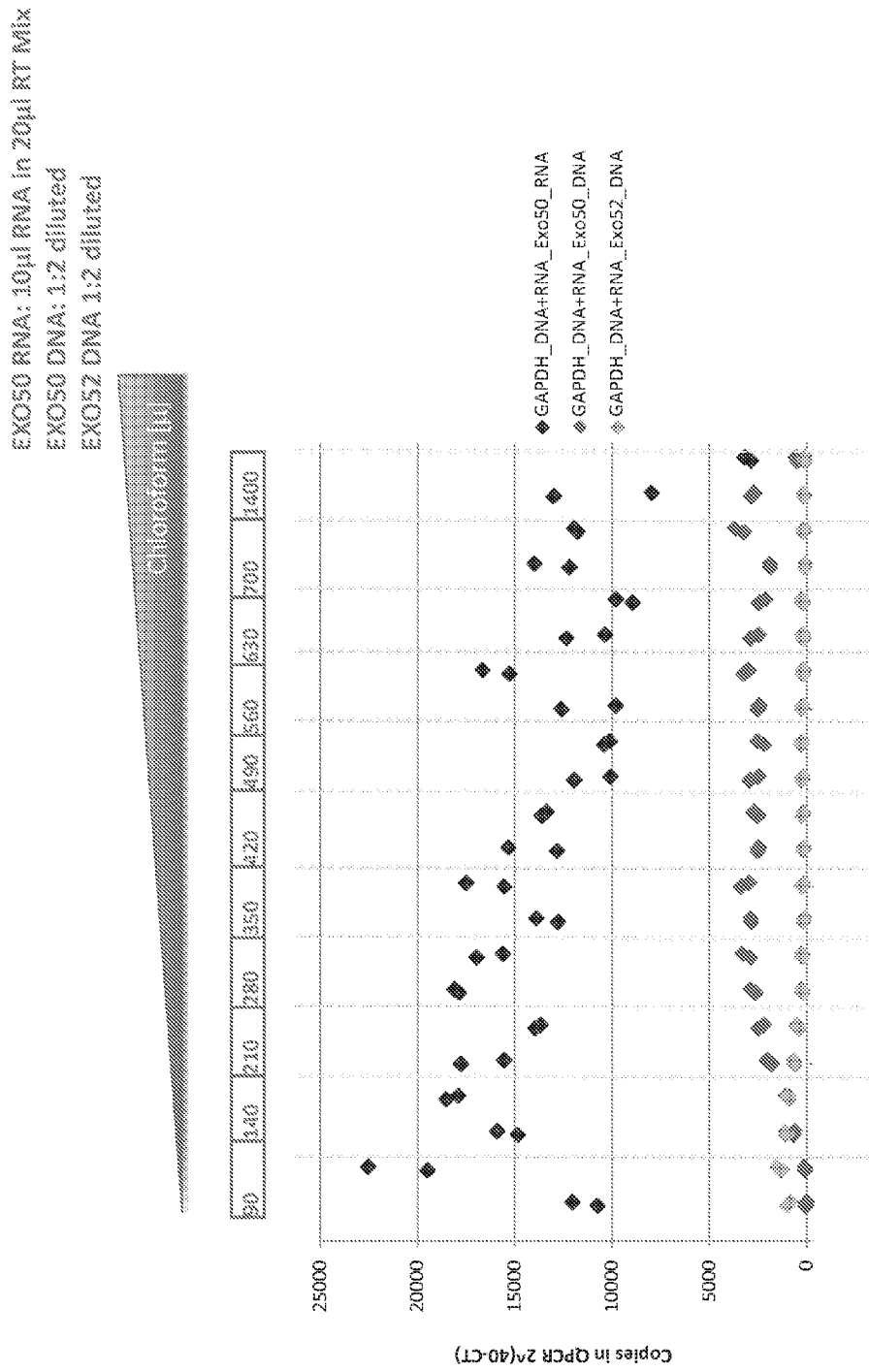

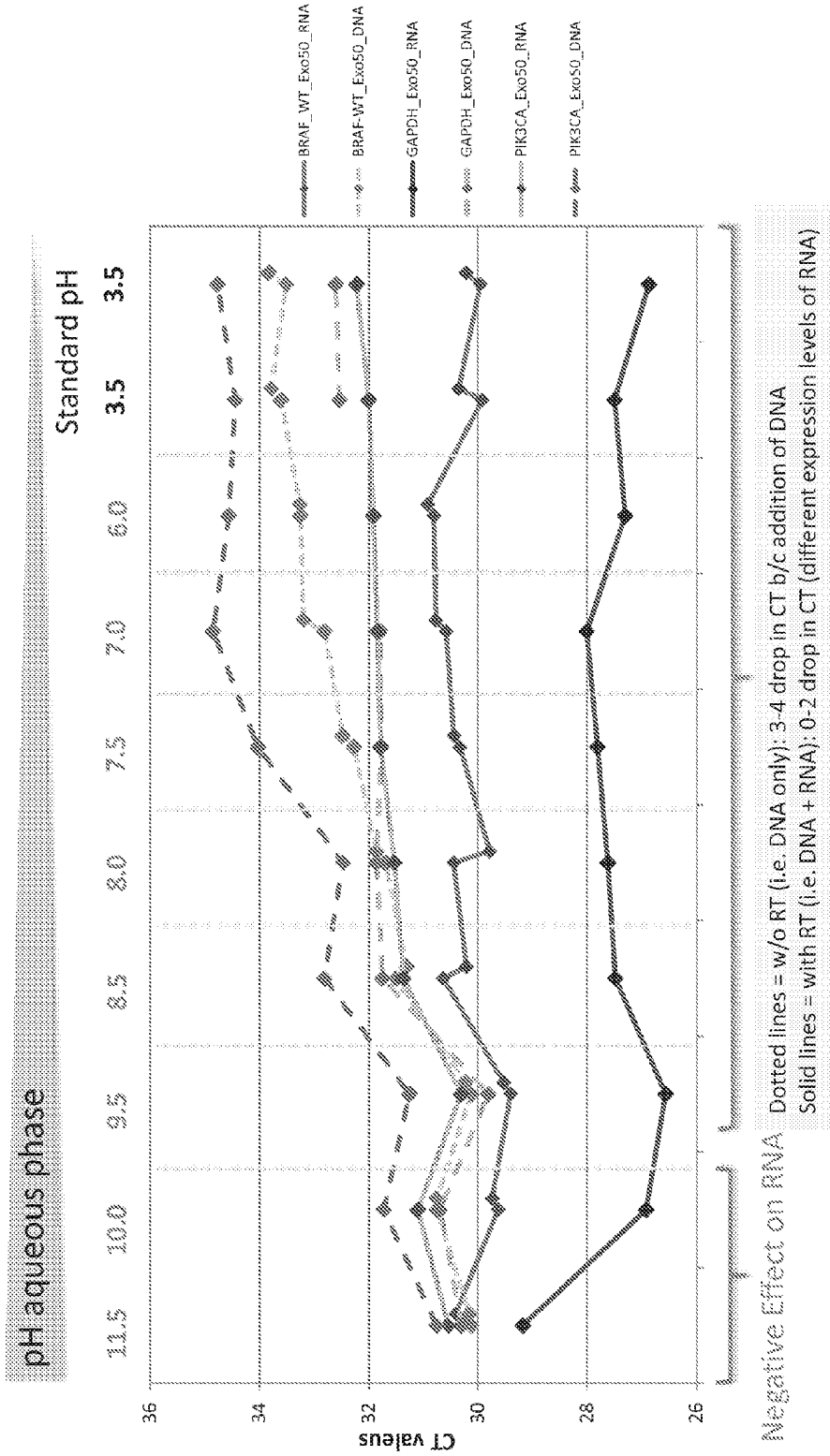

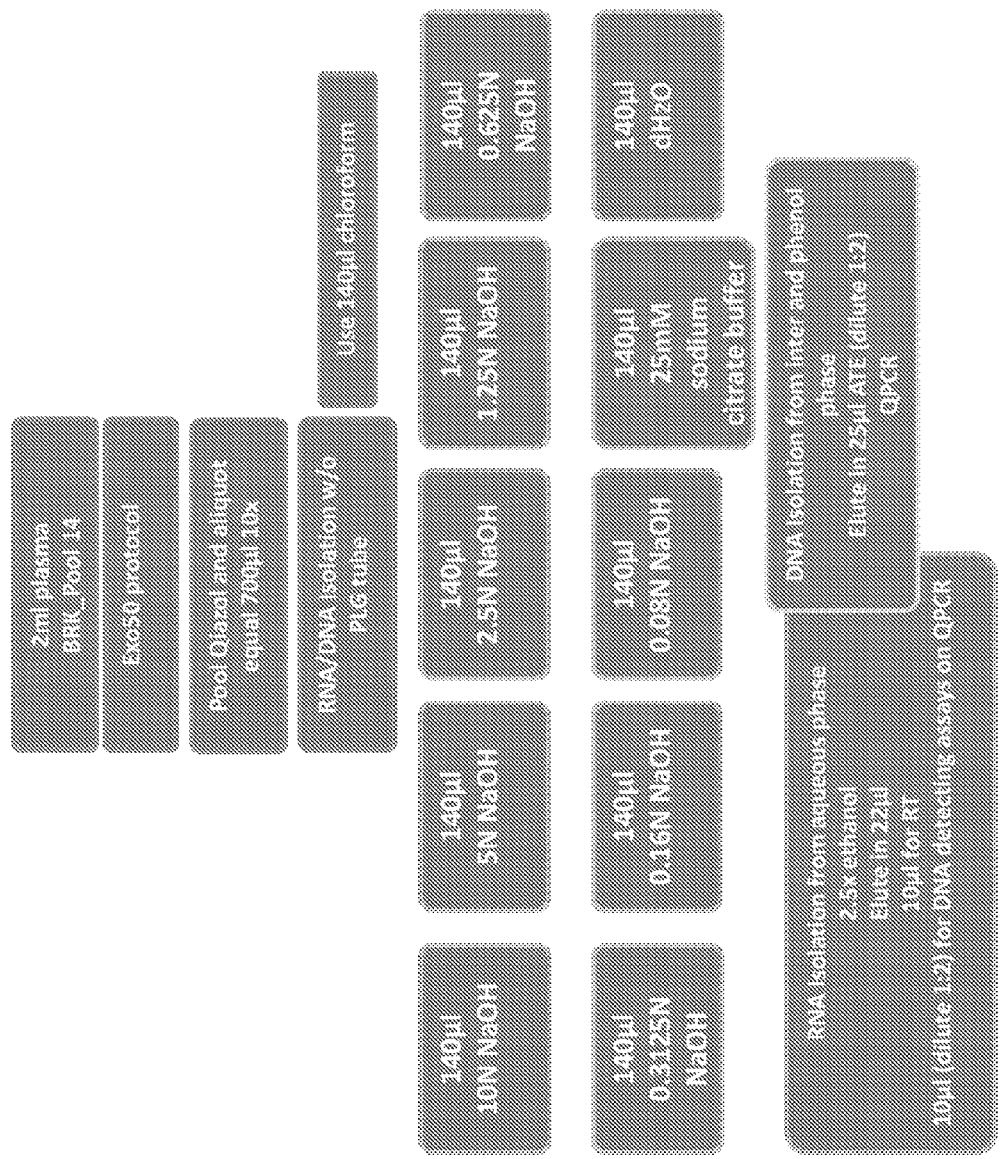

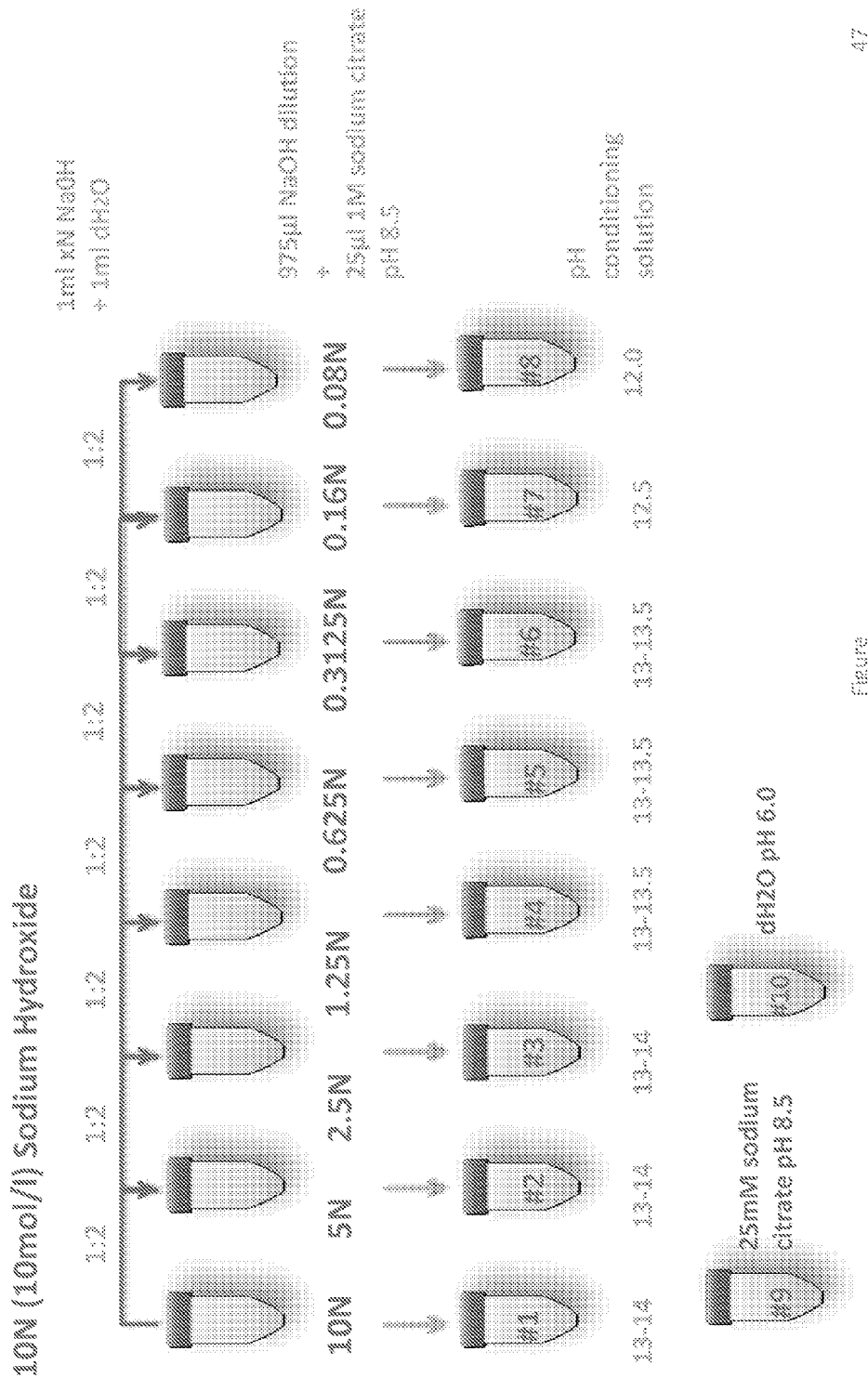

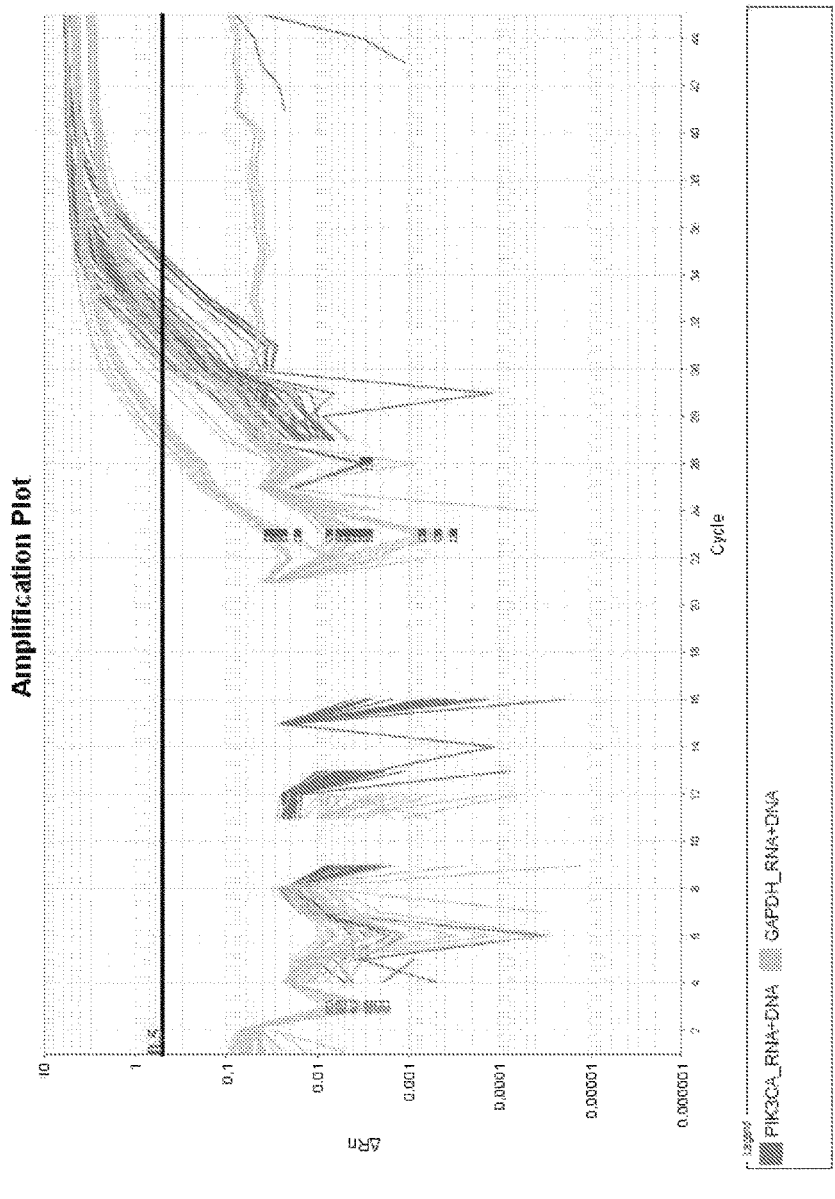

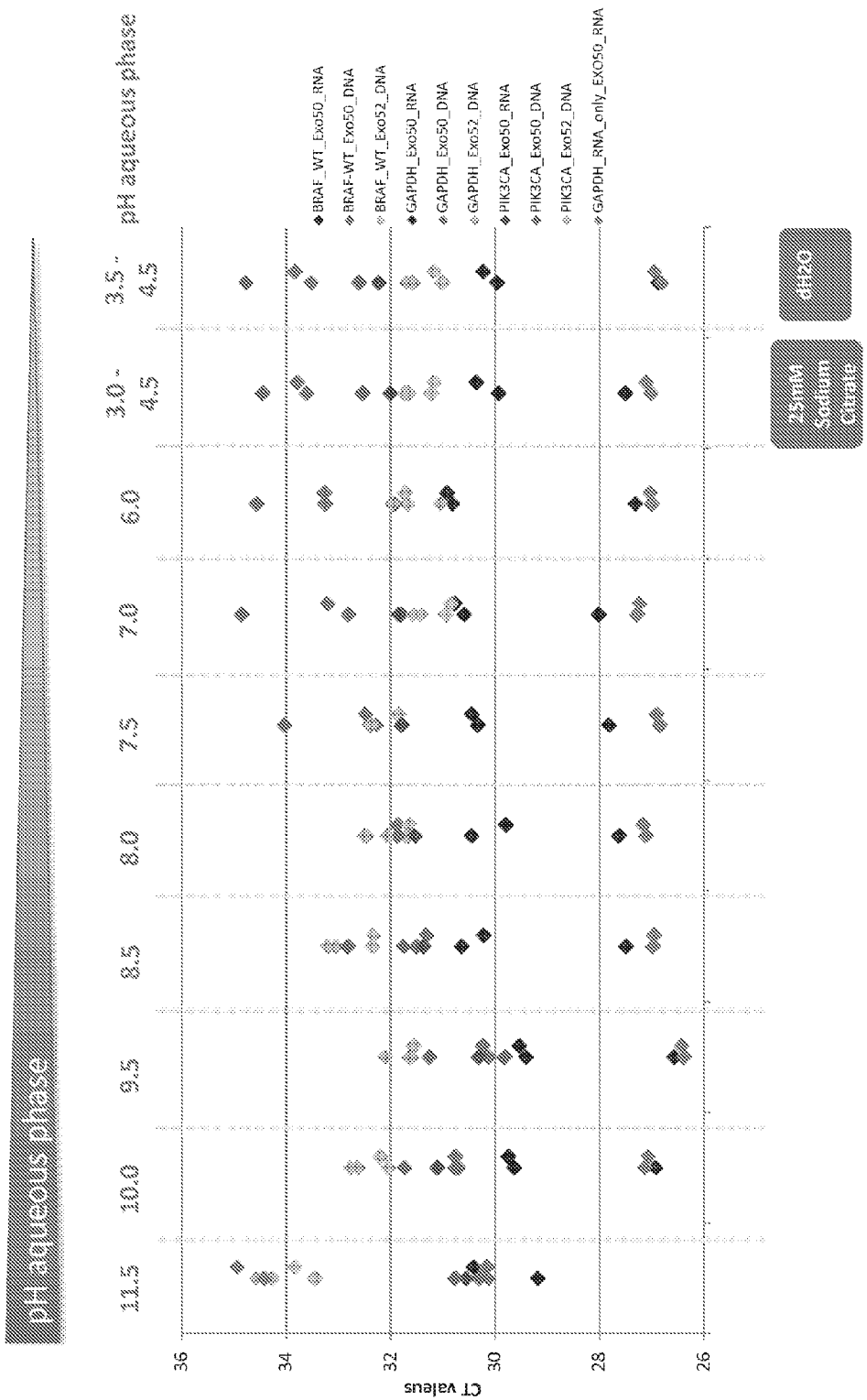

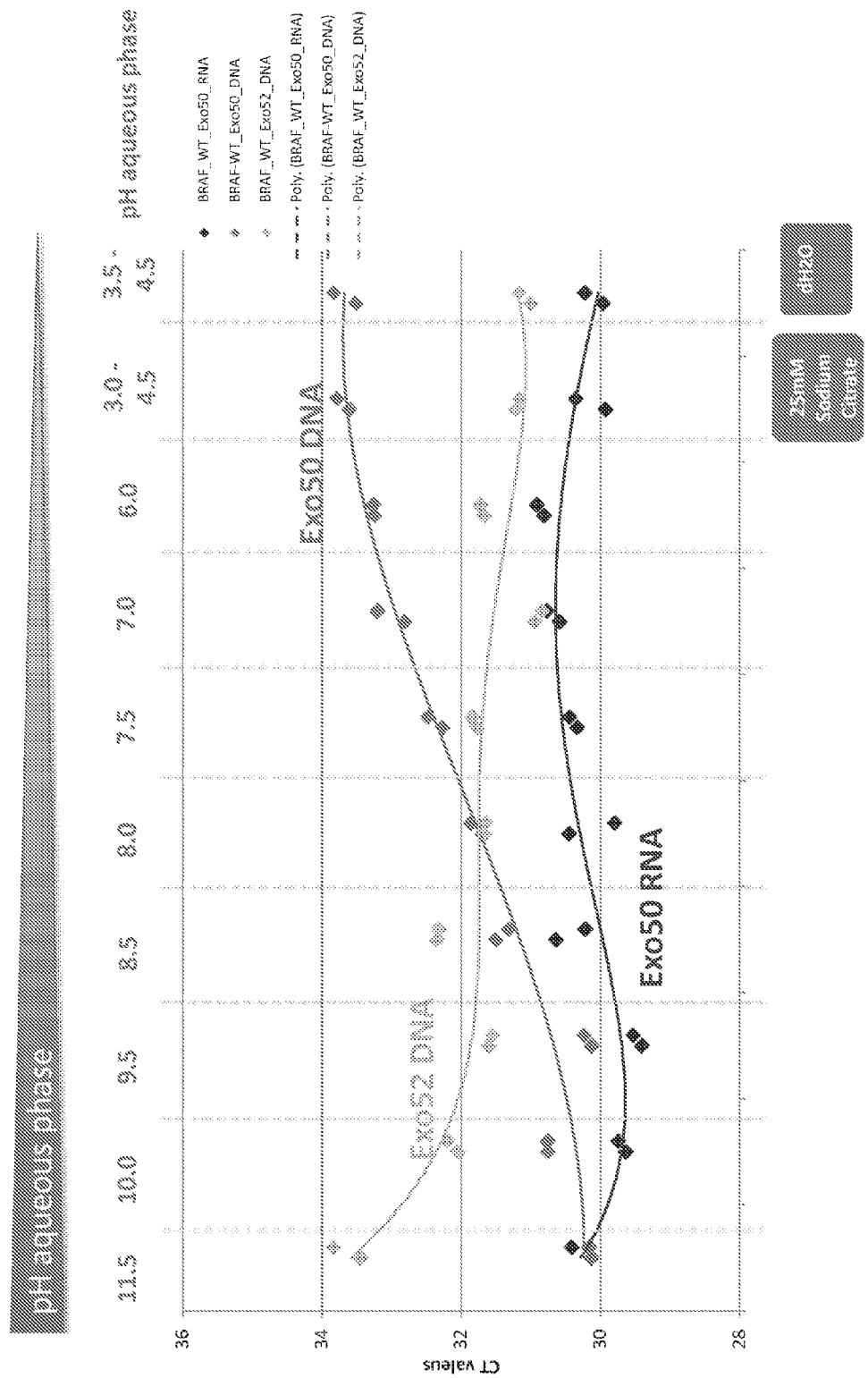

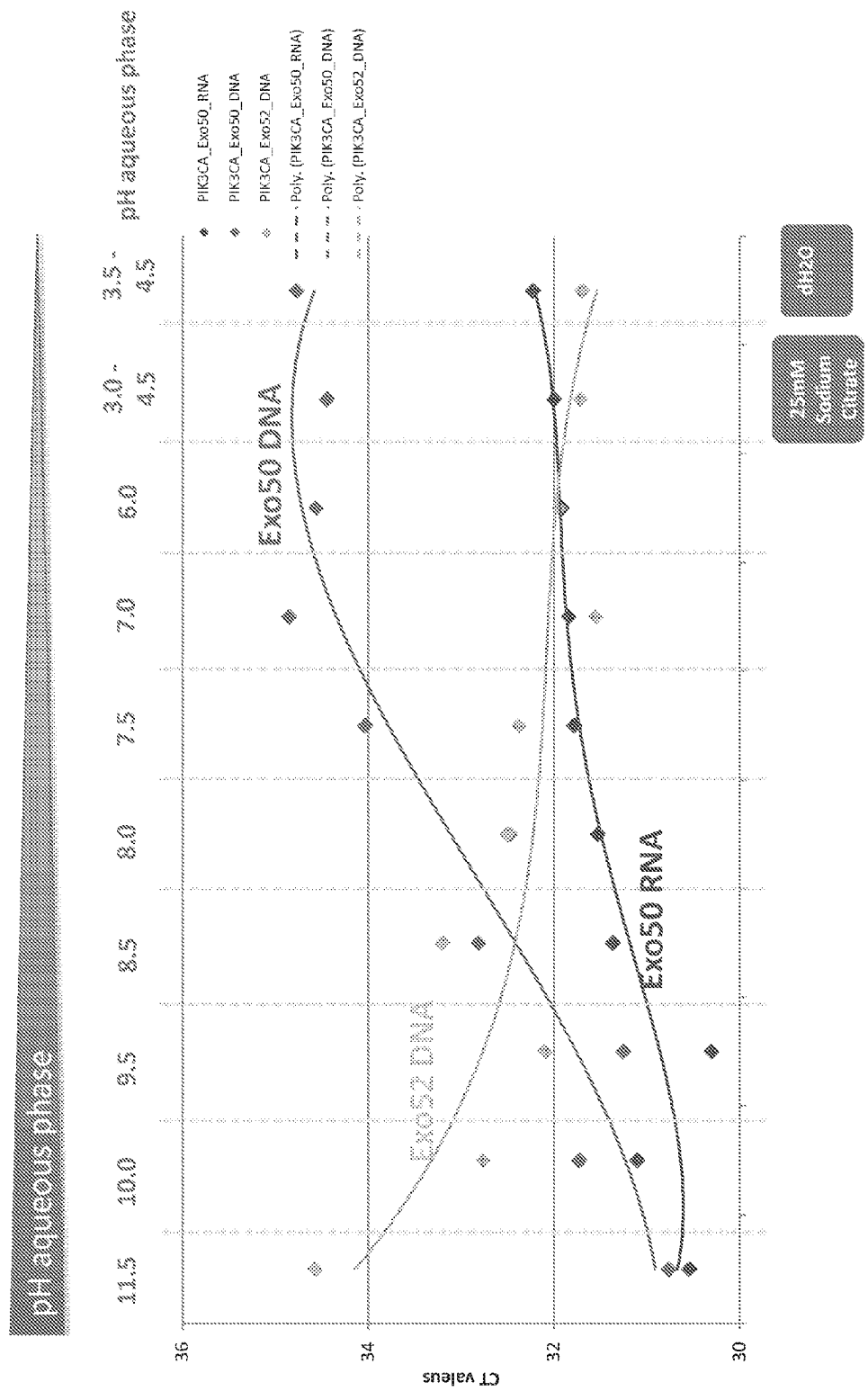

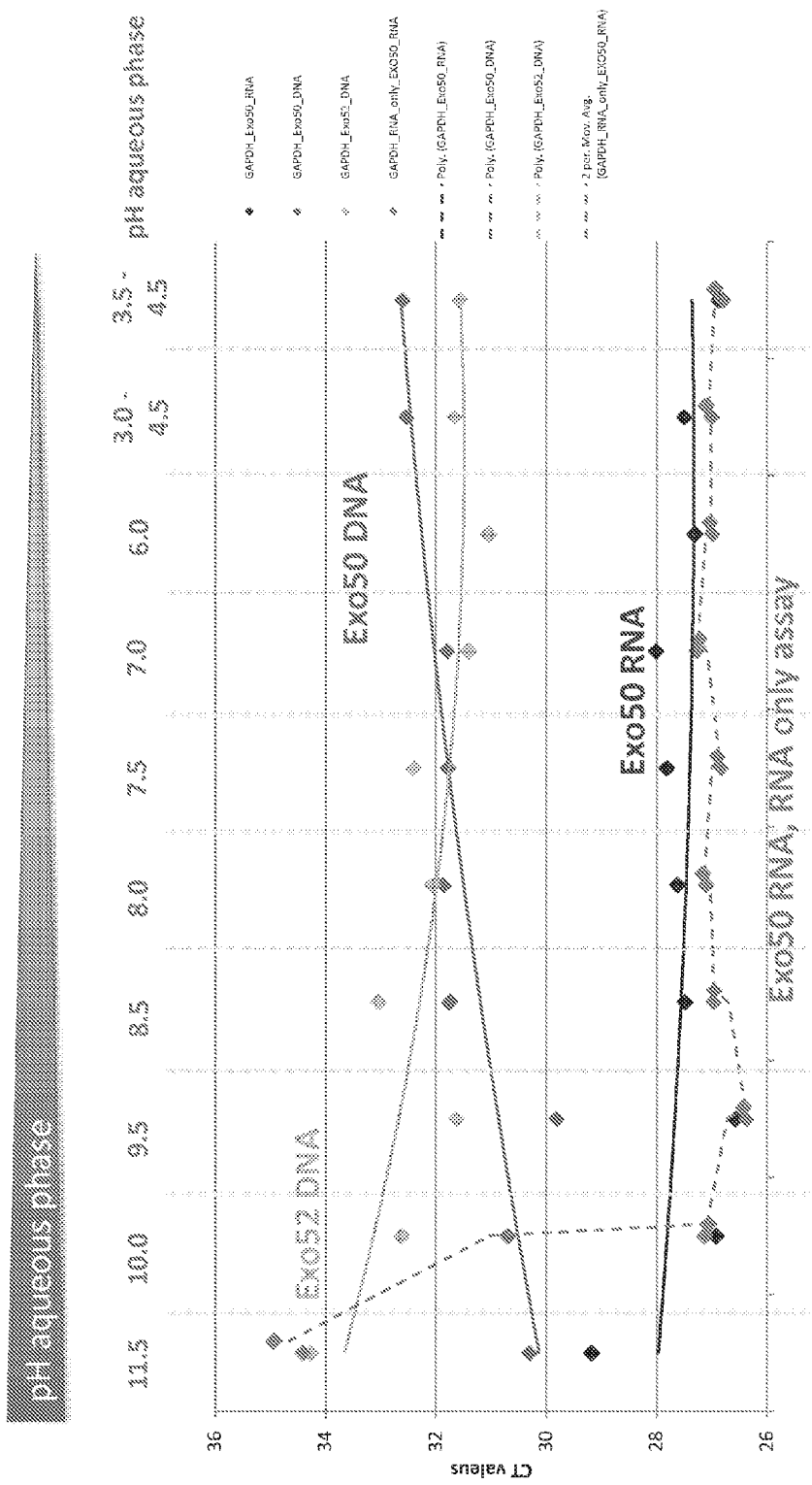

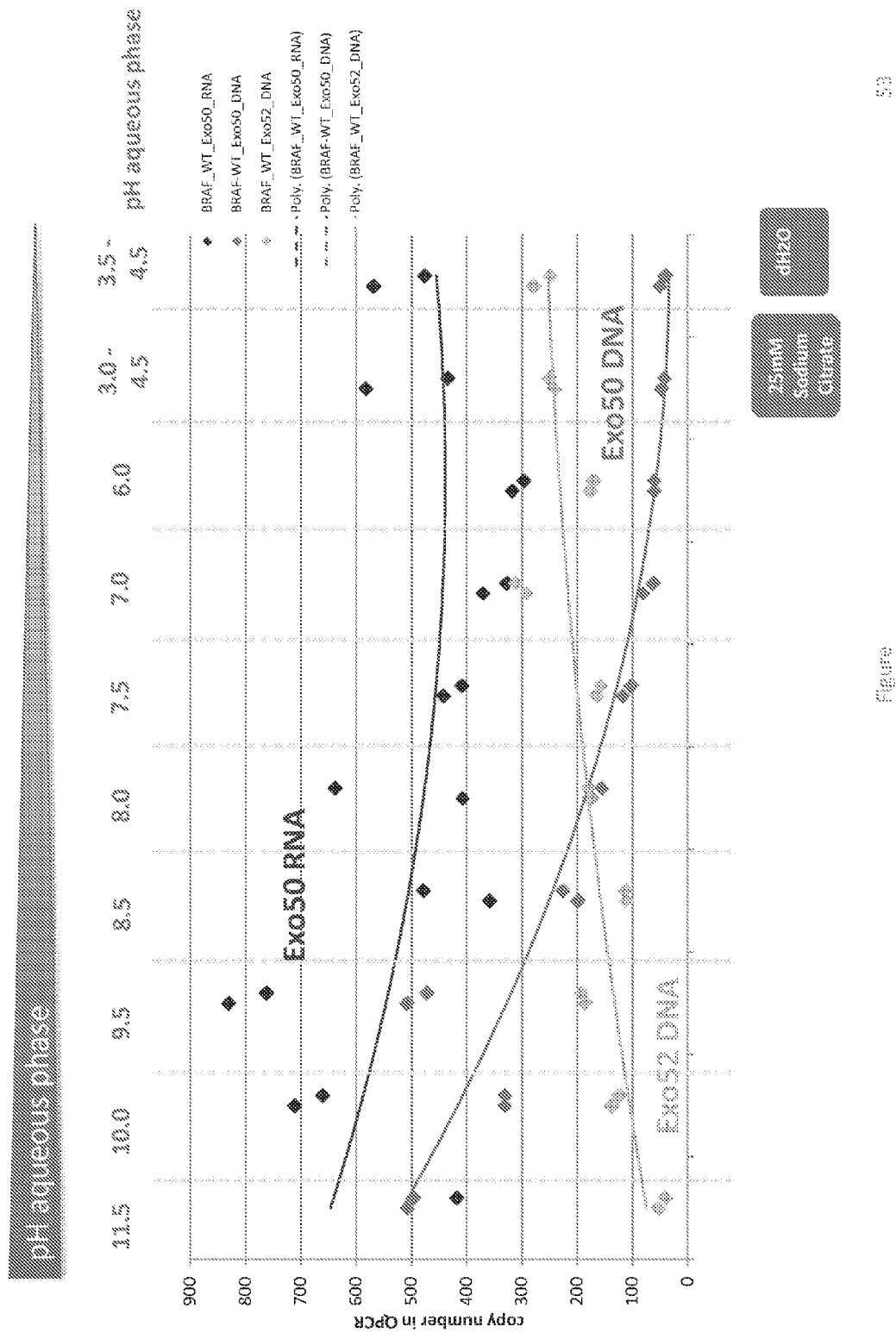

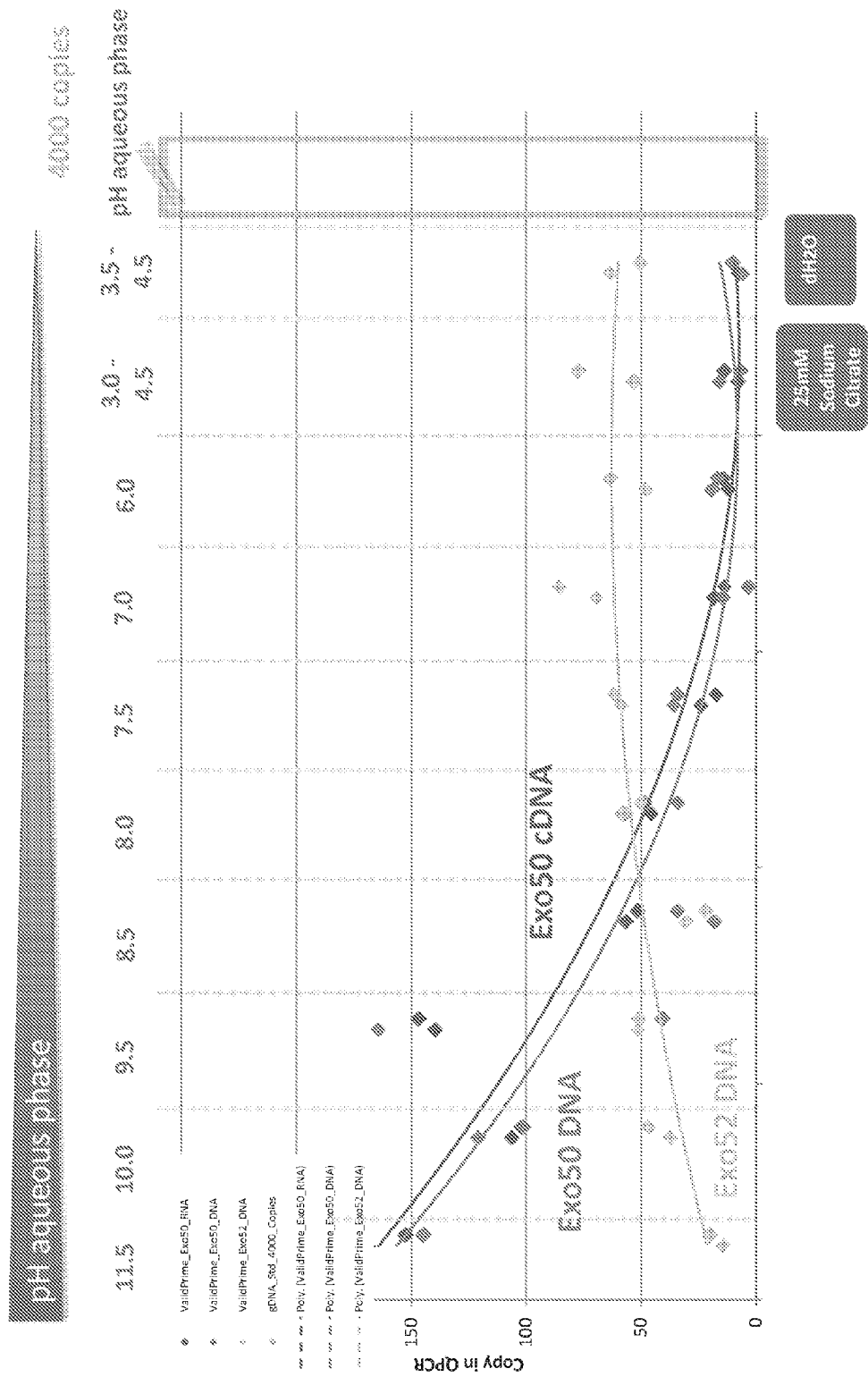

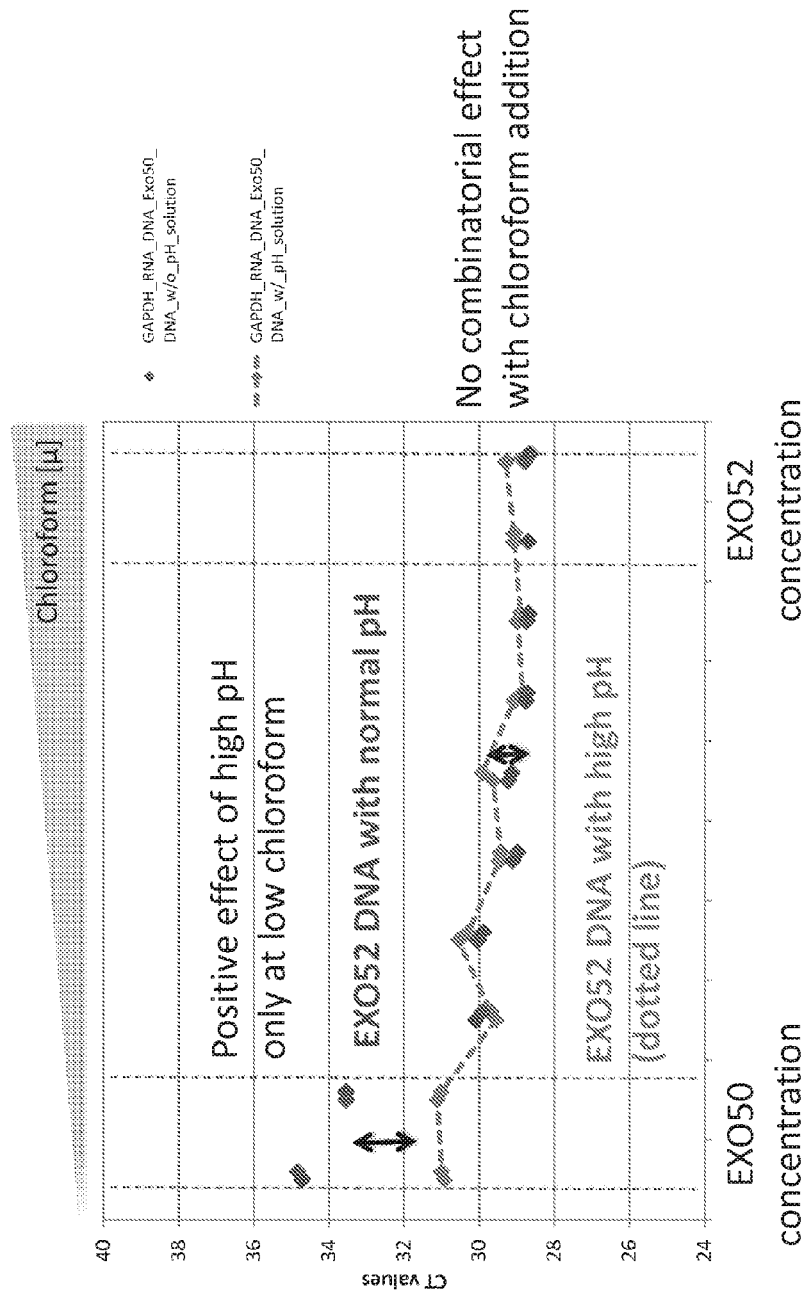

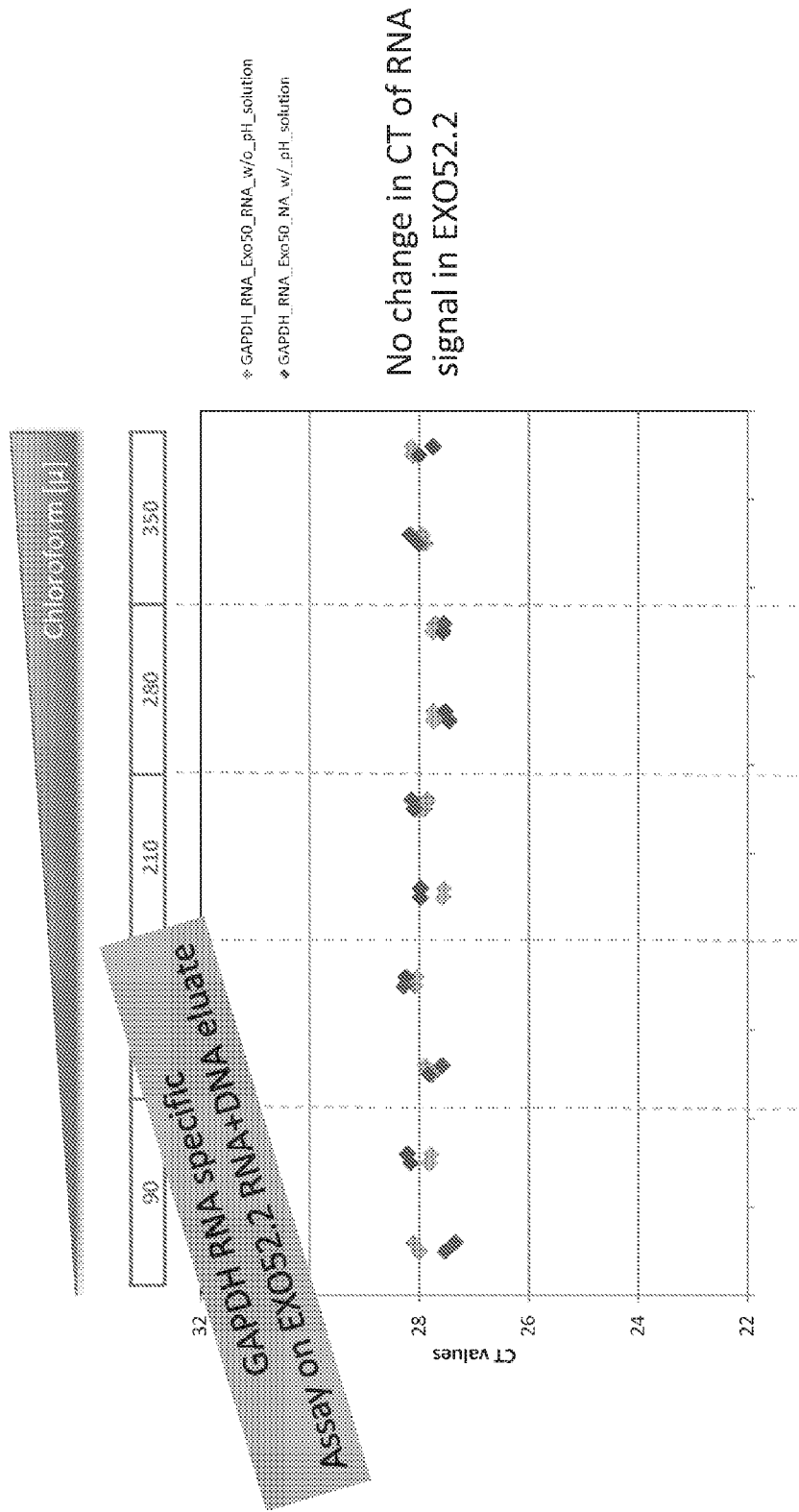

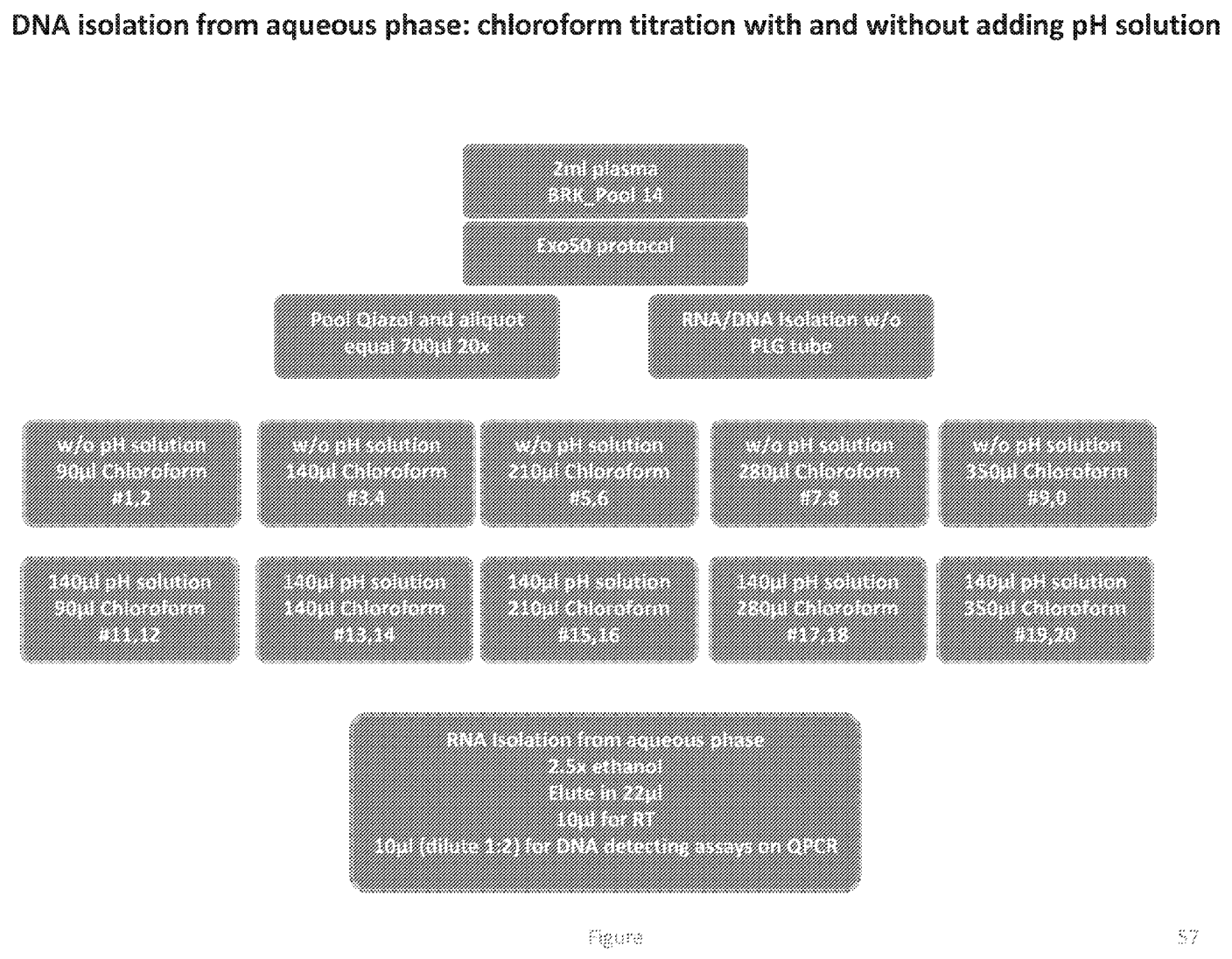

DNA isolation from aqueous phase: chloroform titration with and without adding pH solution

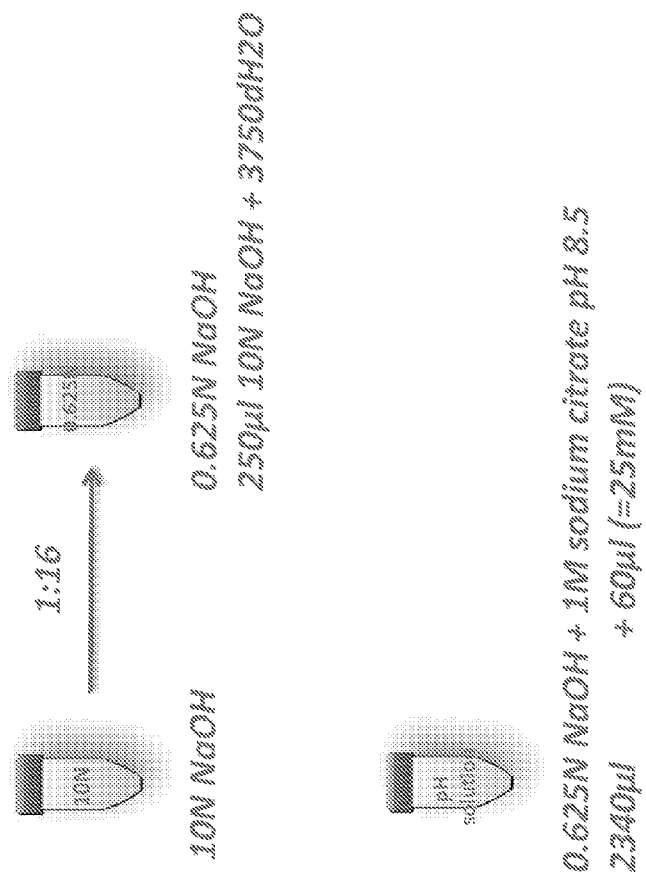

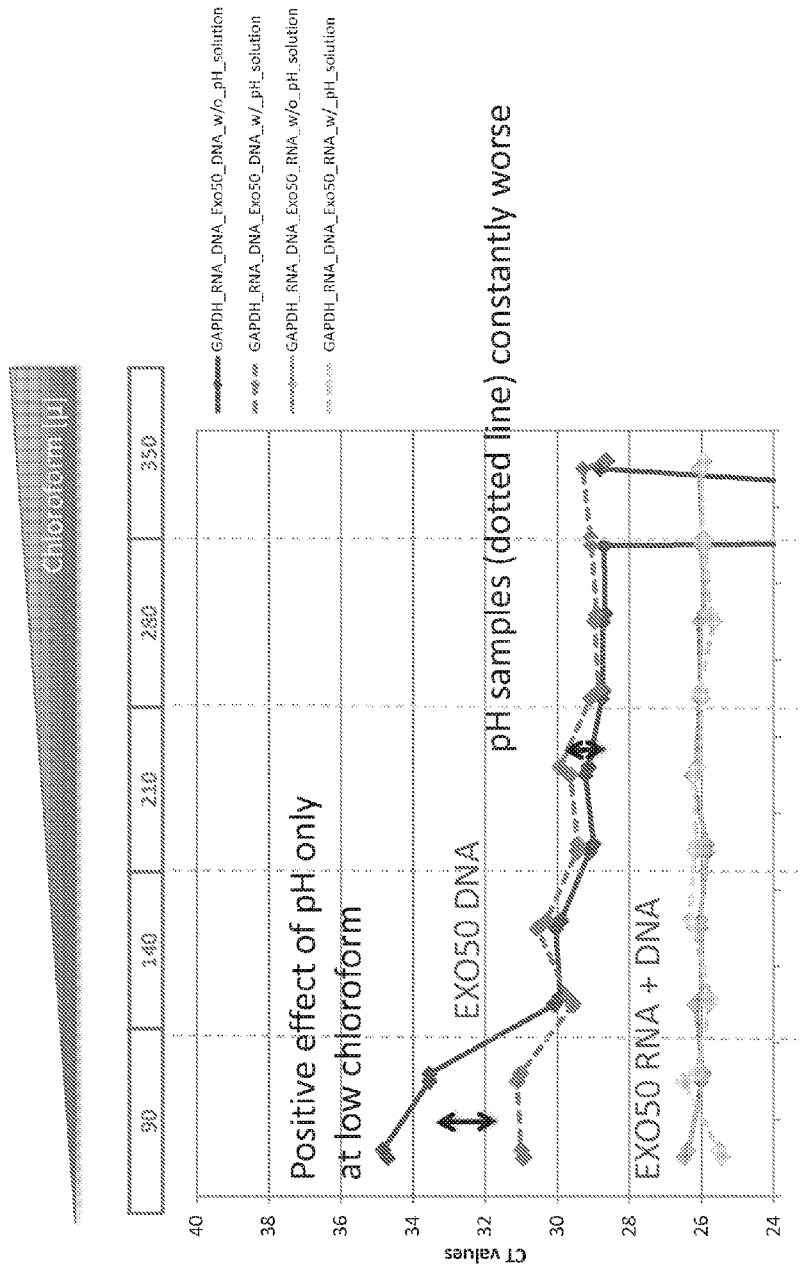

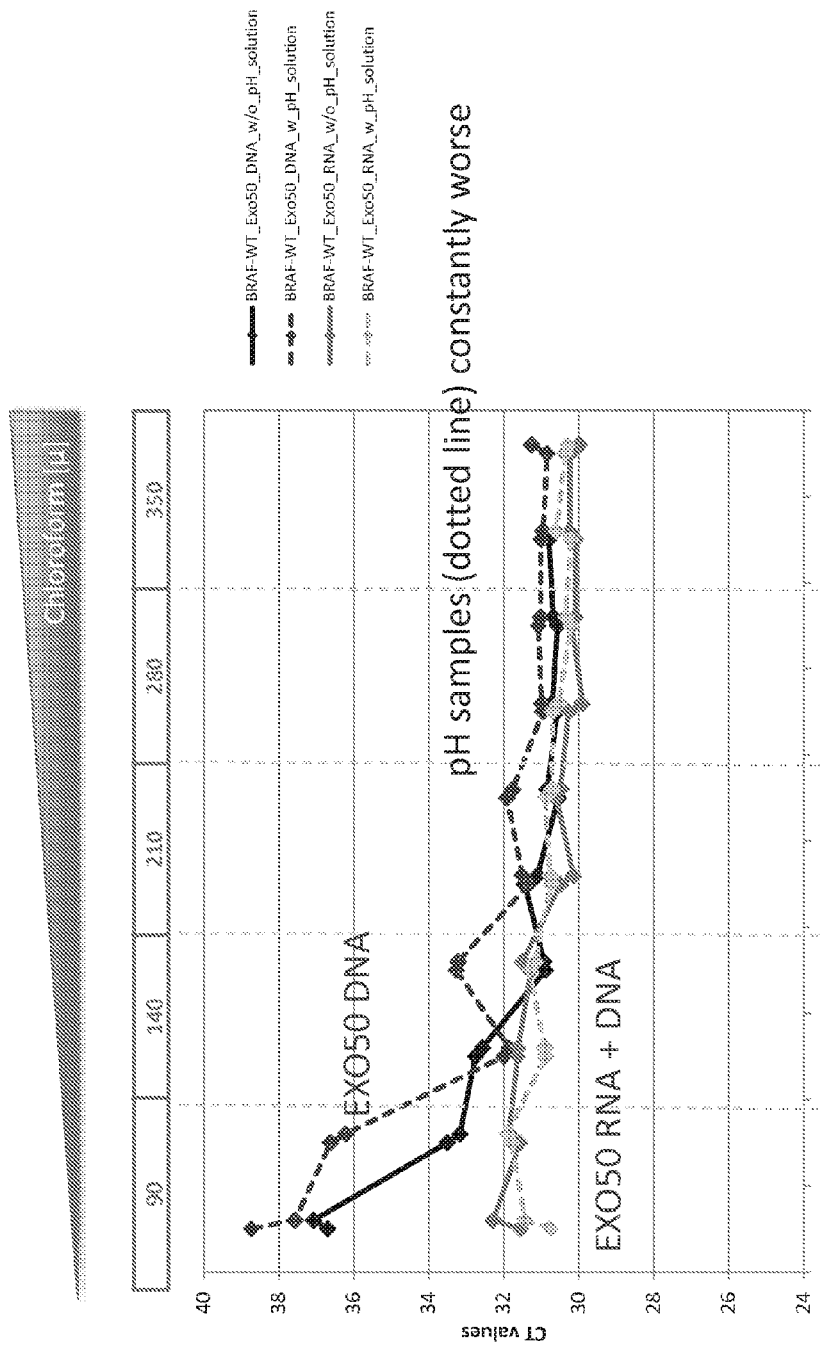

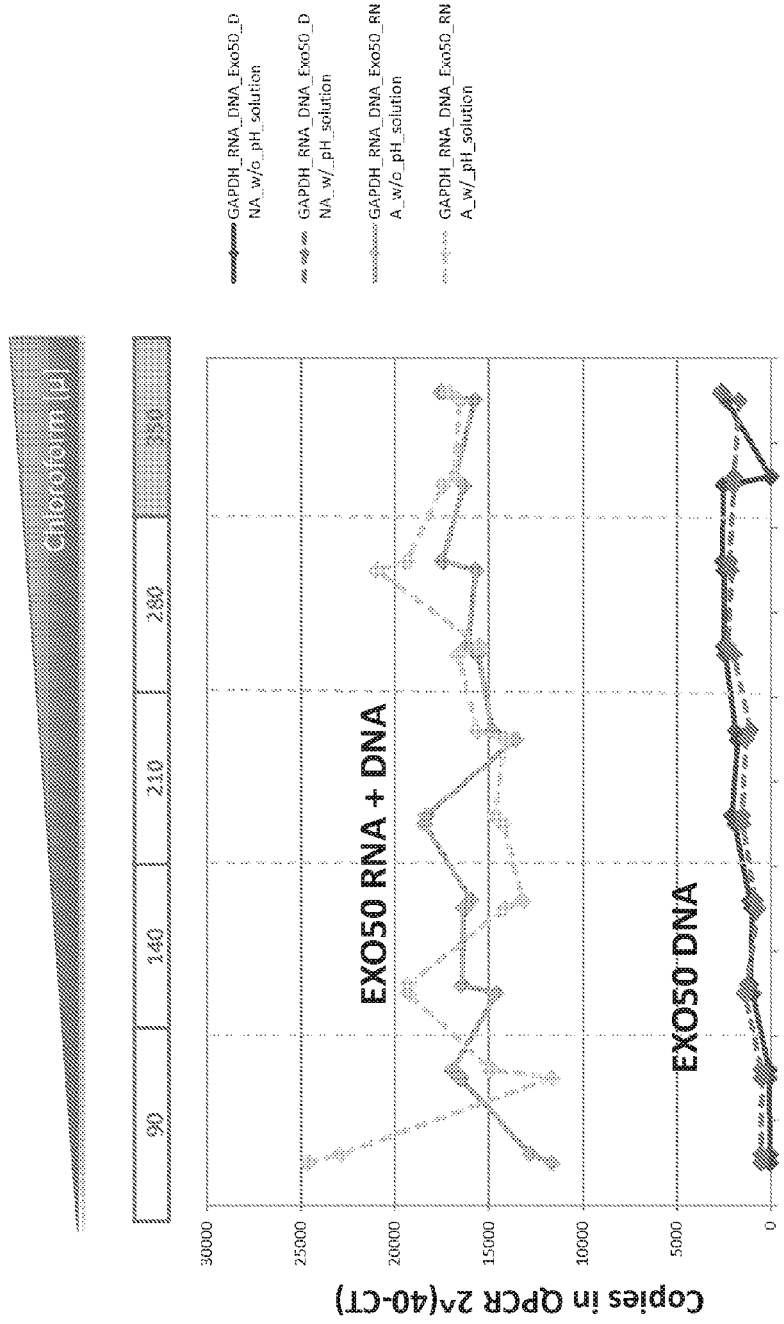

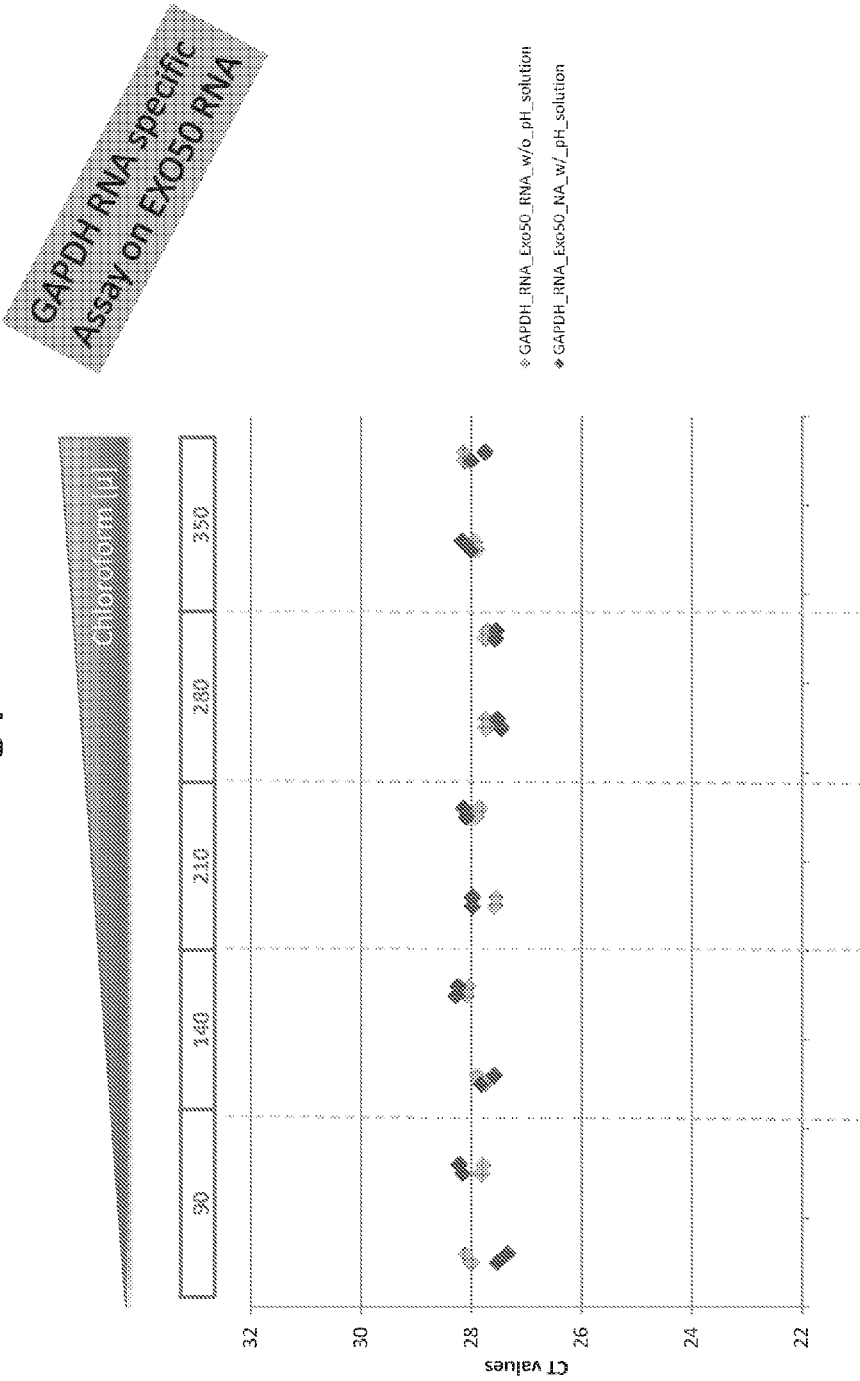

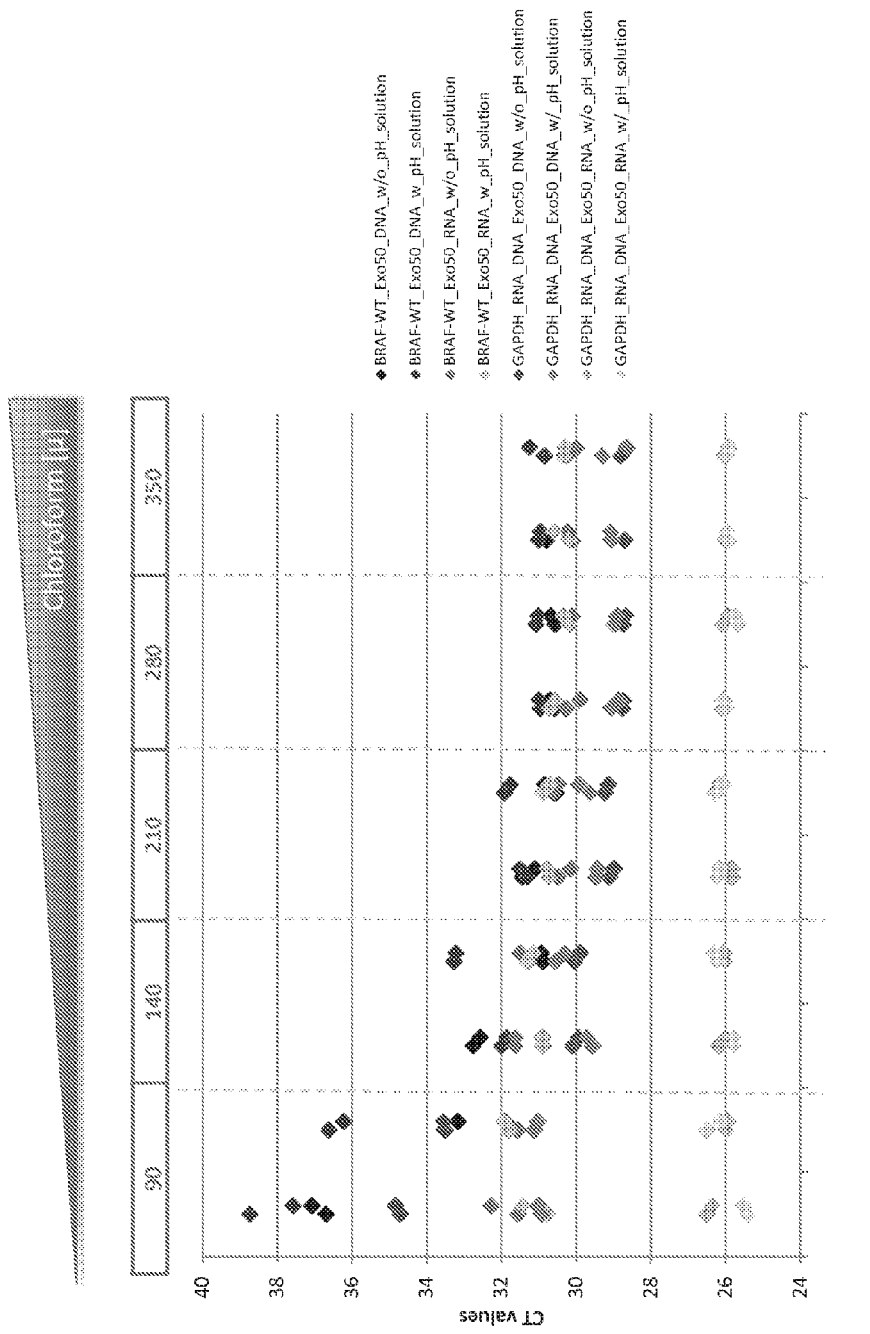

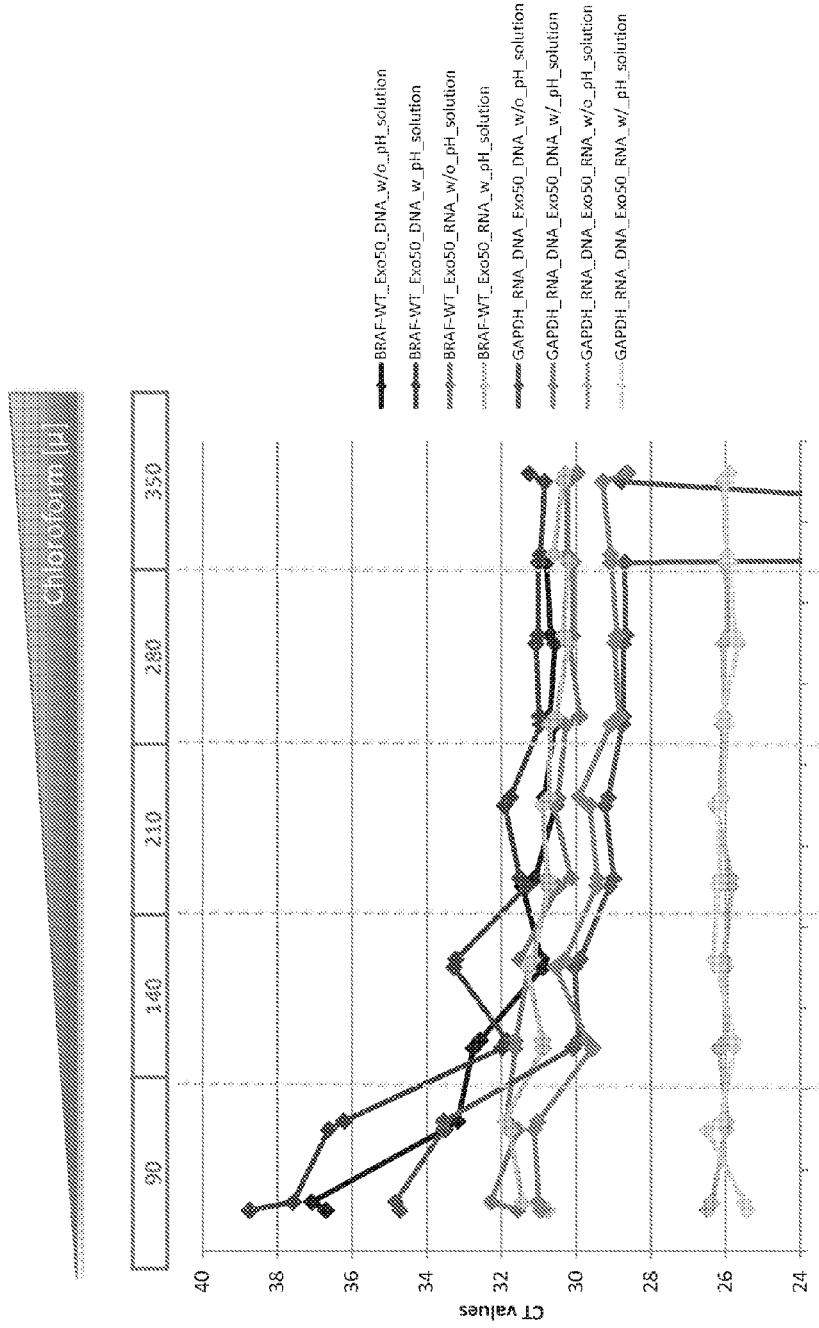

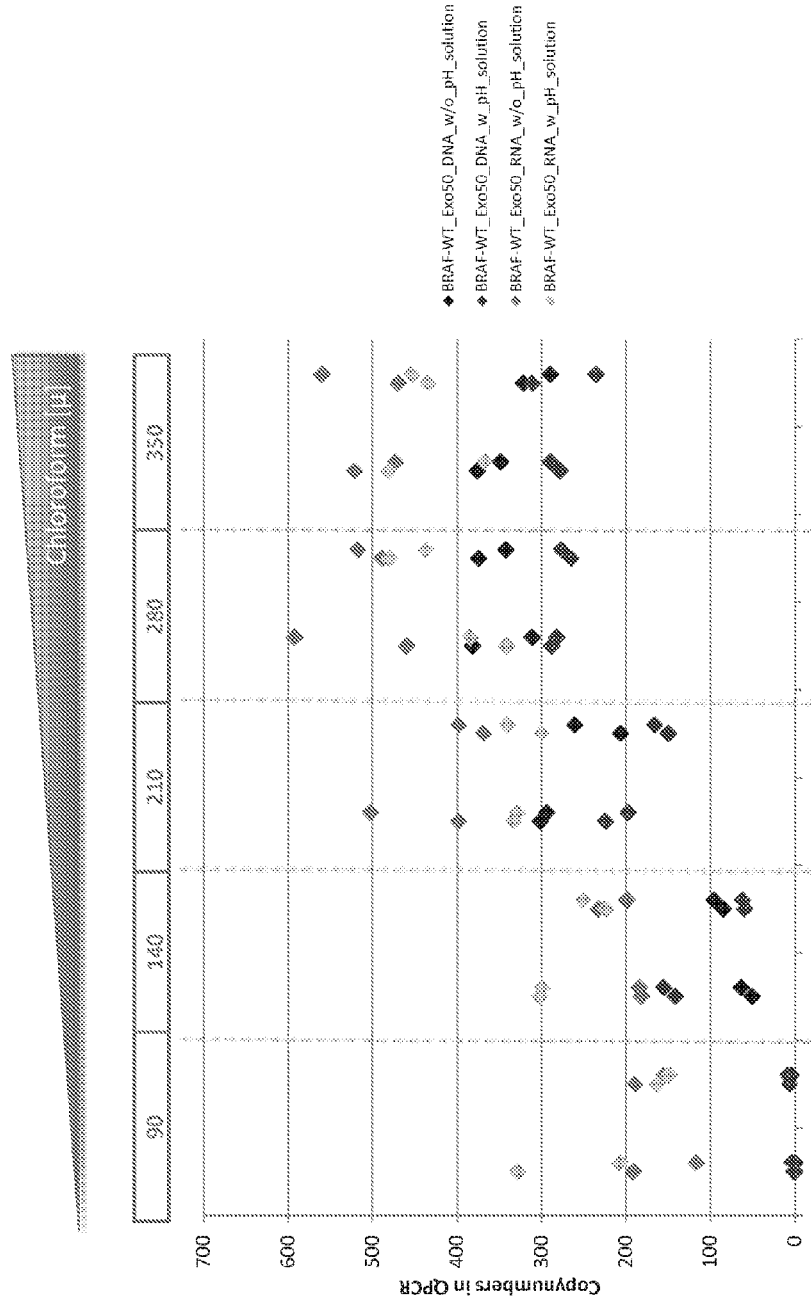

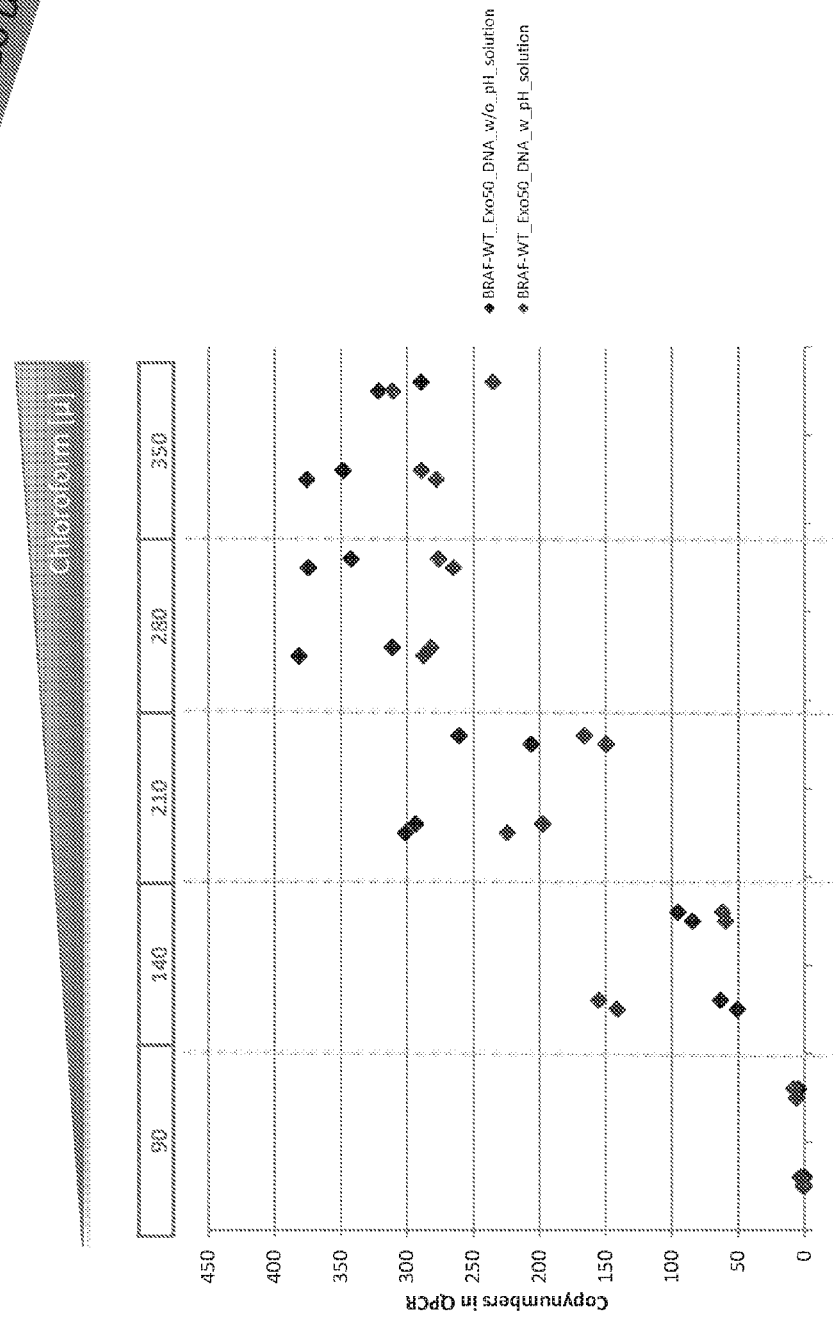

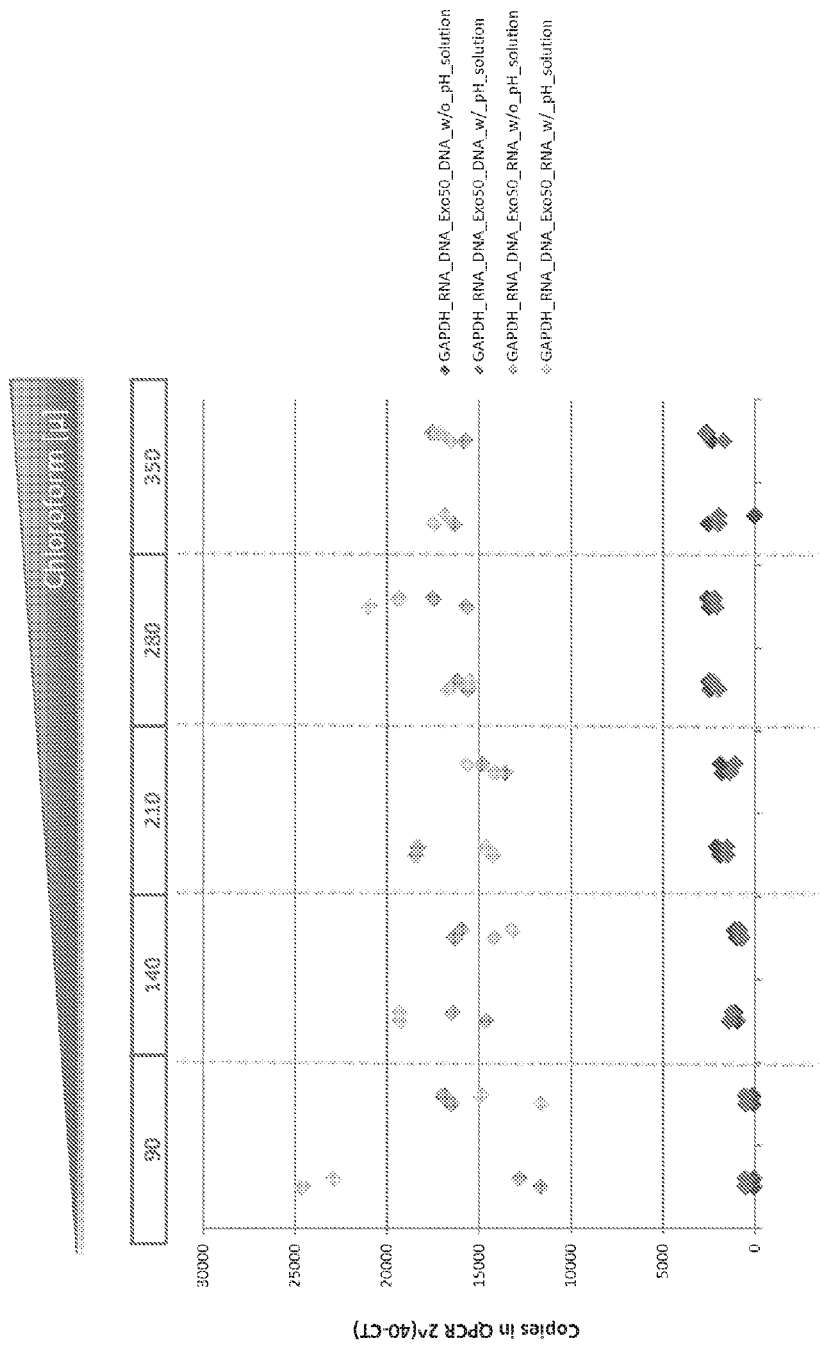

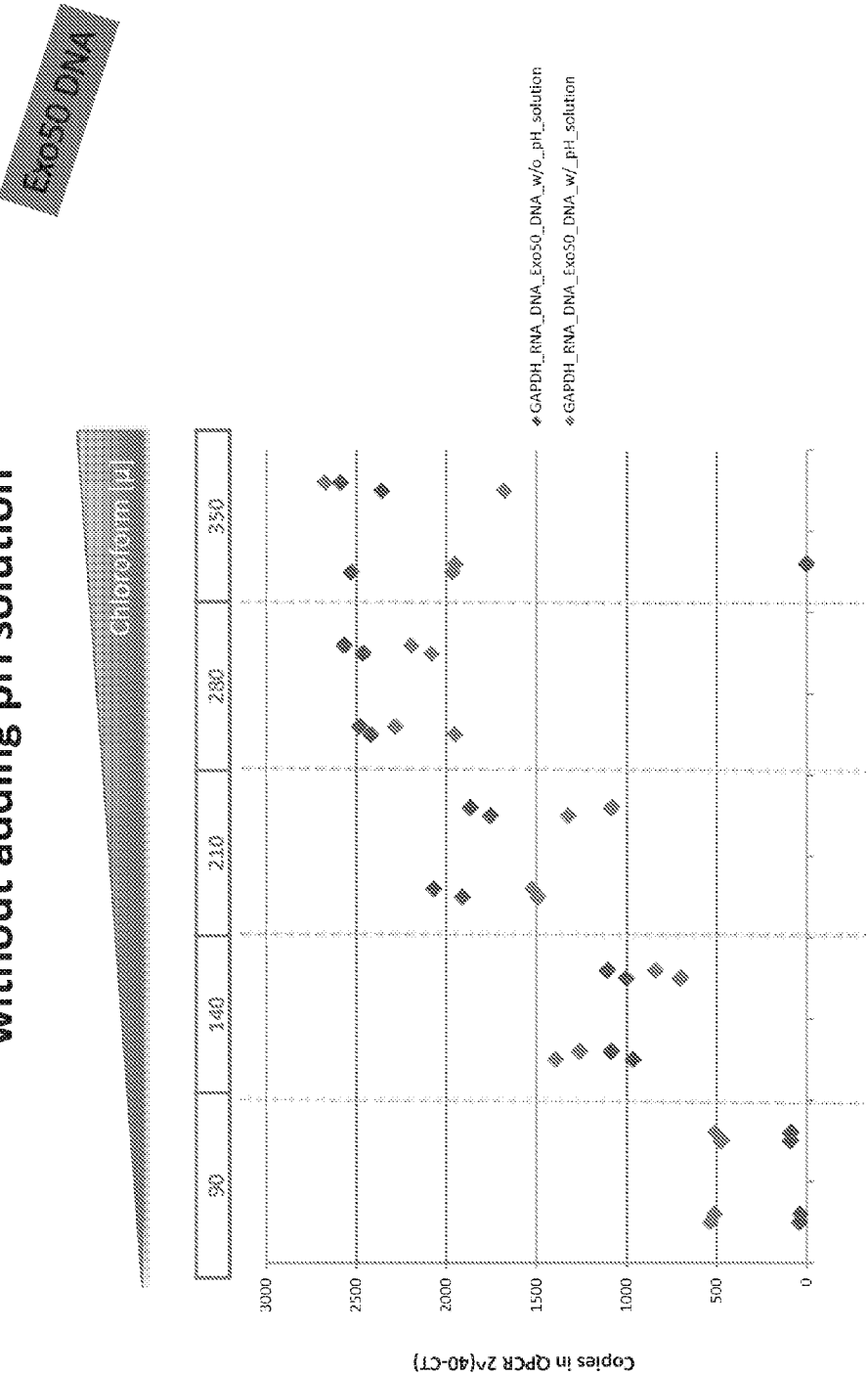

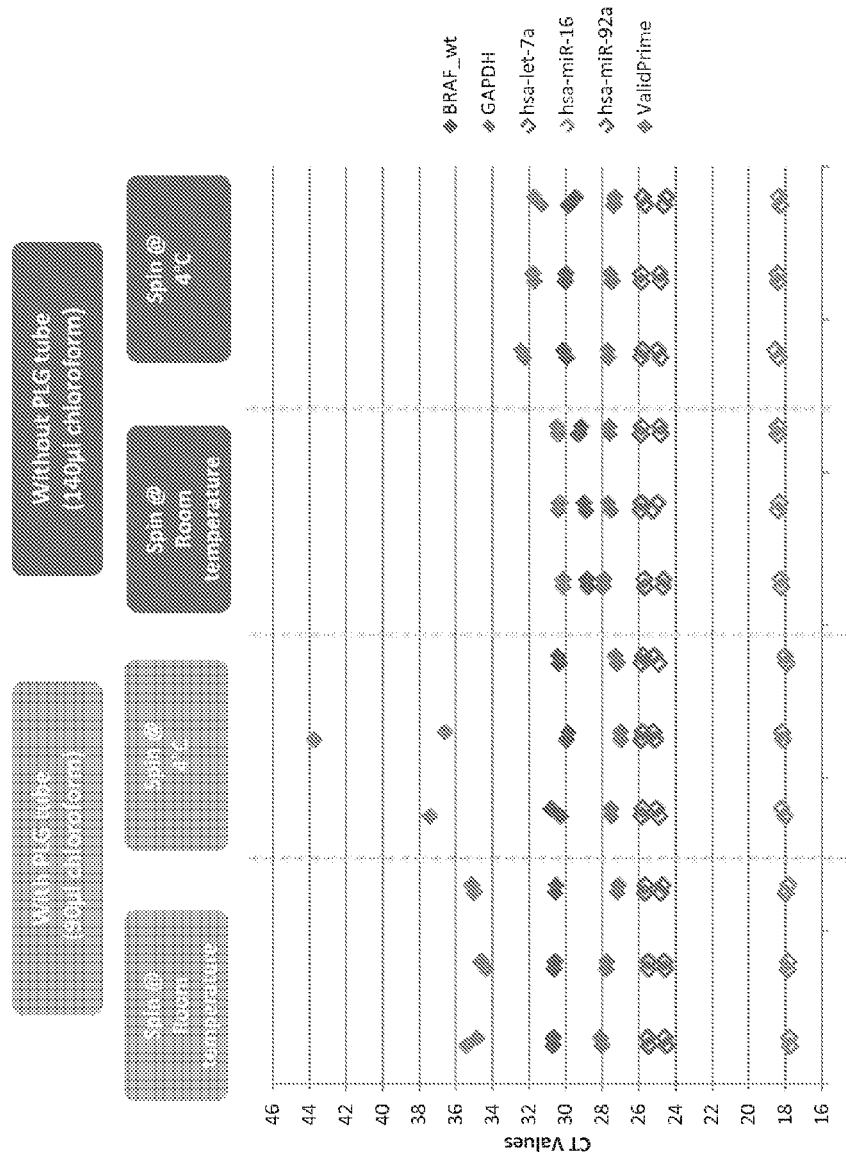

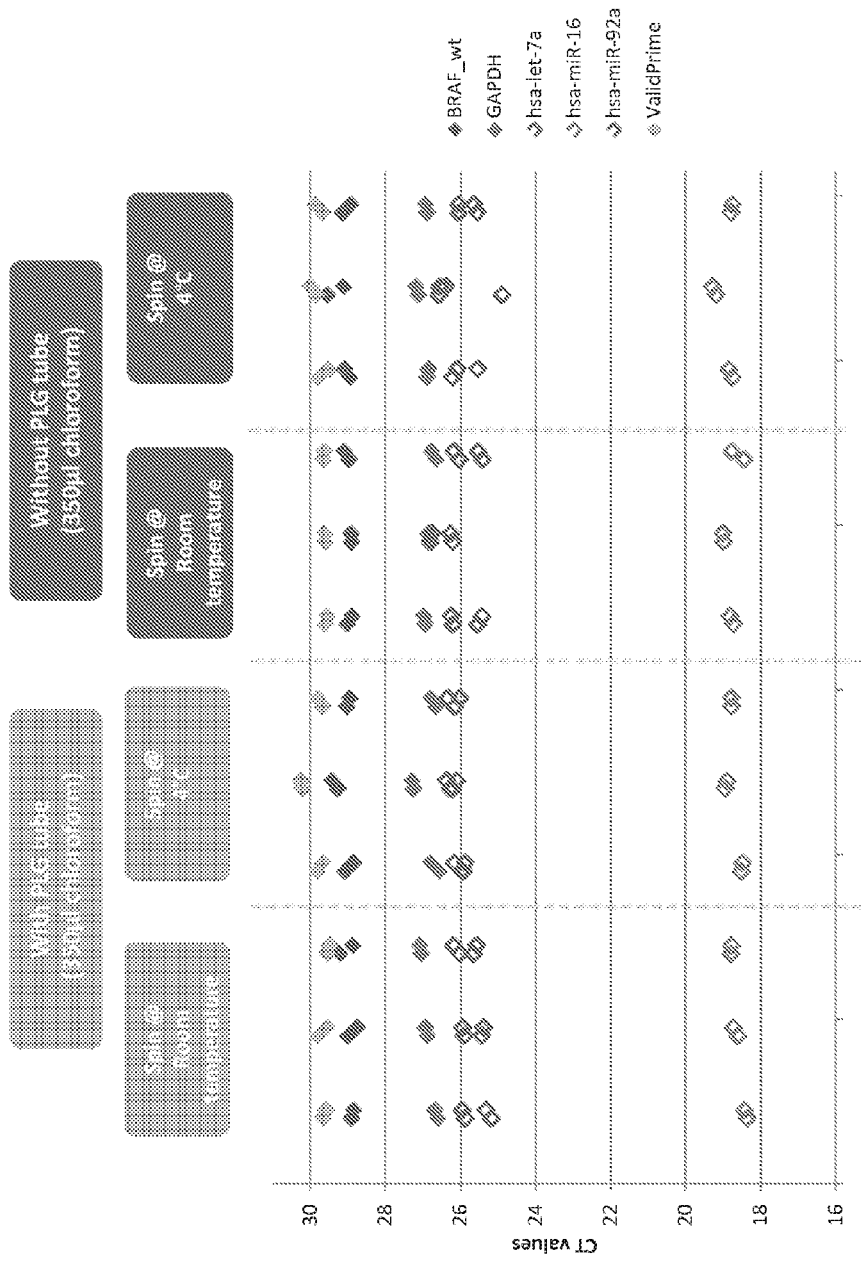

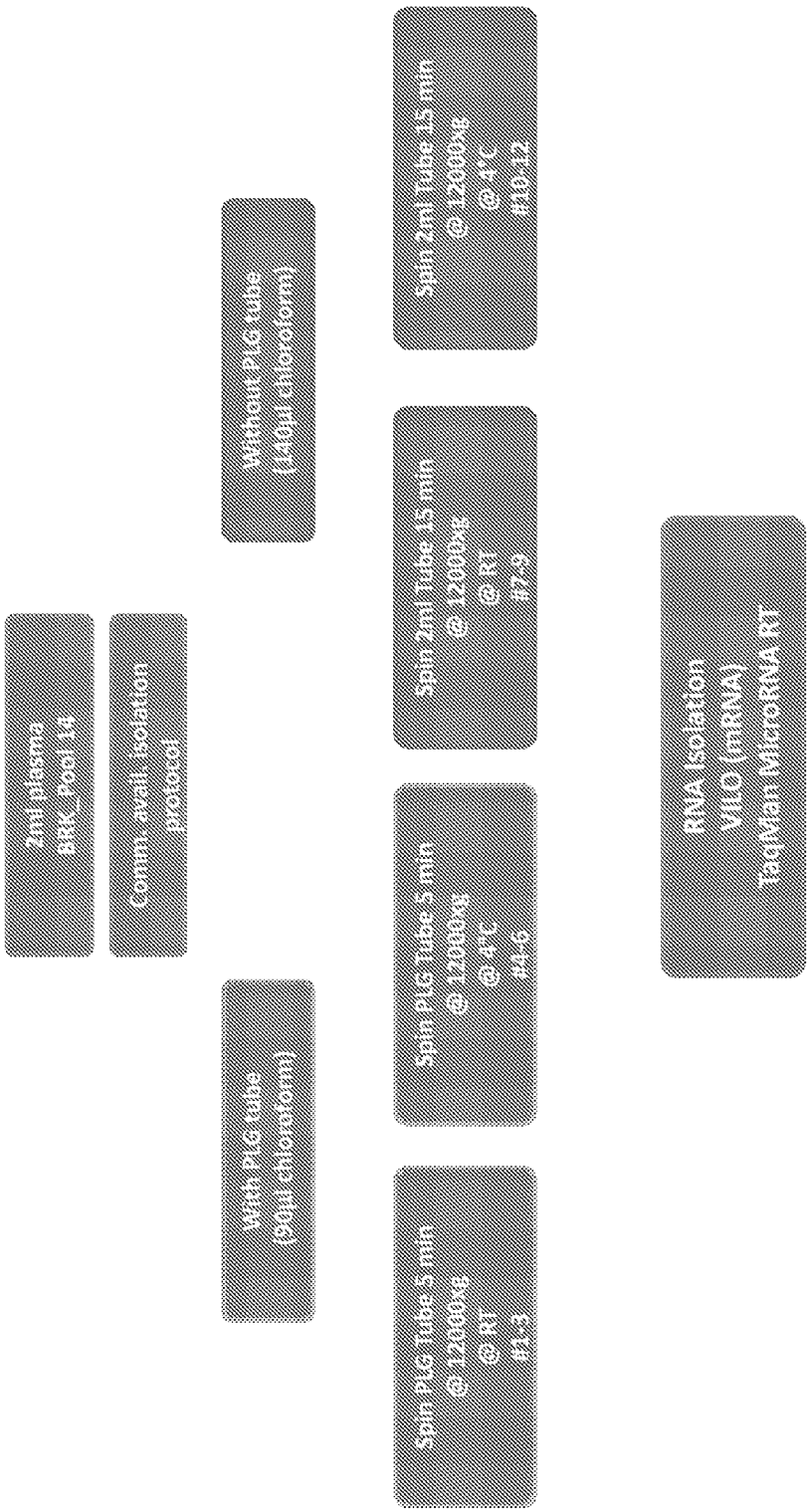

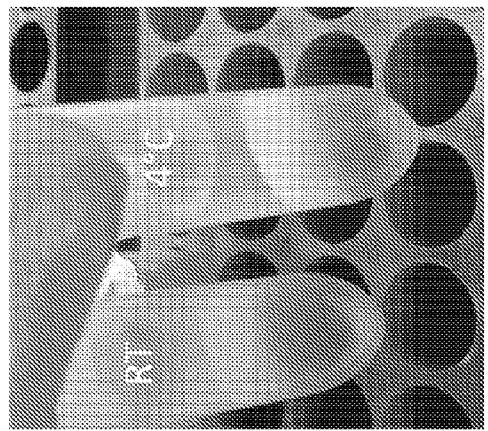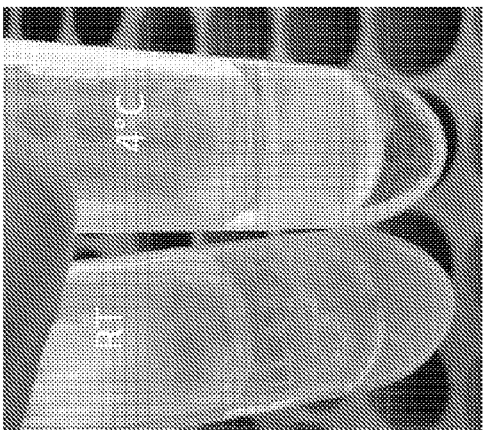
Figure 72

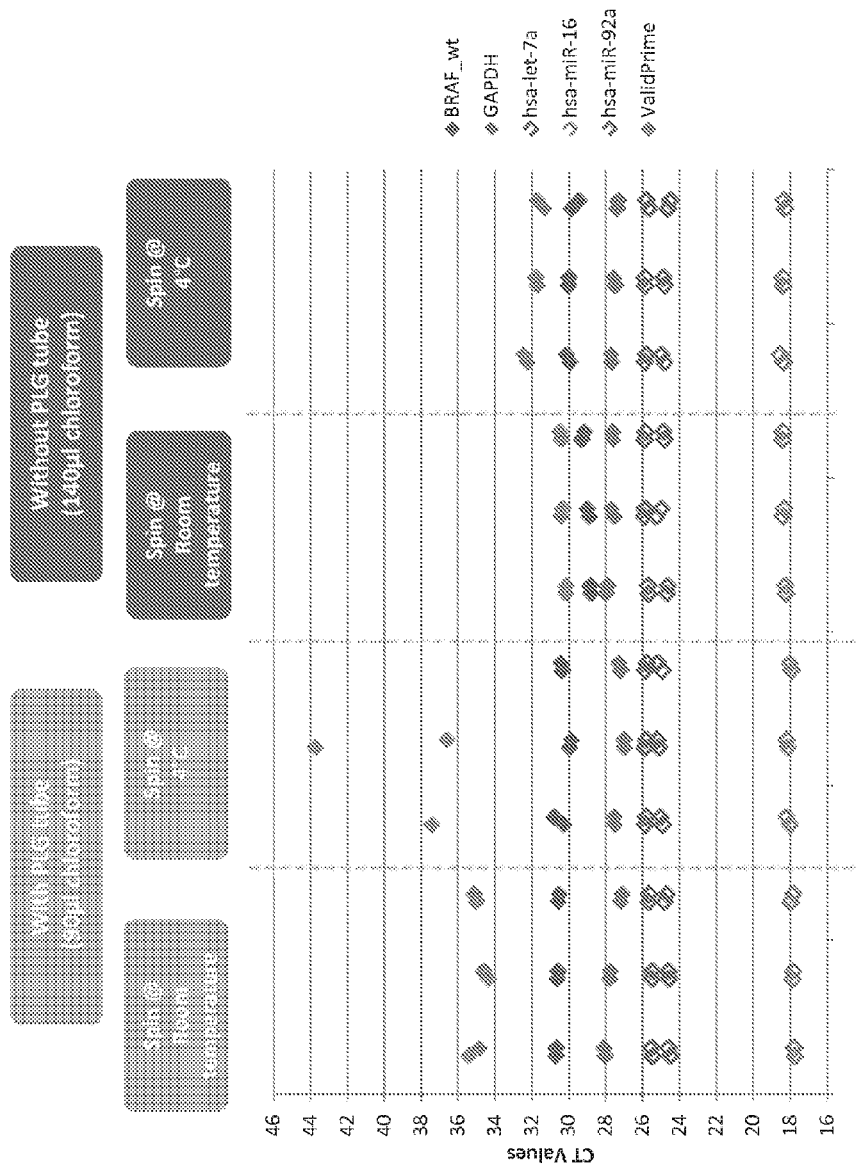

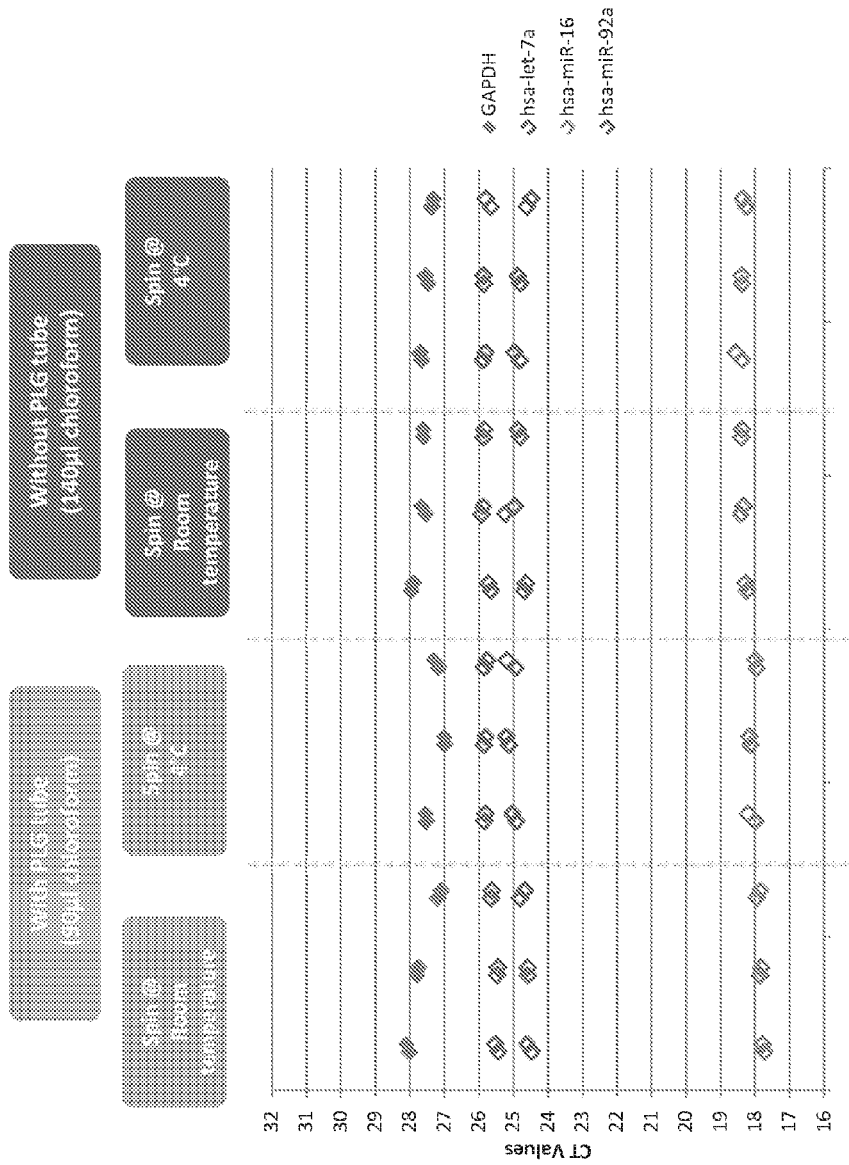

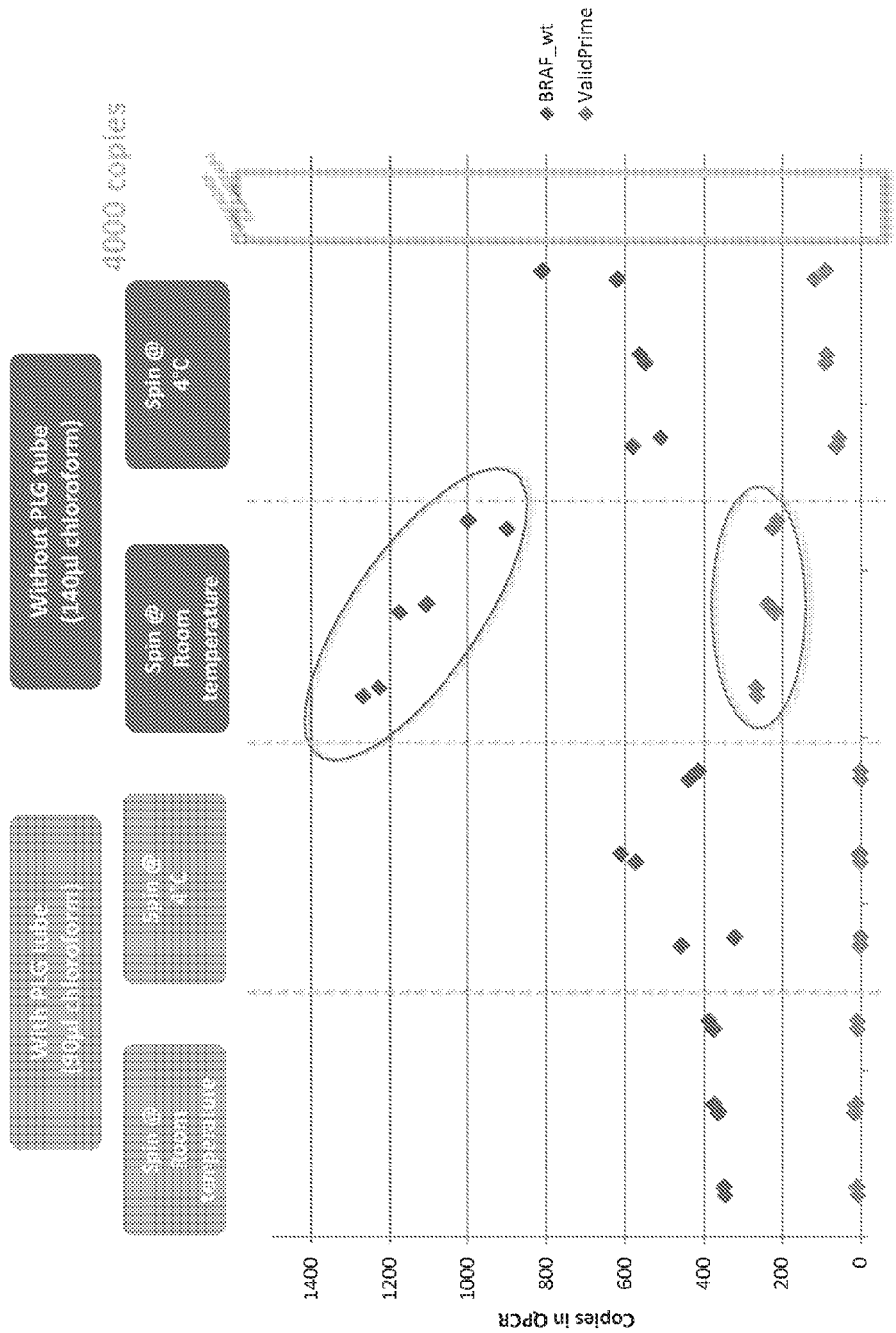

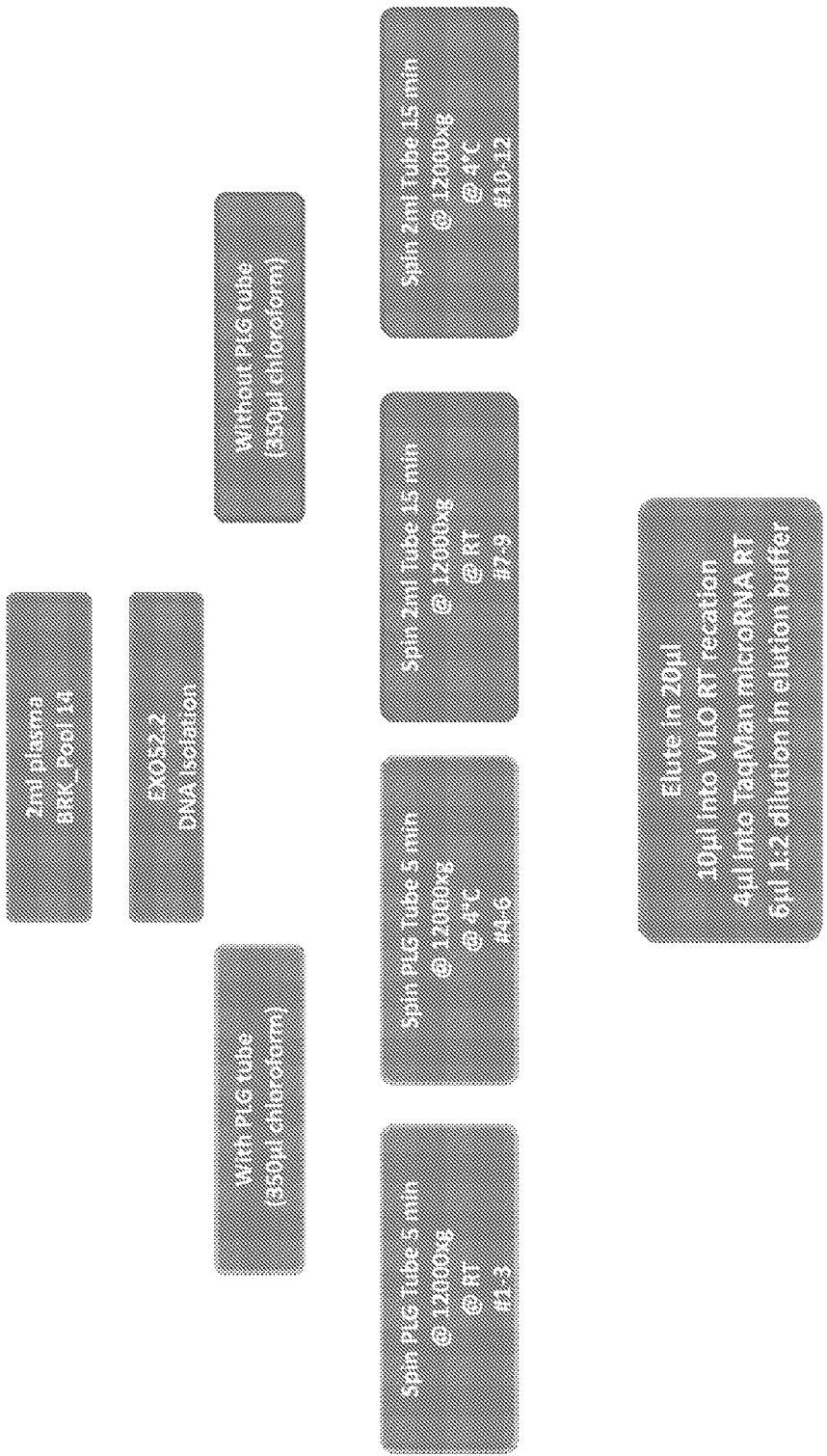

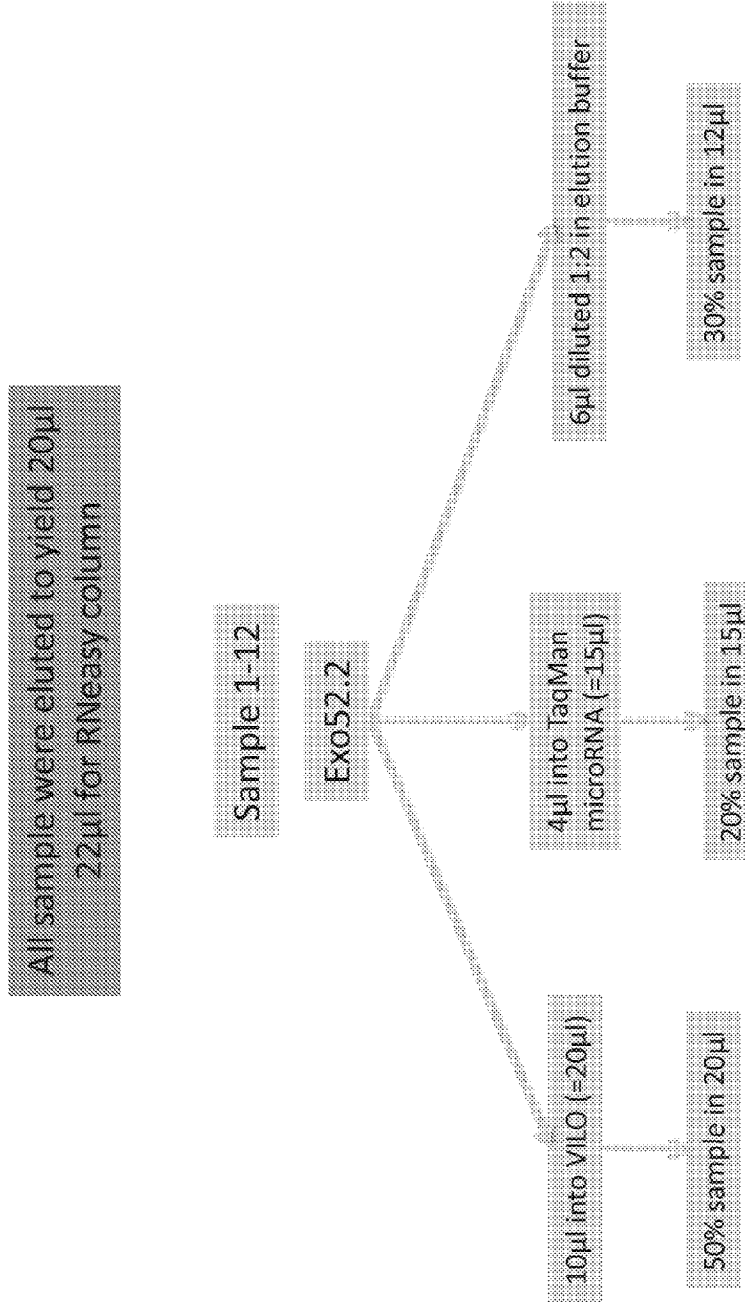

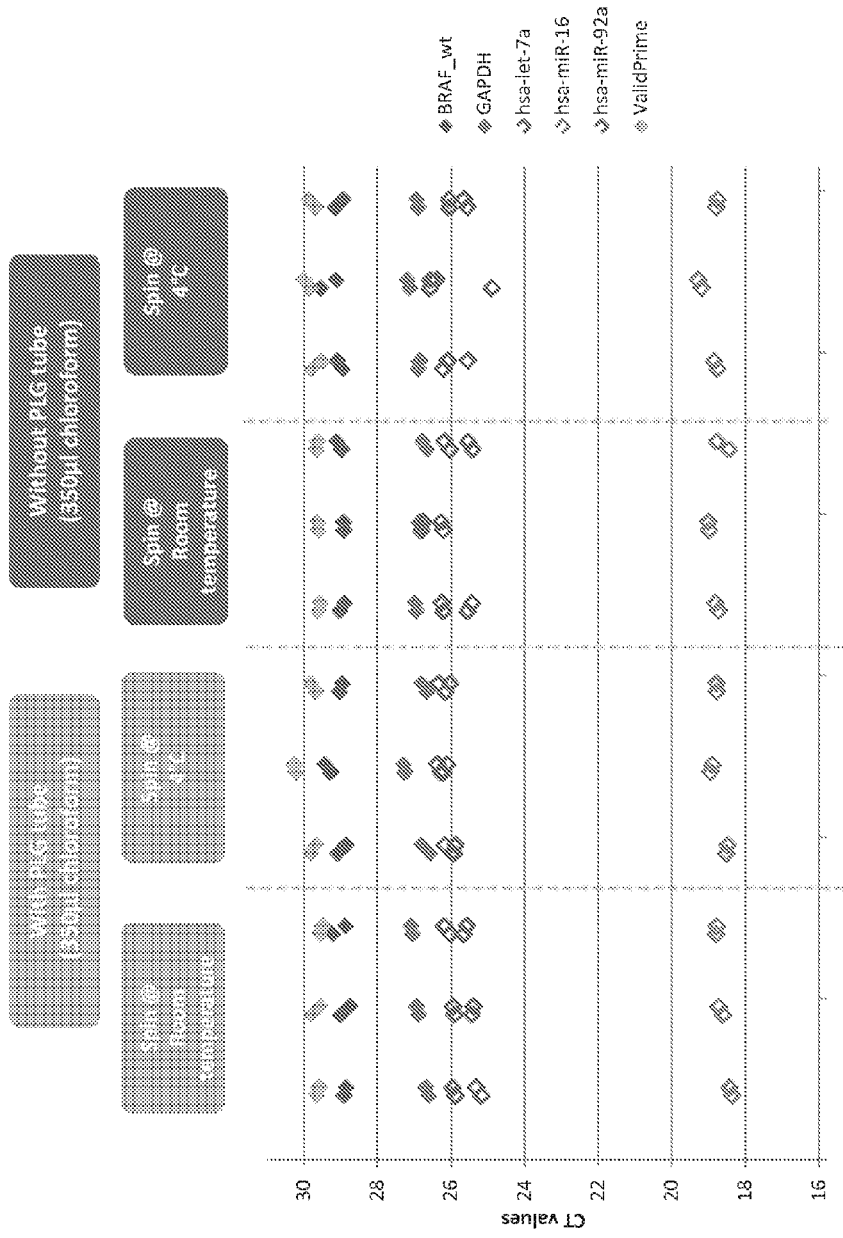

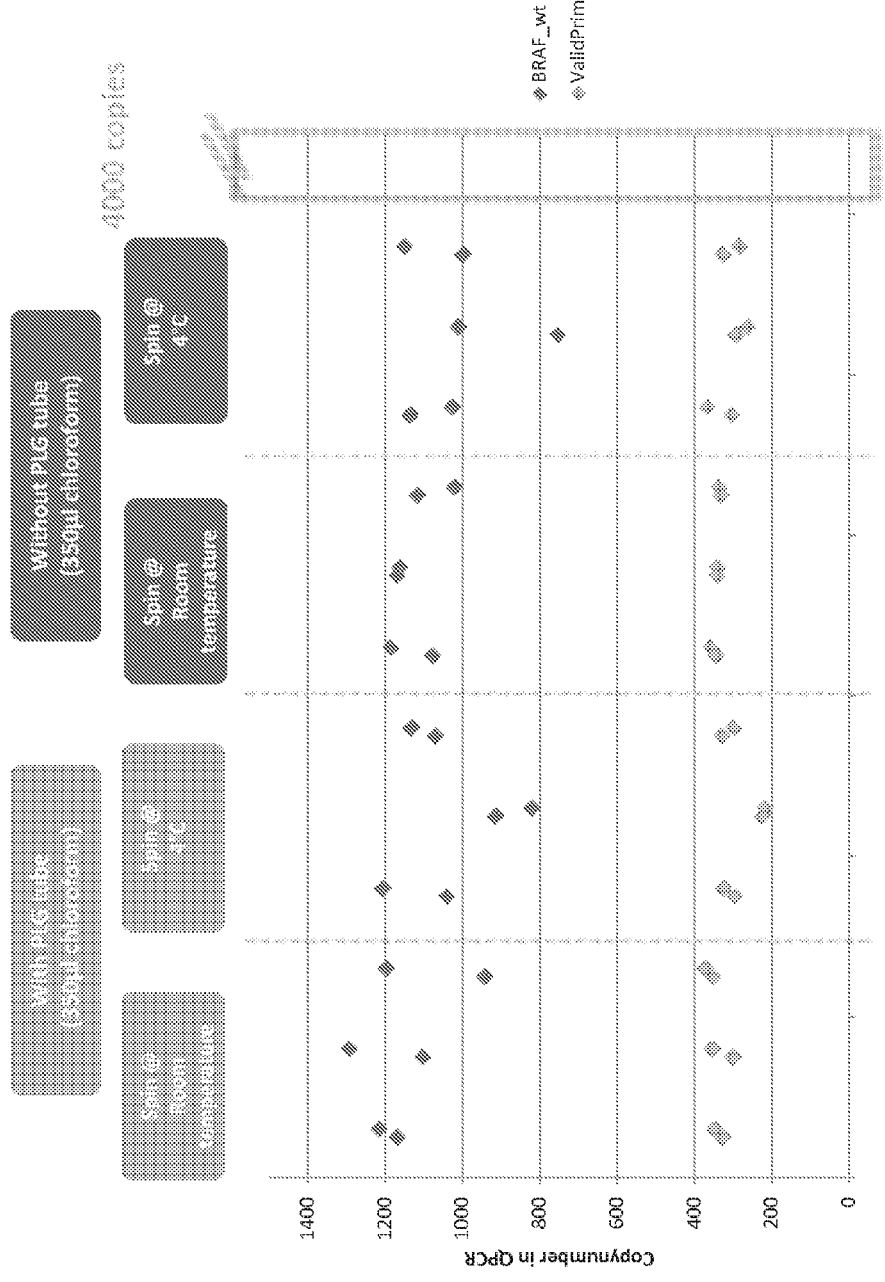

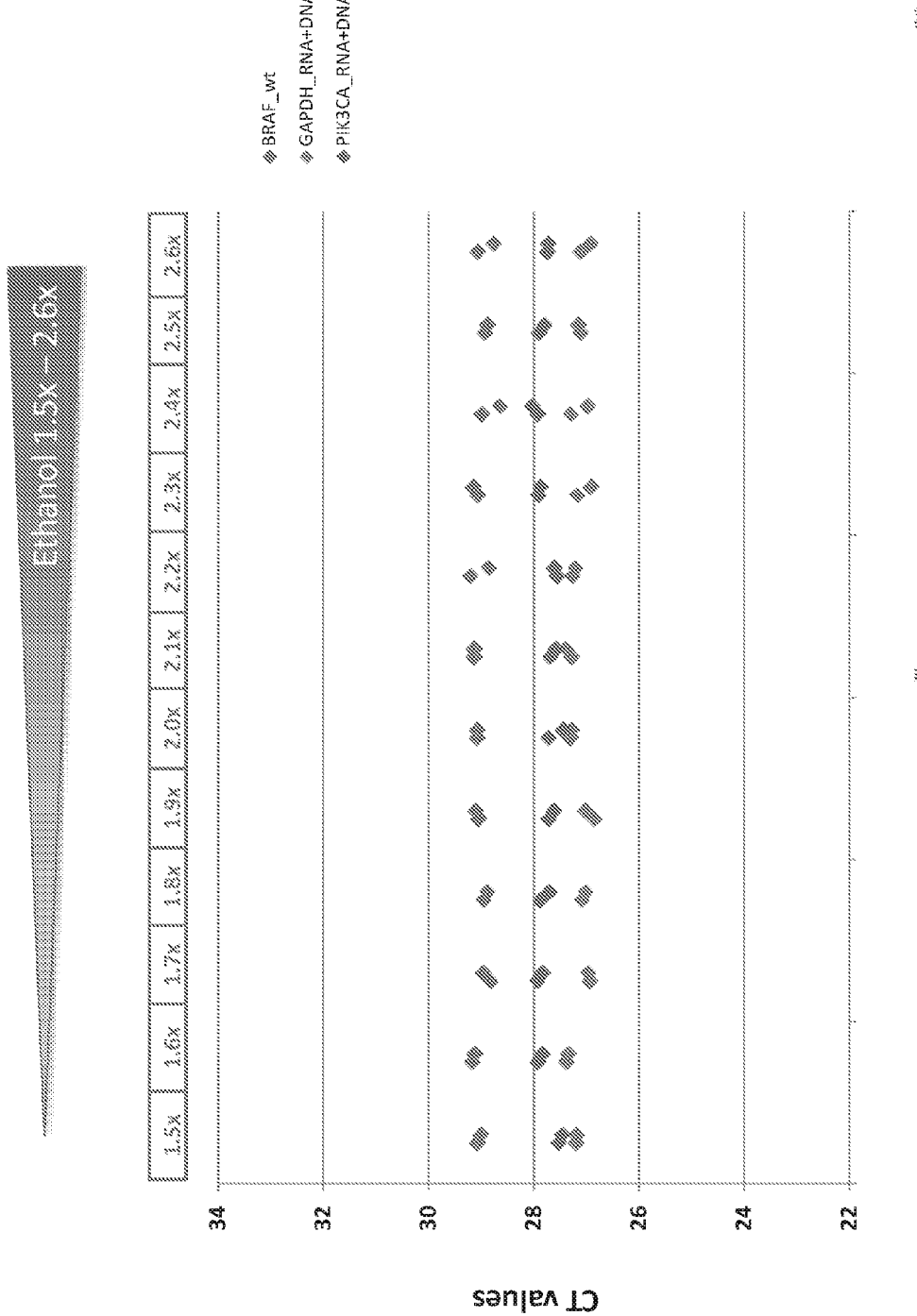

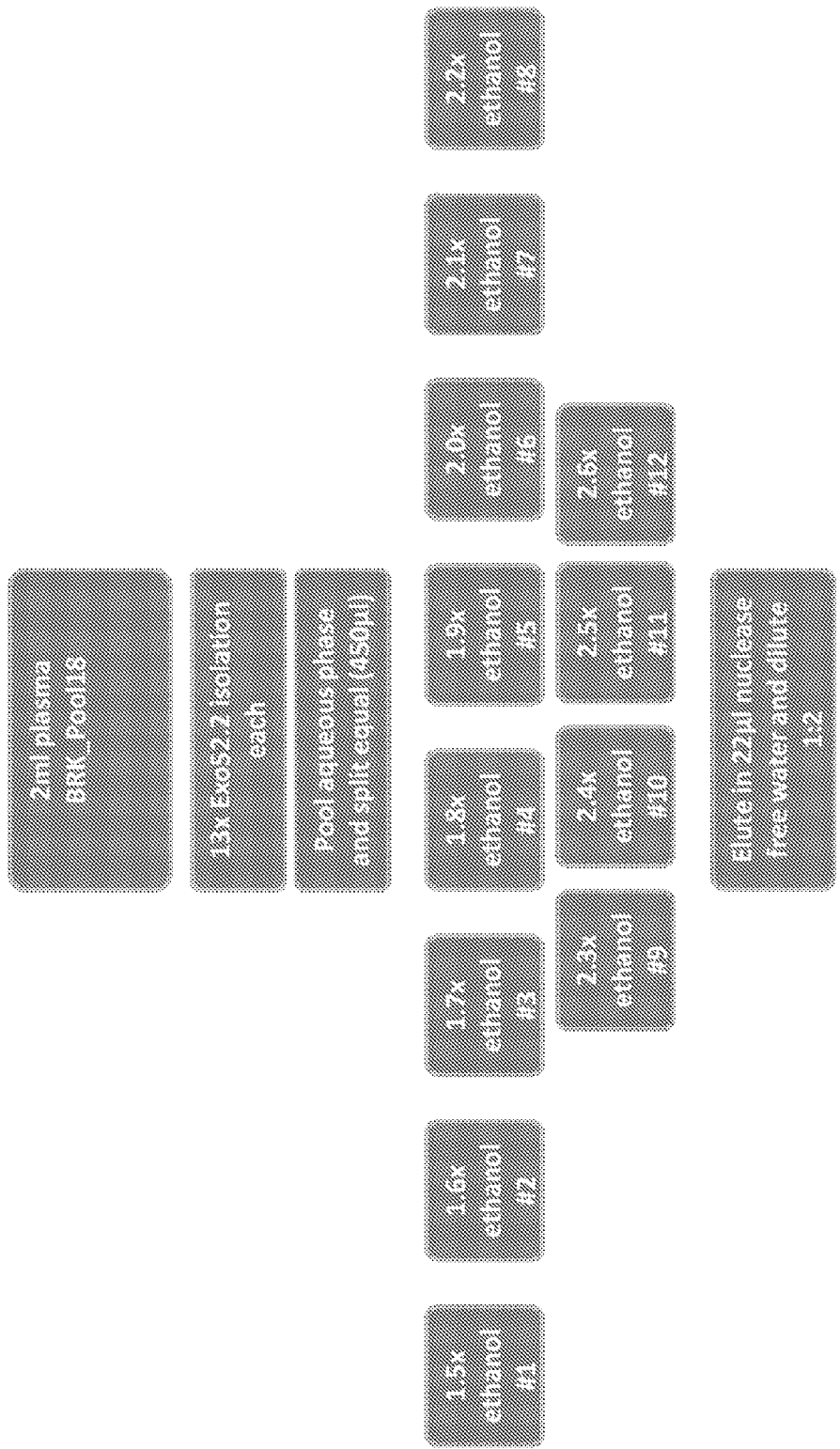

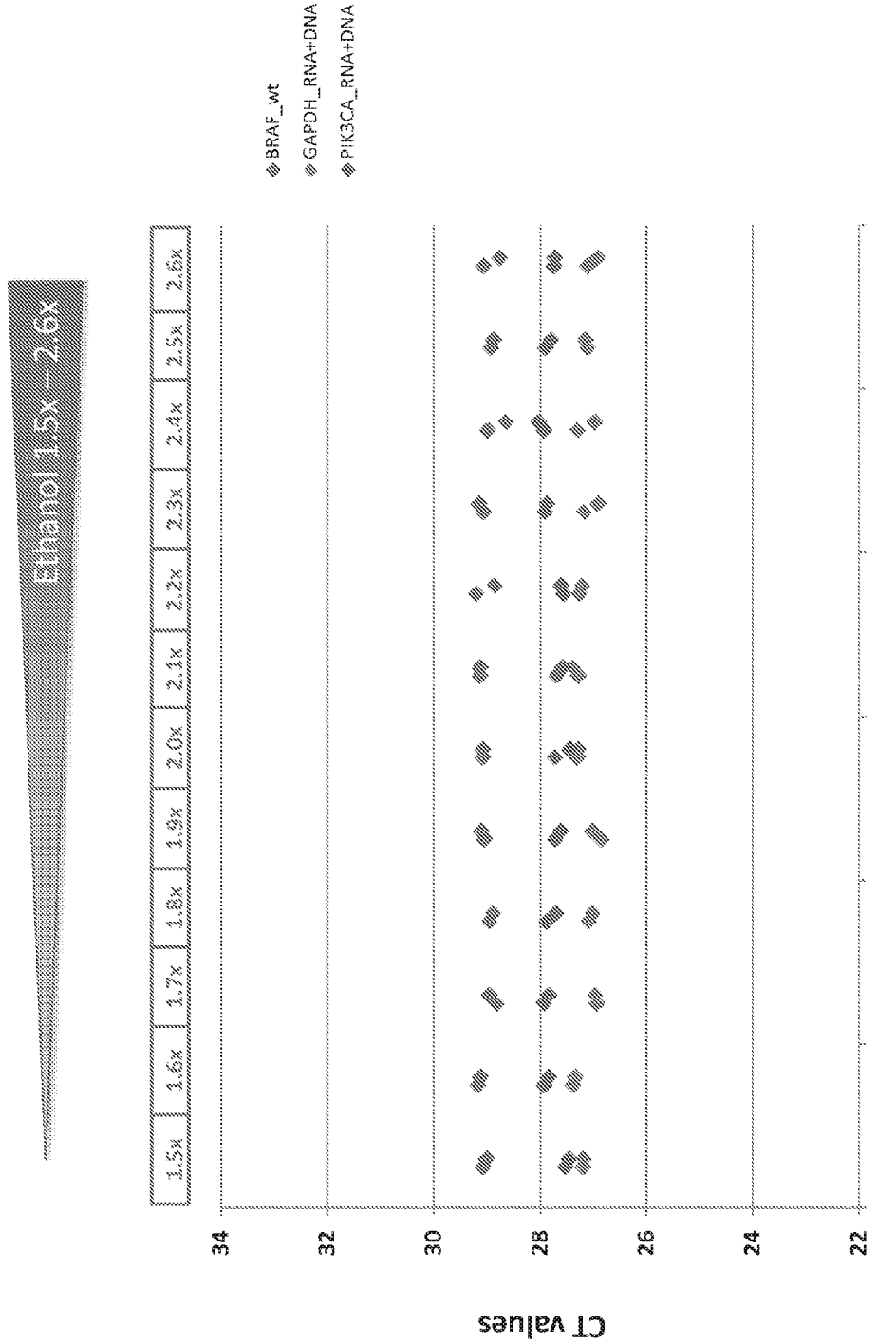

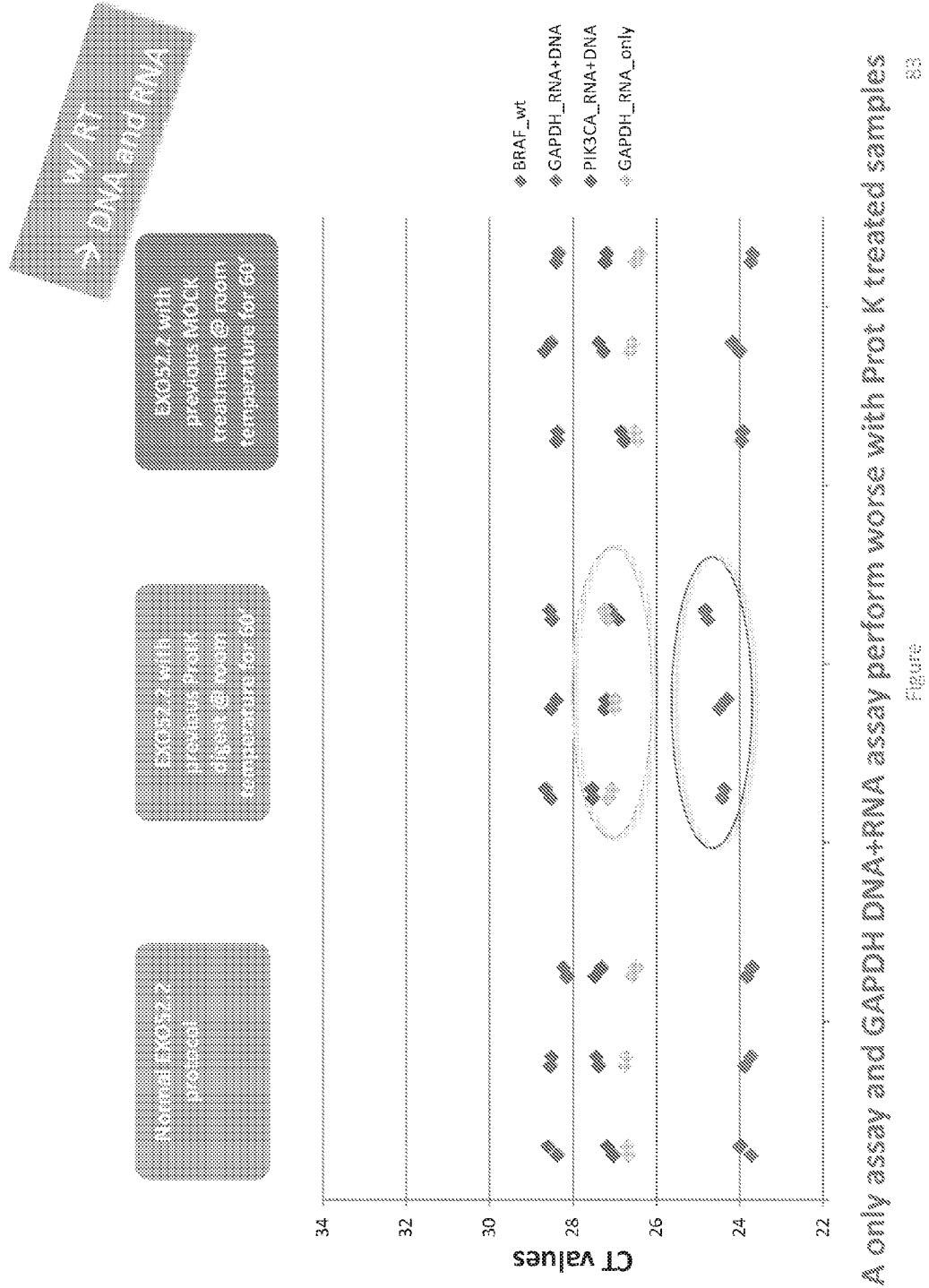

Exo52.2 : ProtK digest @ room temperature before EXO52.2 binding step

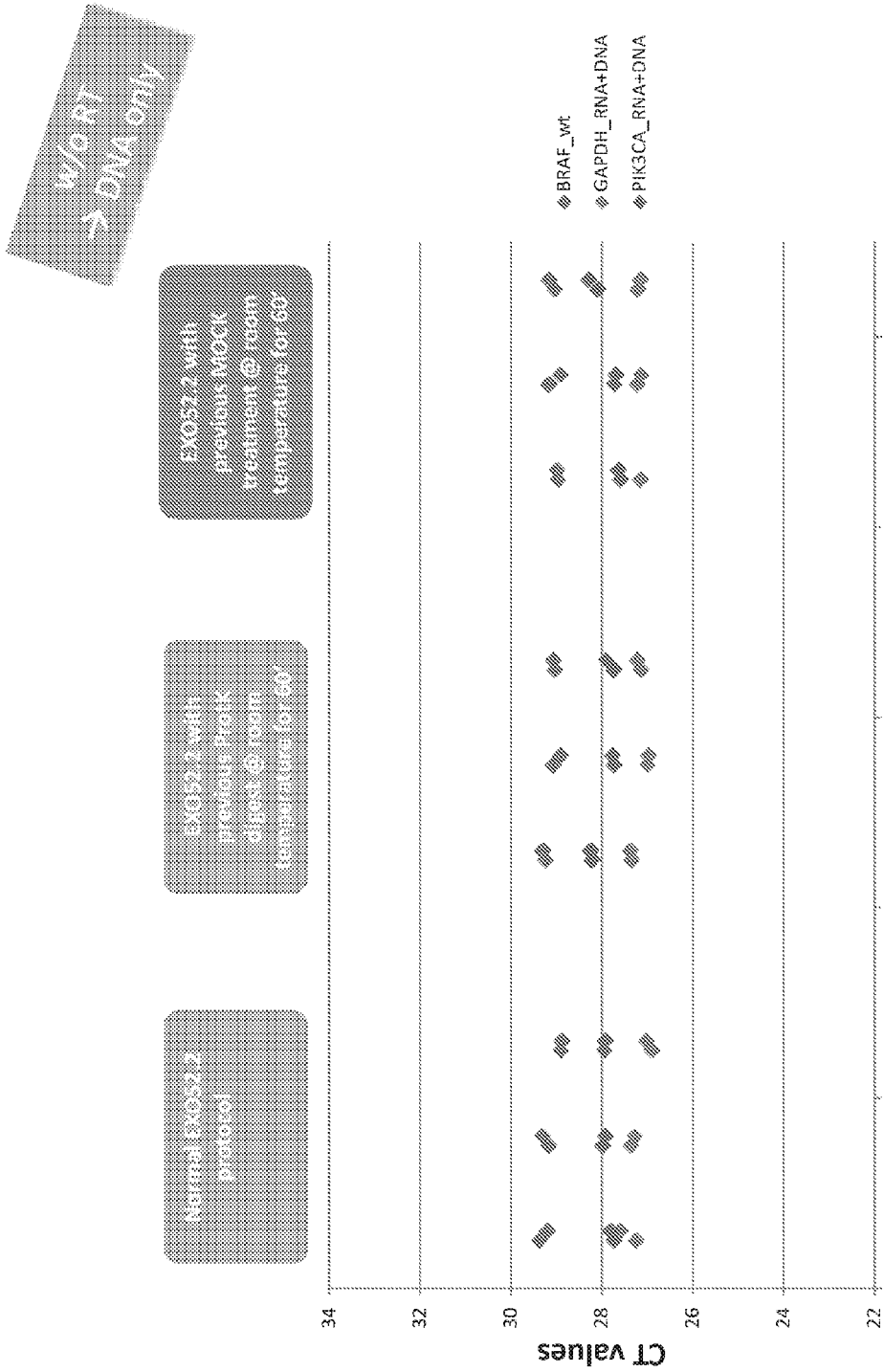

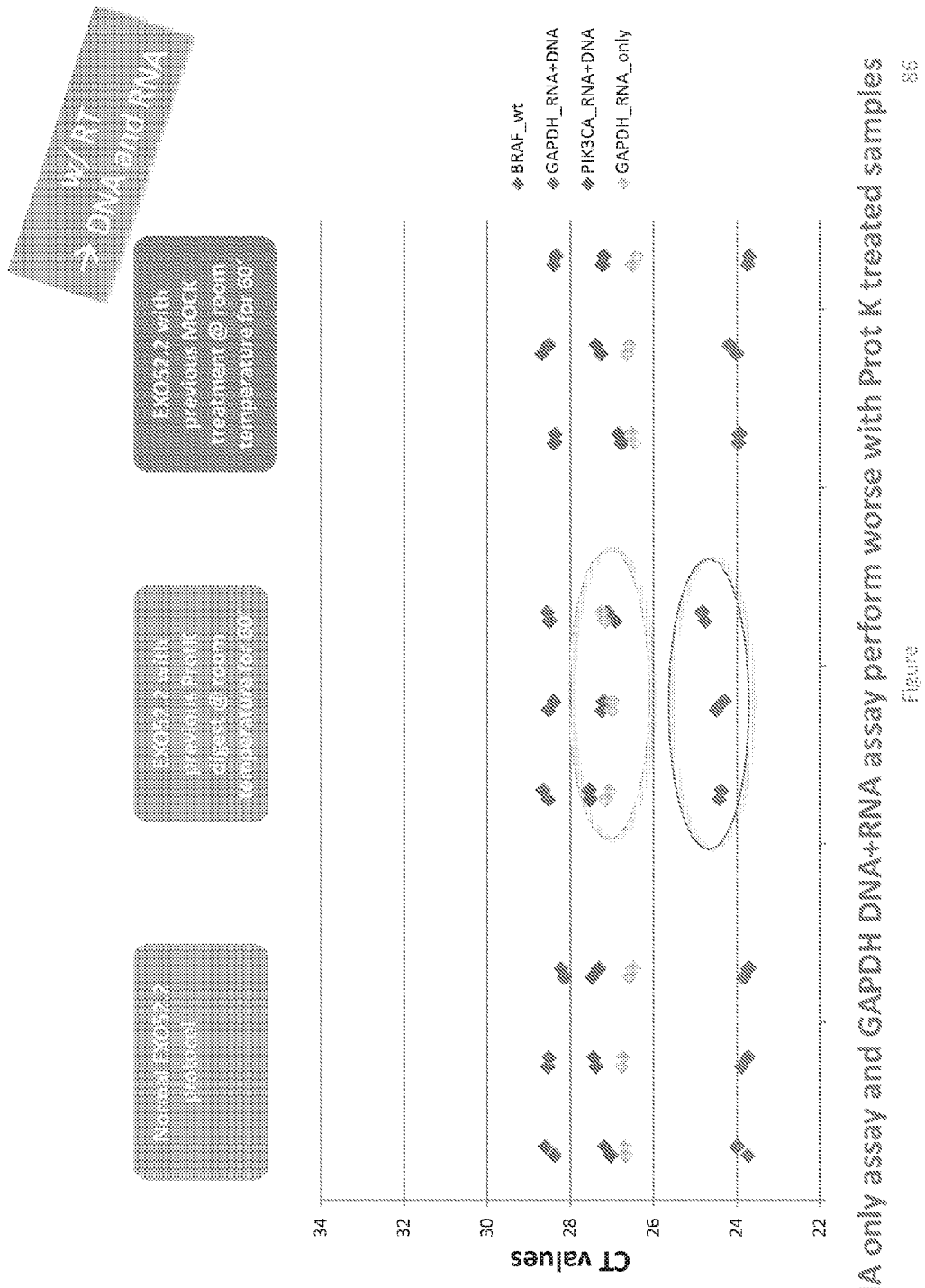

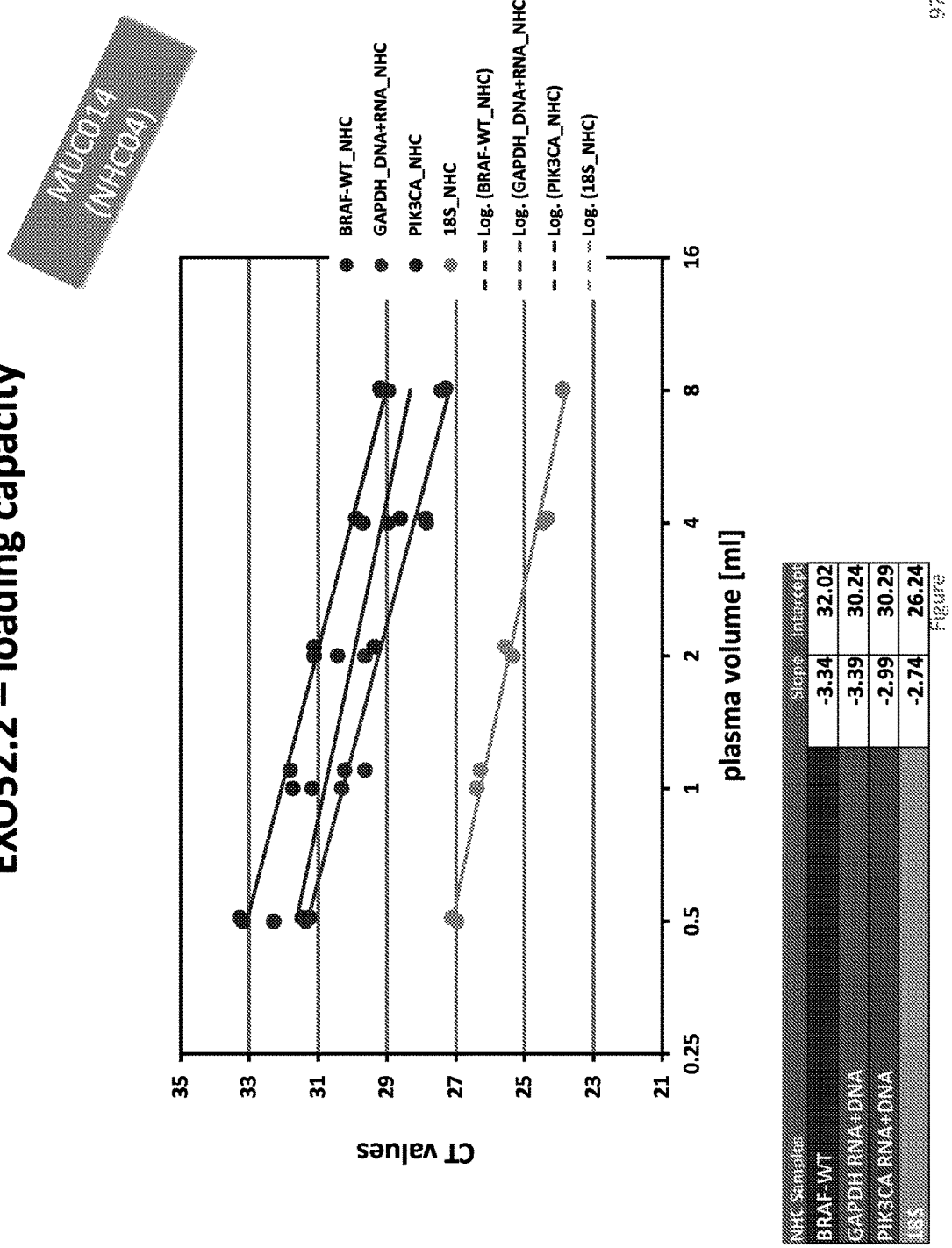

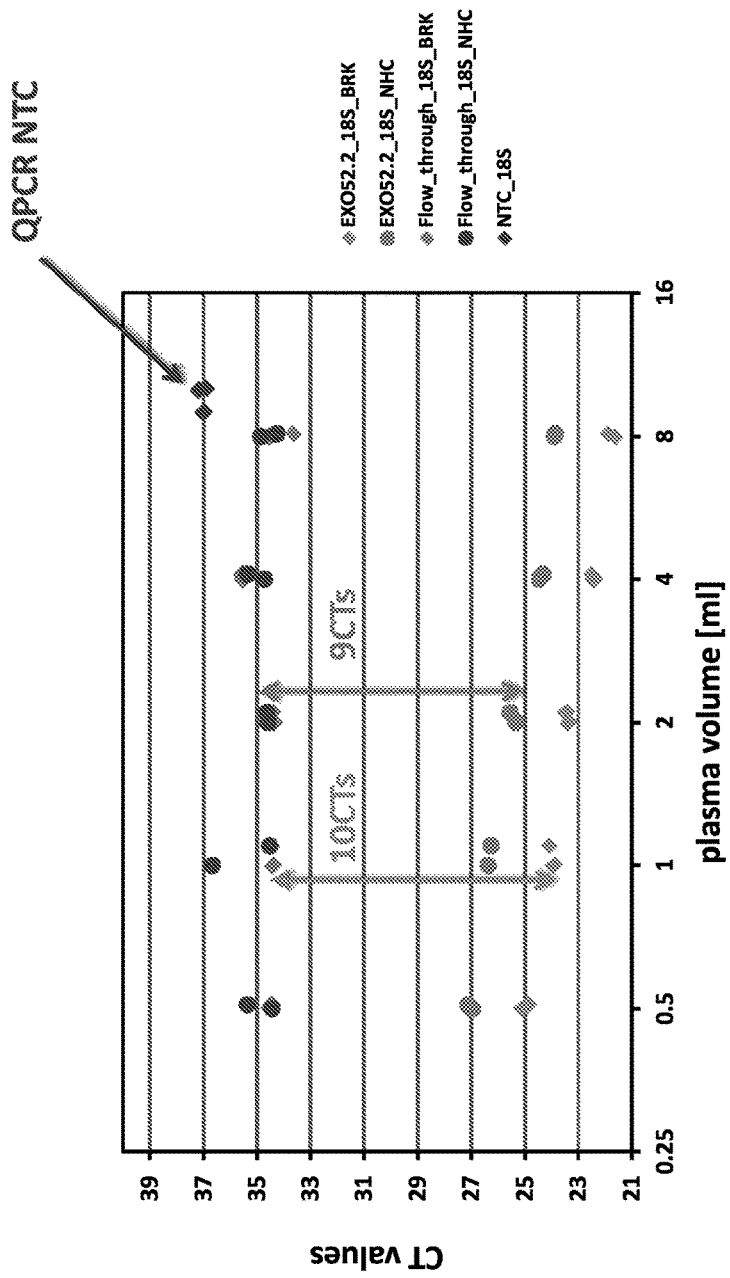

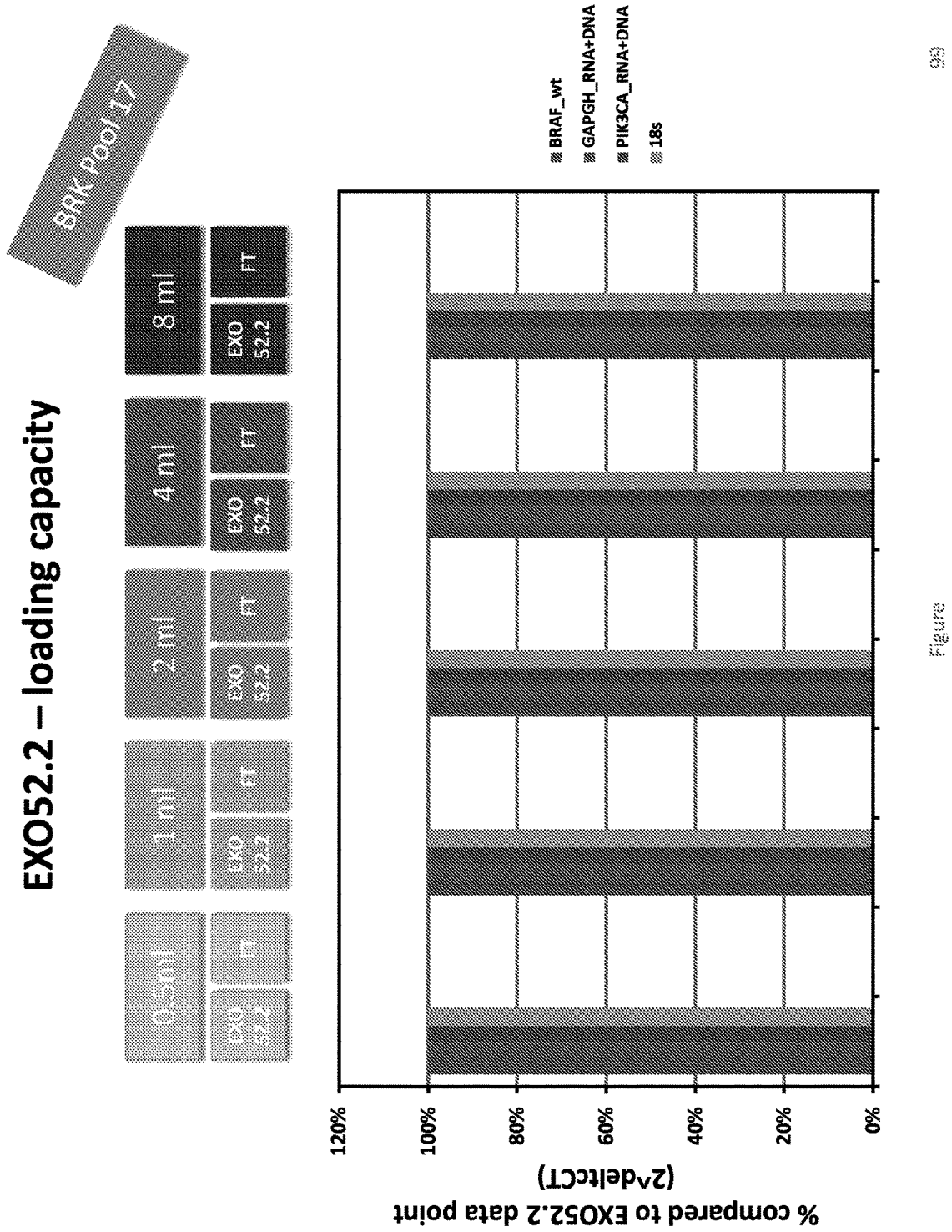

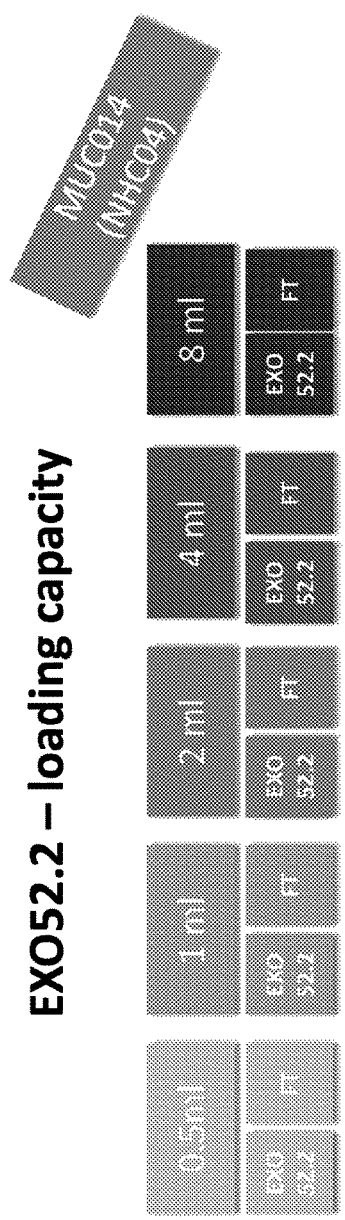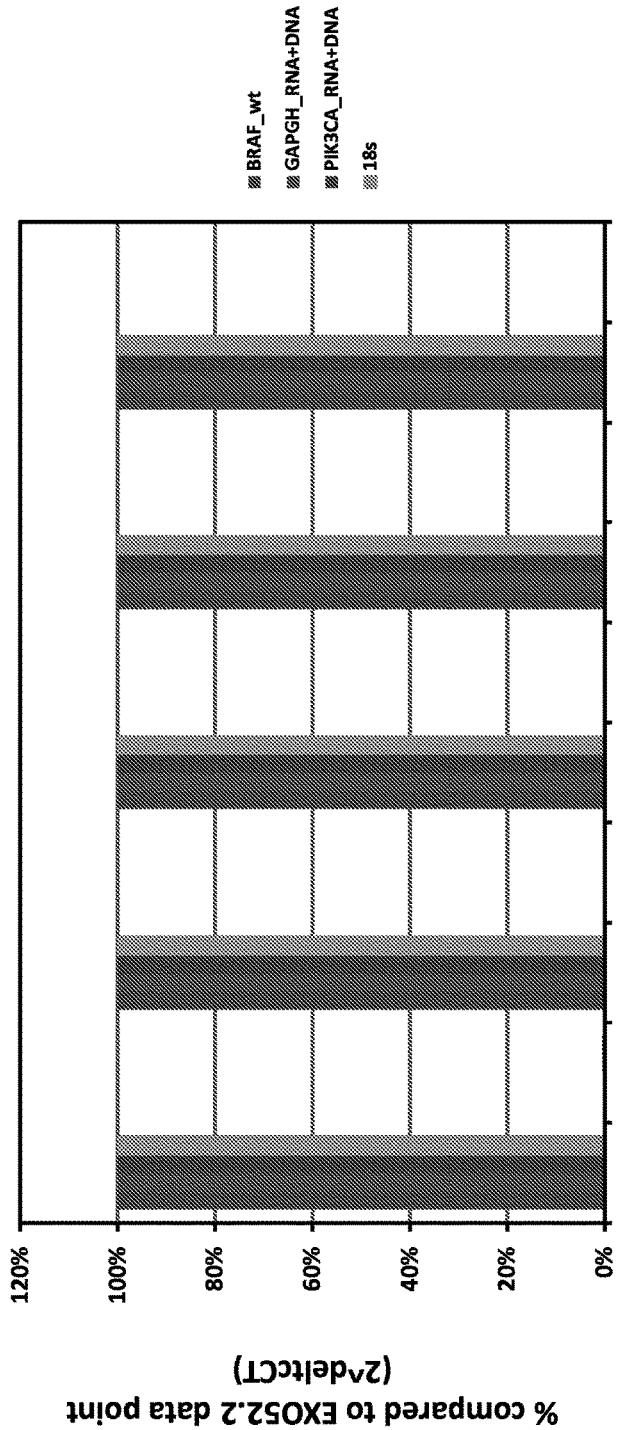

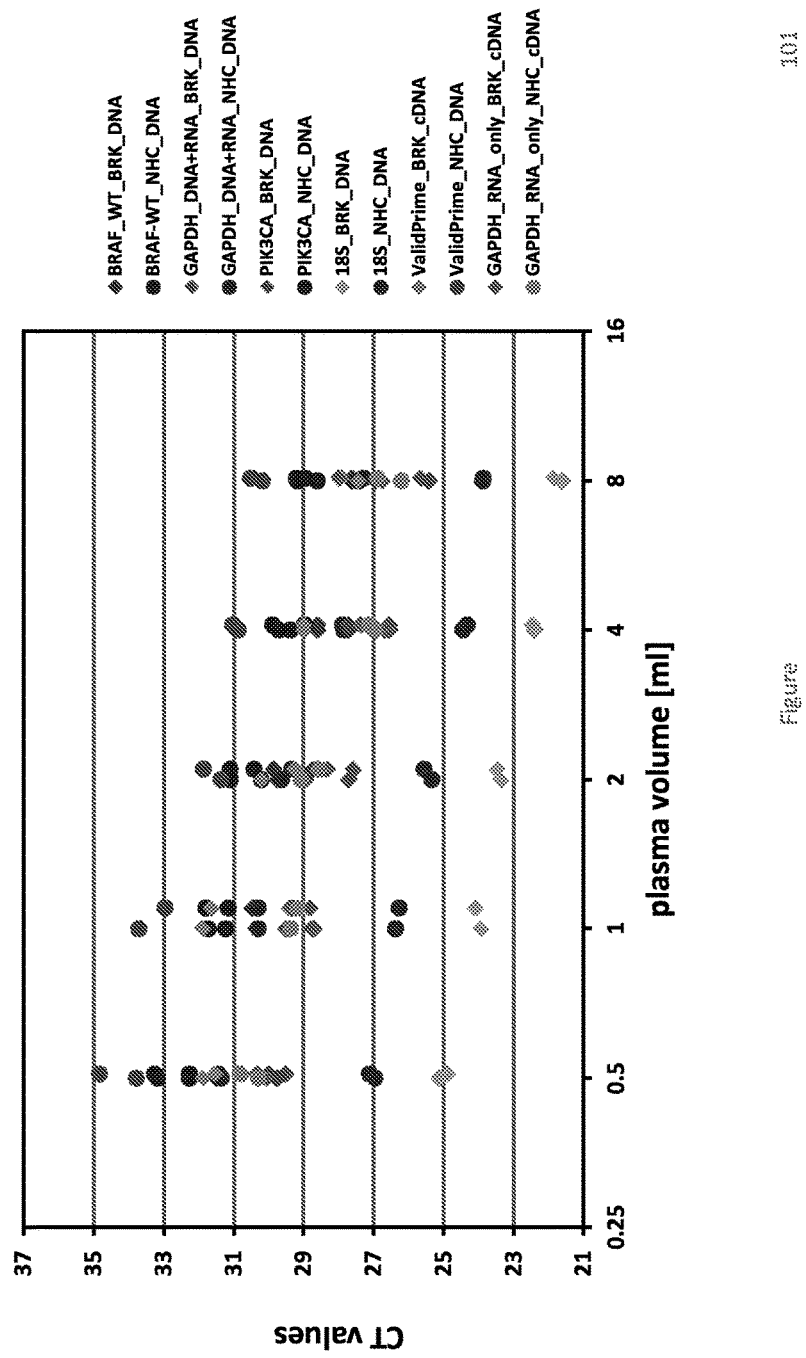

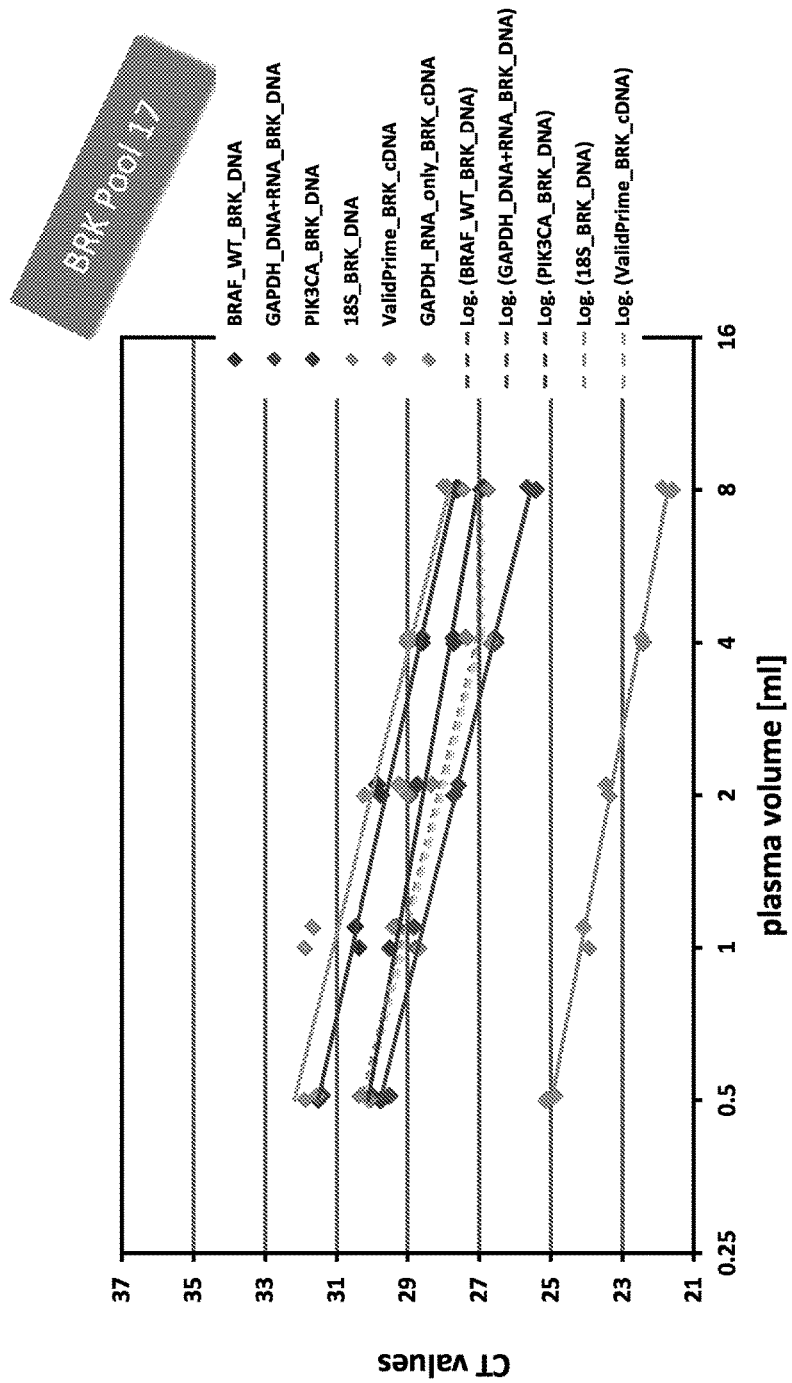

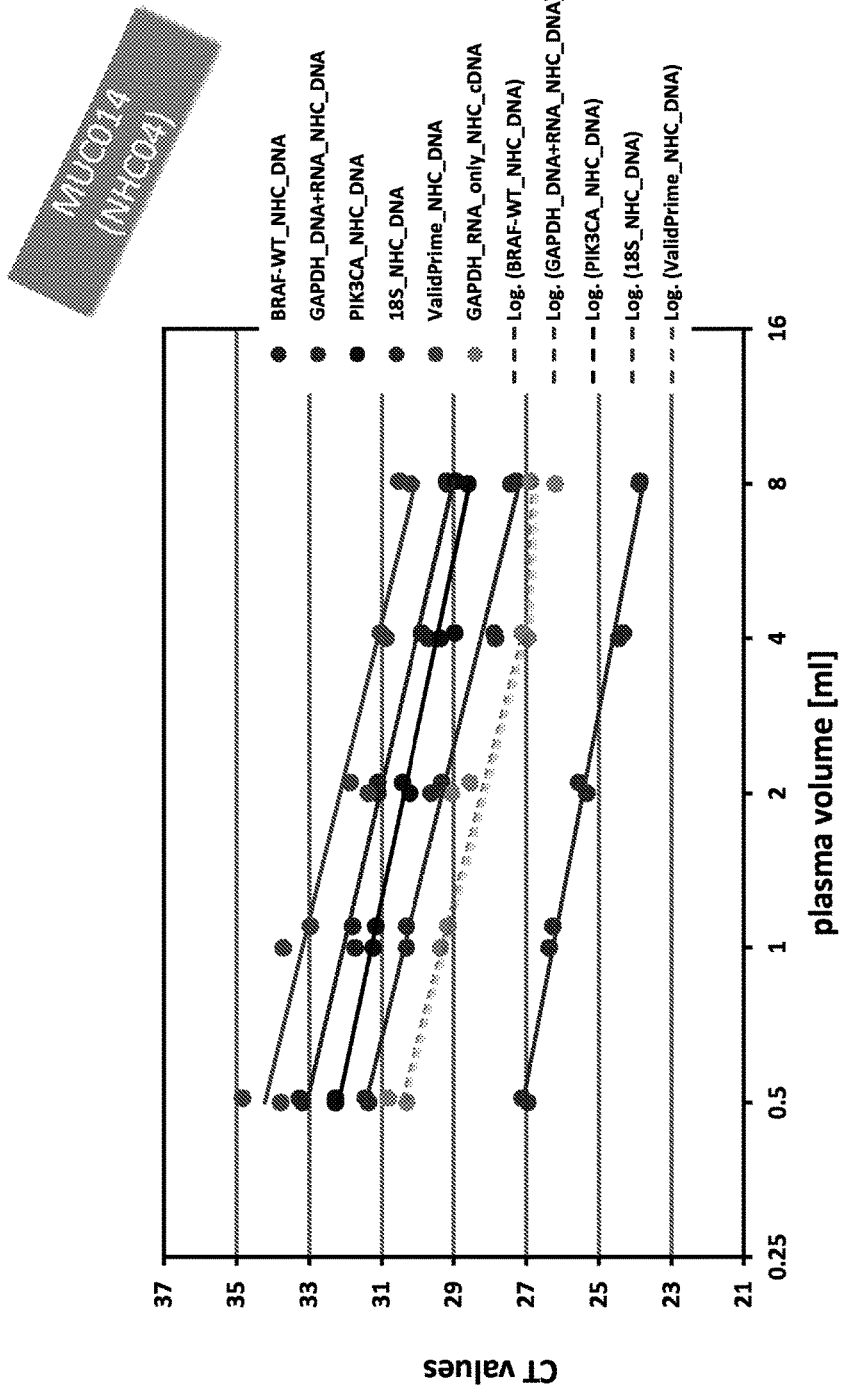

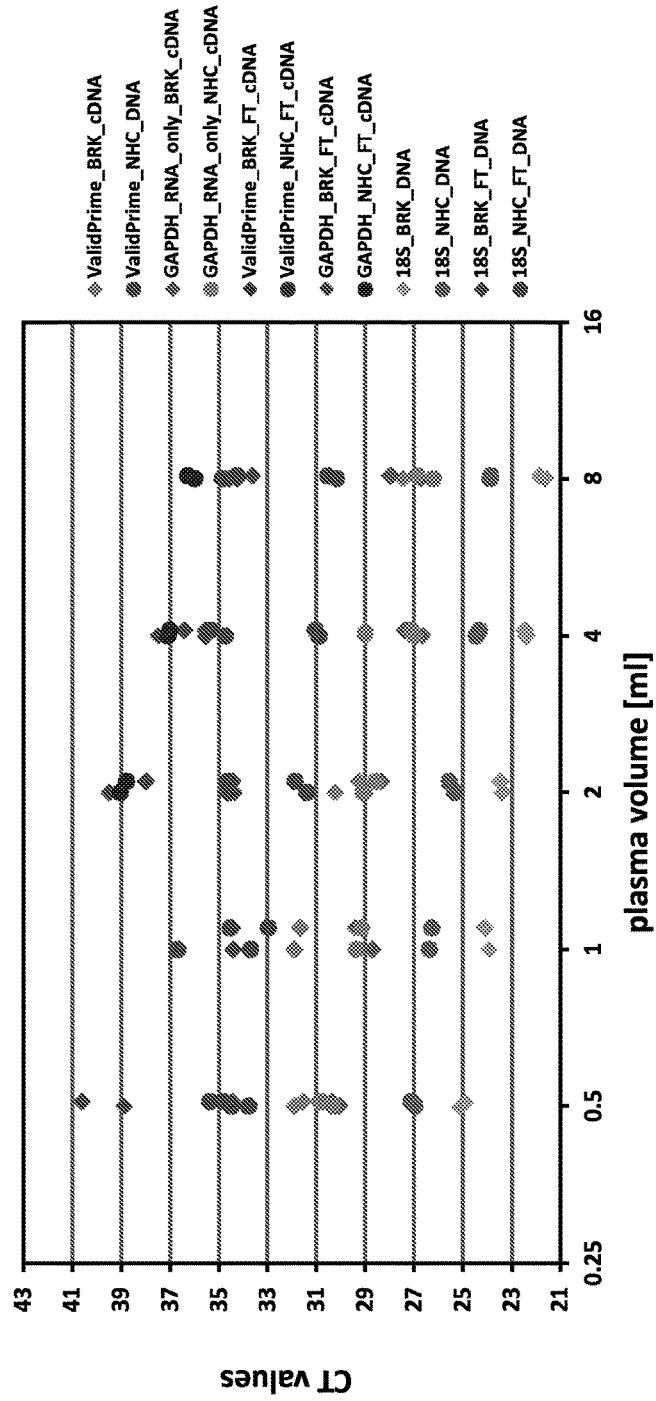

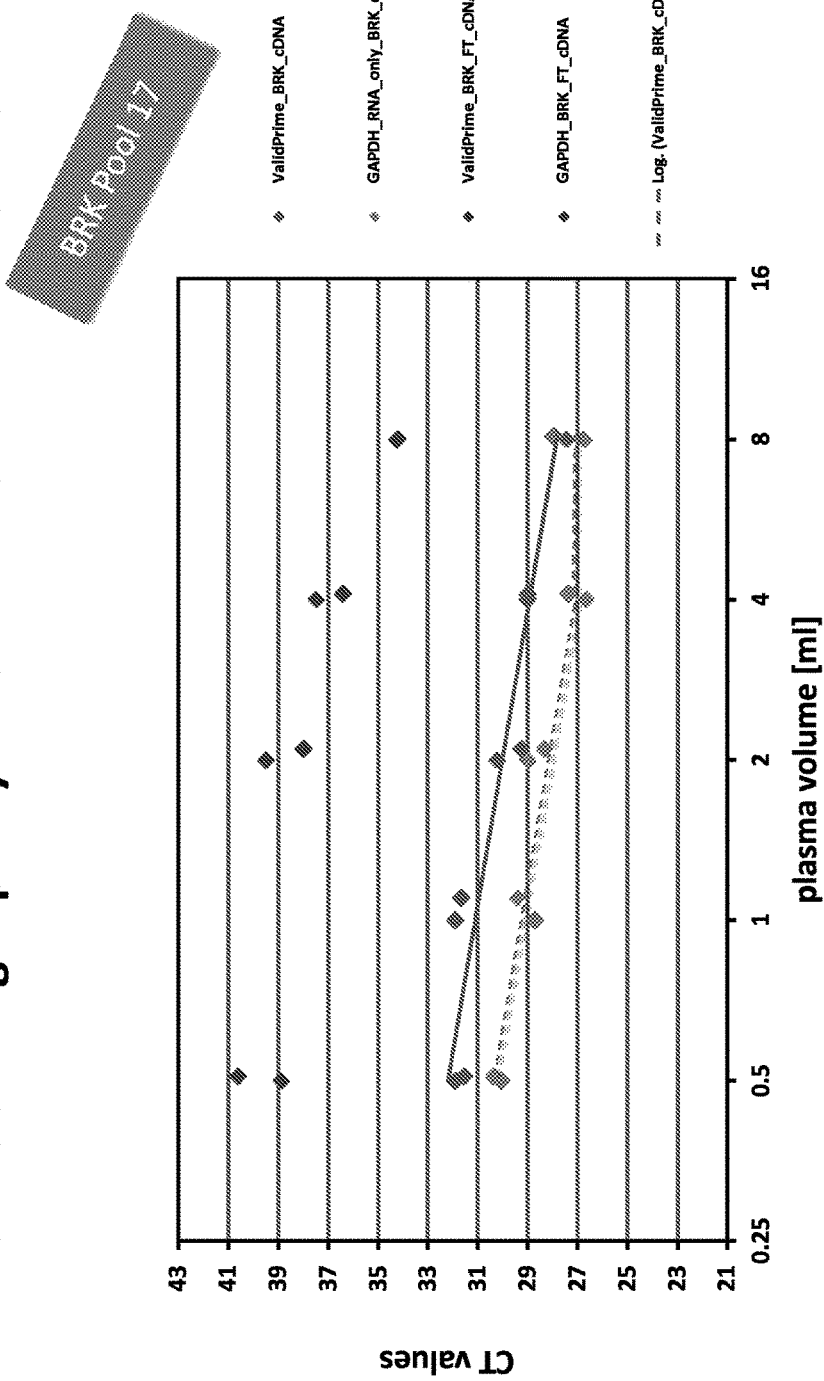

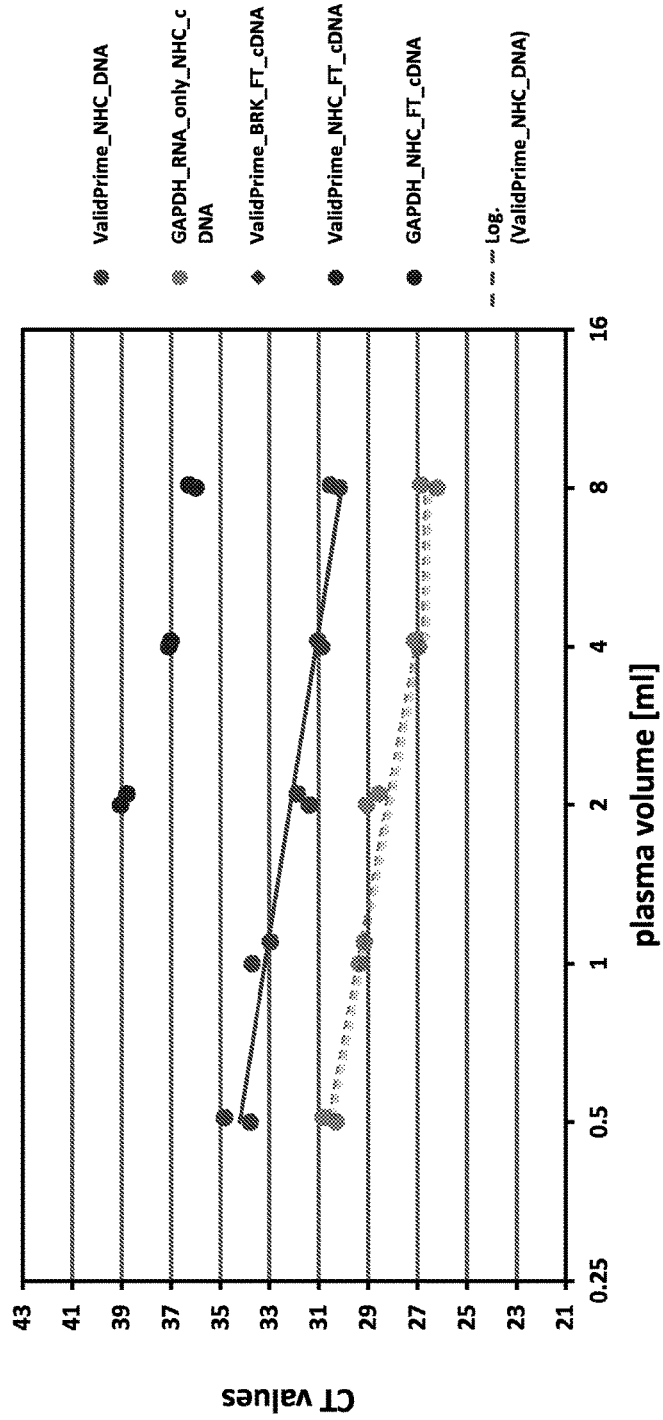

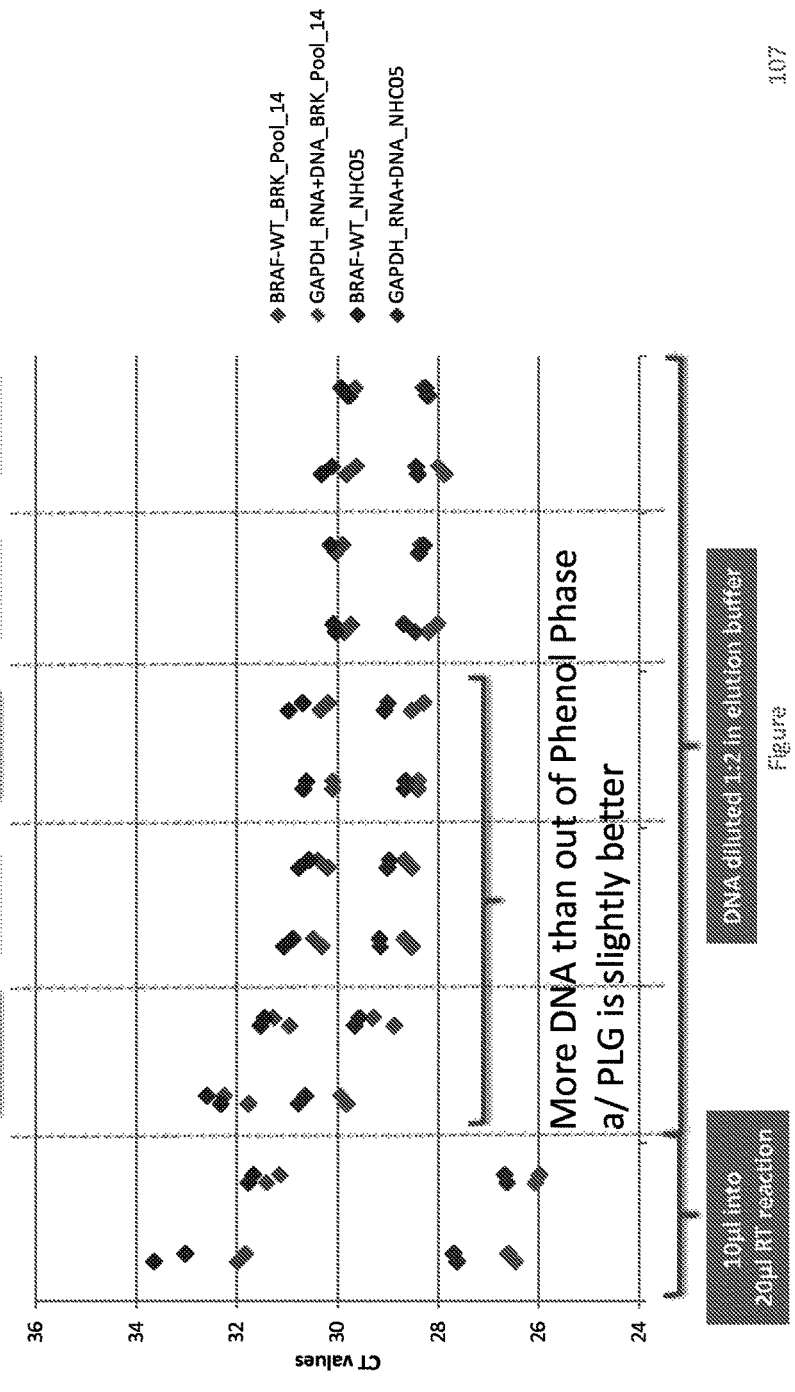

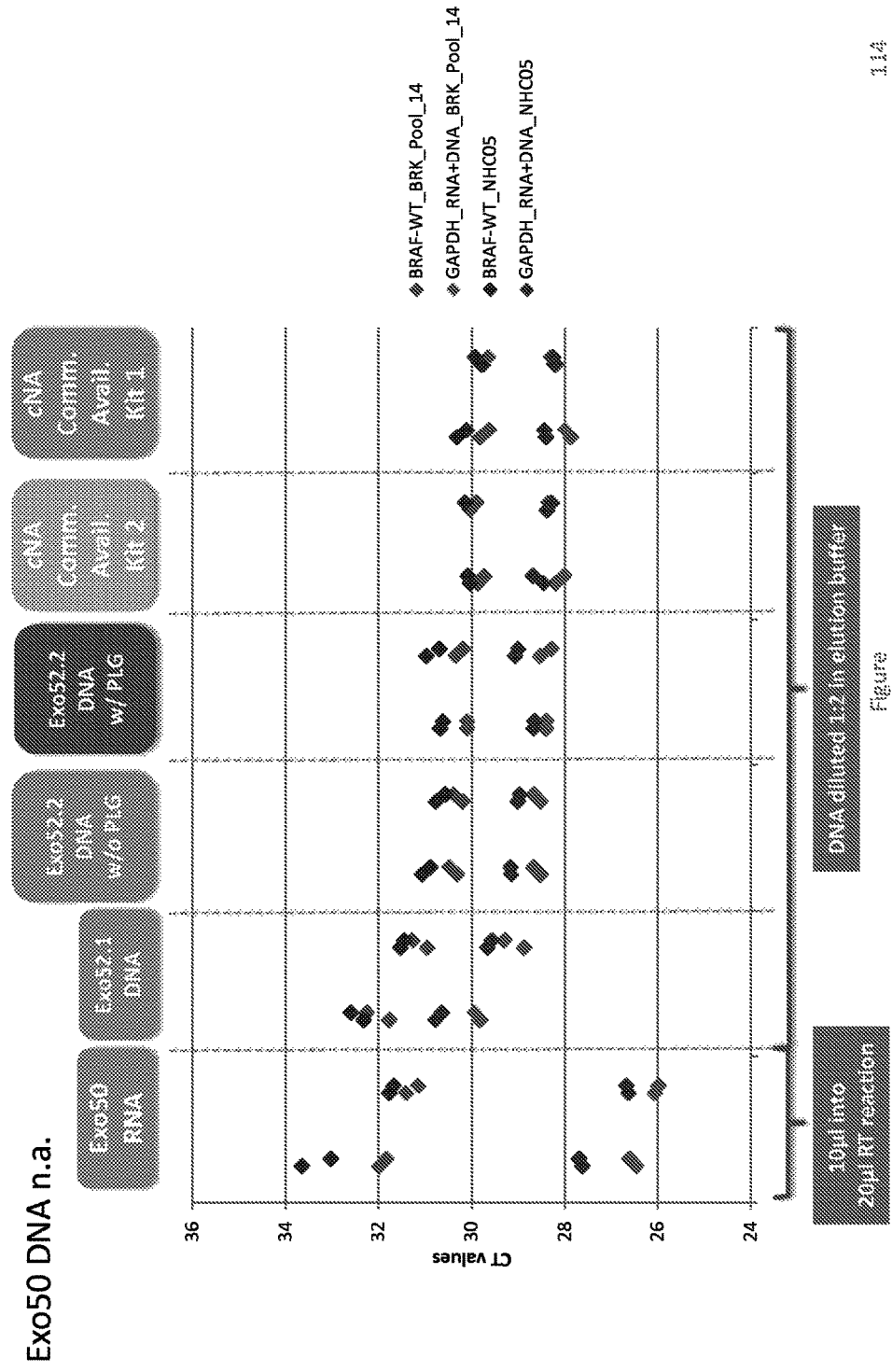

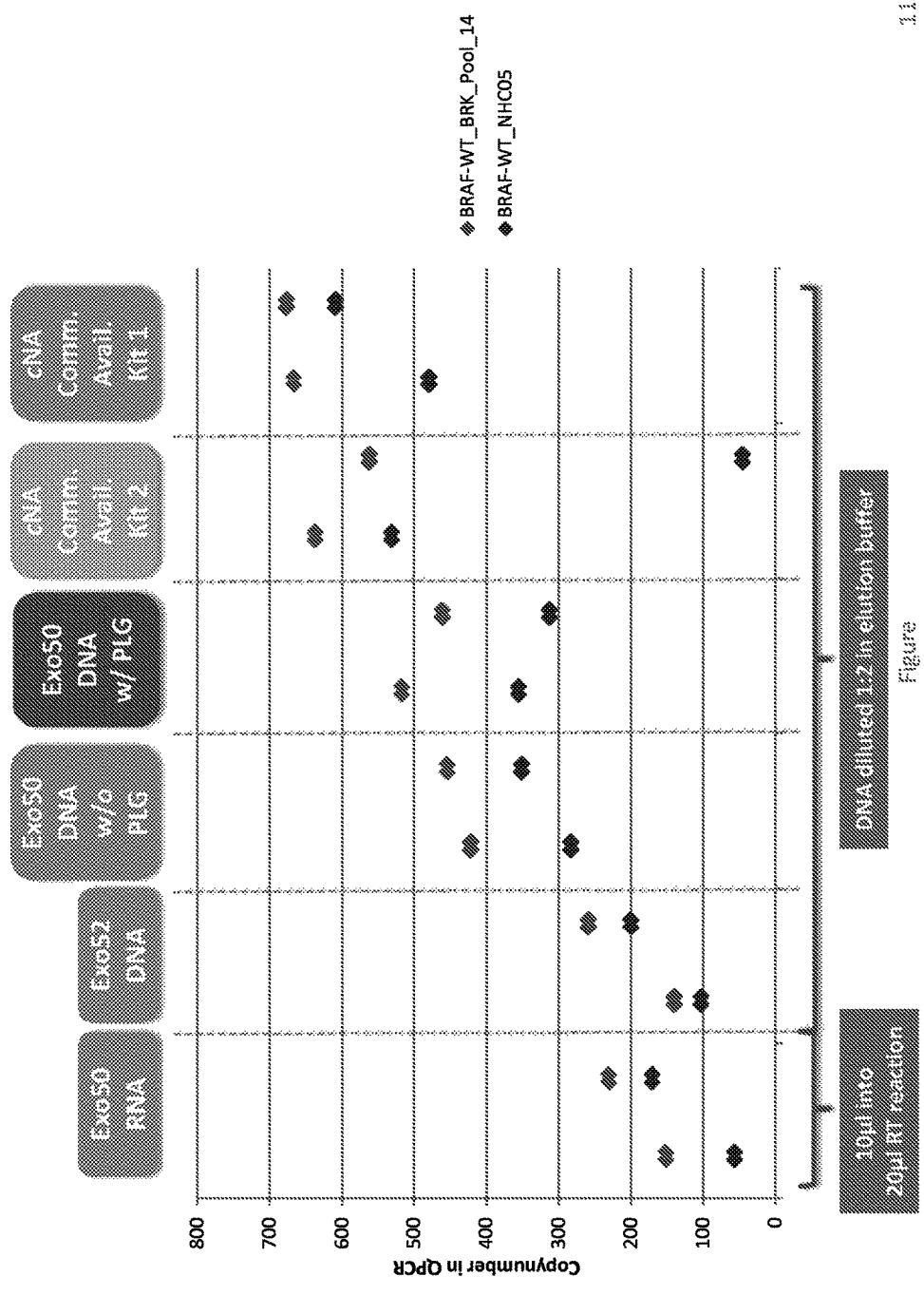

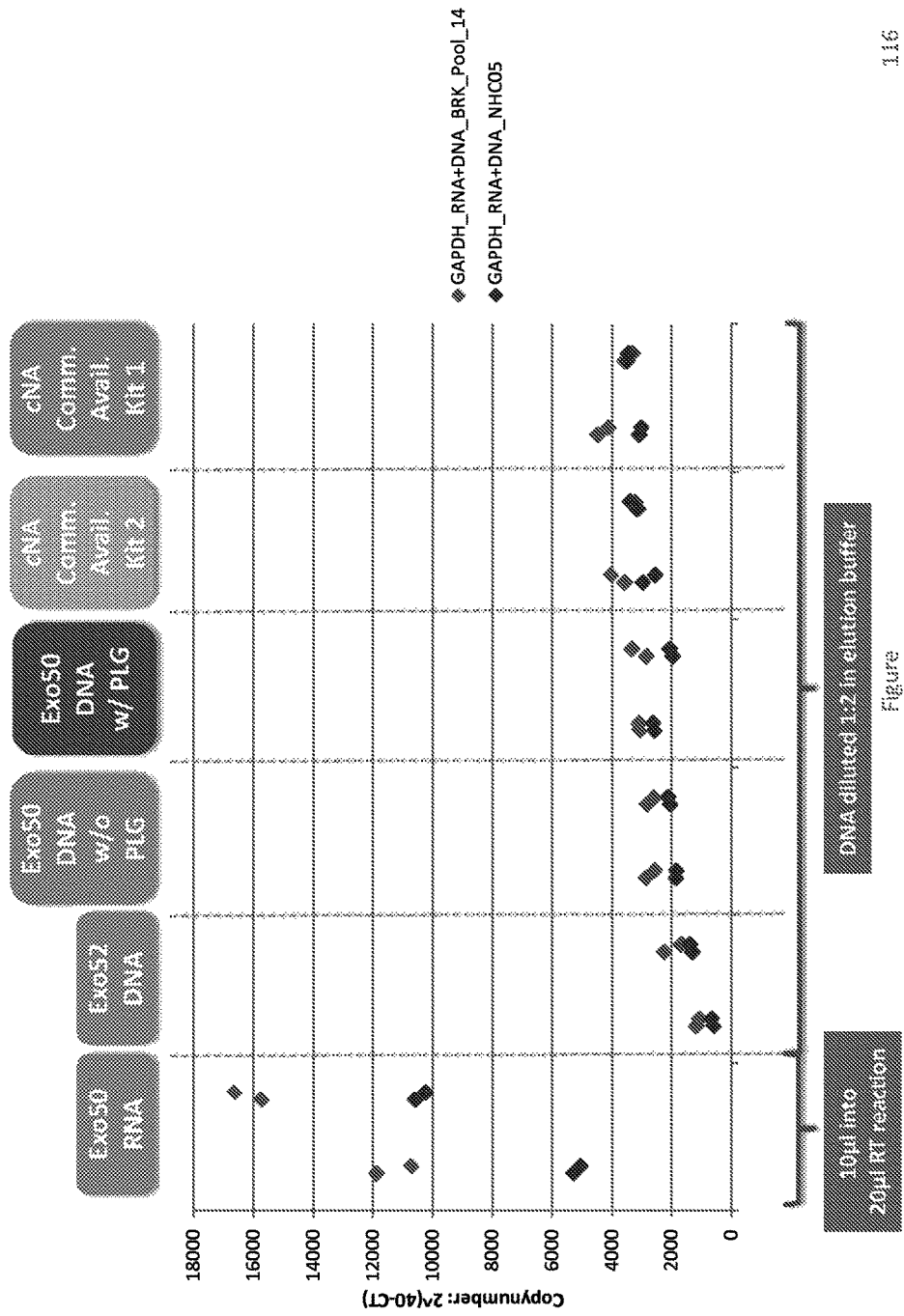

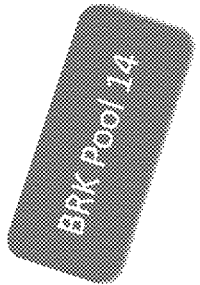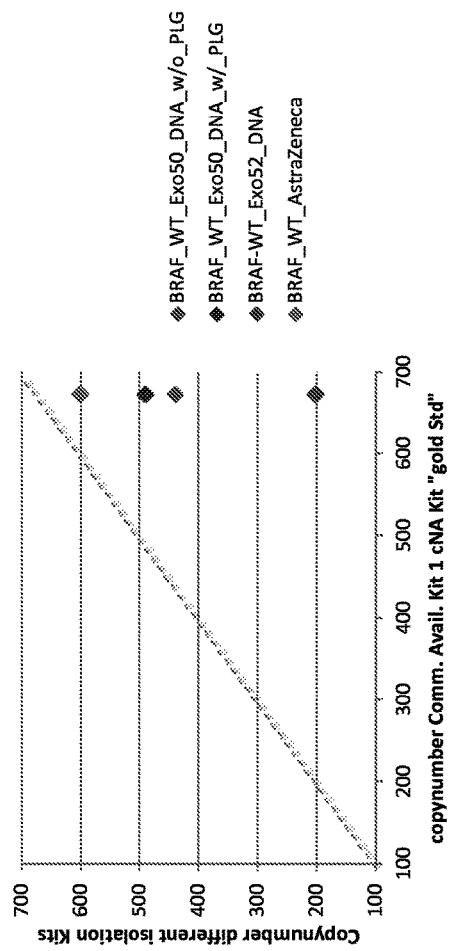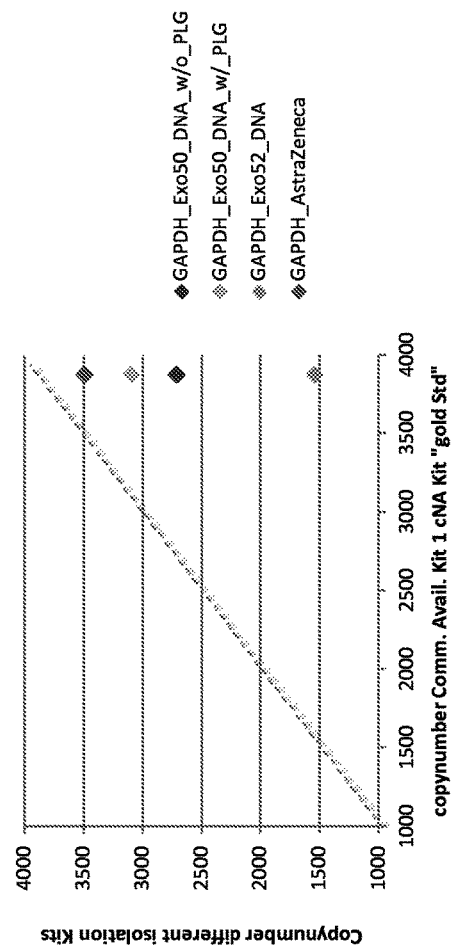

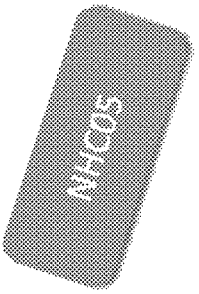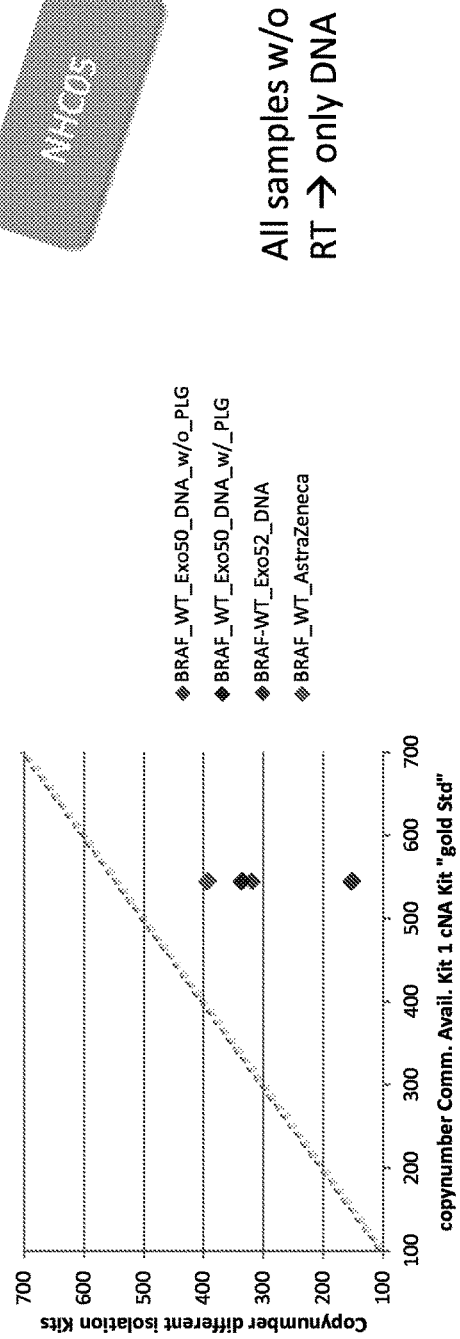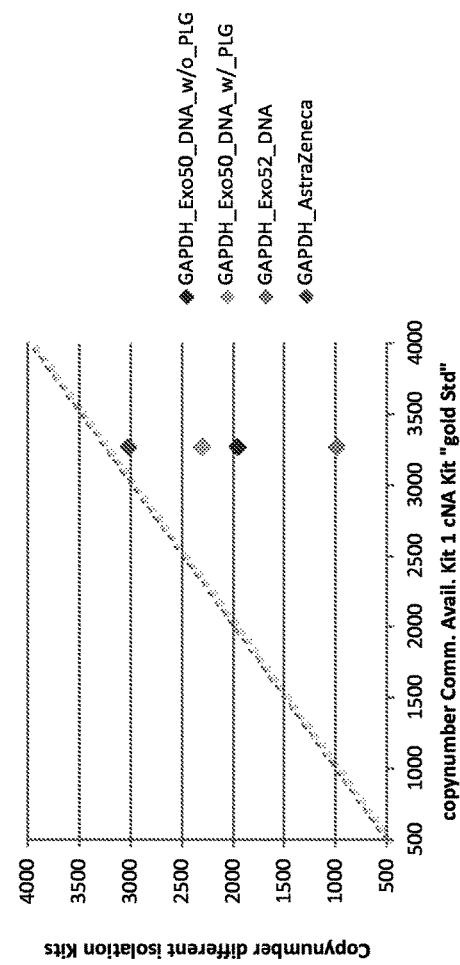

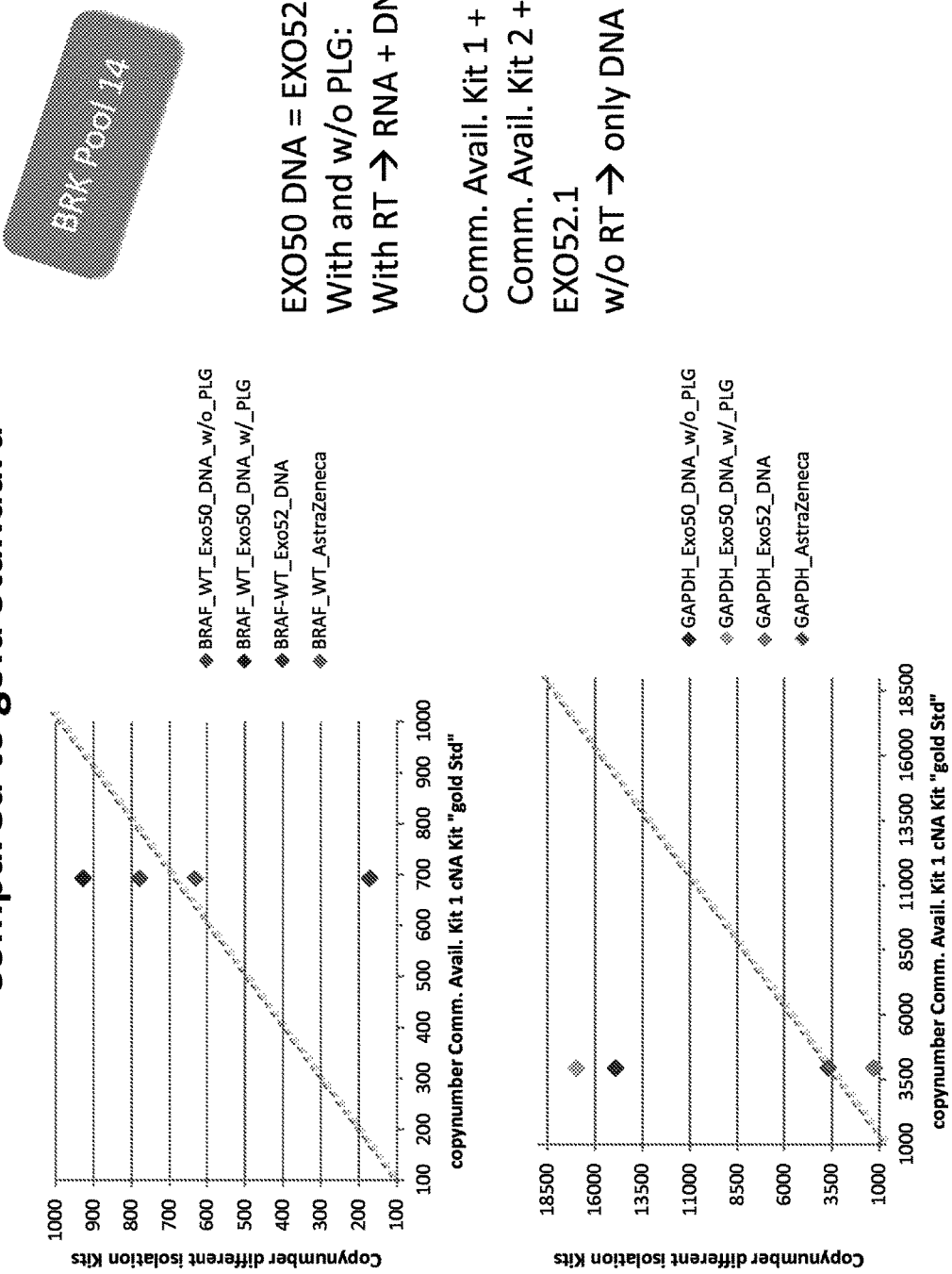

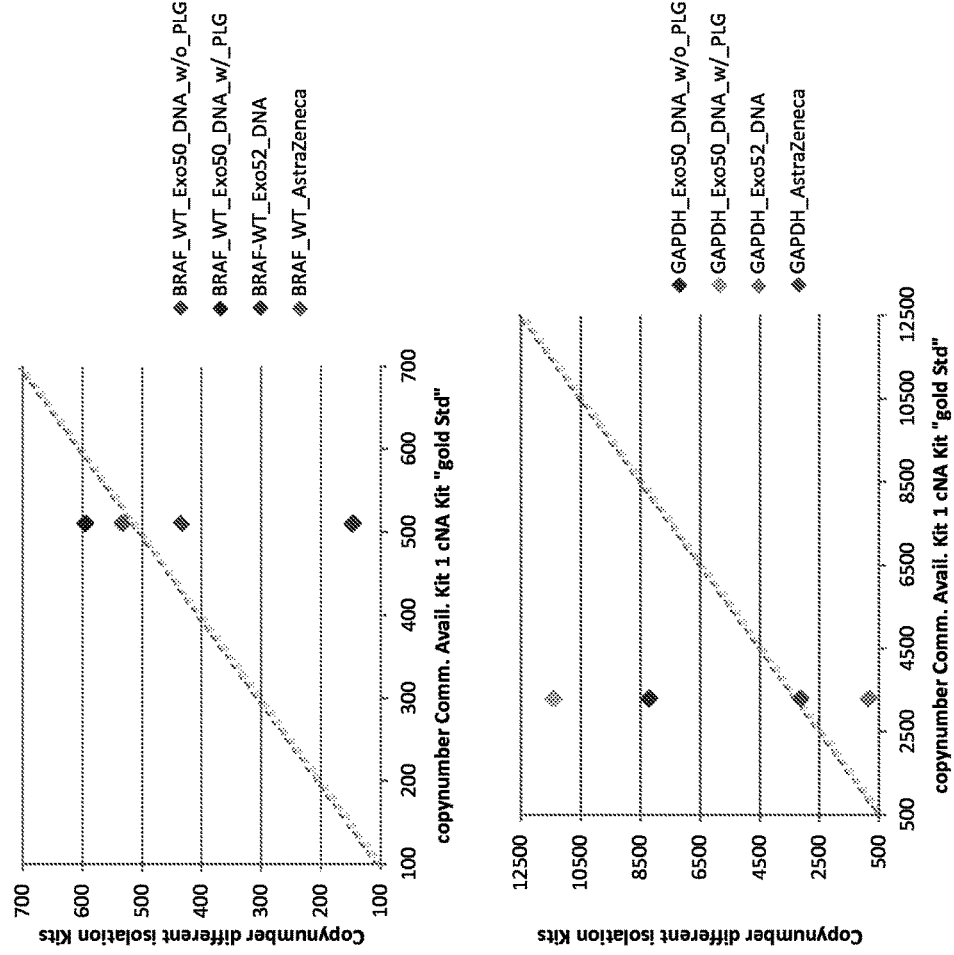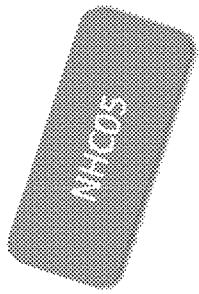

Result: Comparison of cfDNA copy number within different KITs

| Copynumber in QPCR | BRAF-WT | | GAPDH_RNA+DNA | |
|---|---|---|---|---|
| | Min | Max | Min | Max |
| Qiagen QIAamp circulating nucleic acid Kit * | 500 | 700 | 3000 | 4000 |
| AstraZeneca * | 400 | 700 | 3000 | 3500 |
| Exo50 DNA Isolation w/o PLG * | 350 | 450 | 2000 | 2500 |
| Exo50 DNA Isolation with PLG * | 350 | 500 | 2500 | 3000 |
| Exo52 DNA Isolation * | 150 | 300 | 1000 | 1500 |

| Copynumber in QPCR | BRAF-WT | | GAPDH_RNA+DNA | |
|---|---|---|---|---|
| | MIN | MAX | MIN | MAX |
| Qiagen QIAamp circulating nucleic acid kit* | 500 | 800 | 3000 | 4000 |
| AstraZeneca* | 500 | 750 | 3000 | 4000 |
| EXO50 DNA isolation w/o PLG (Exo52.2)** | 400 | 800 | 7500 | 10500 |
| EXO50 DNA isolation w/ PLG (Exo52.2)** | 500 | 500 | 10000 | 17000 |
| EXO52.1 DNA Isolation* | 100 | 250 | 700 | 1000 |
| EXO50 RNA Isolation** | 100 | 250 | 10000 | 15000 |

\* samples without RT step → only DNA
\*\* samples with RT step → contain transcript RNA and DNA

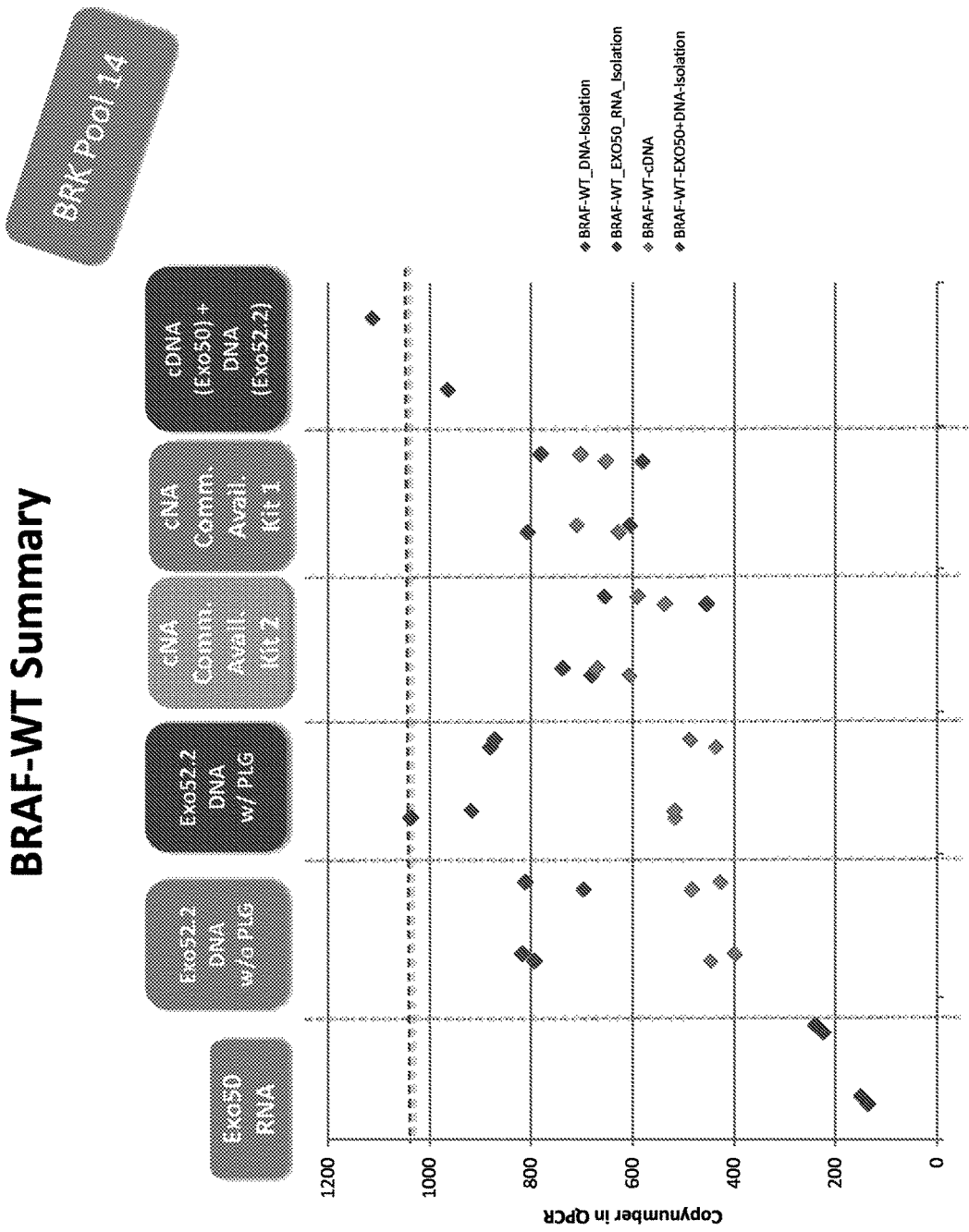

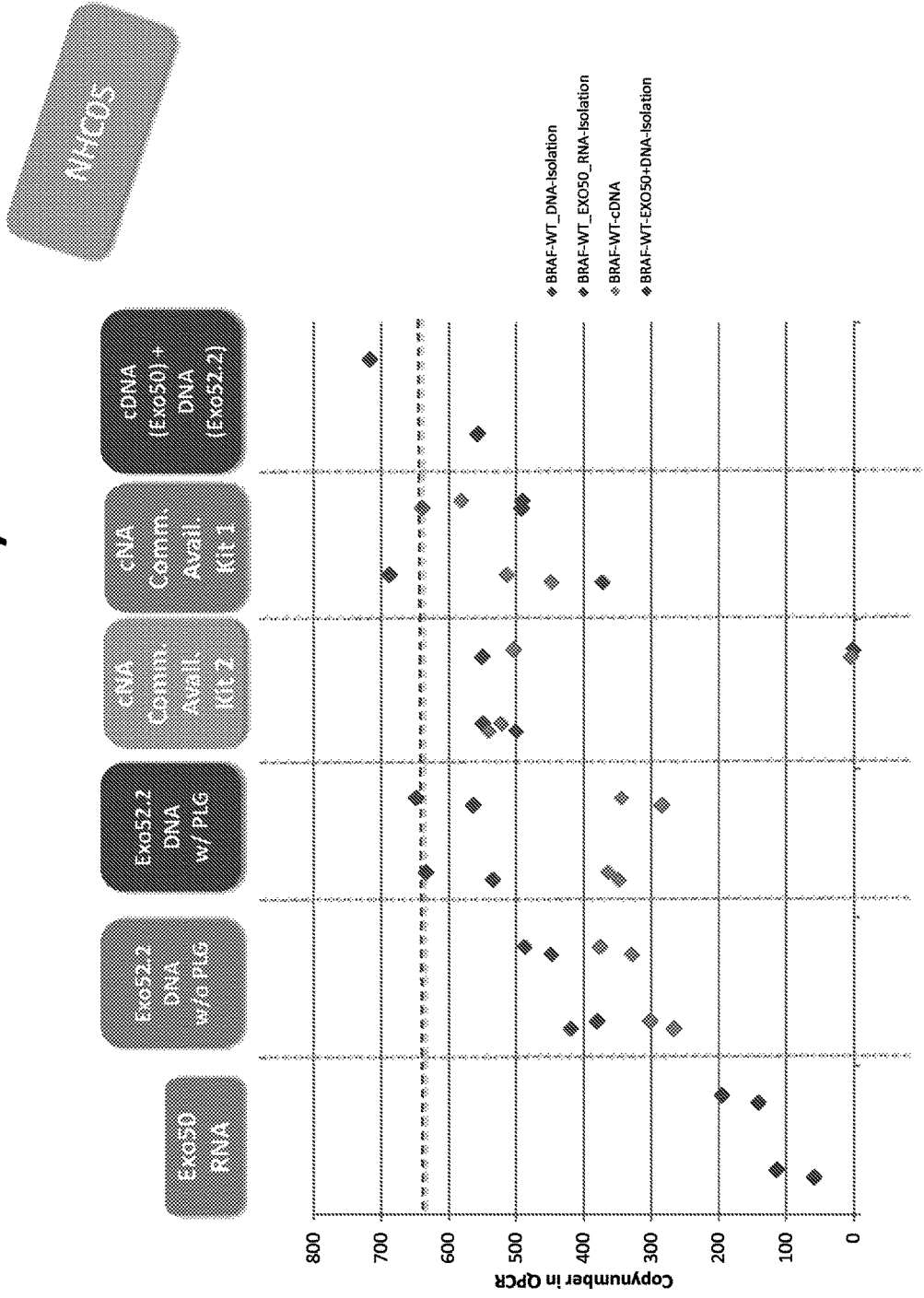

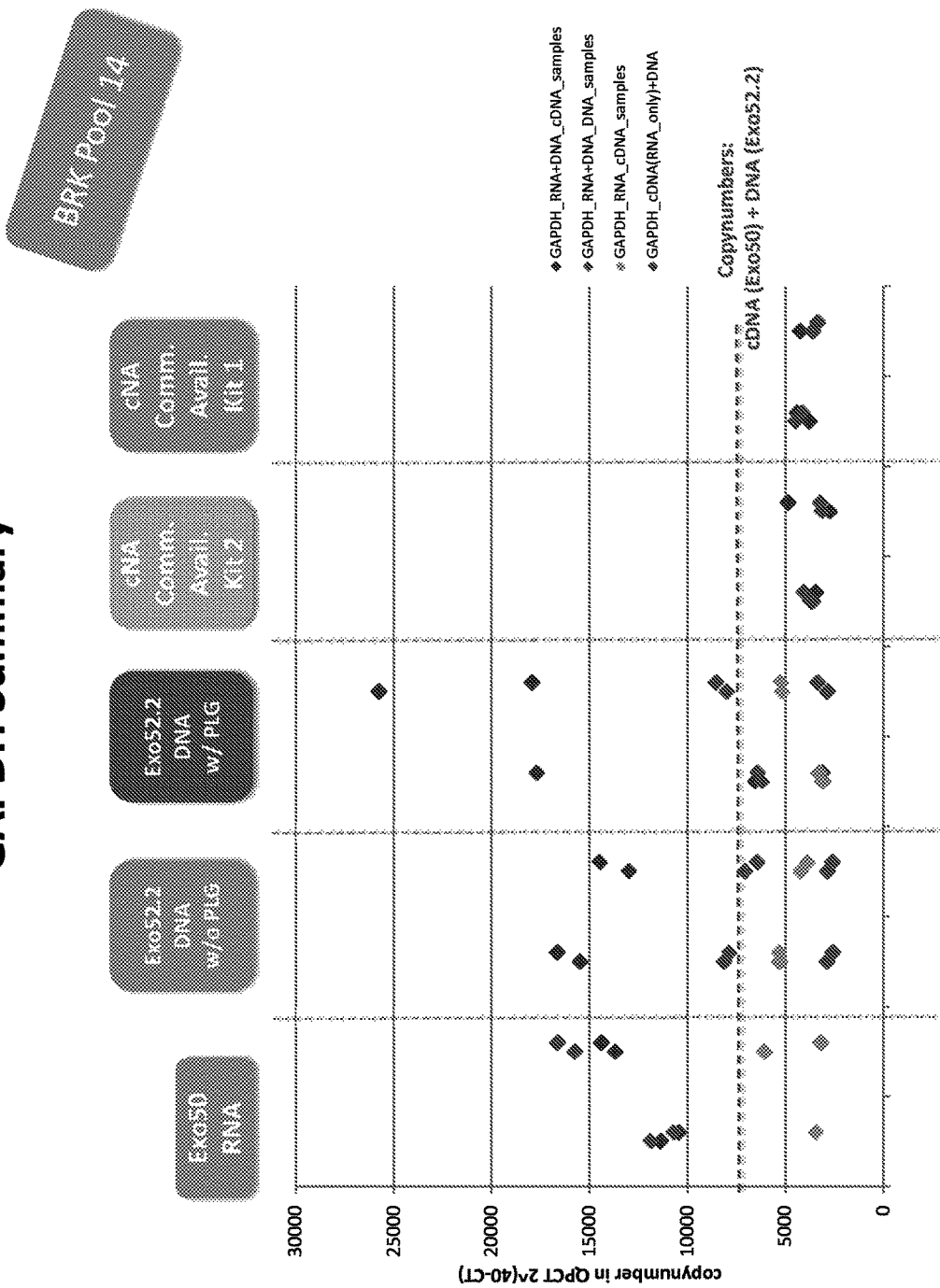

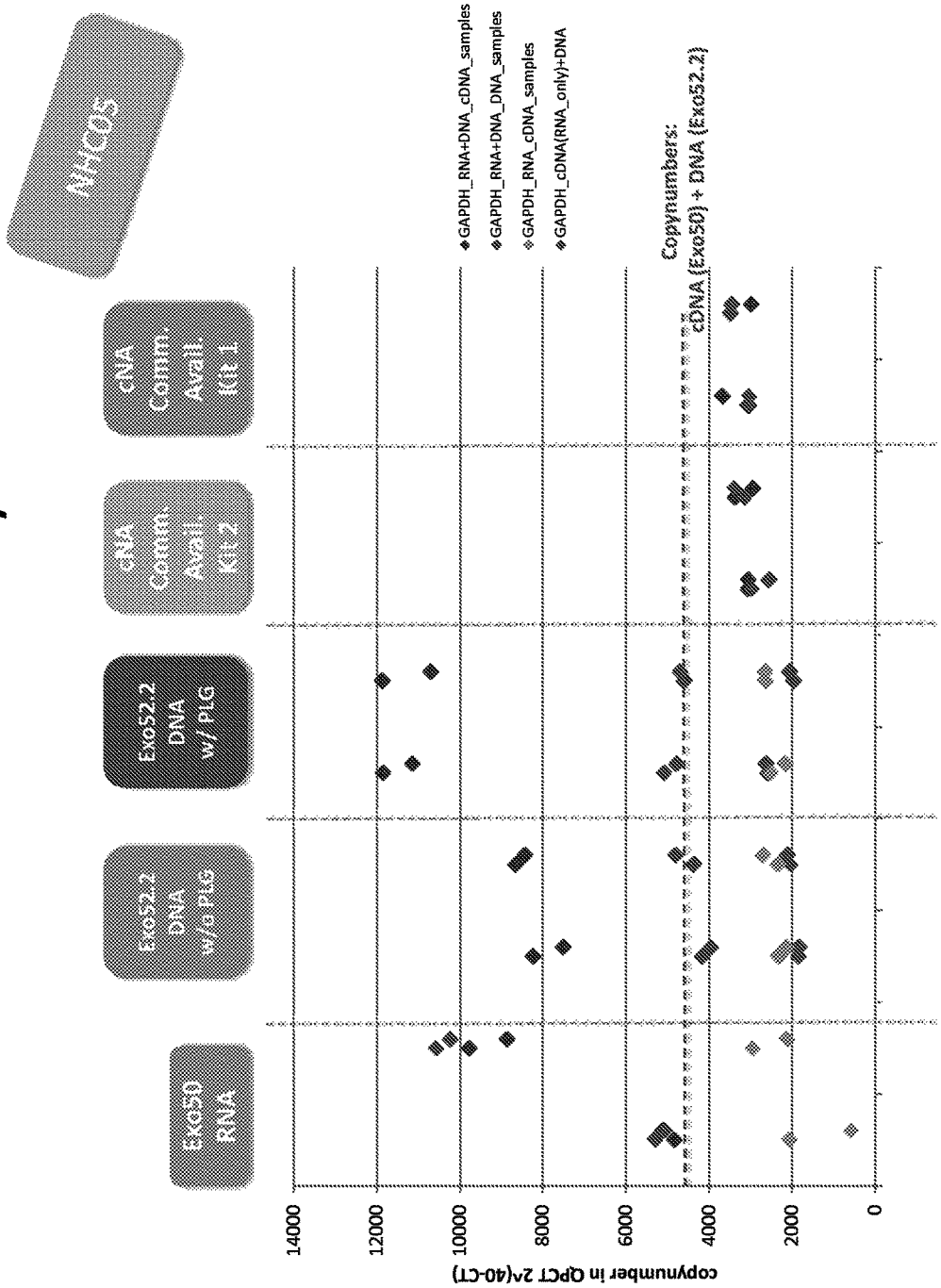

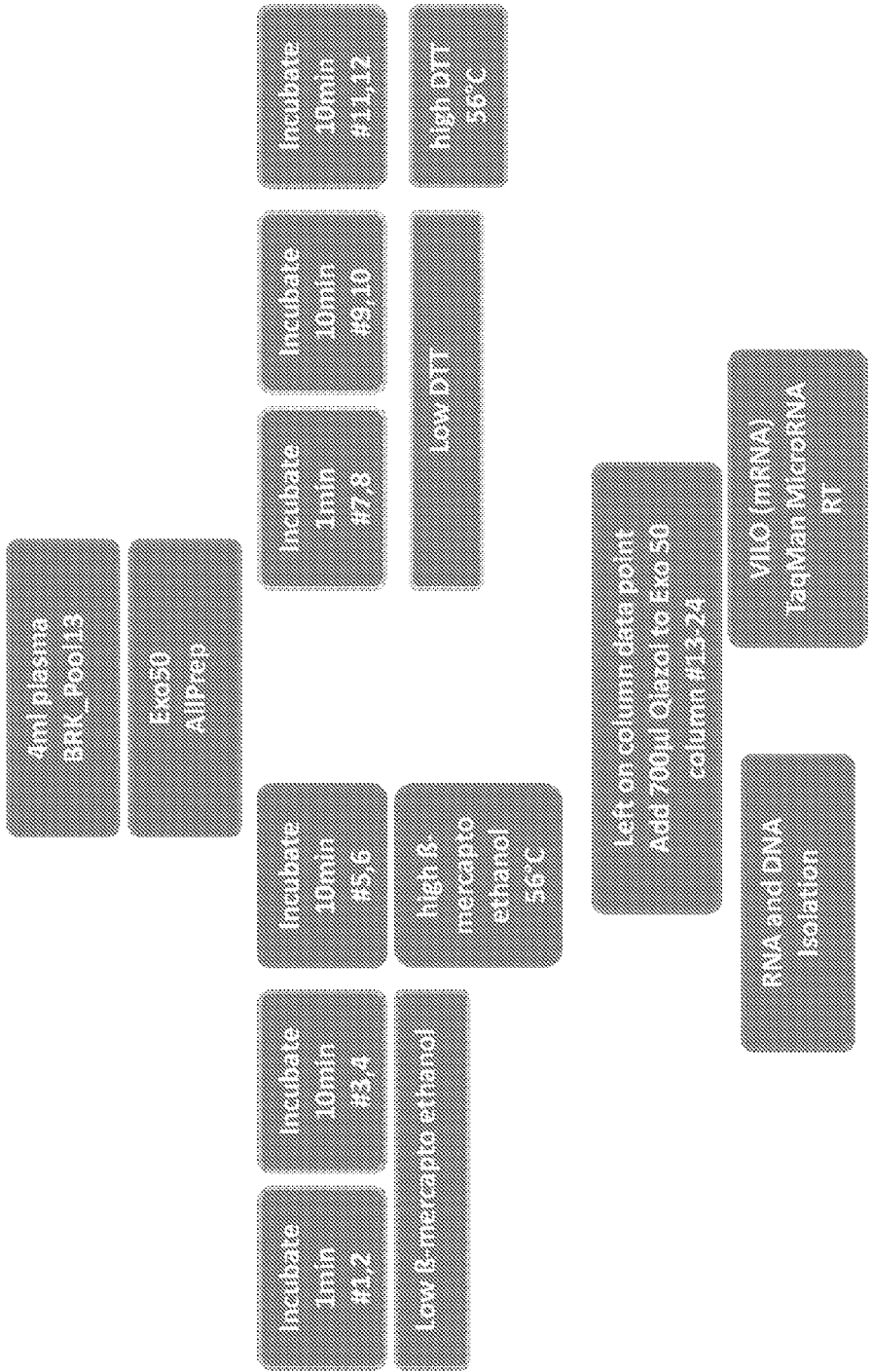

Notes:

Carrier RNA: polyA from commercially available kit   0.2μg/μl = 200ng/μl → Dilute to 4ng/μl (1:50) and use 5μl per sample β-mercaptoethanol 14.3 M
Low concentration: 10μl per 1ml RLT buffer → 143M
High concentration: 50μl per 1ml RLT buffer → 715M DTT 1M
Kit recommendation 20μl of 2M DTT per 1ml RLT buffer
→ 40μl of 1M DTT per 1ml RLT (=low concentration) → 40M
→ 200μl of 1M DTT per 1ml RLT (=high cocnentration) → 200M

Figure 130

RNA Isolation

| | recommendation AllPrep MicroKit | homemade protocol Exo50 |
|---|---|---|
| Isolation mRNA | 1x 70% Ethanol | 1.5x 100% Ethanol |
| Isolation total RNA (containing small RNAs) | 1.5x 100% Ethanol | 2x 100% Ethanol |

RNeasy Mini Elute Columns clogging during binding step; further steps are also affected

DNA Isolation

| Specification | AllPrep DNA spin column | RNeasy MinElute spin column |
|---|---|---|
| Maximum binding capacity | 100 μg DNA* | 45 μg RNA |
| Maximum loading volume | 700 μl | 700 μl |
| Nucleic acid size distribution | DNA of 1.5–30 kb† | RNA >200 nucleotides† |
| Minimum elution volume | 30 μl ⟹ 25μl | 10 μl ⟹ 20μl |
| Maximum amount of starting material | | |
| Animal and human cells | 5 × 10⁶ cells | Entire flow-through from AllPrep DNA spin column |
| Animal and human tissues | 5 mg | Entire flow-through from AllPrep DNA spin column |

Figure

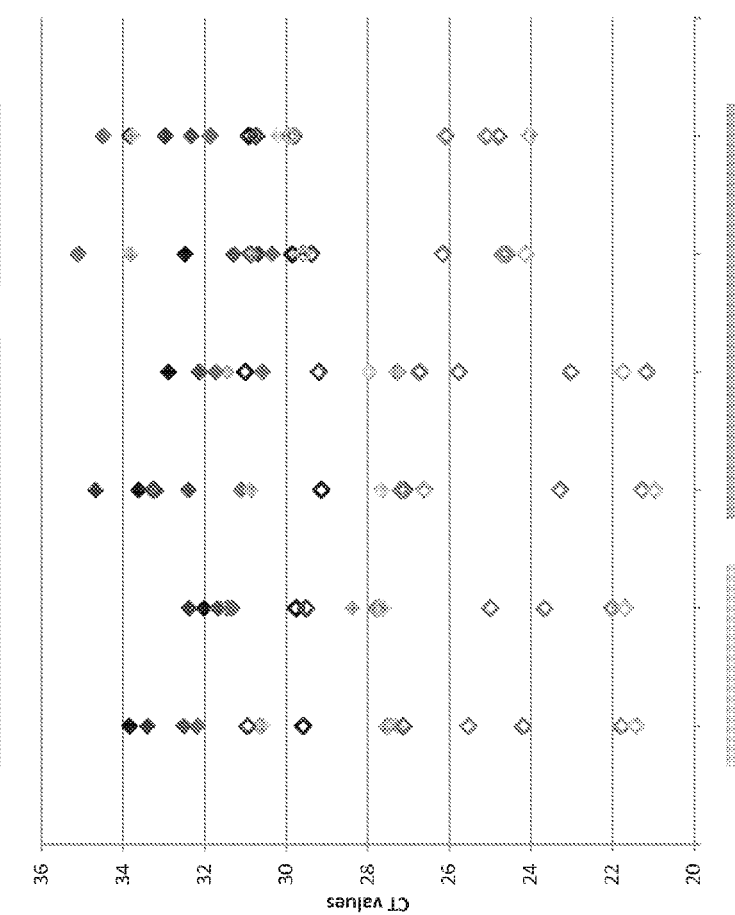

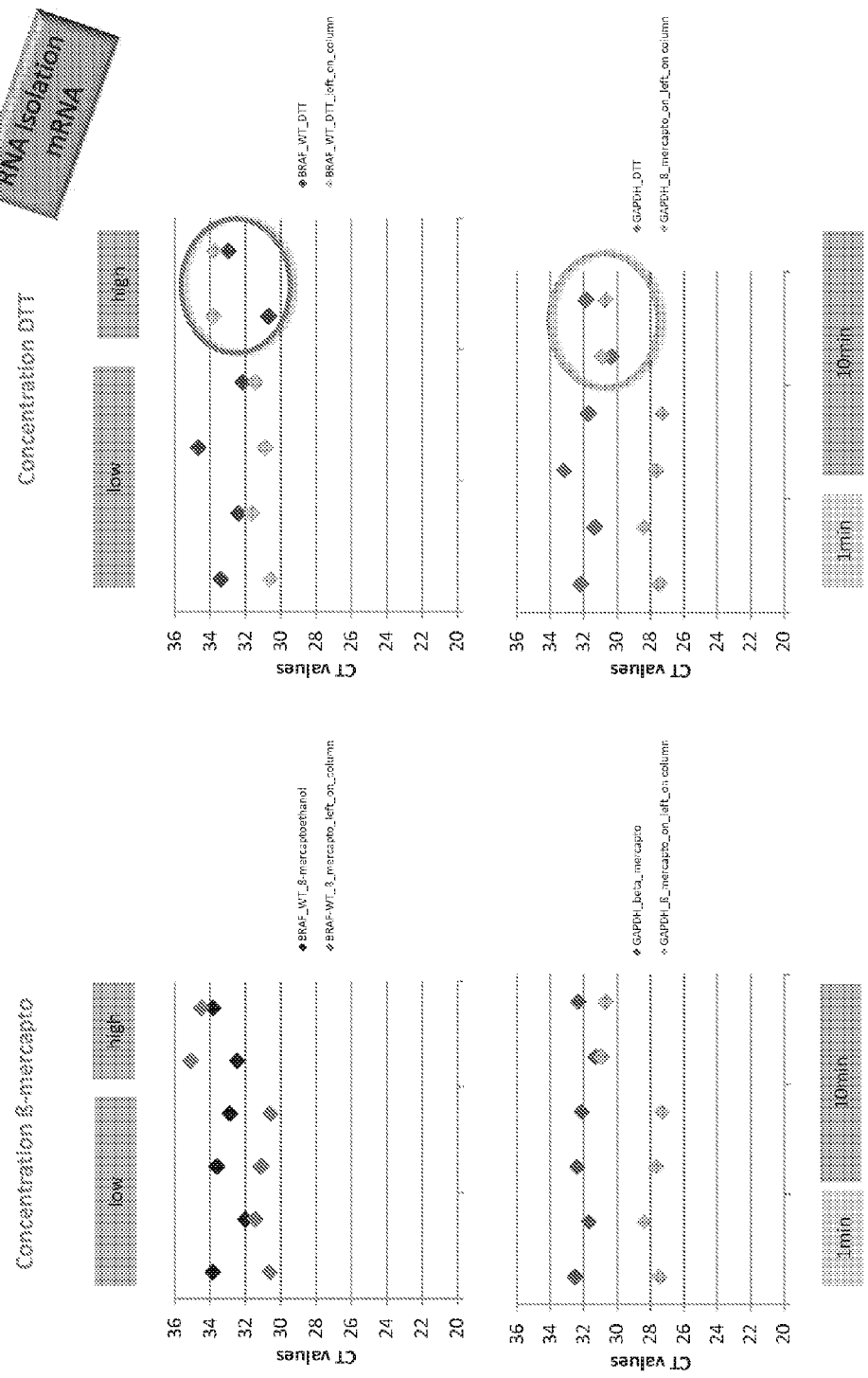

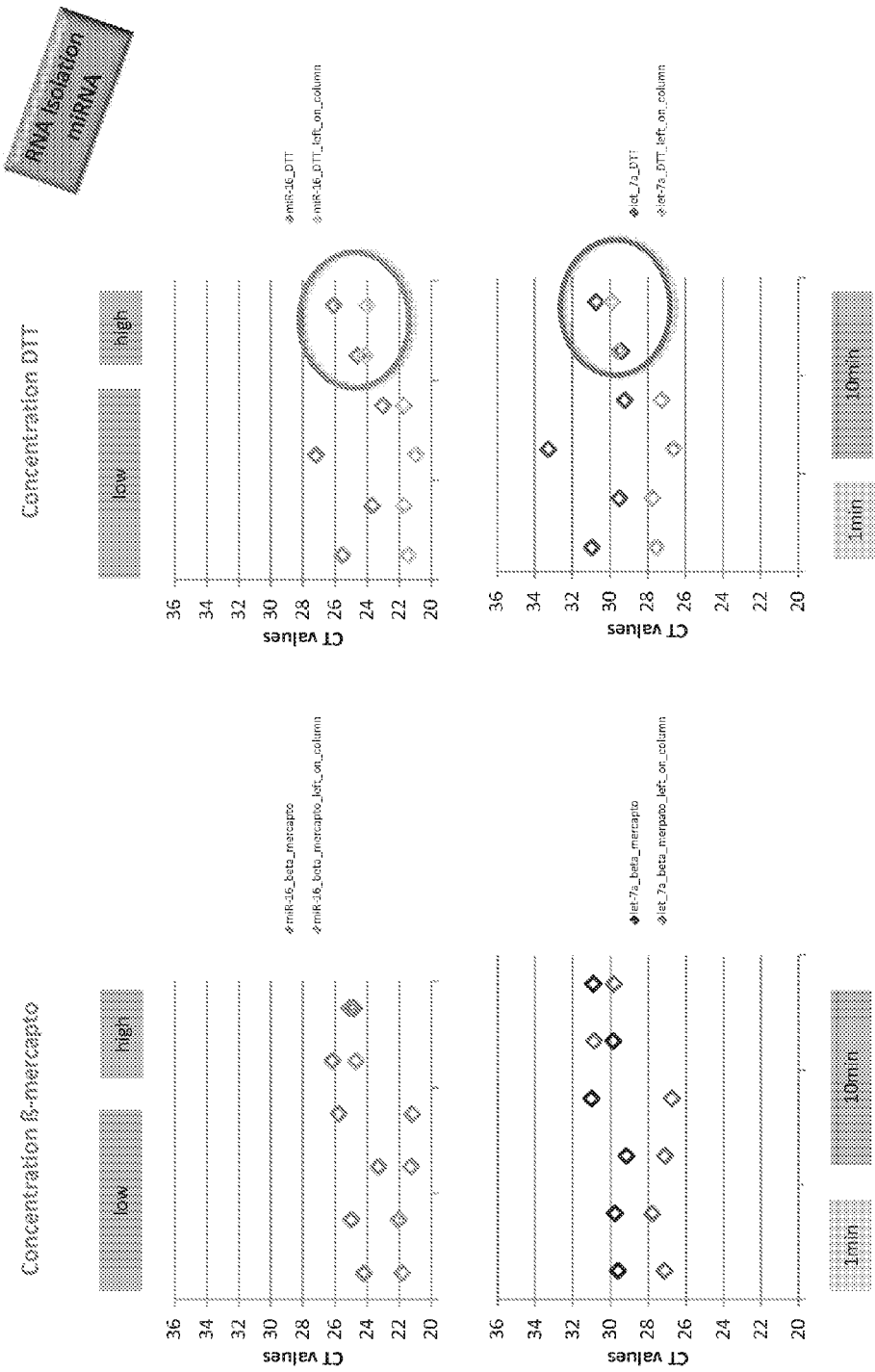

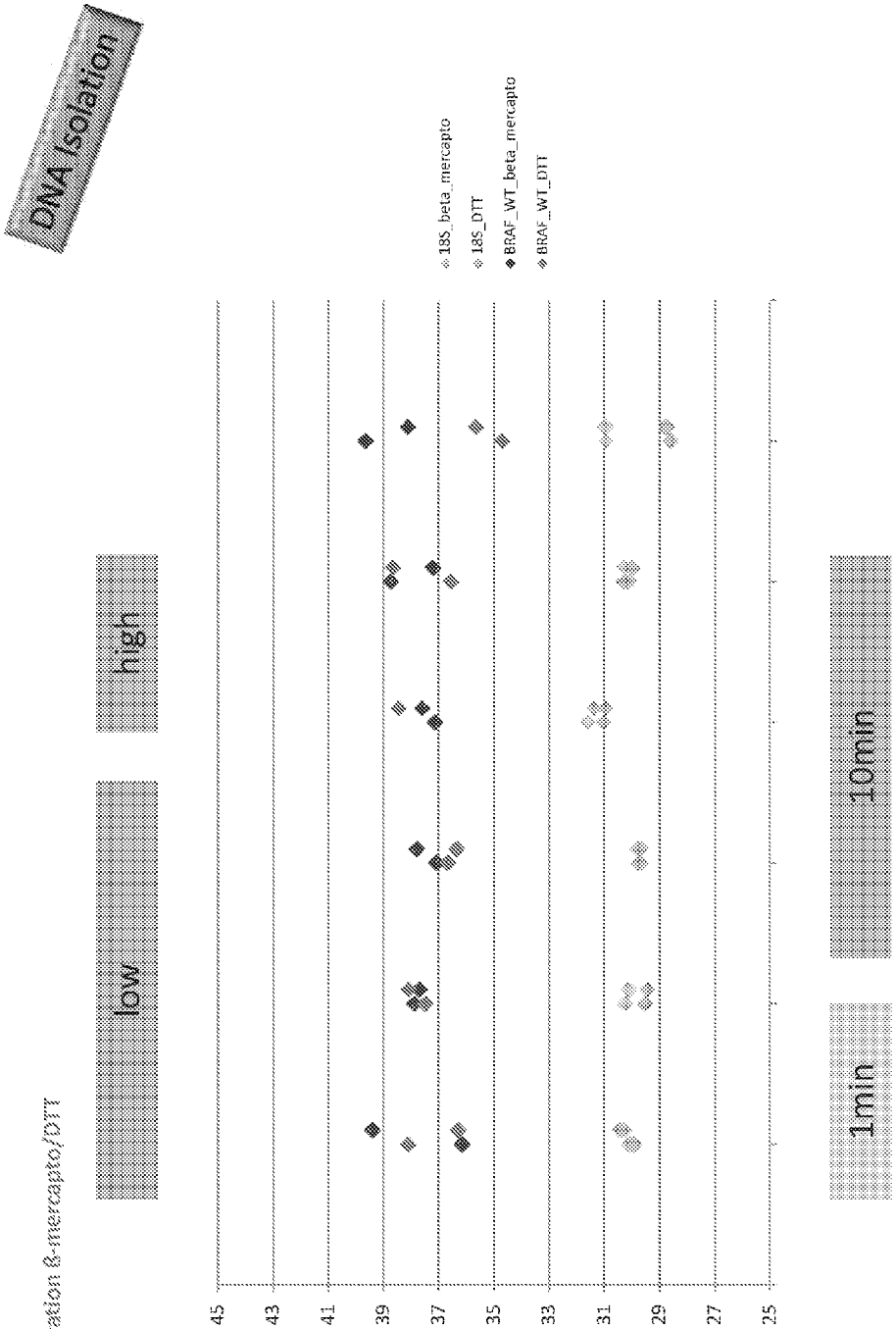

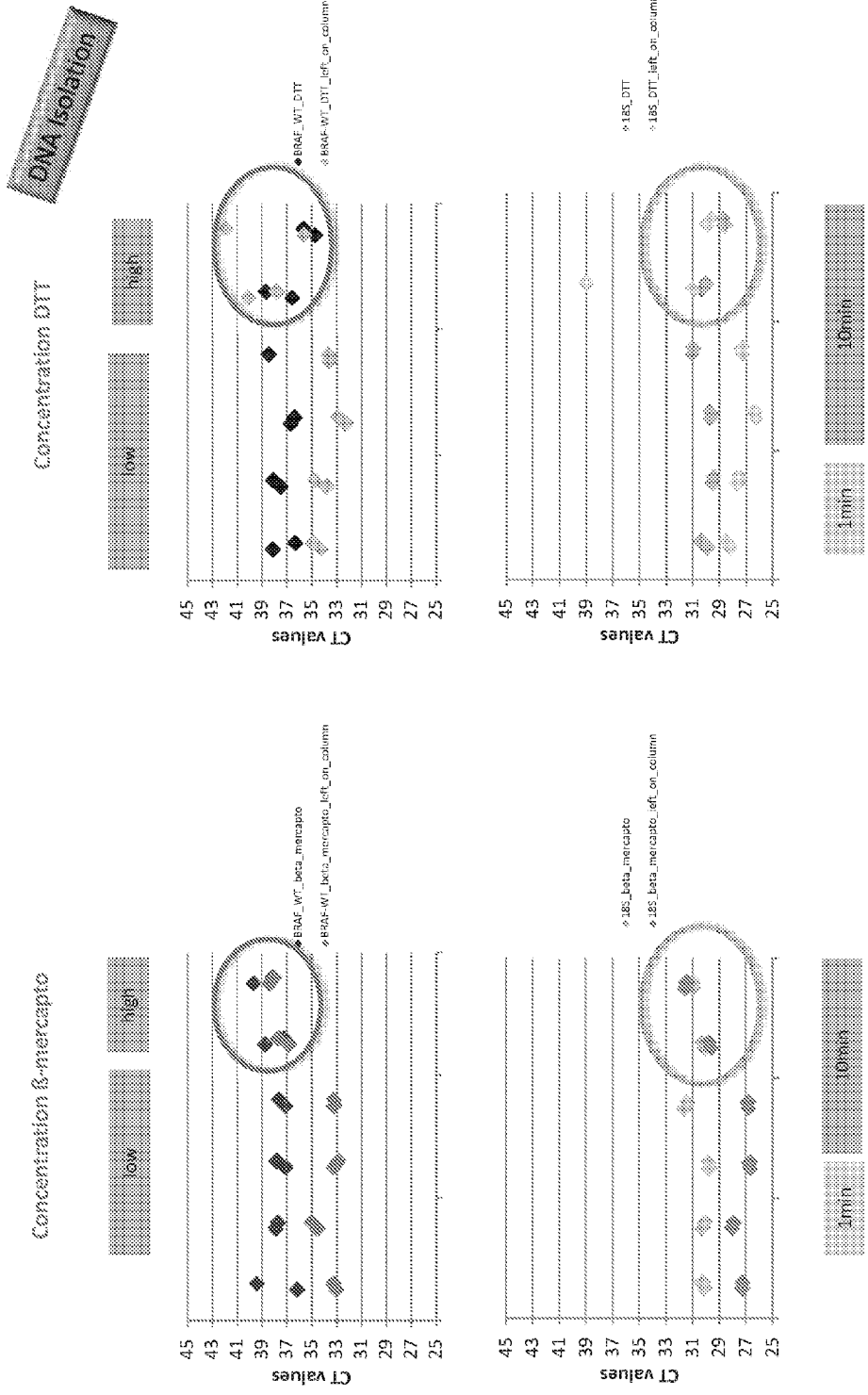

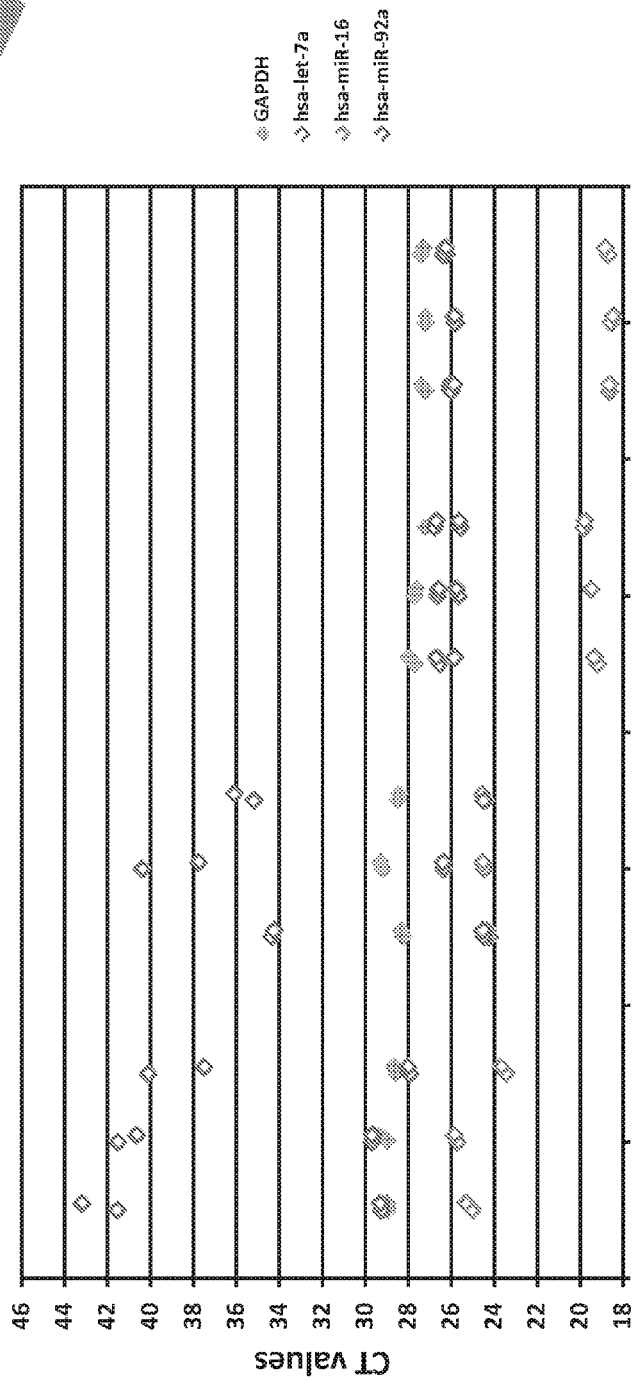

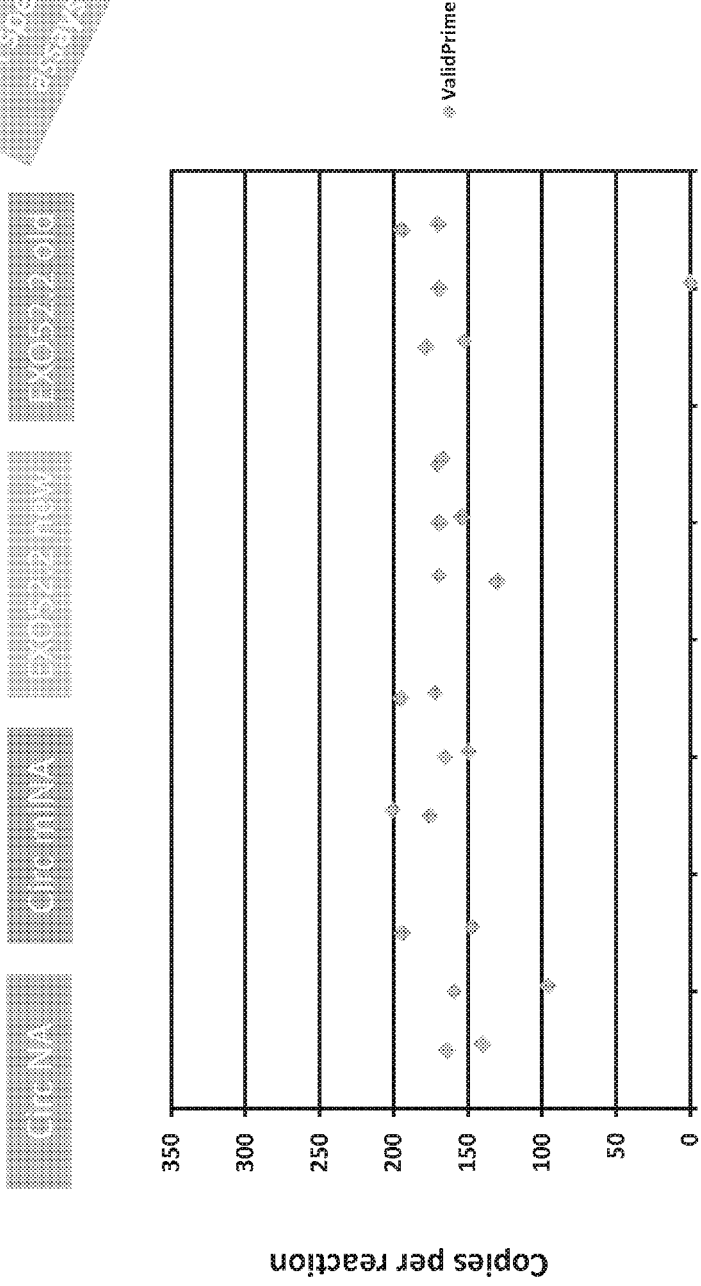

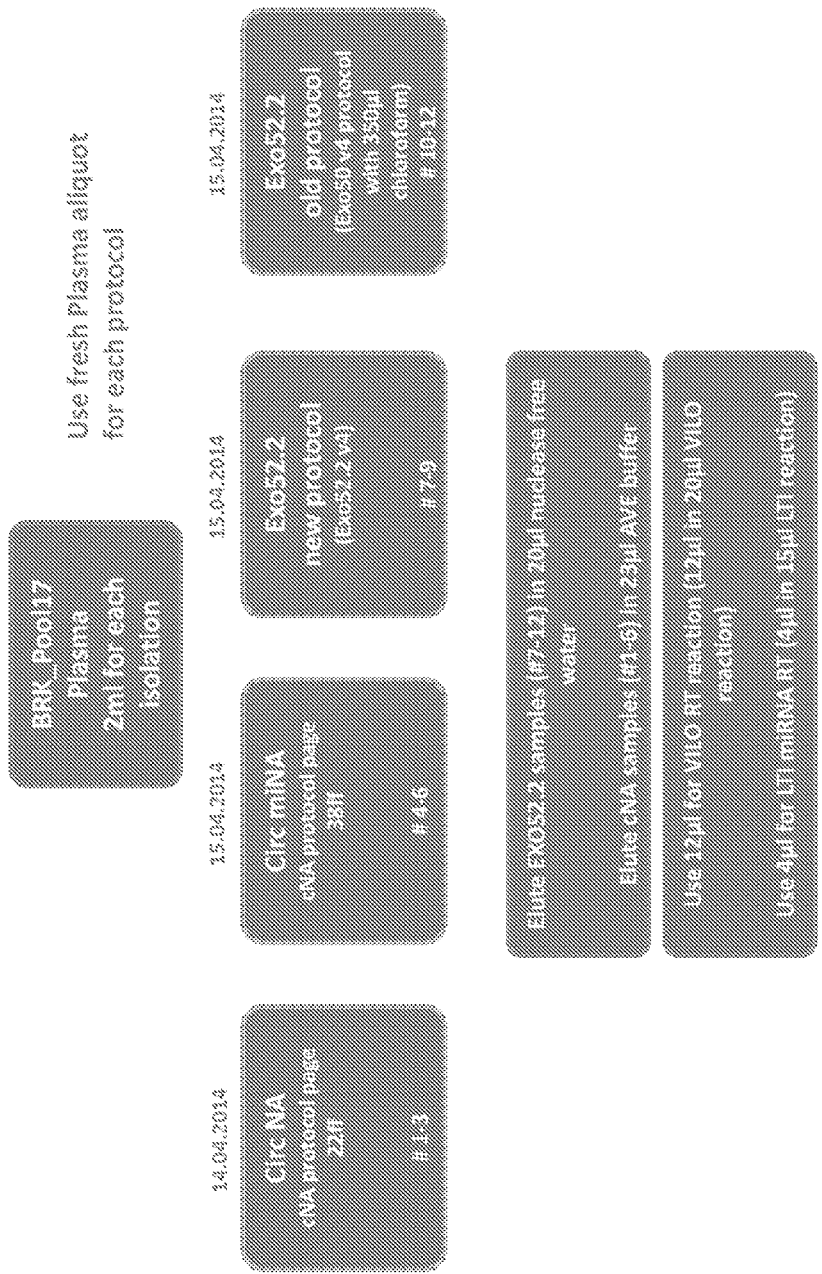

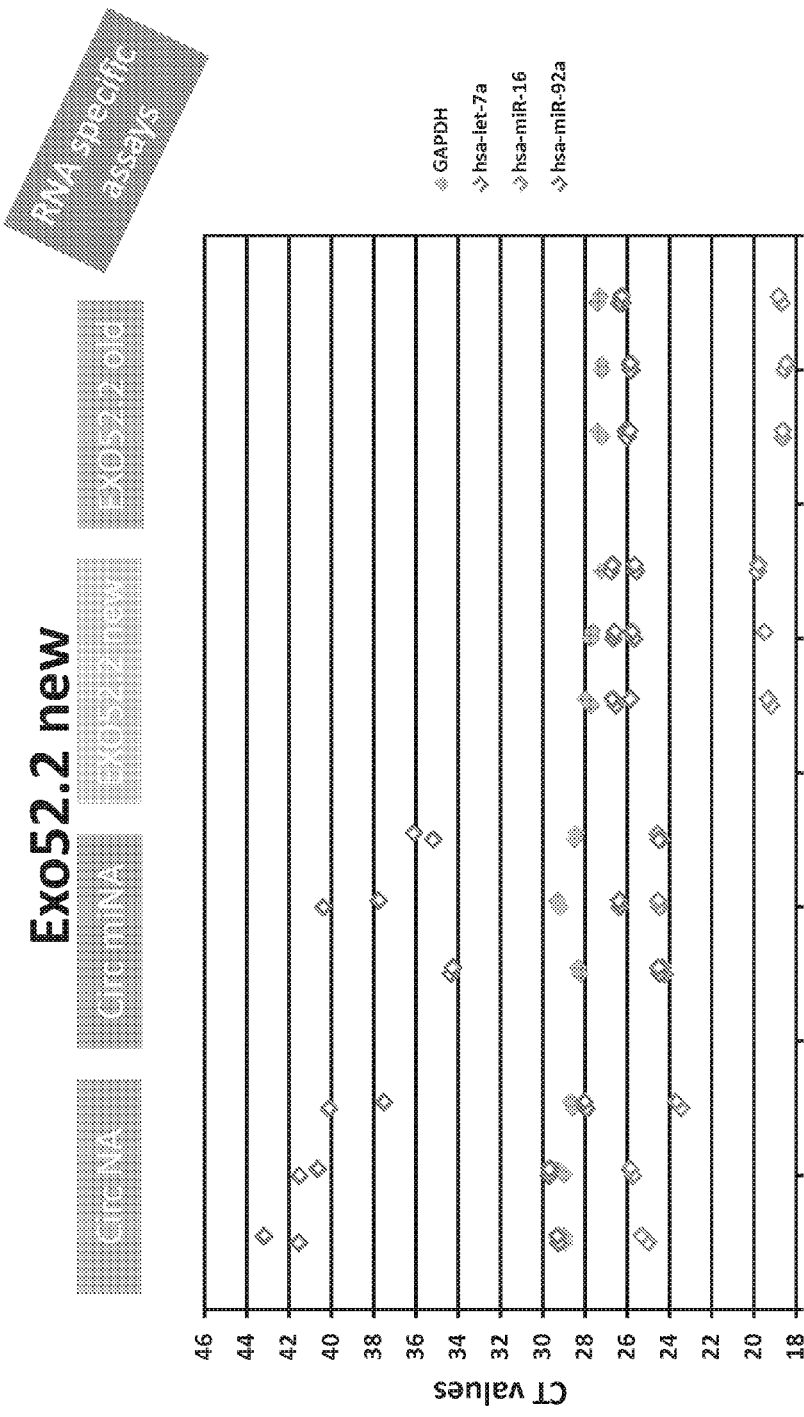

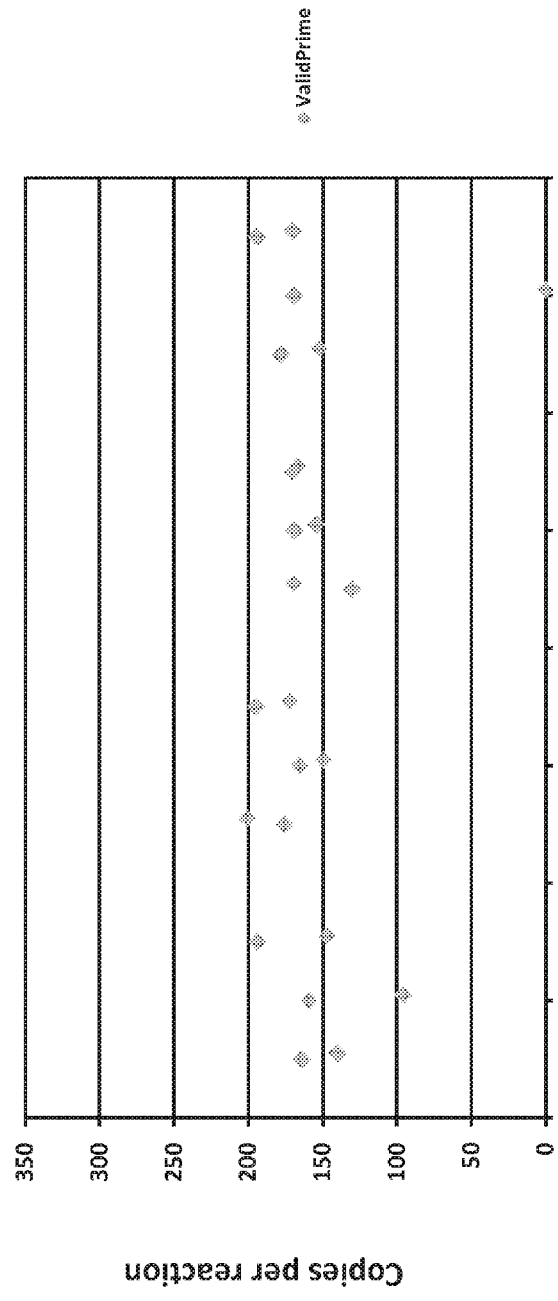

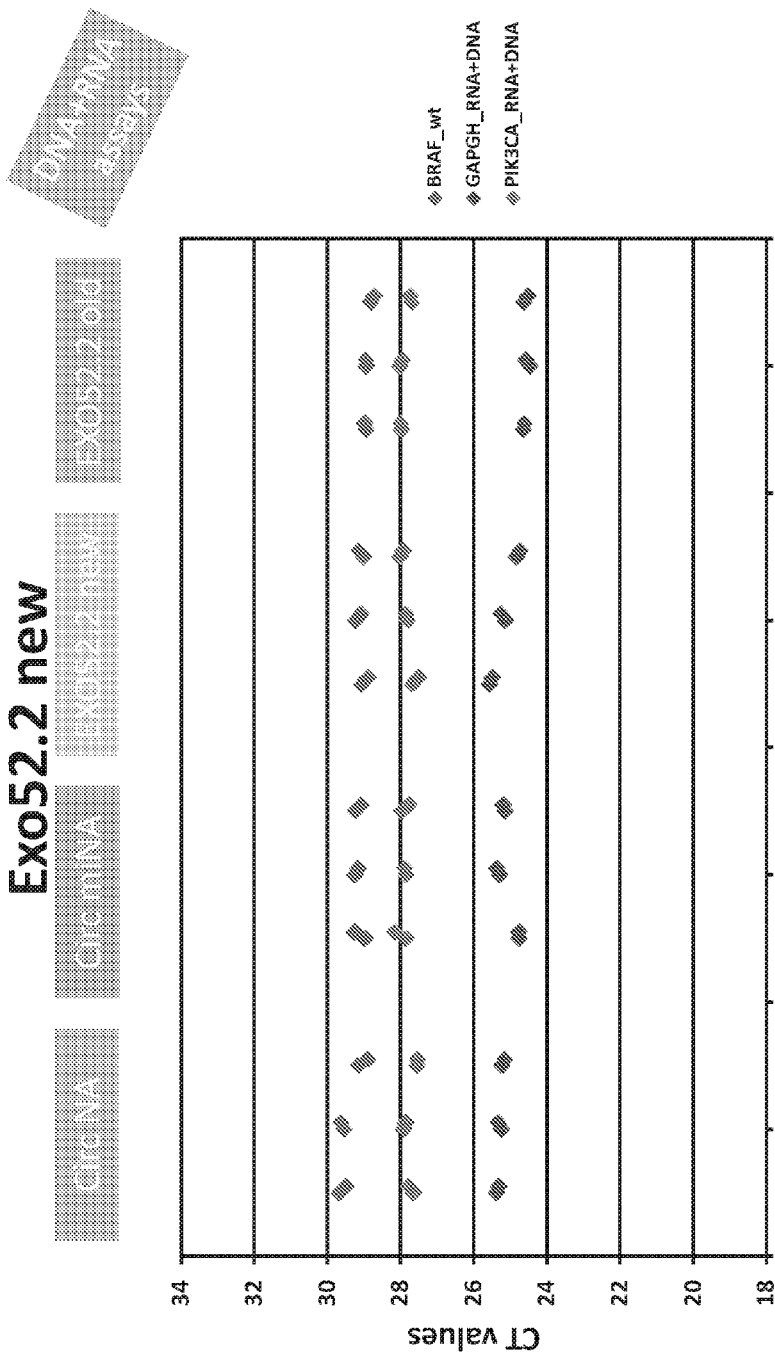

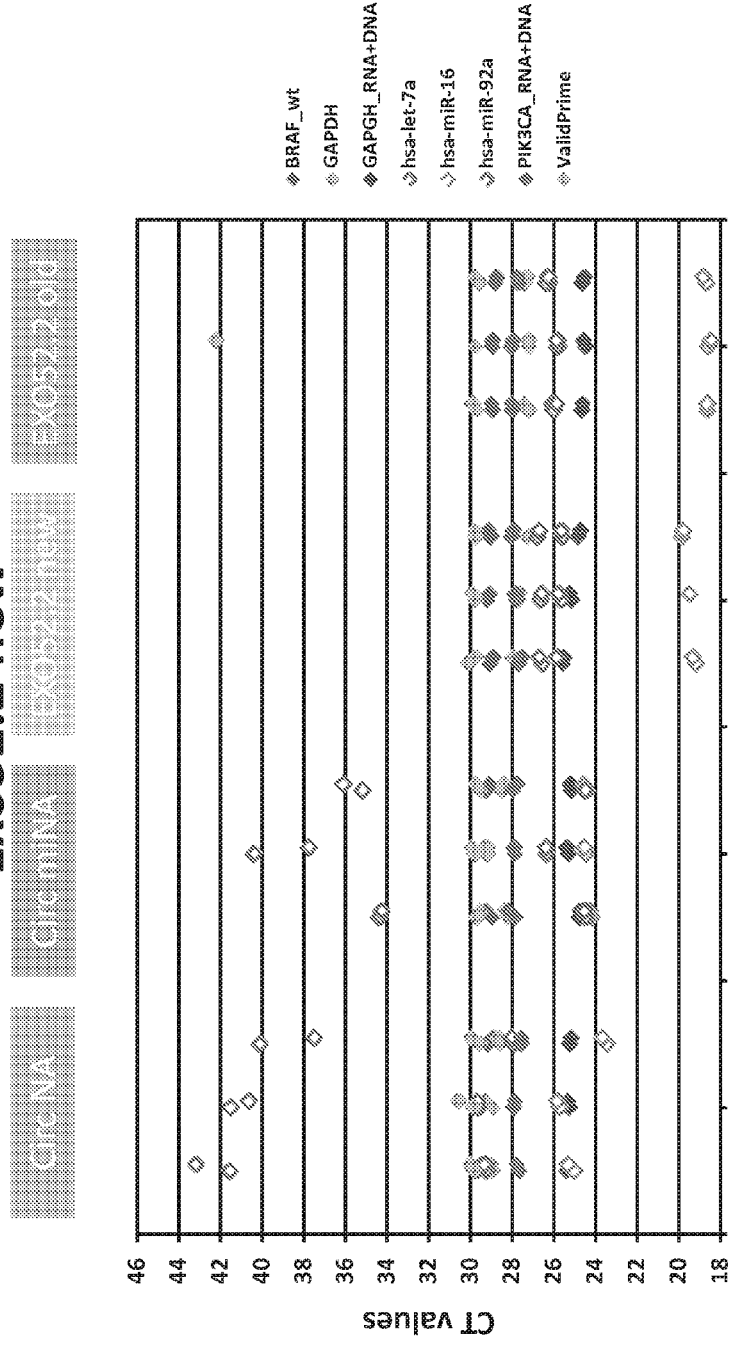

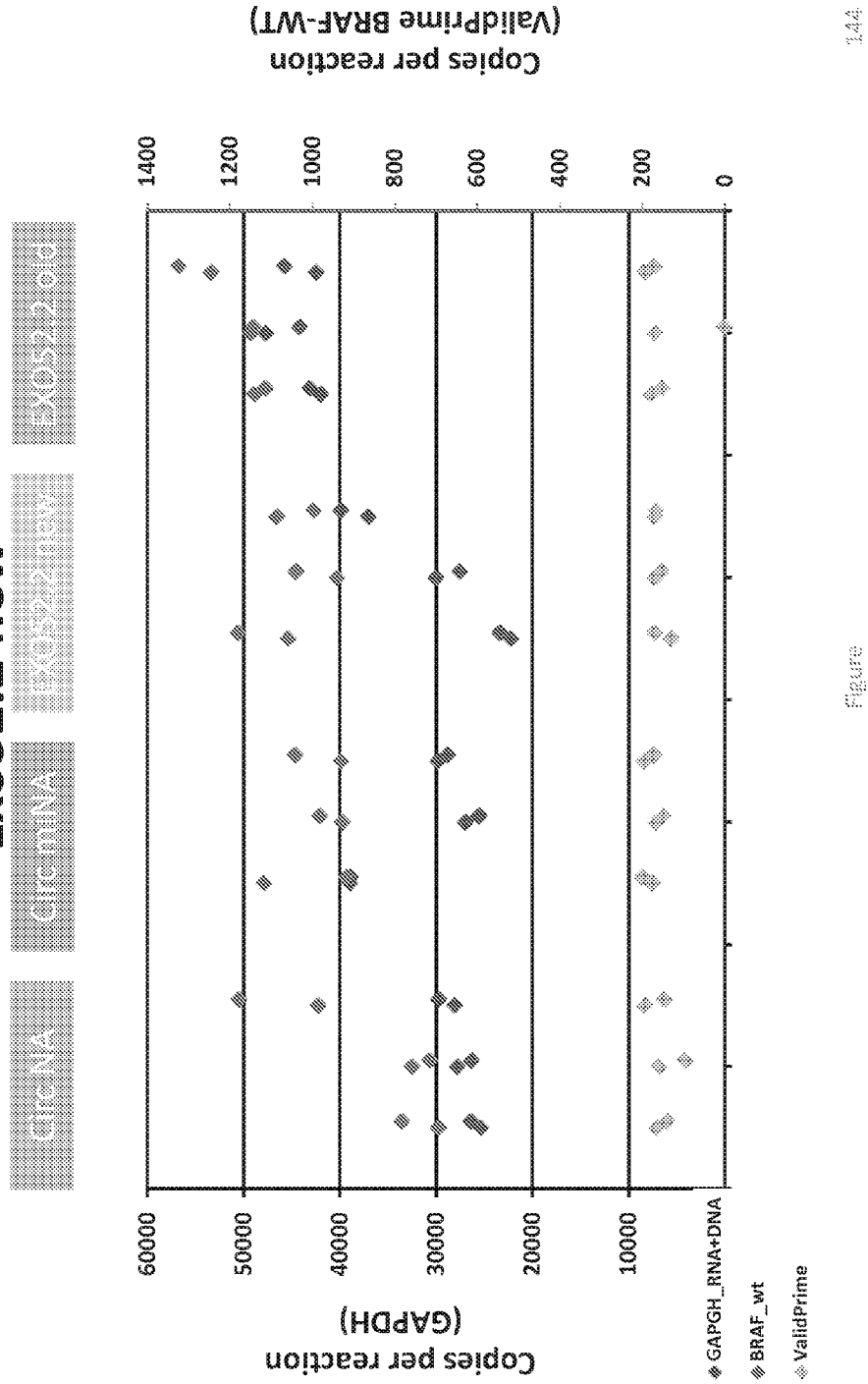

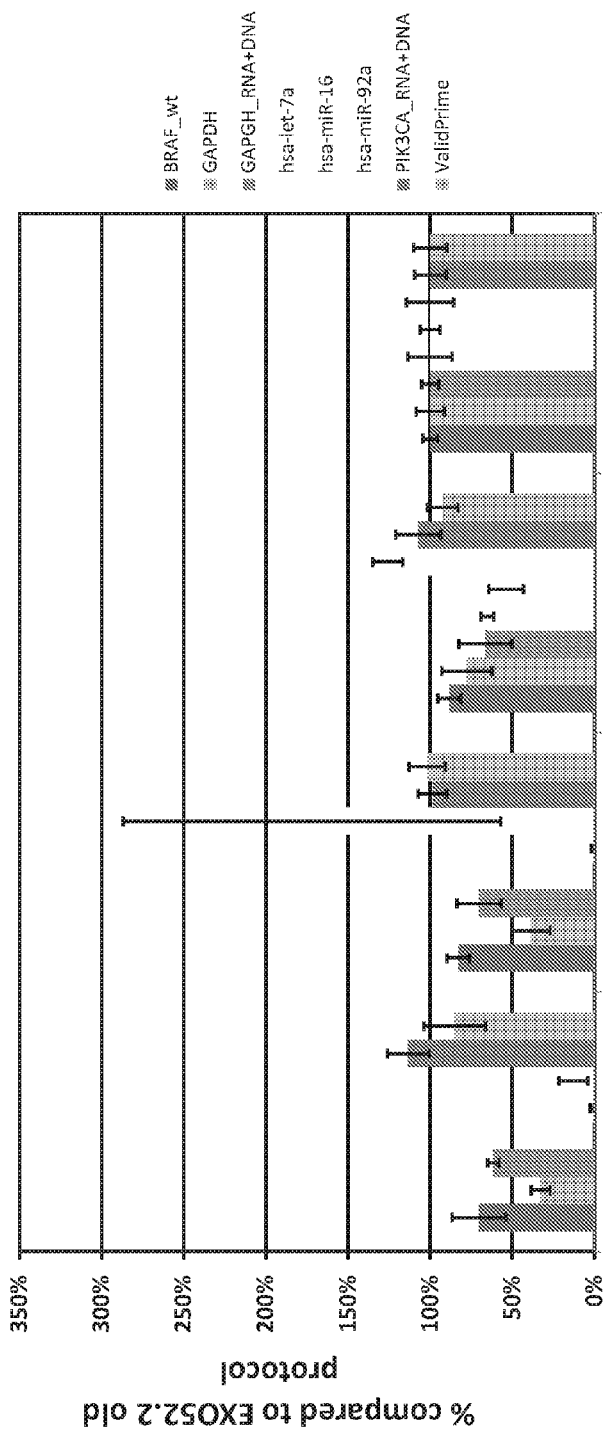

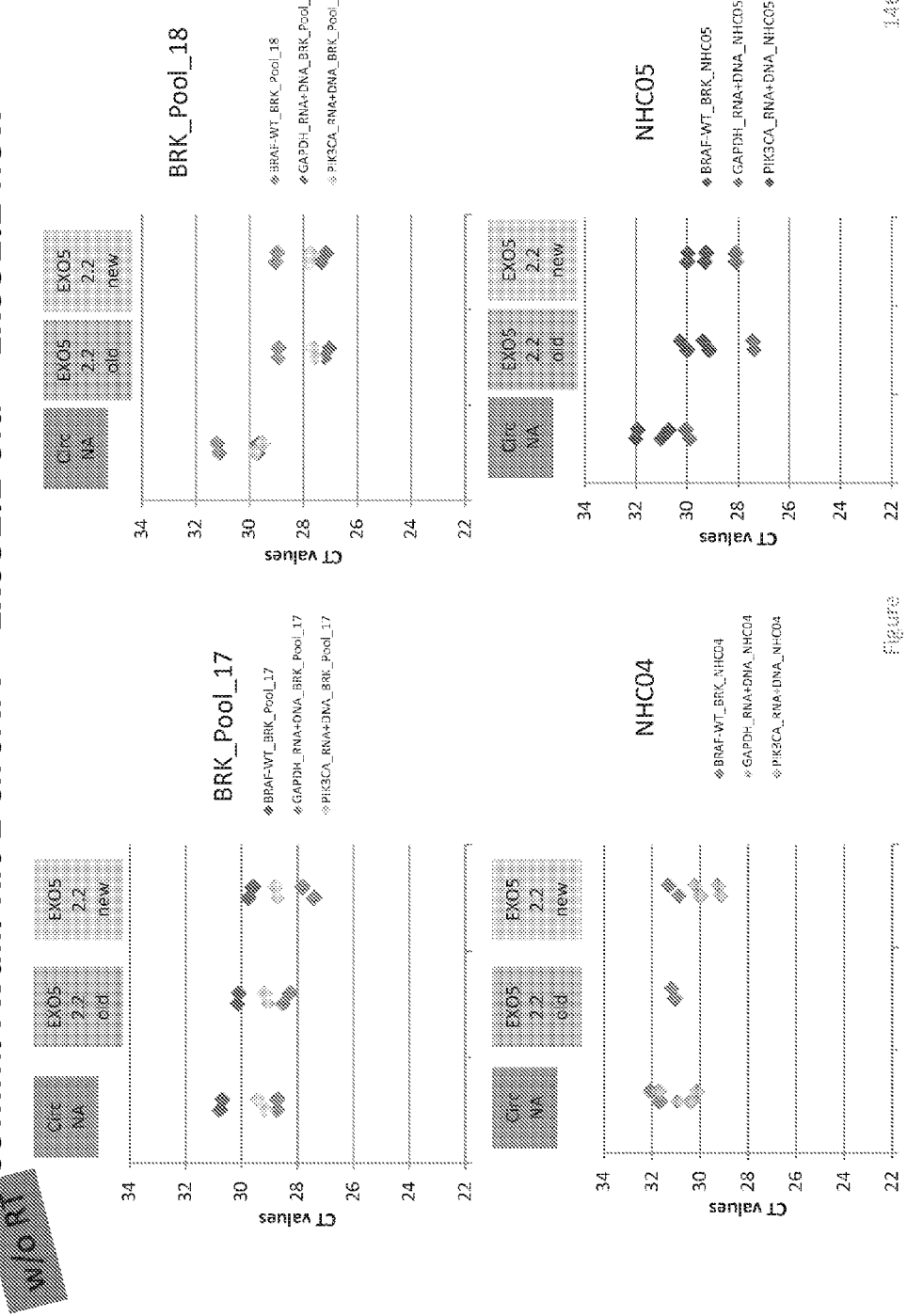

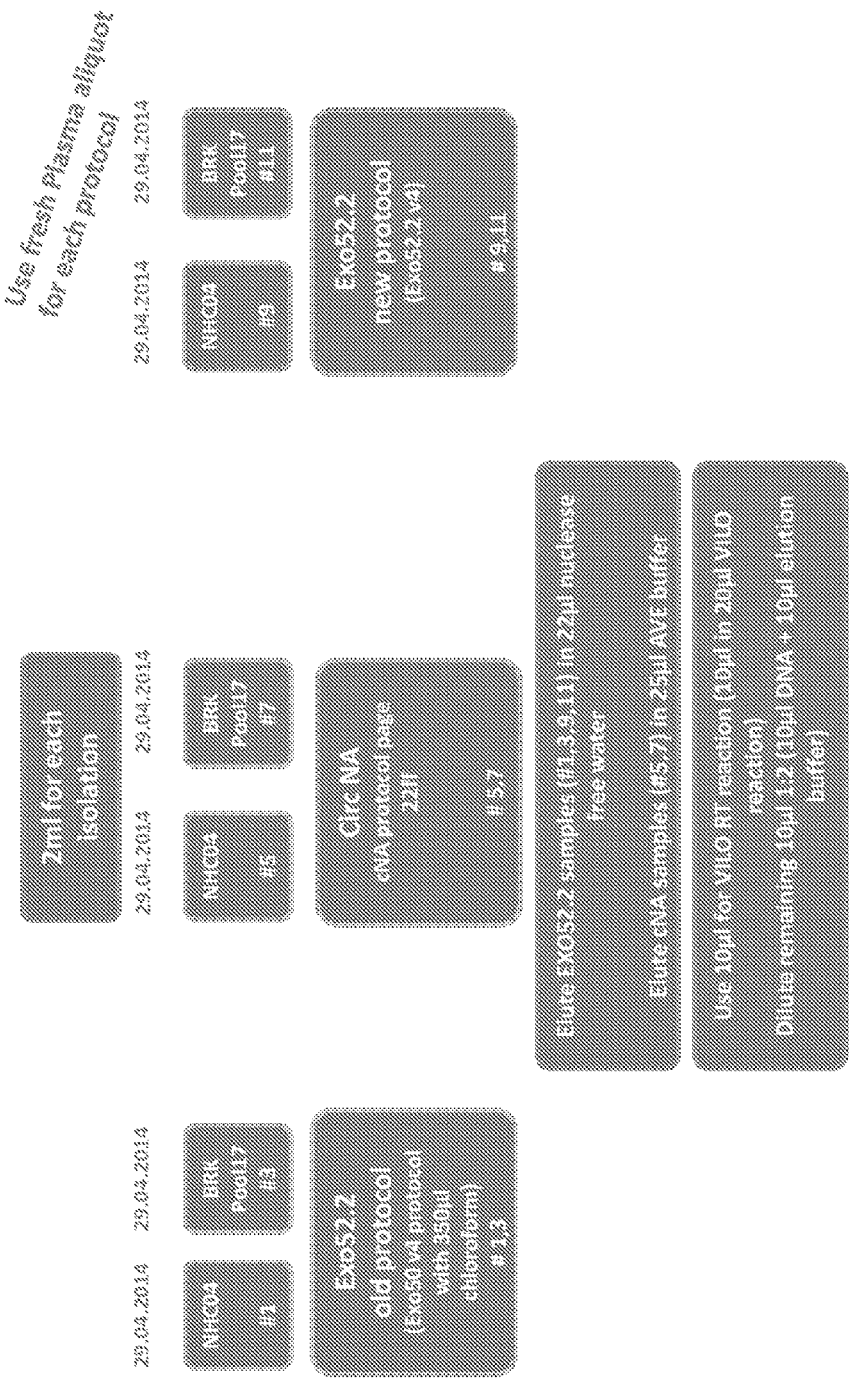

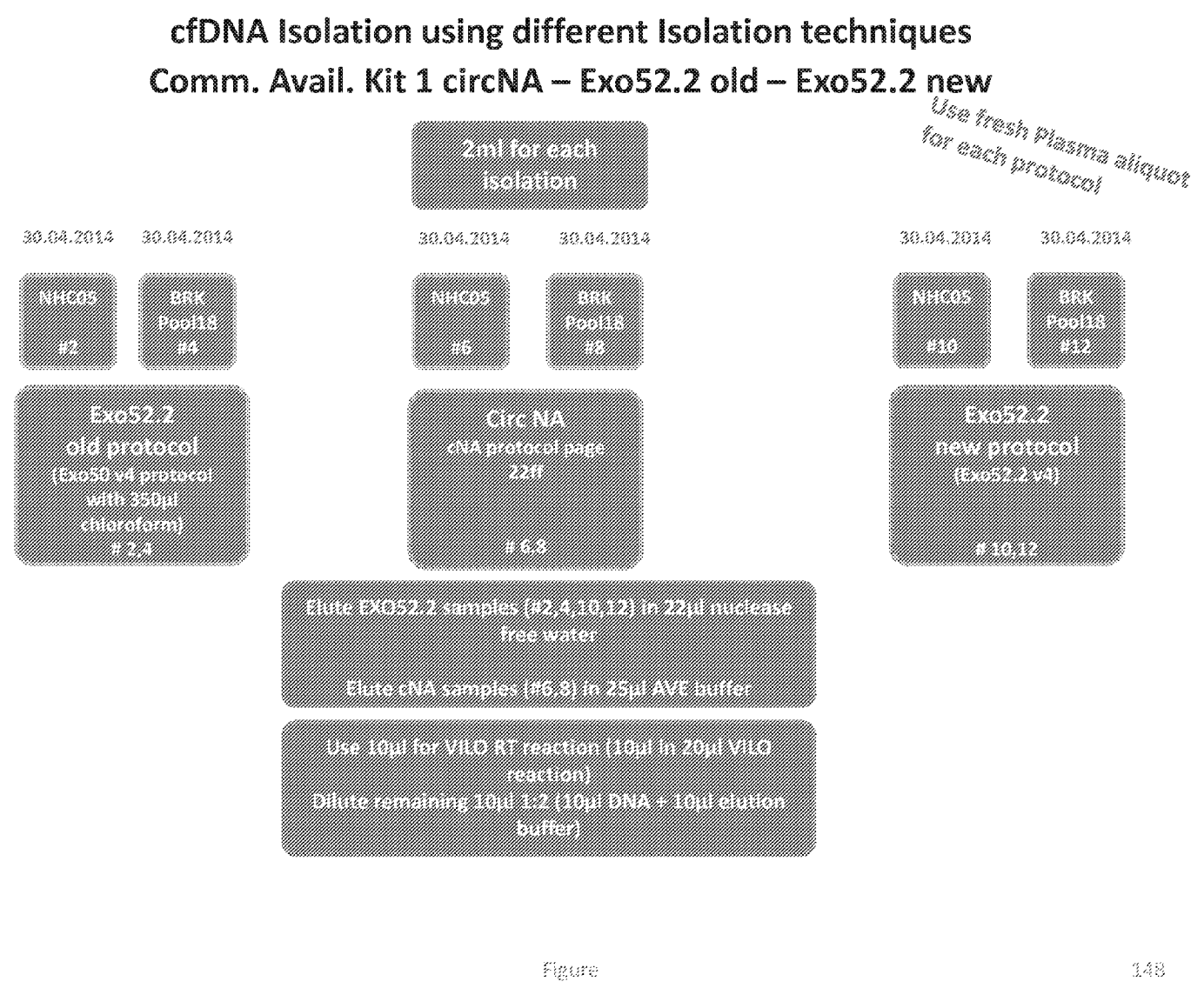

Figure

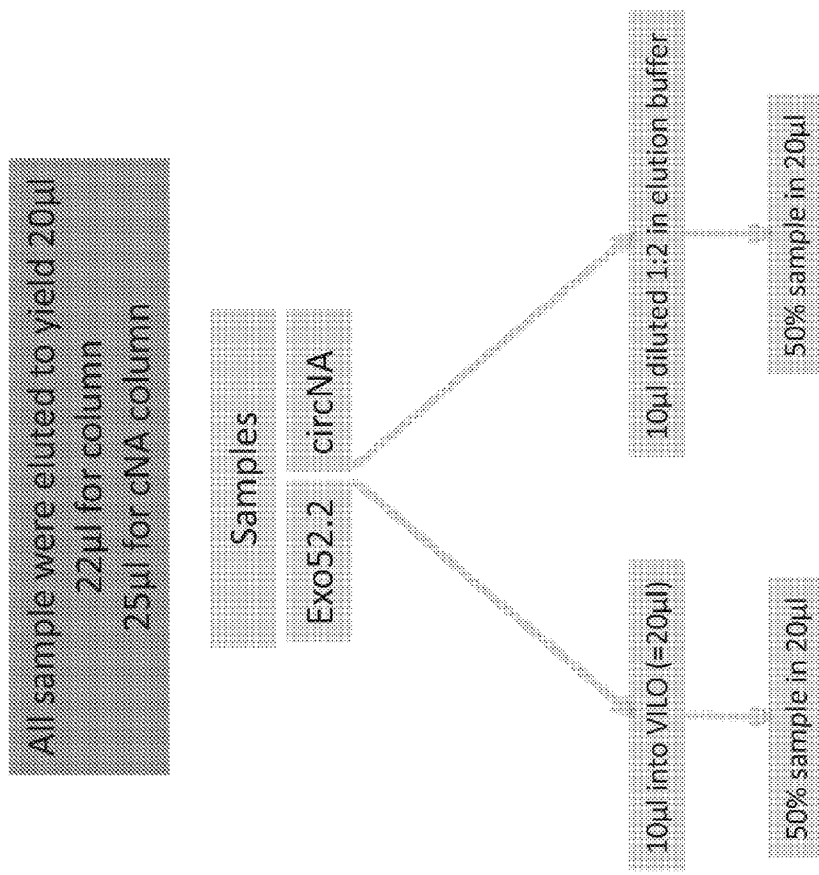

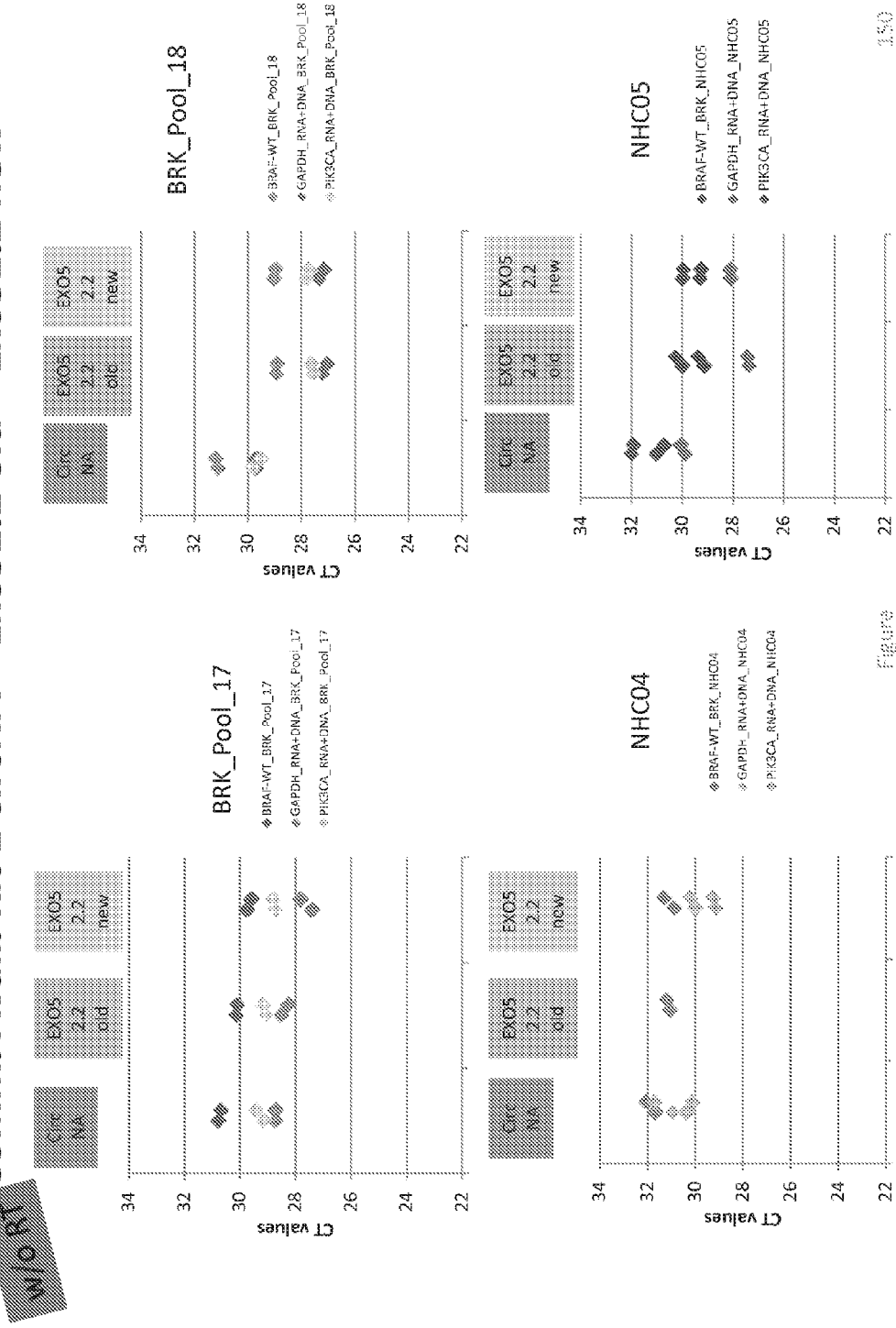

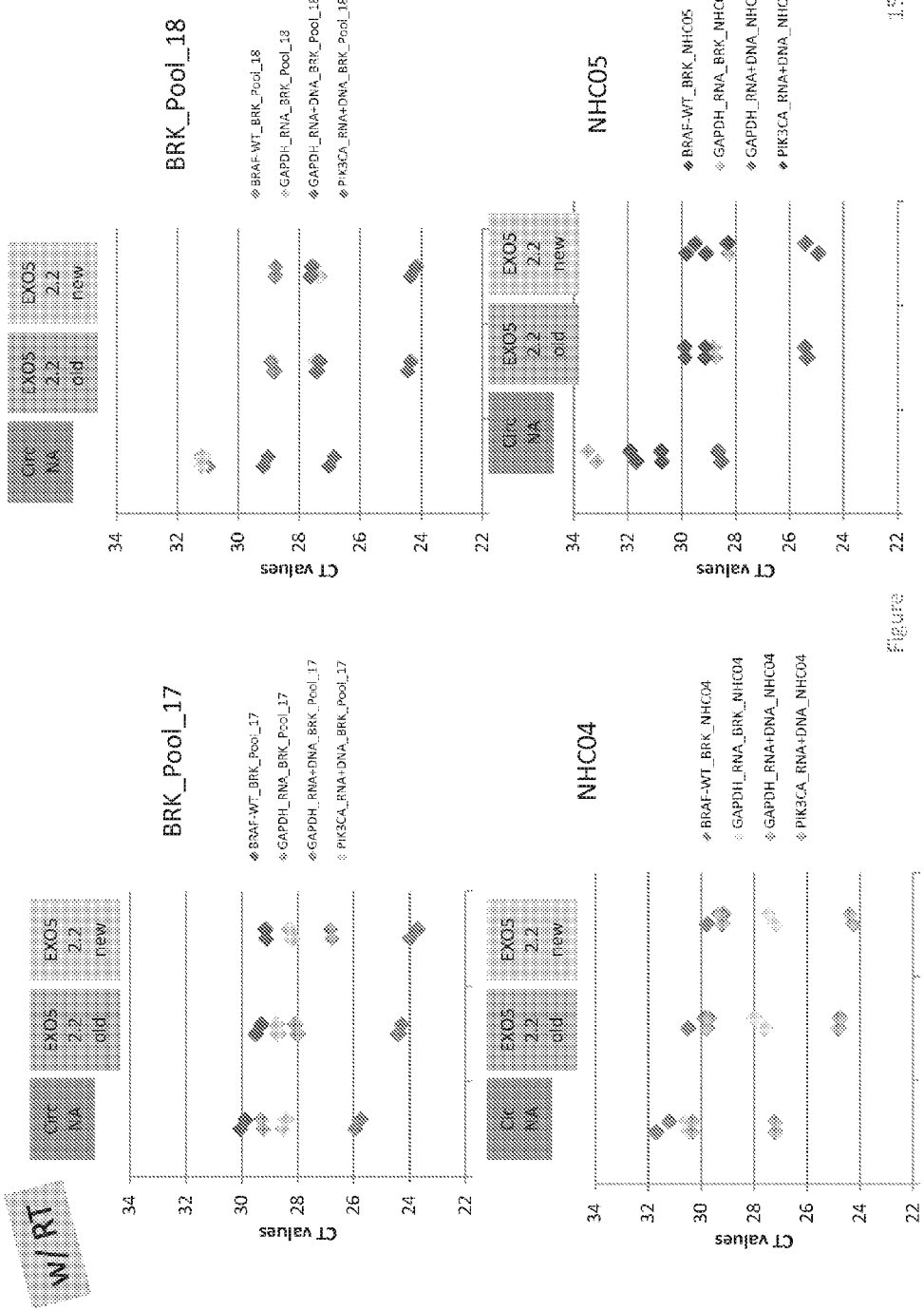

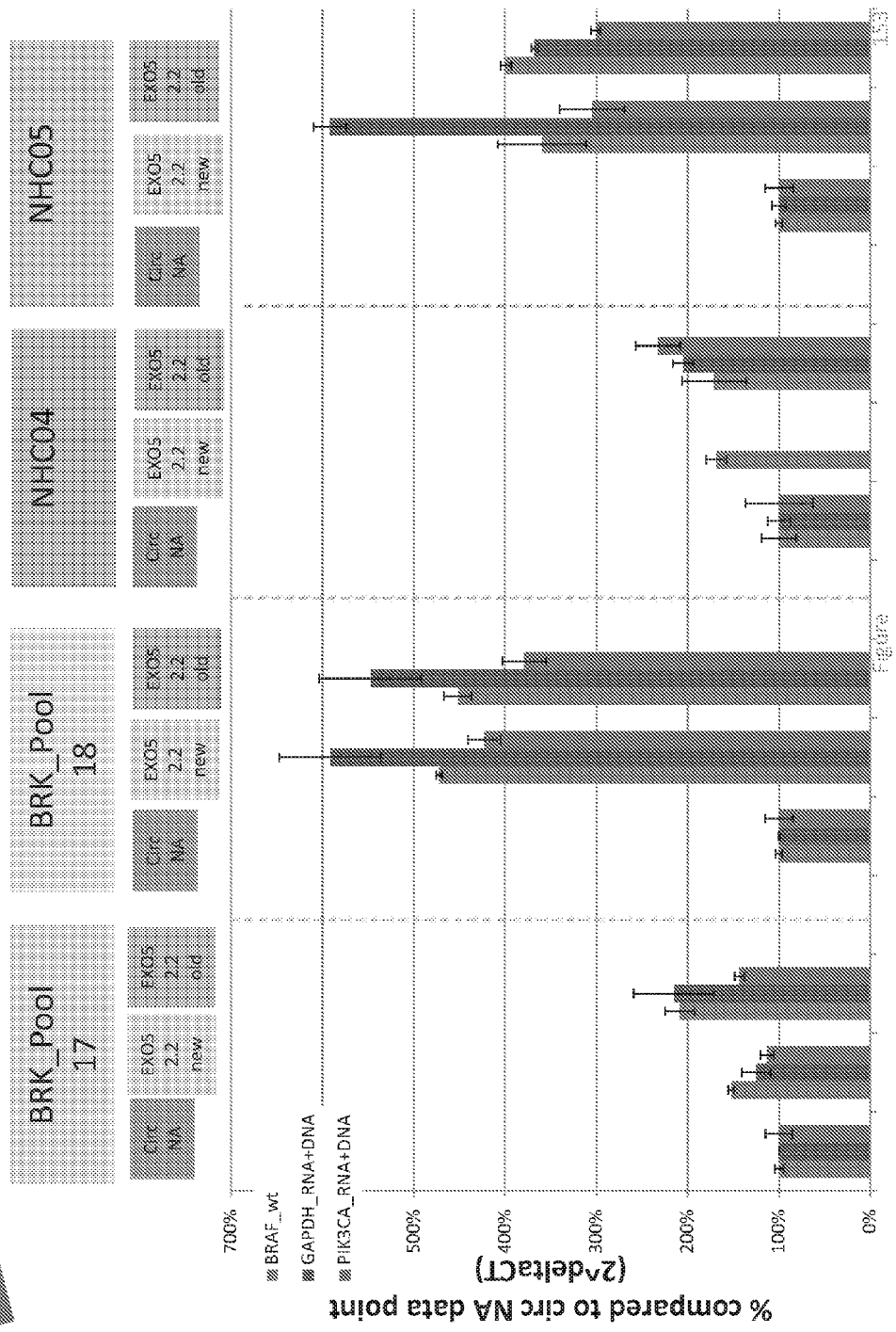

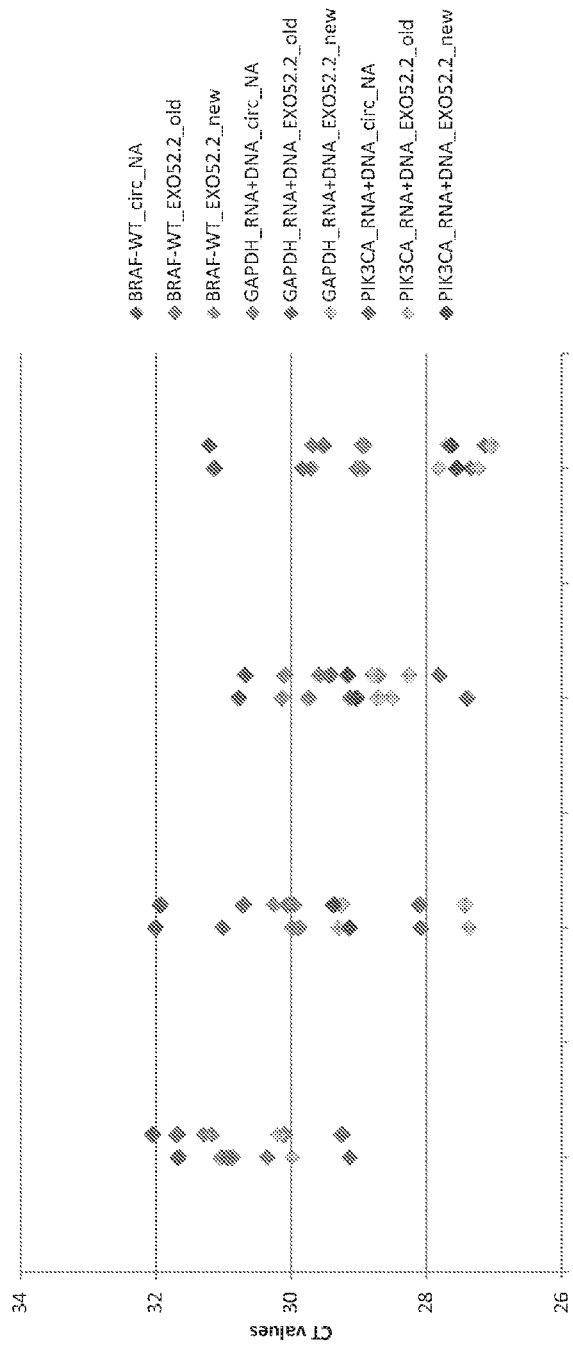

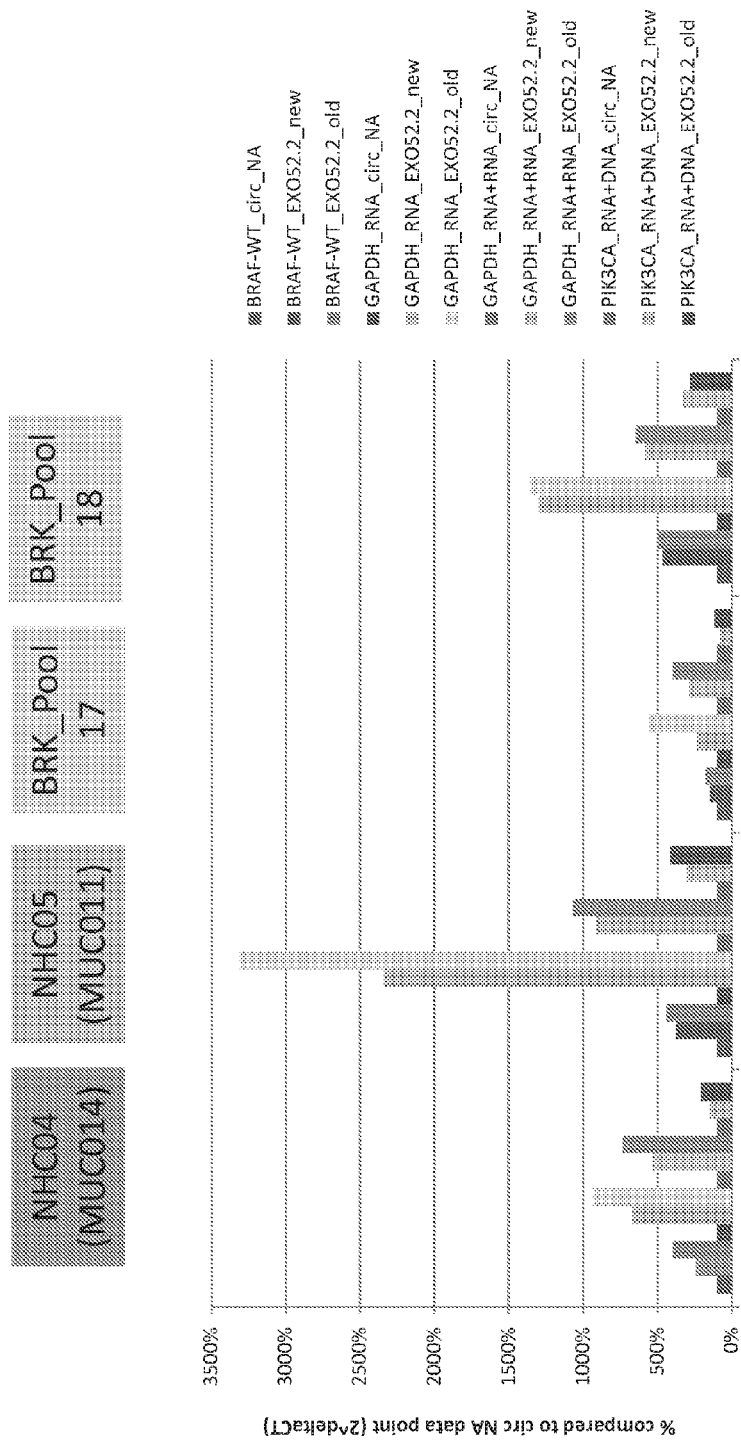

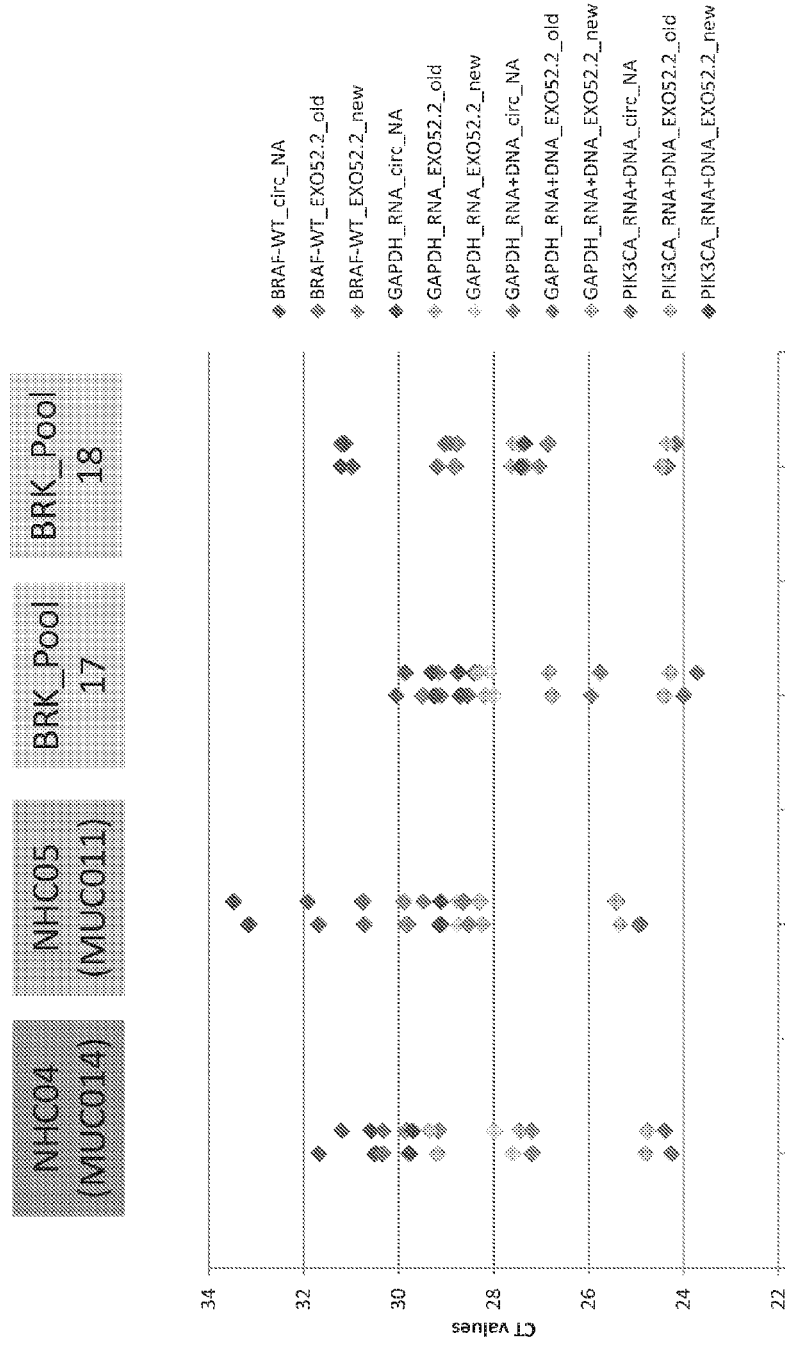

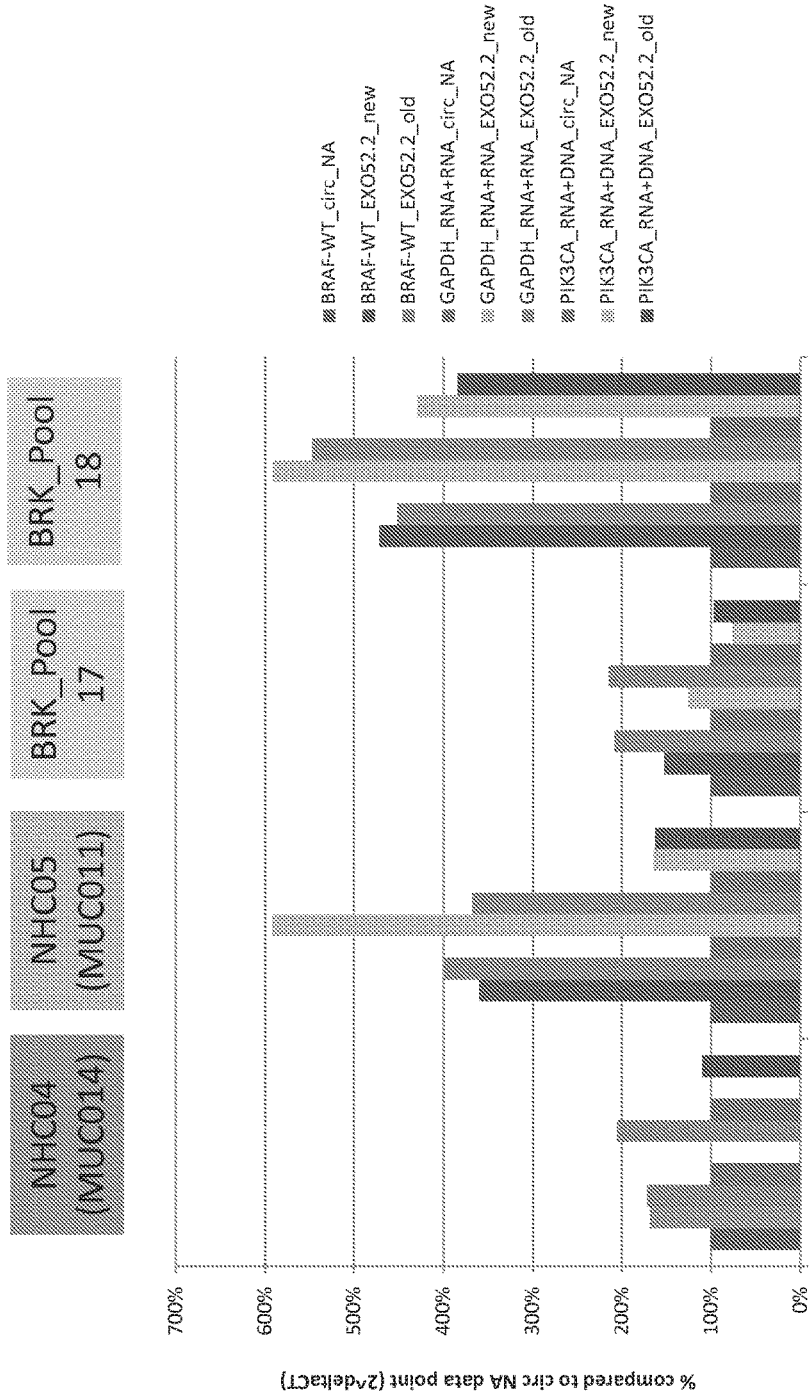

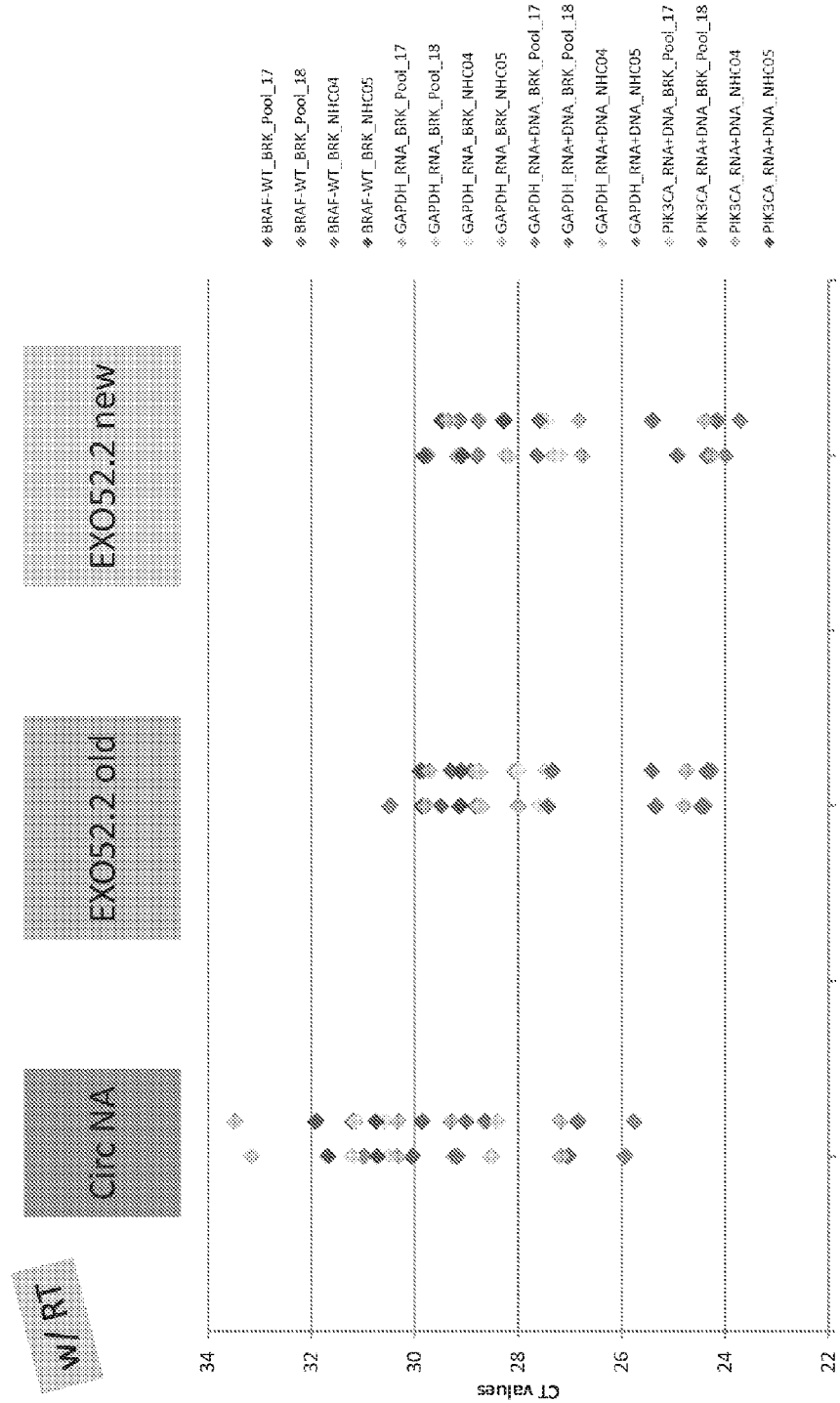

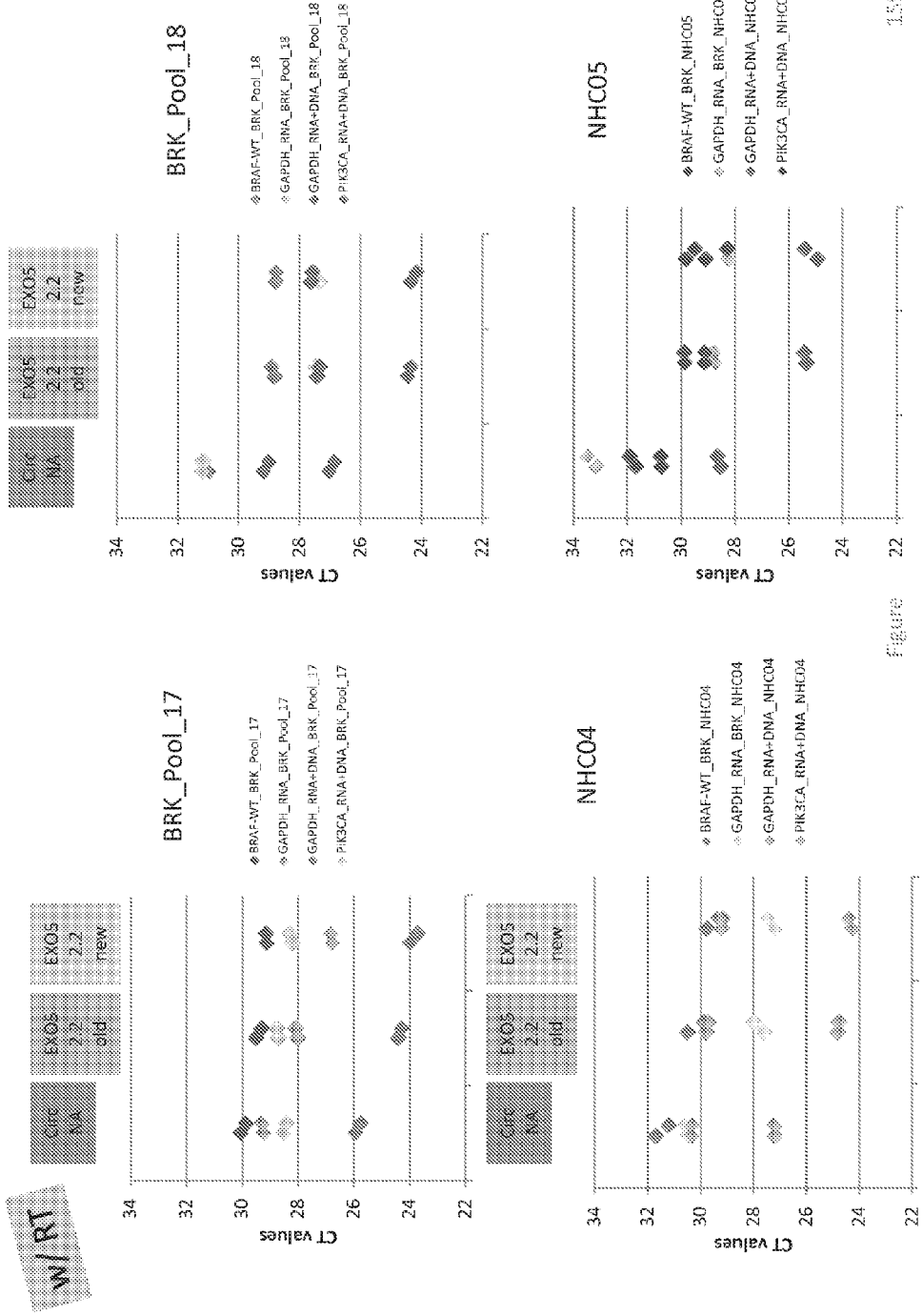

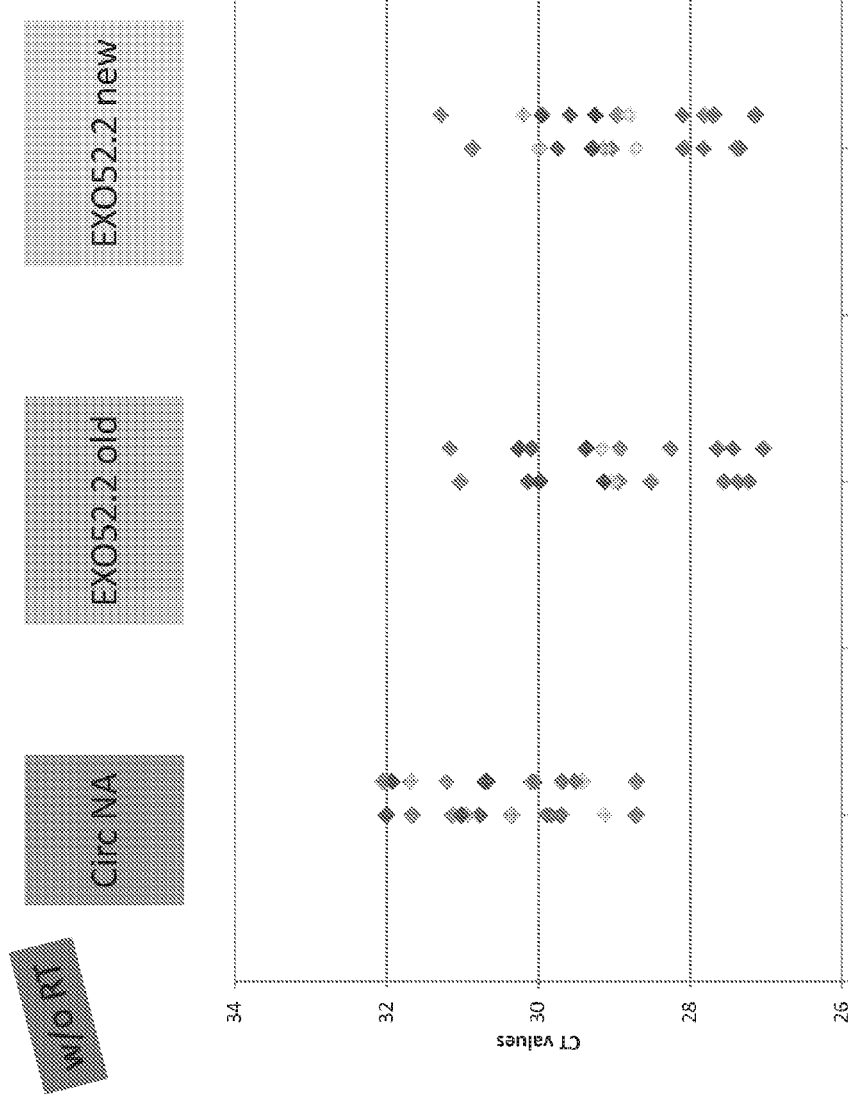

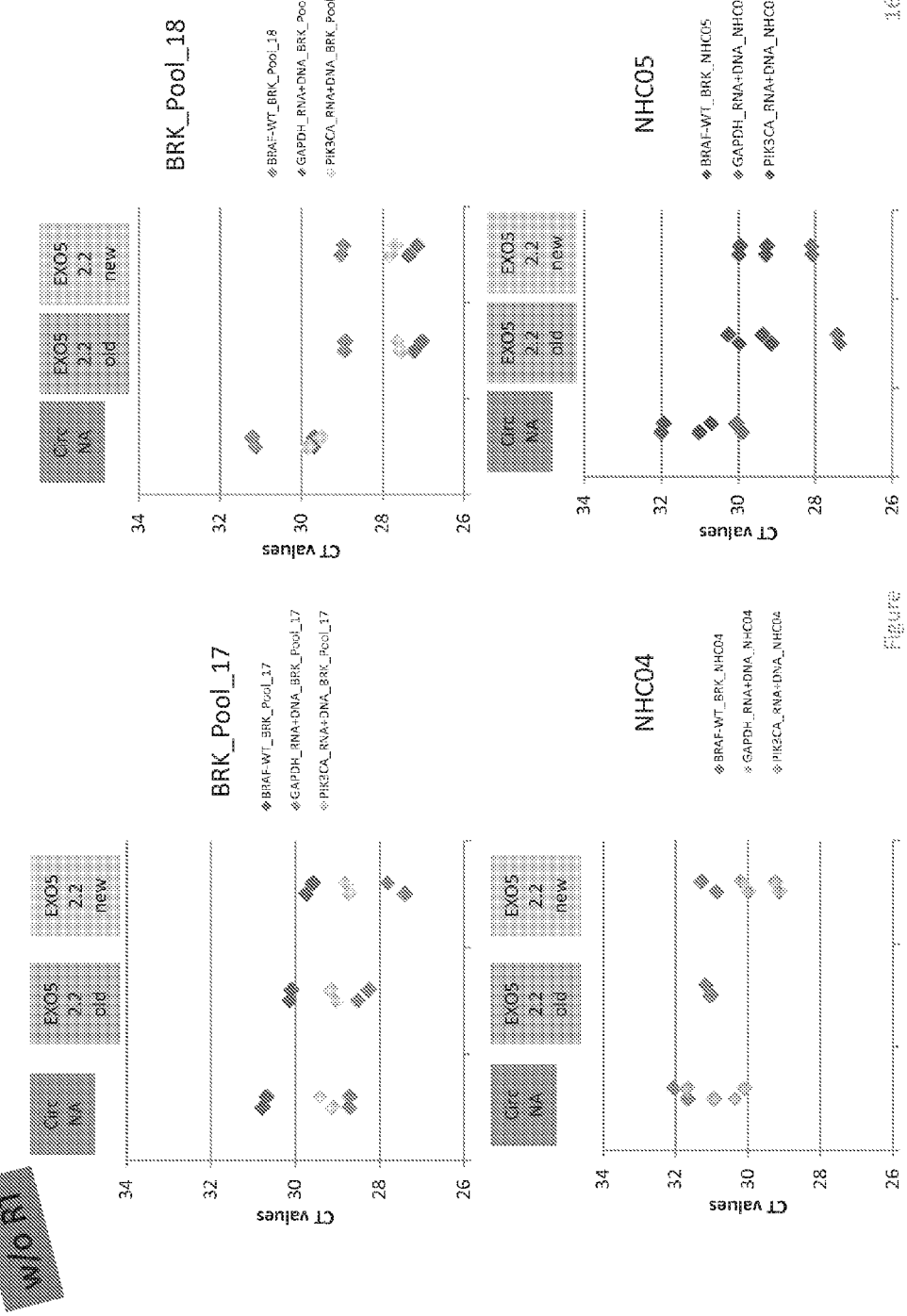

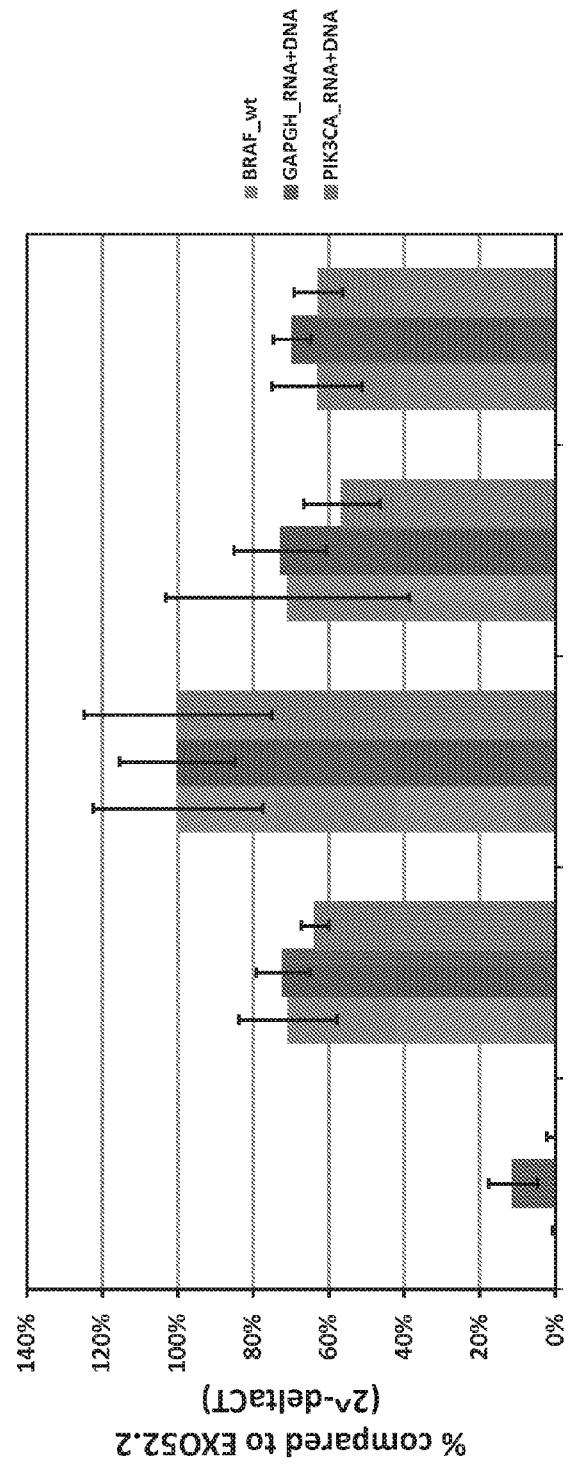

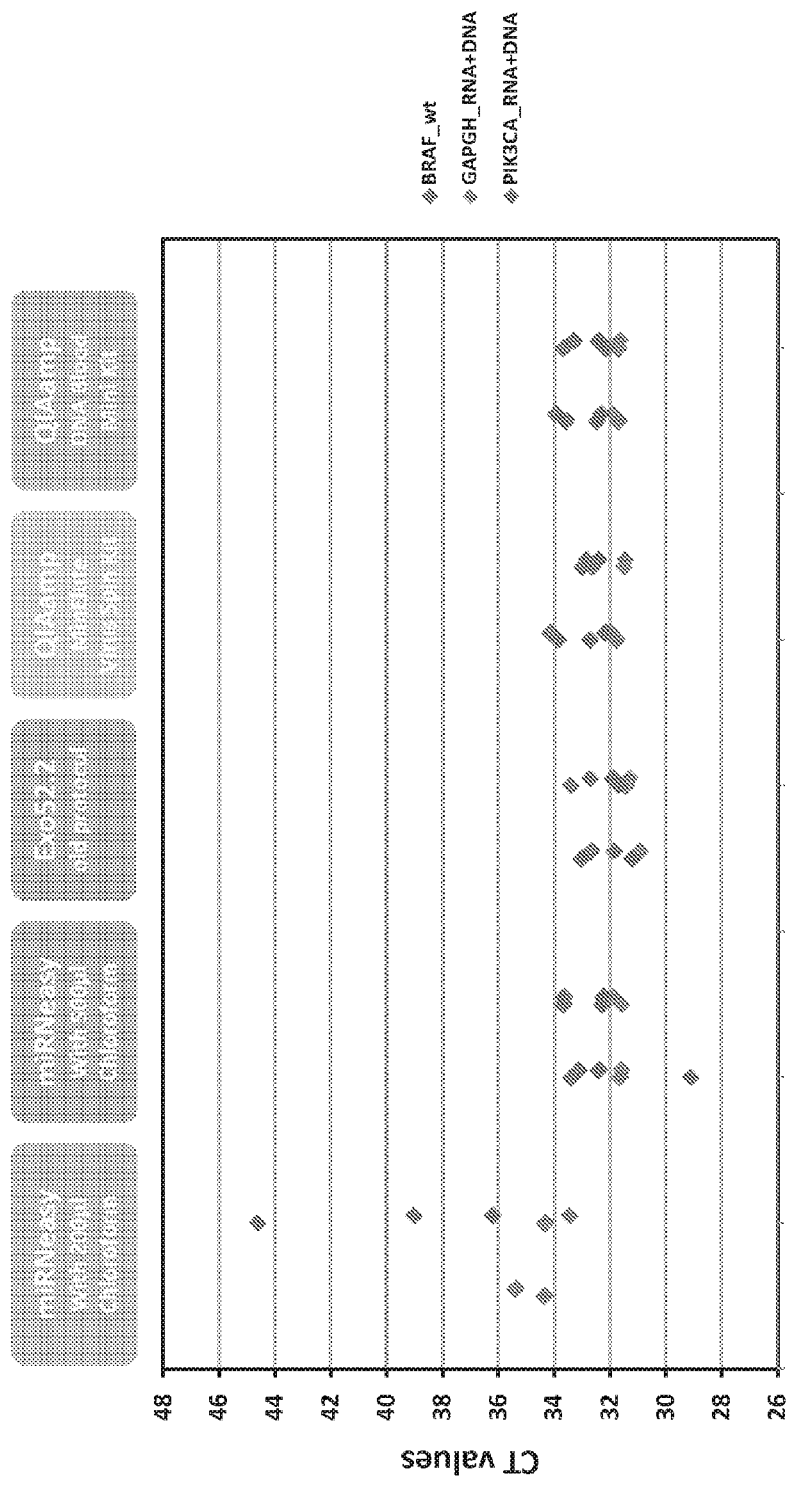

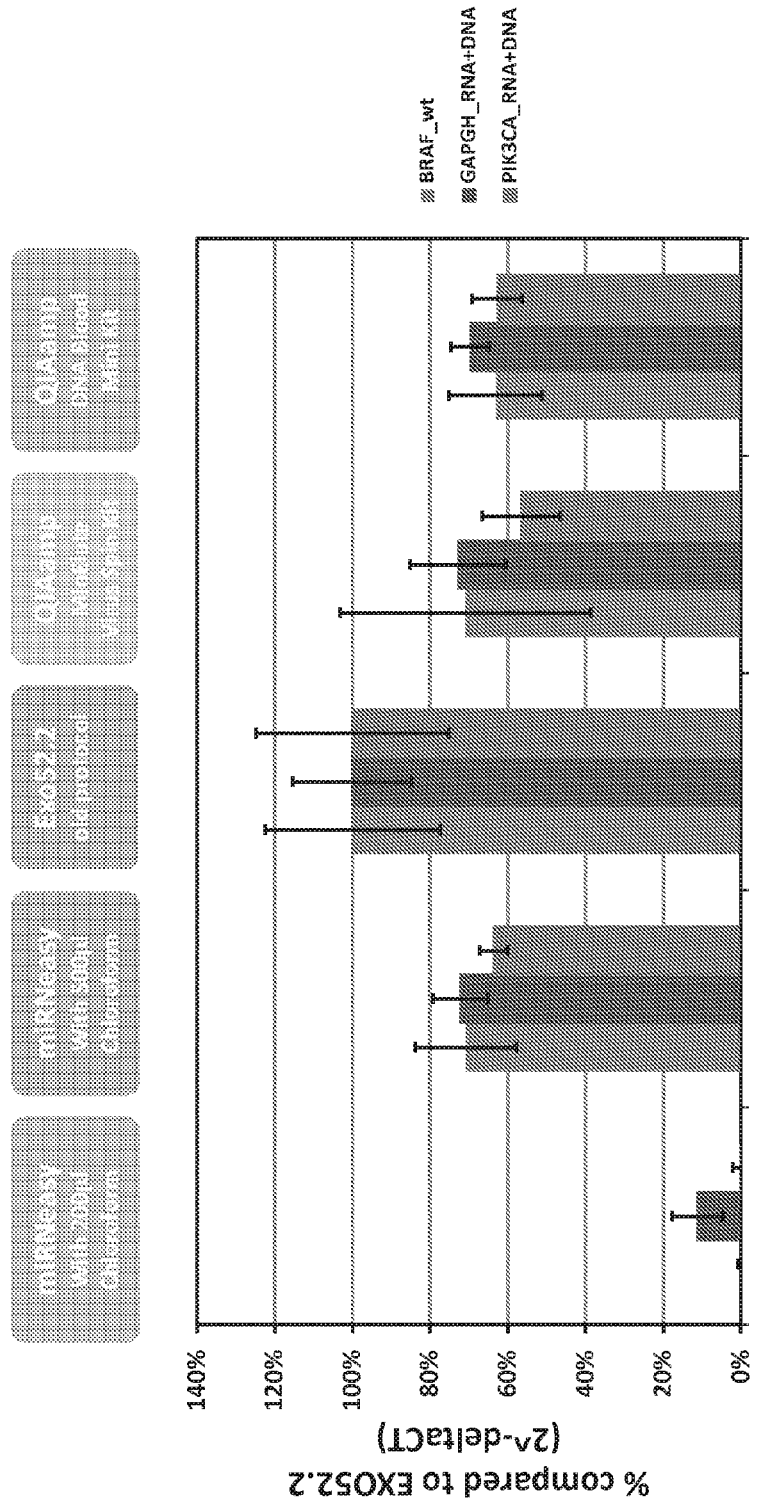

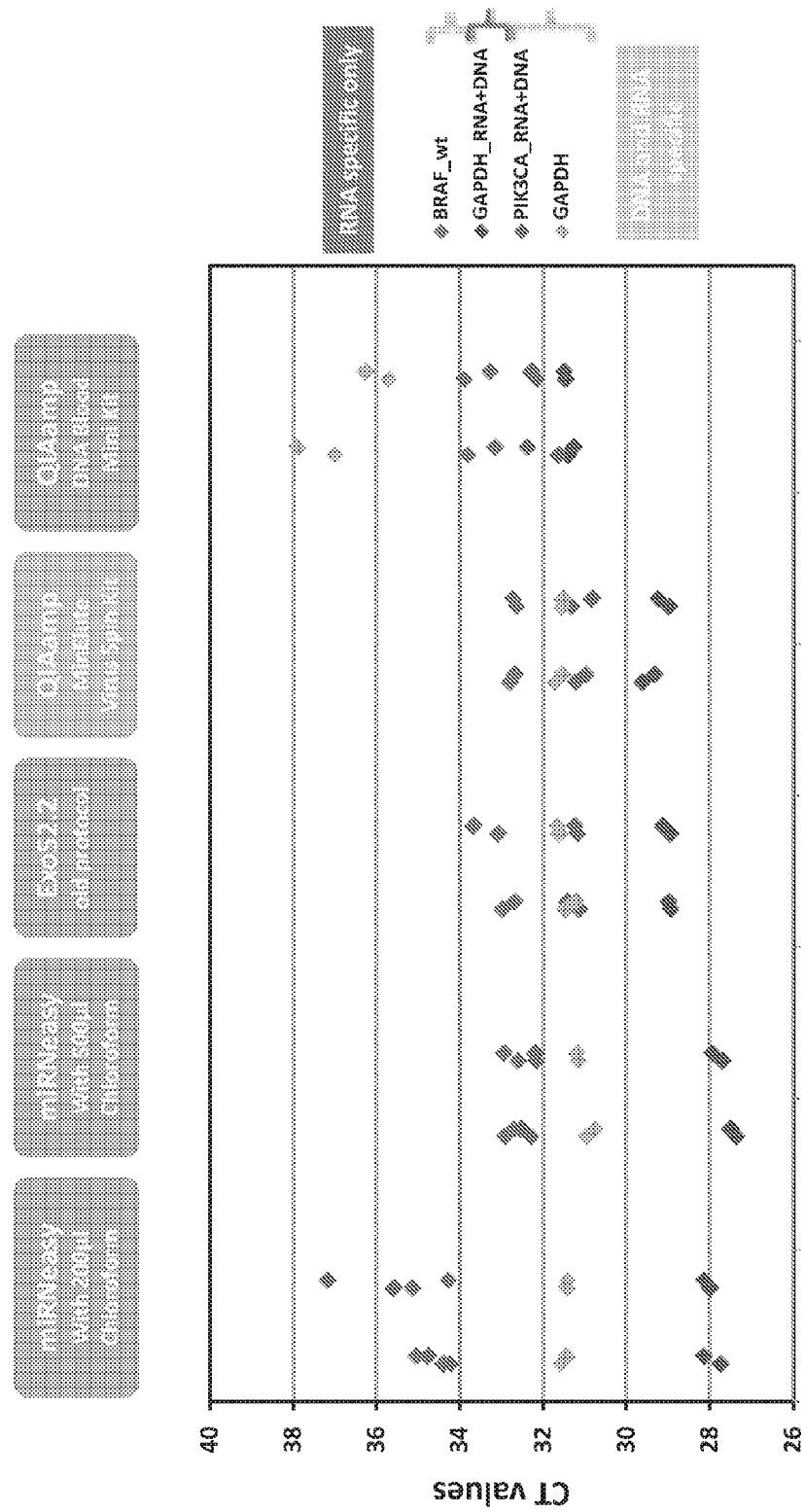

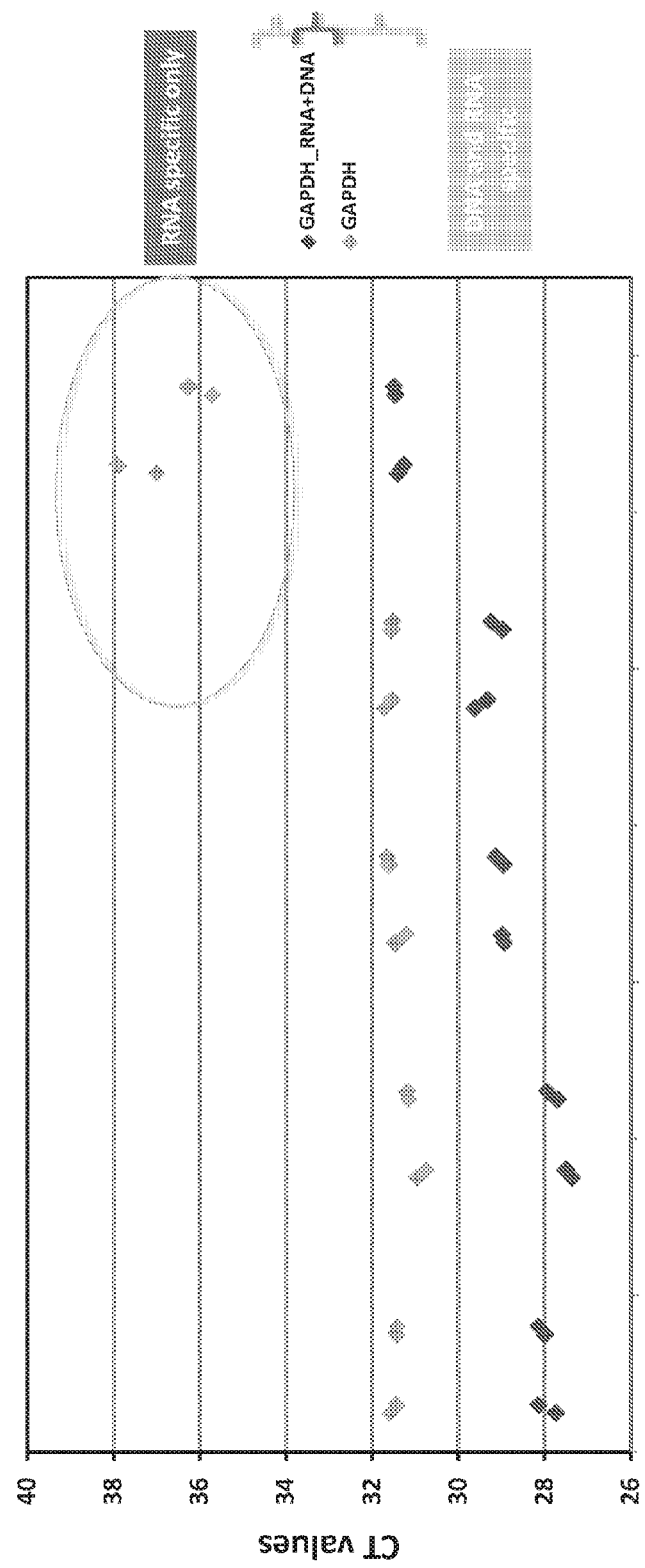

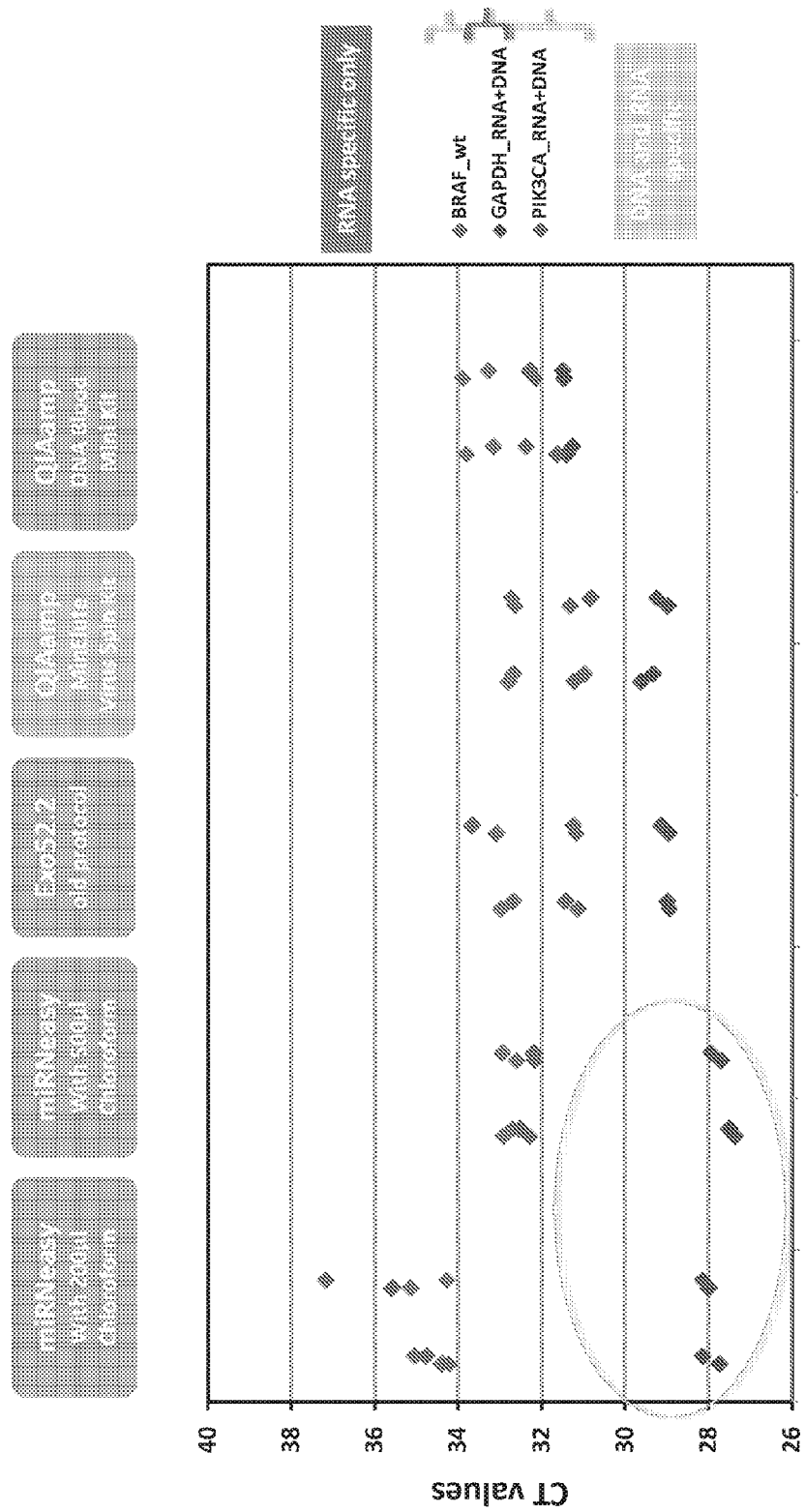

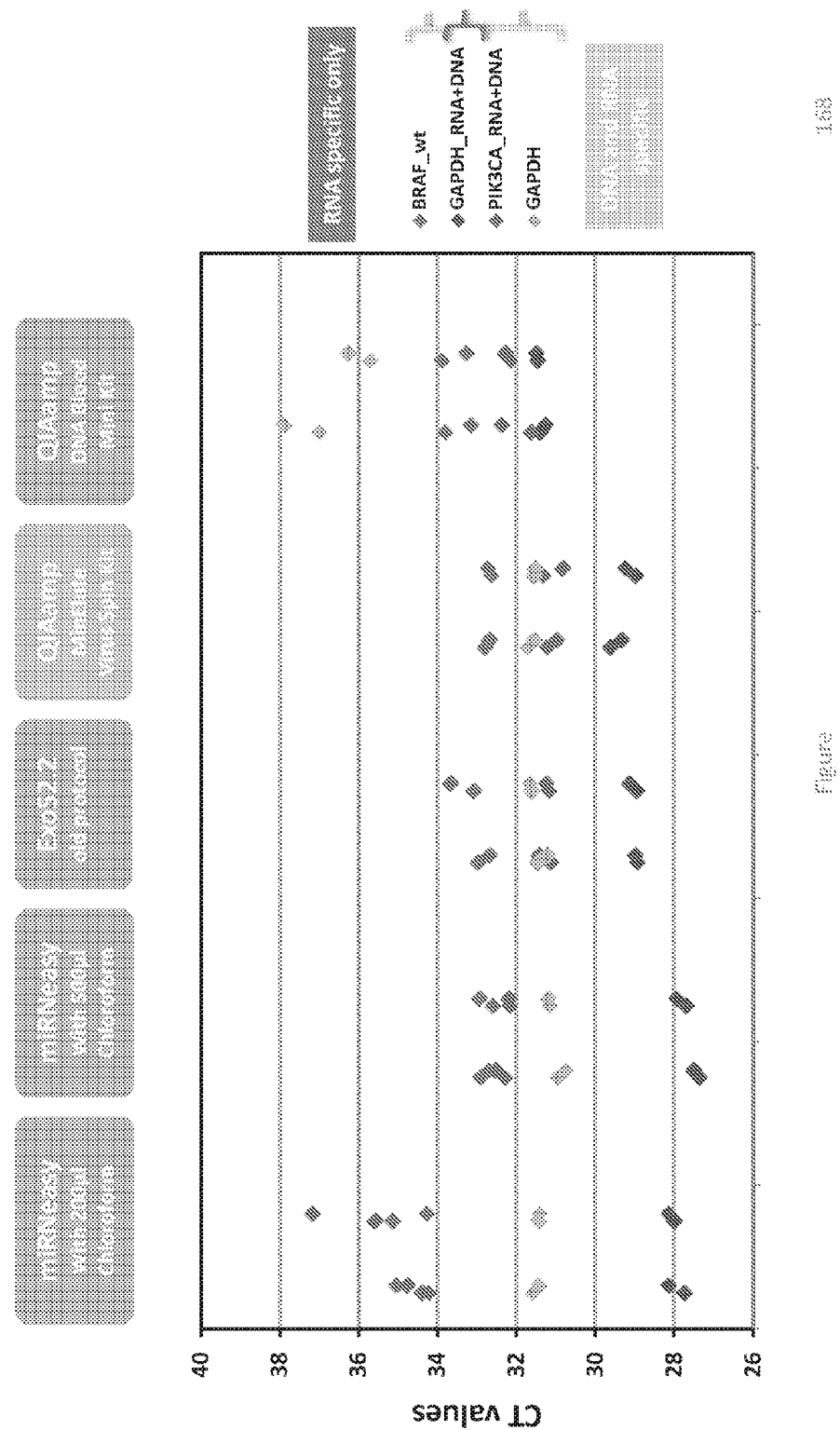

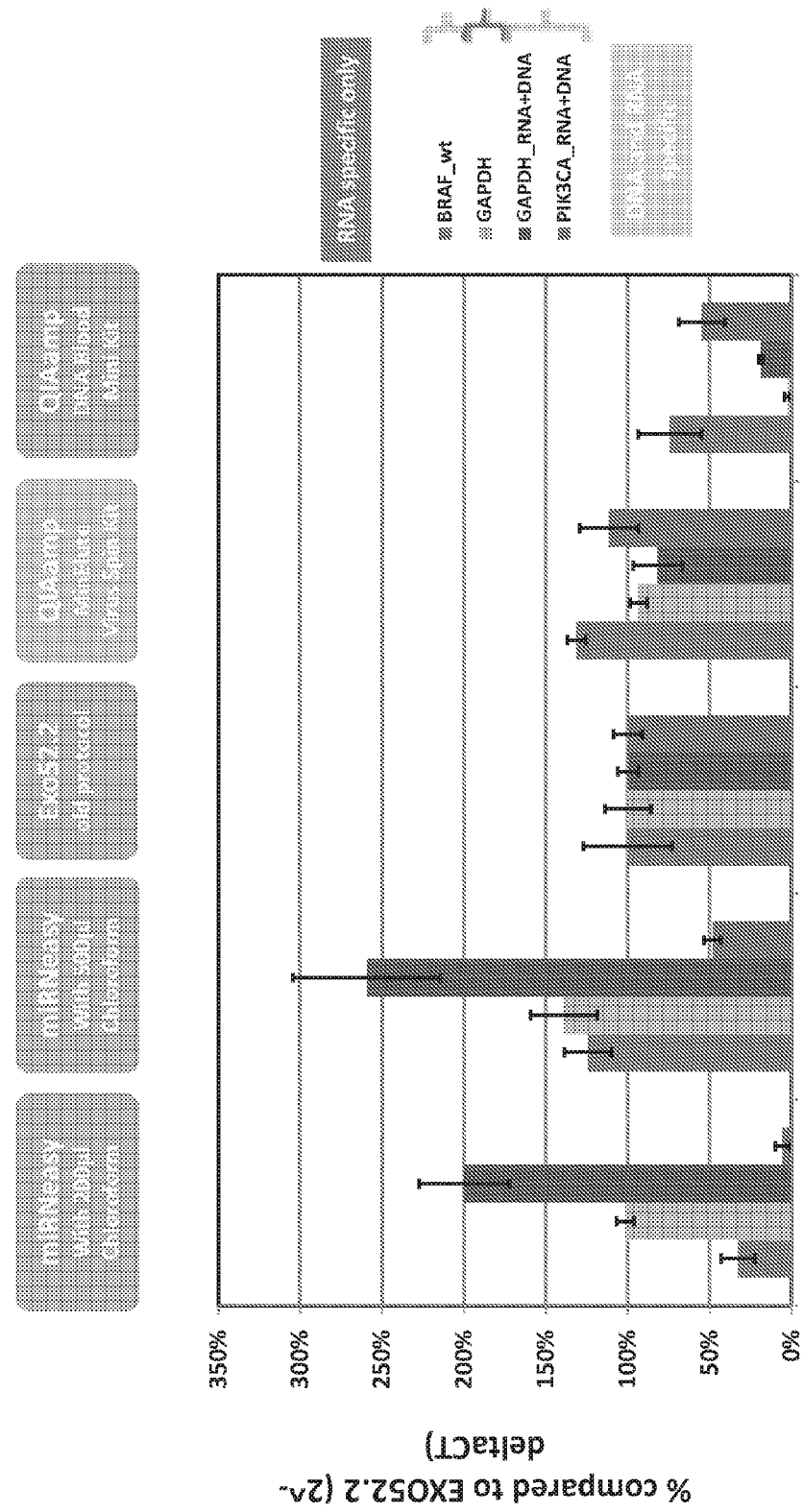

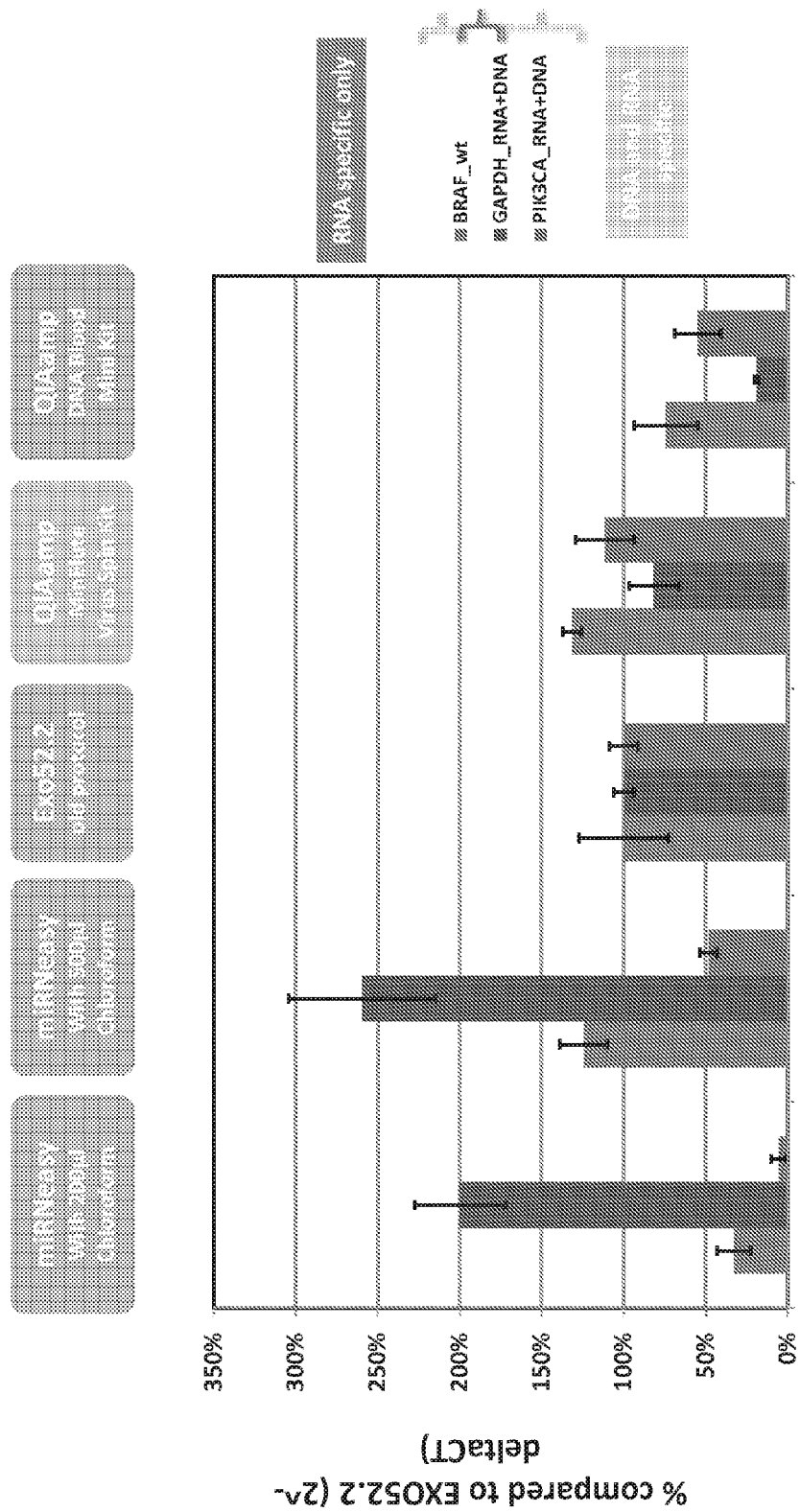

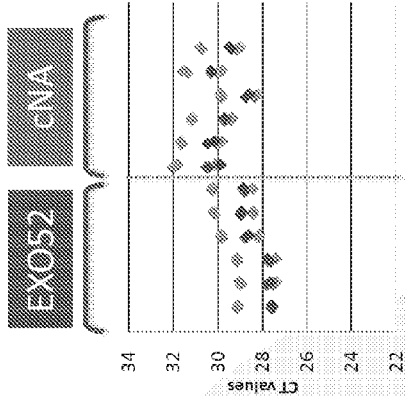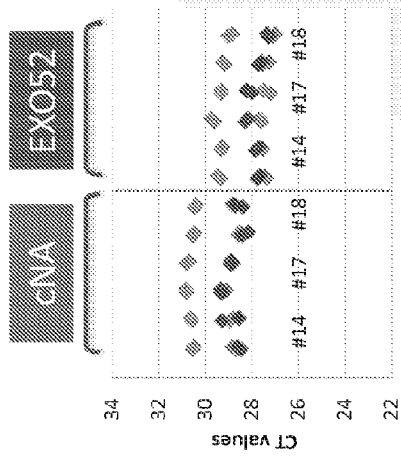

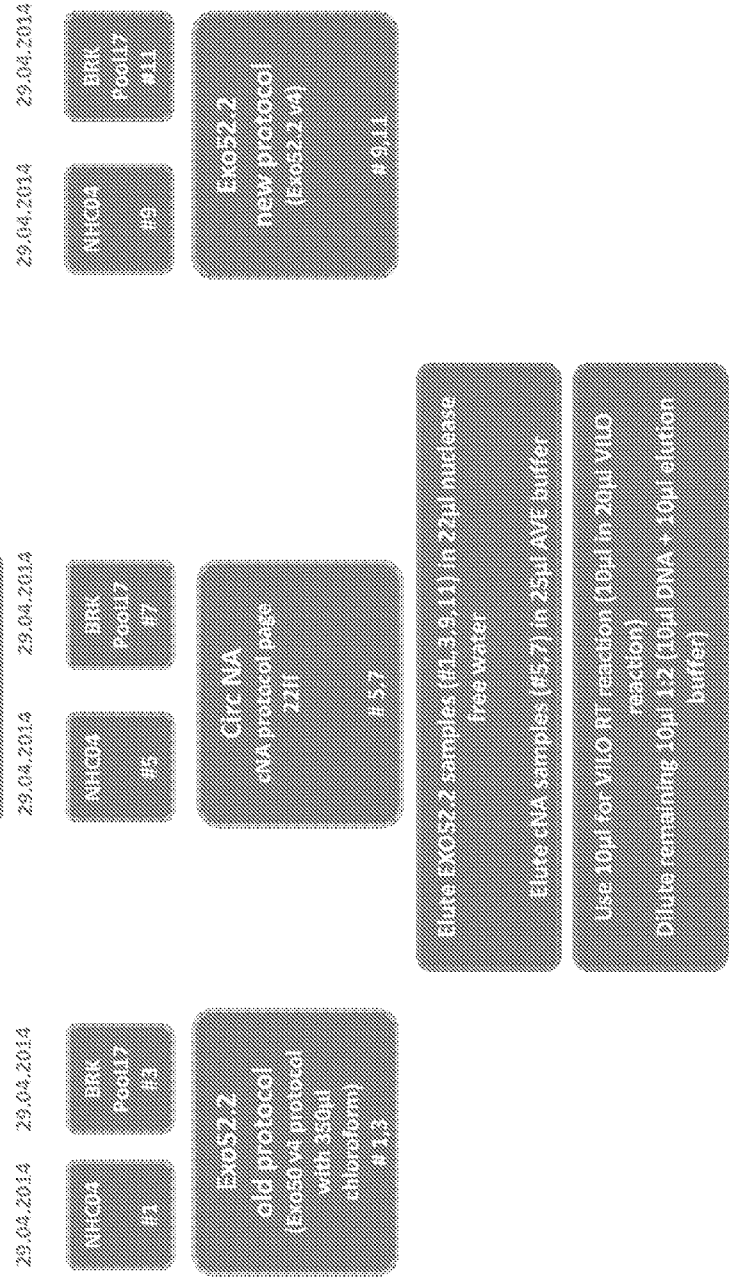

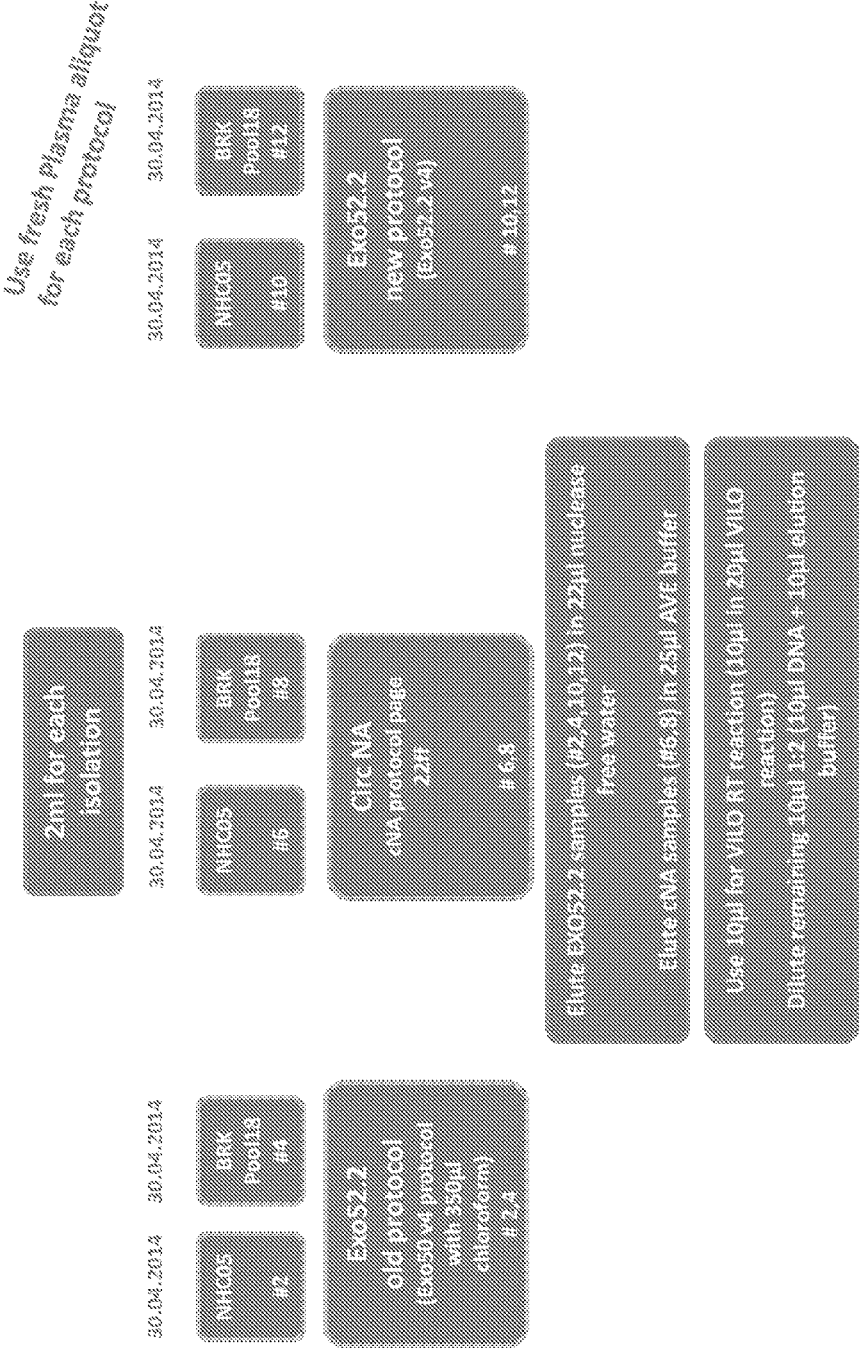

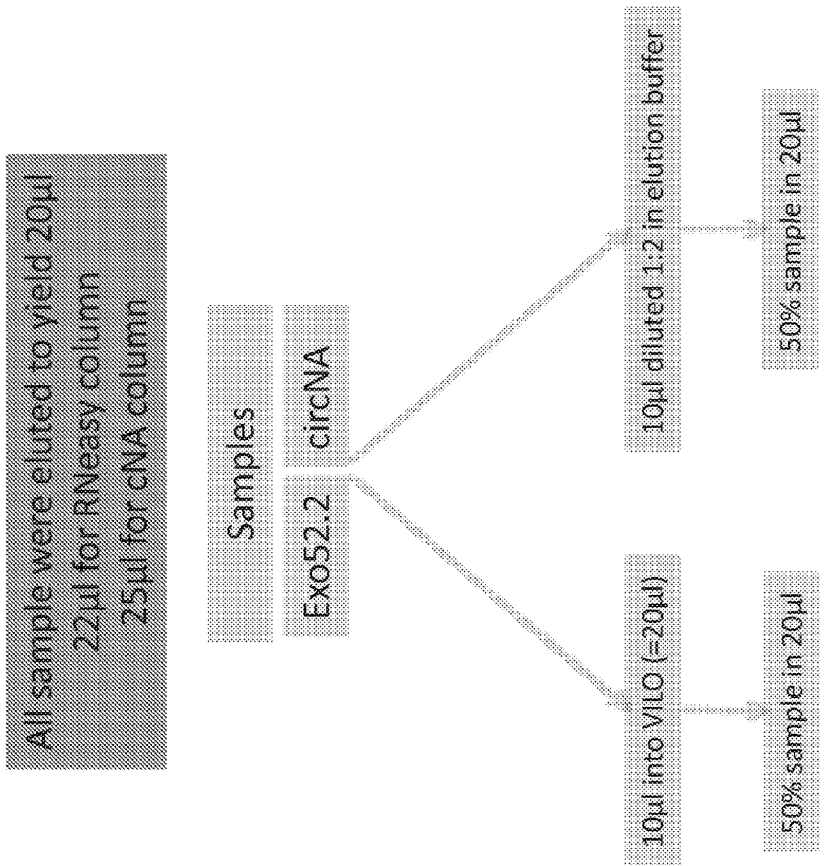

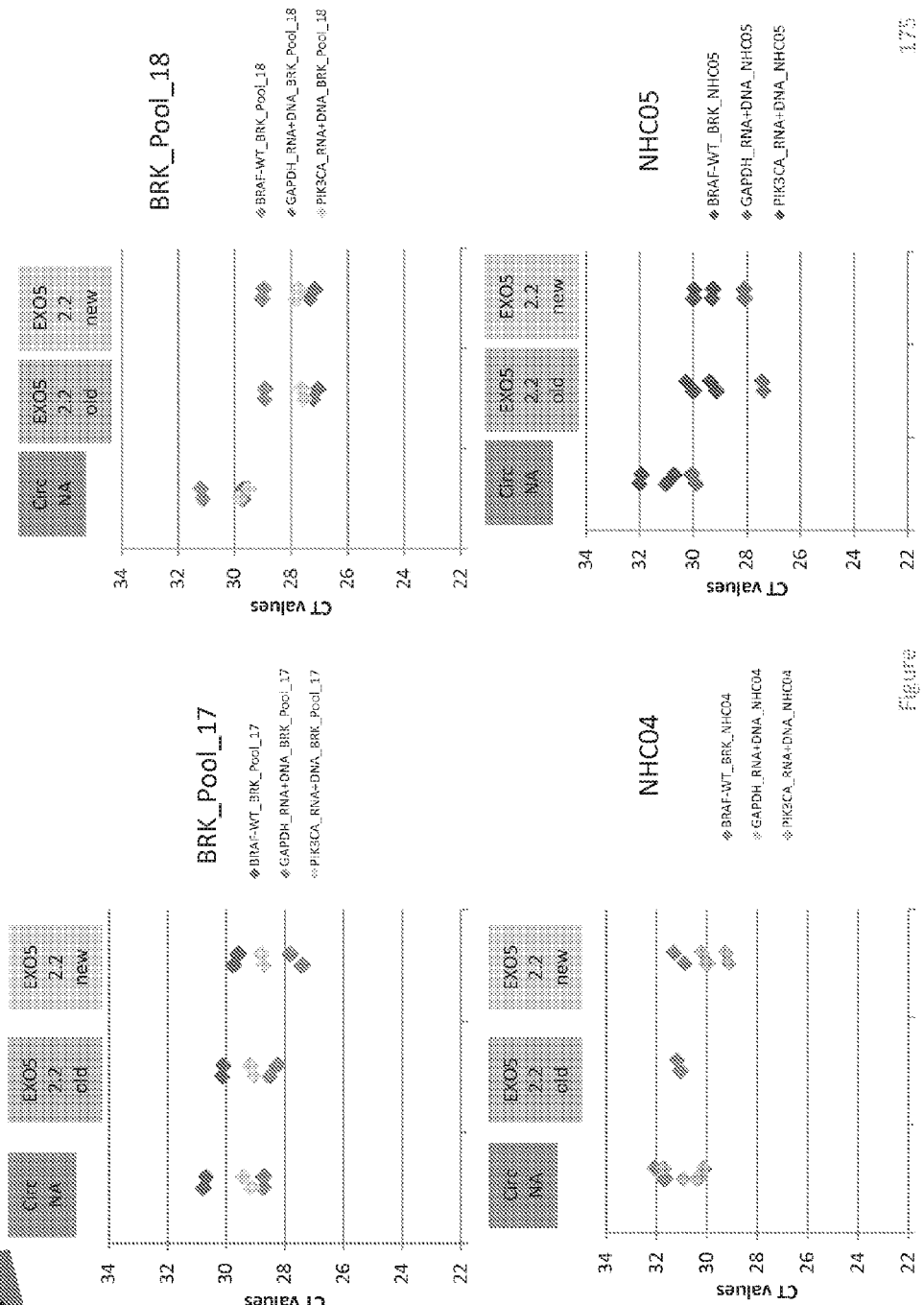

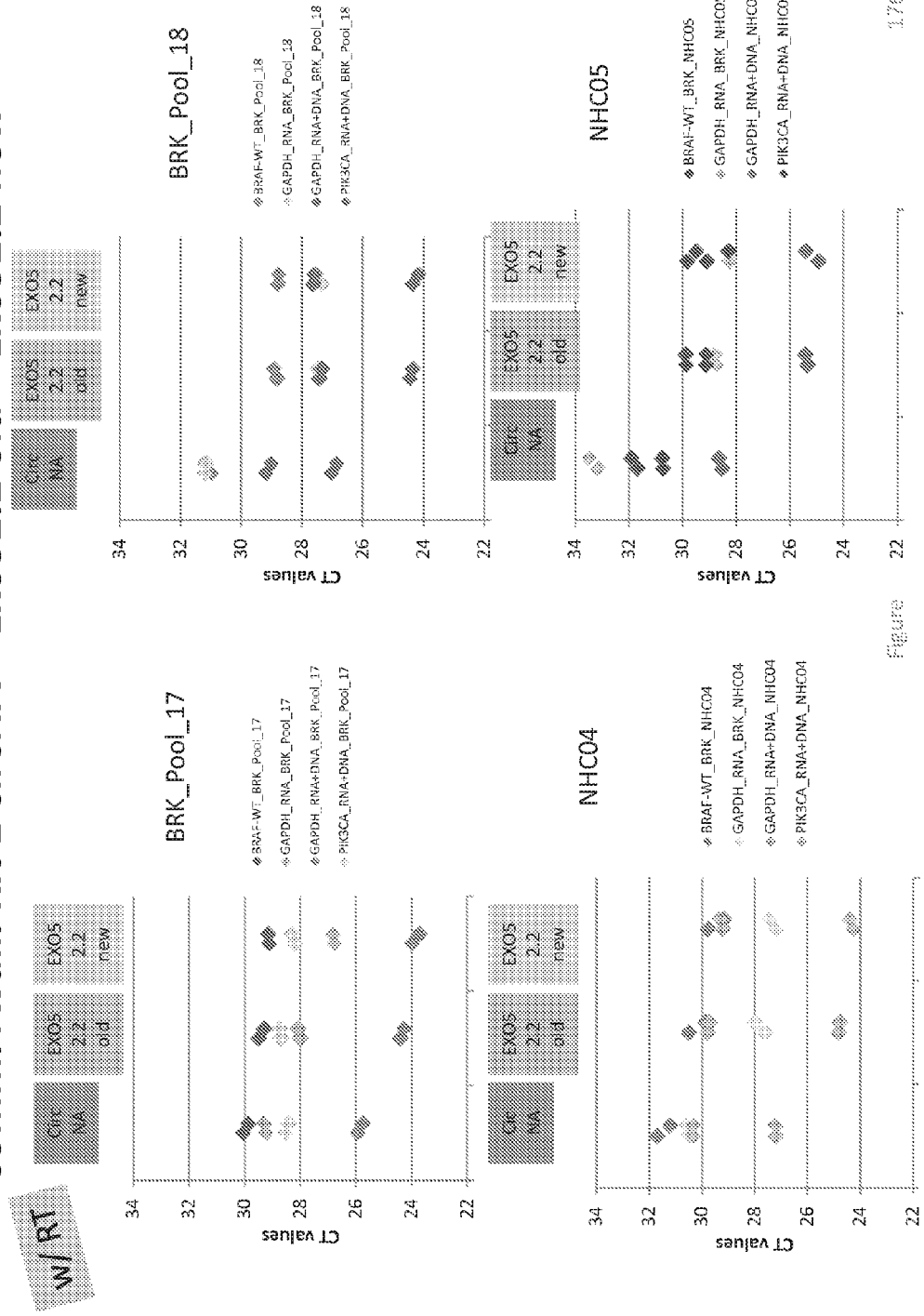

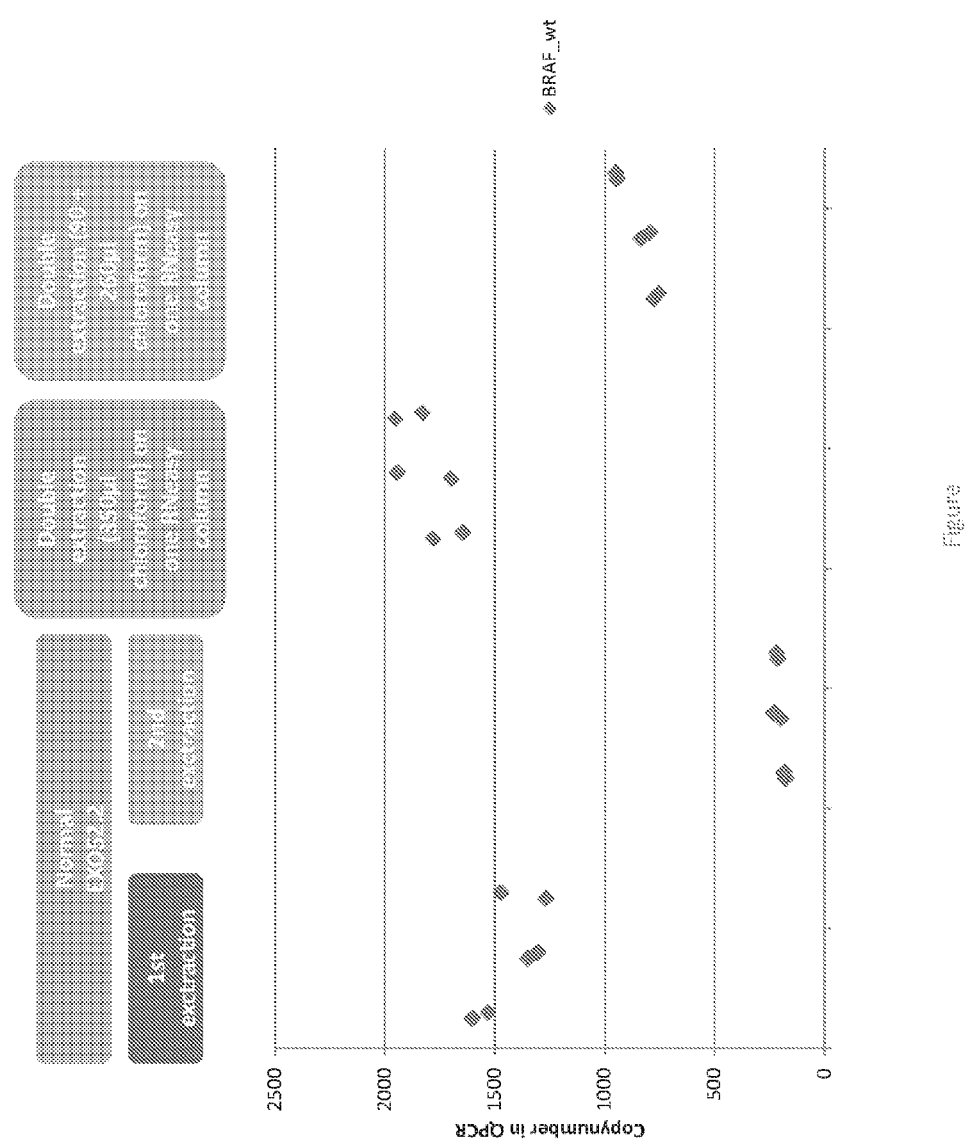

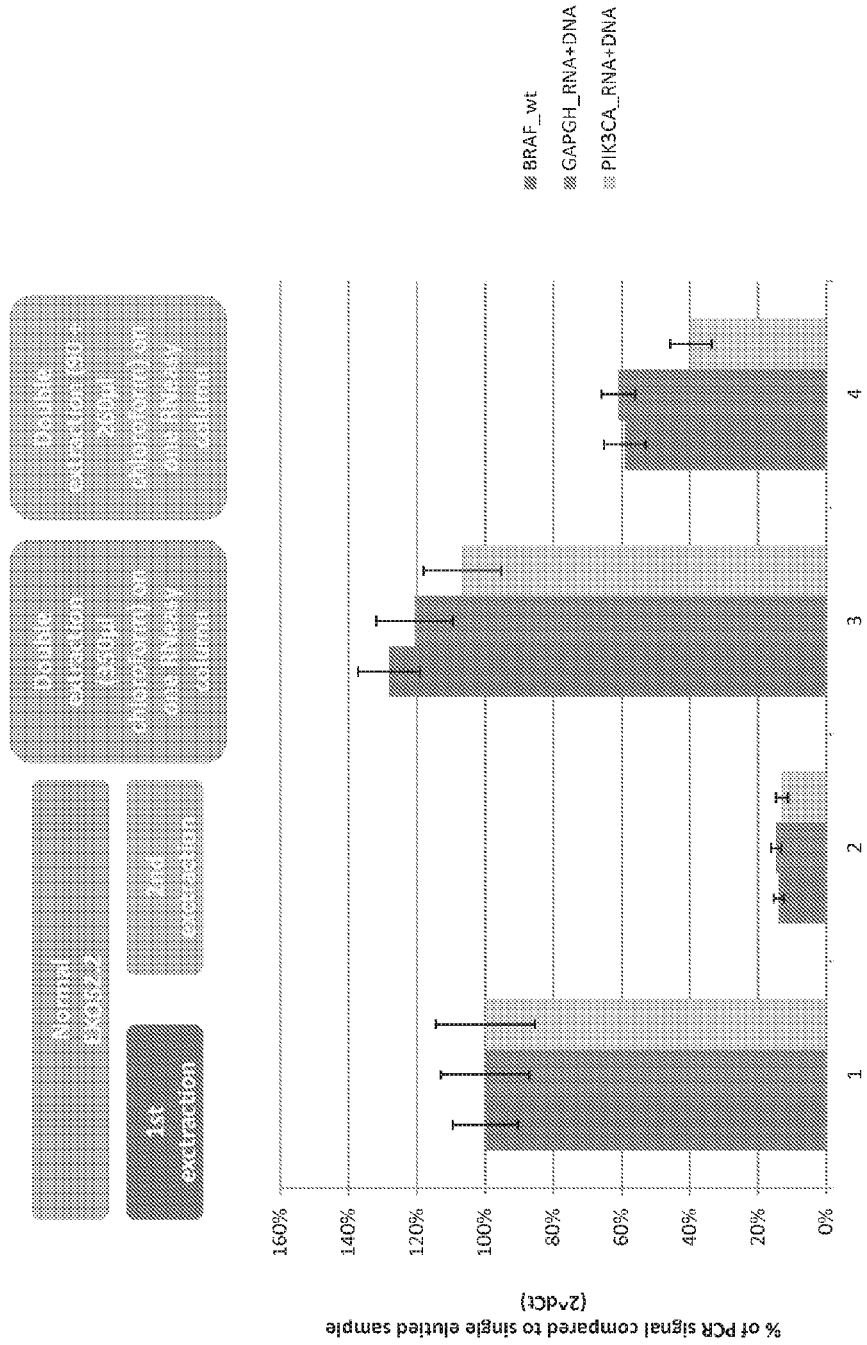

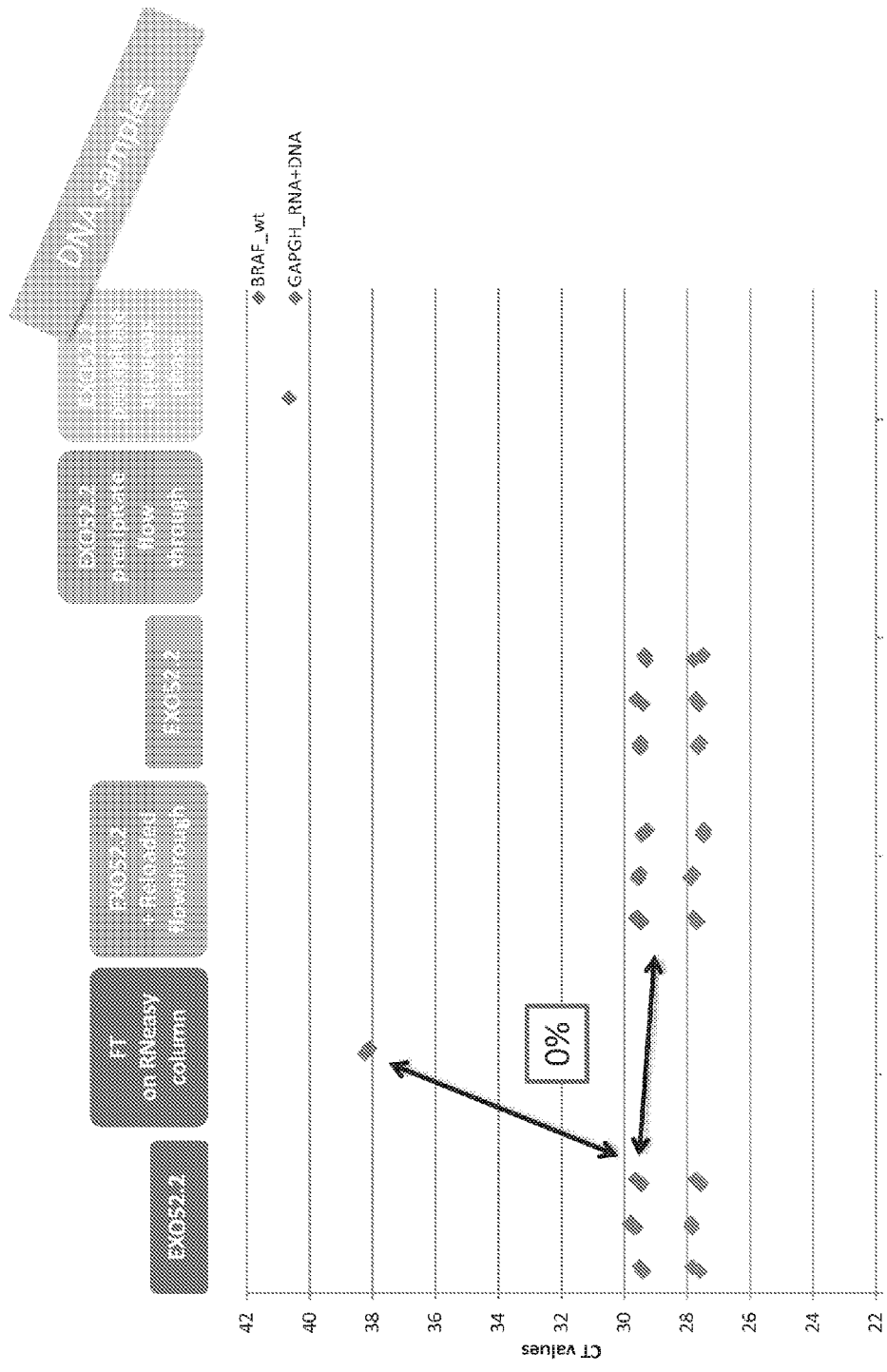

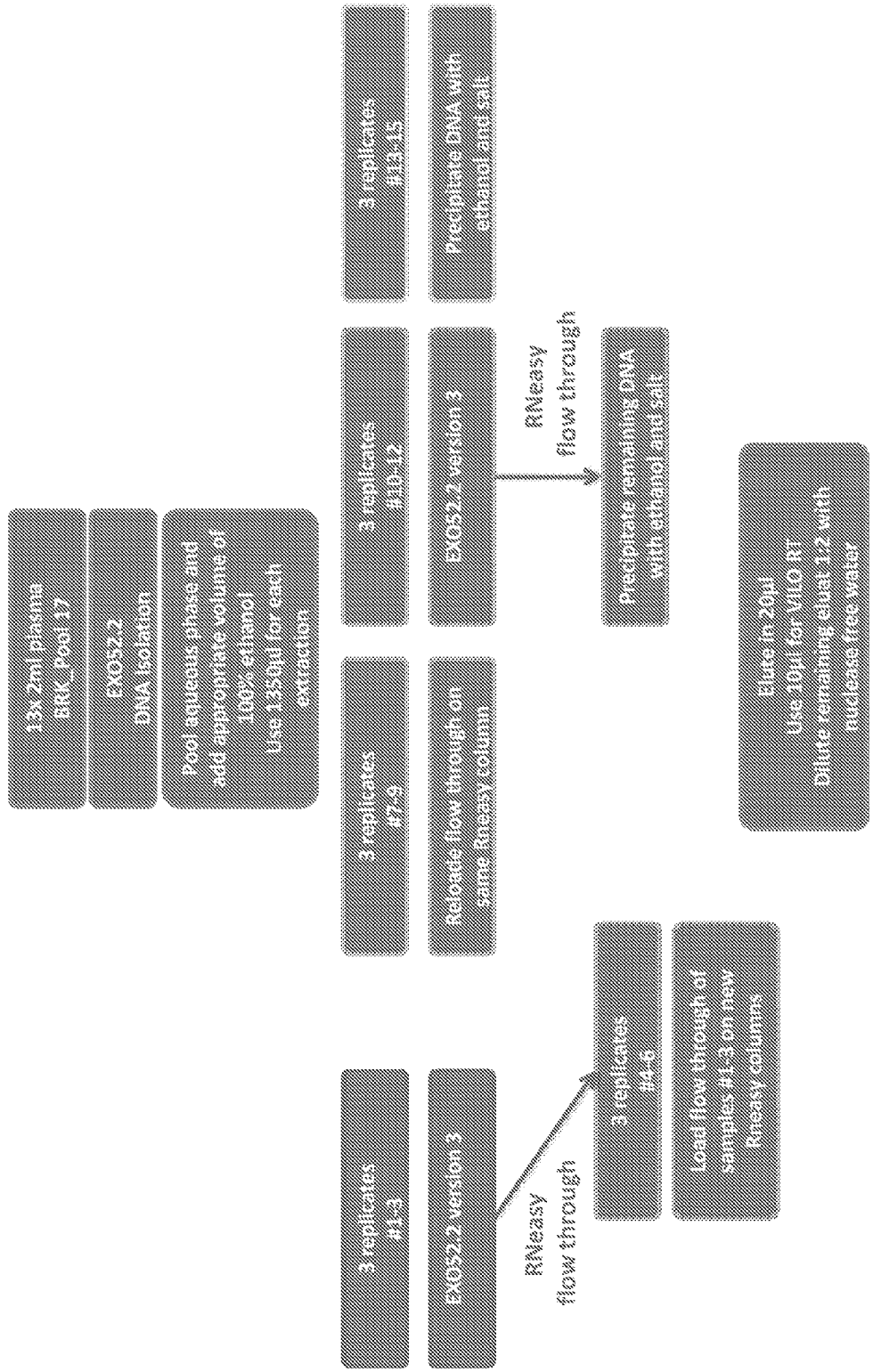

Protocol ethanol precipitation

Nucleic acid ethanol precipitation from aqueous phase (EXO52.2 procedure):

Reagents:
* 3M sodium acetate pH 5.5
* 100% ethanol
* 20µg/µl Glycogen

Protocol:

1. Transfer the upper aqueous phase to a new collection tube. Avoid transfer of any interphase material. Add 2 volumes of 100% ethanol and mix thoroughly by pipetting up and down several times. Do not centrifuge
2. Measure the volume of the aqueous phase (containing RNA and DNA) and added ethanol 1350µl (450µl aqueous phase + 900µl 100% ethanol)
3. Add 1/10 volume (relative to aqueous phase volume) of sodium acetate pH 5.2. → 45µl
4. Add up to 2.5 volumes of 100% ethanol (450µl aqueous phase + 45µl 3M sodium acetate) → 1237.5µl 100% ethanol (900µl already added to aqueous phase see step 1.) → add remaining 100% ethanol (337.5µl)
5. mix thoroughly by pipetting up and down several times. Do not centrifuge
6. Add 25µg Glycogen (1.25µl Glycogen 20µg/µl)
7. mix thoroughly by pipetting up and down several times. Do not centrifuge
8. Place tubes in the freezer @ -20°C over night
9. Thaw samples on the next day
10. mix thoroughly by inverting the tube several time
11. Spin @ maximum speed (16000xg) for 15 min @ 4°C
12. Carefully remove supernatant without destroying nucleic acid pellet
13. If pellet come off the tube wall, re-spin for 2 min @ full speed
14. Add 1ml 70% ethanol. Mix and spin briefly. Carefully remove supernatant
15. If pellet come off the tube wall, re-spin for 2 min @ full speed
16. Remove remaining 70% ethanol using a small pipette
17. Air dry pellet
18. Resuspend pellet in 20µl EB

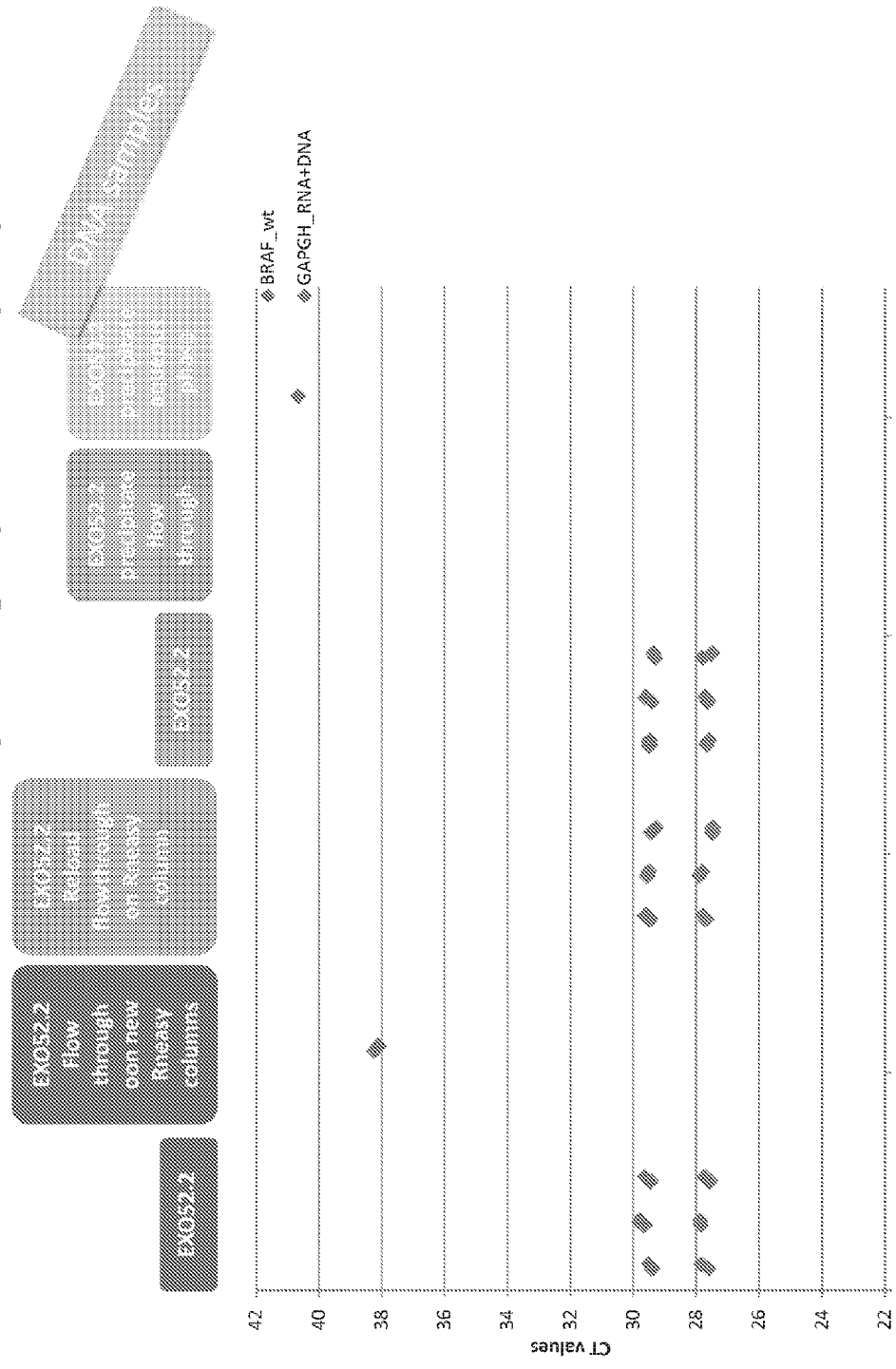

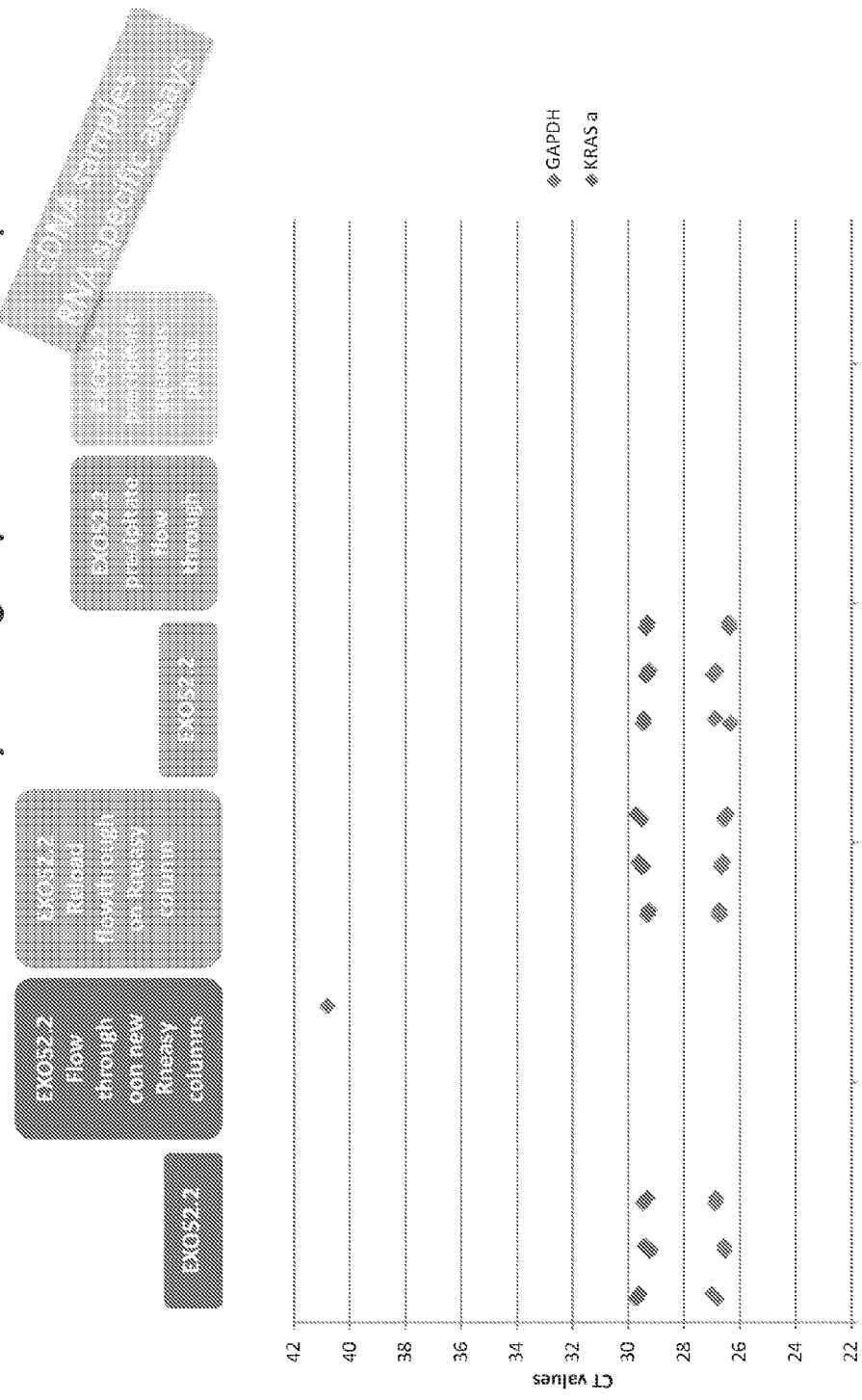

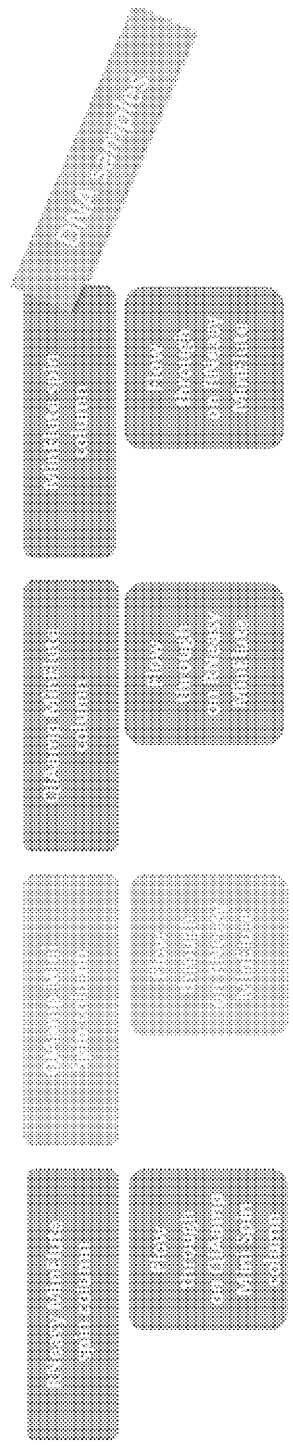
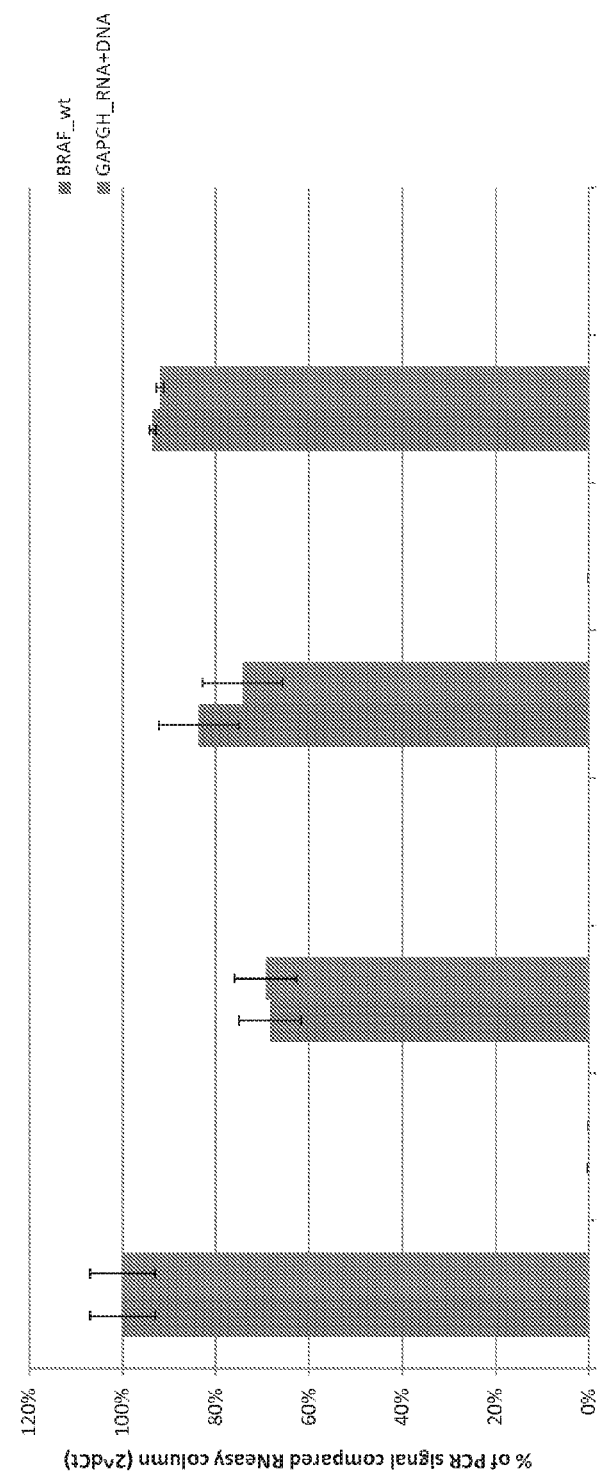

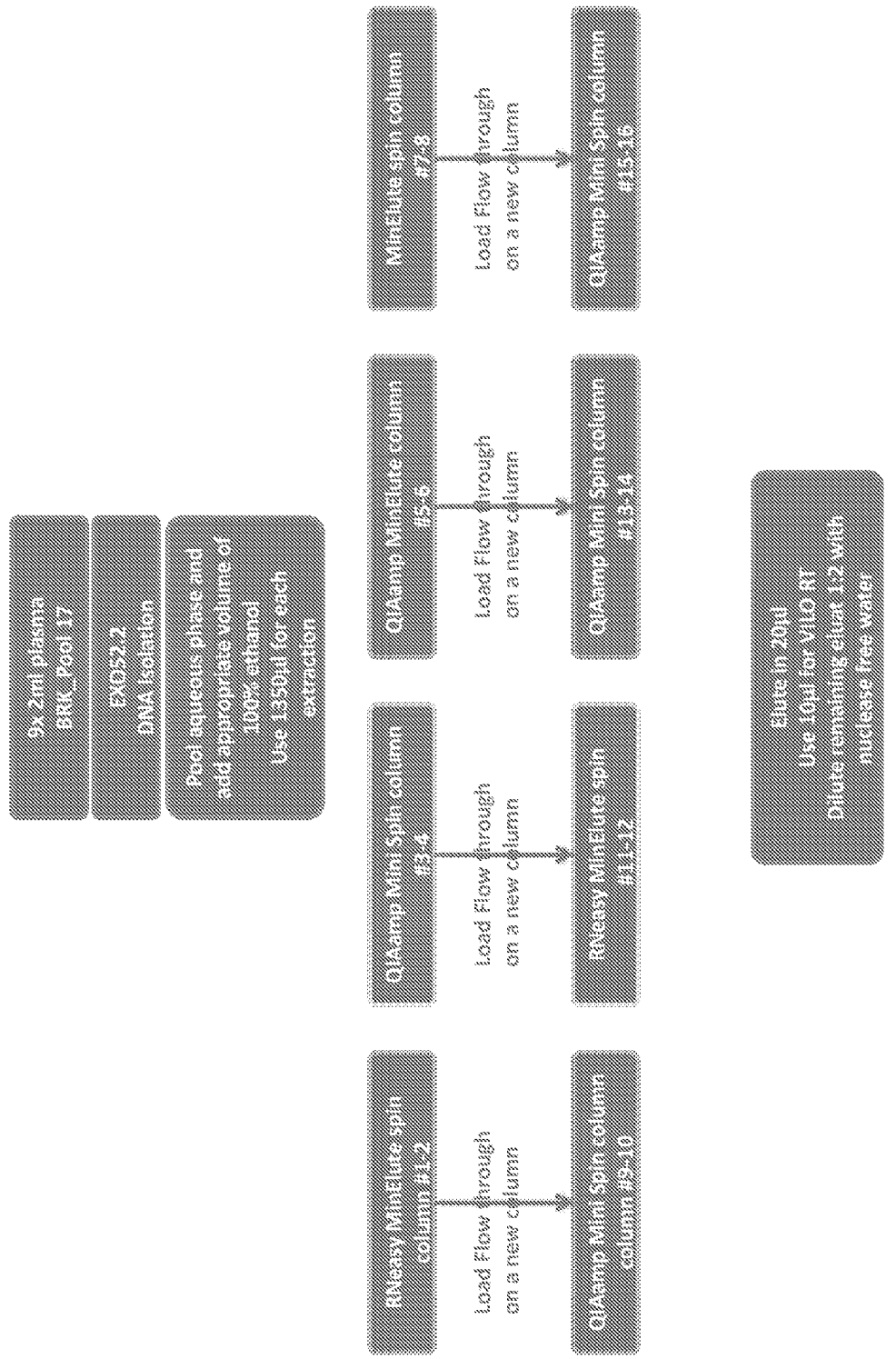

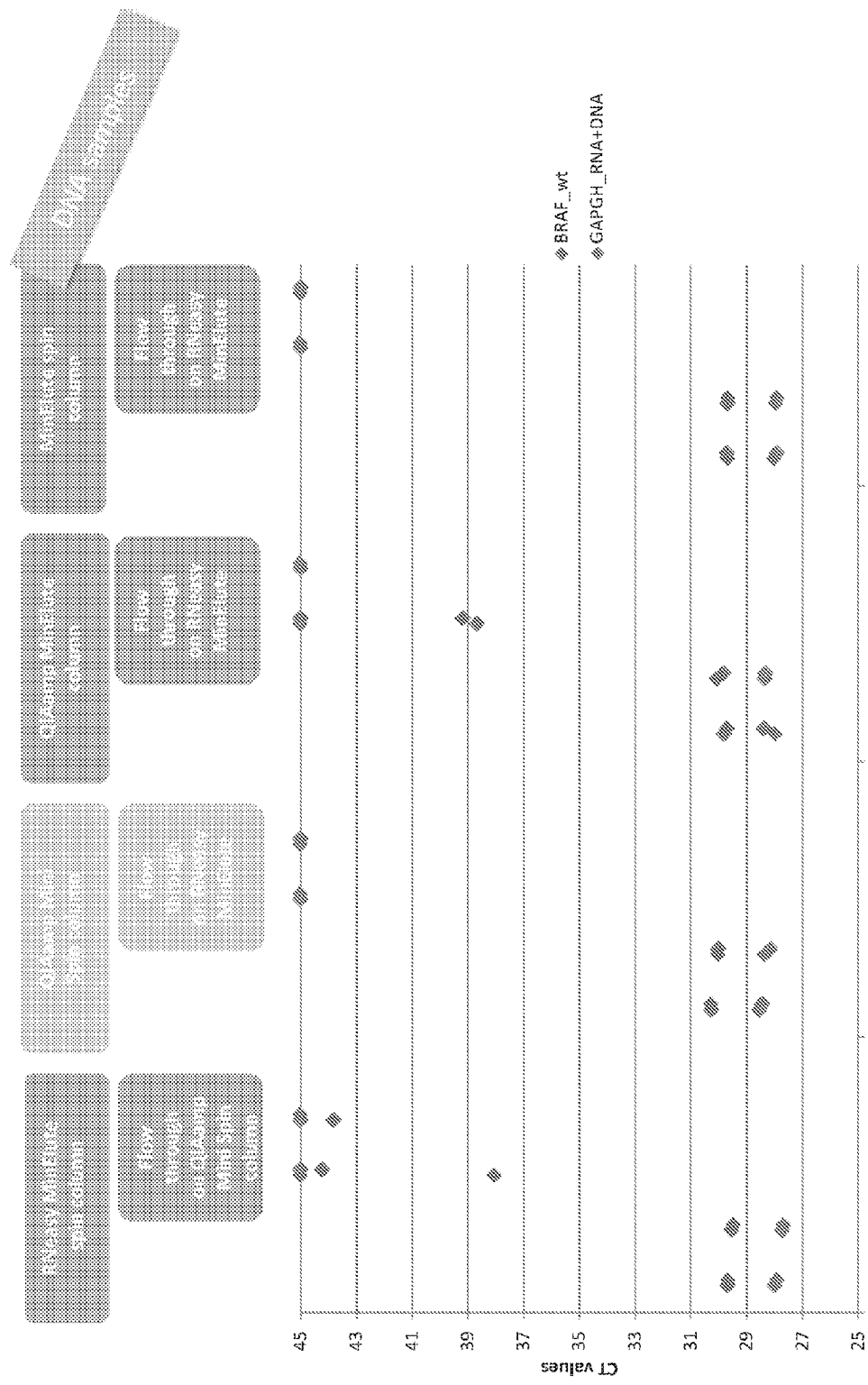

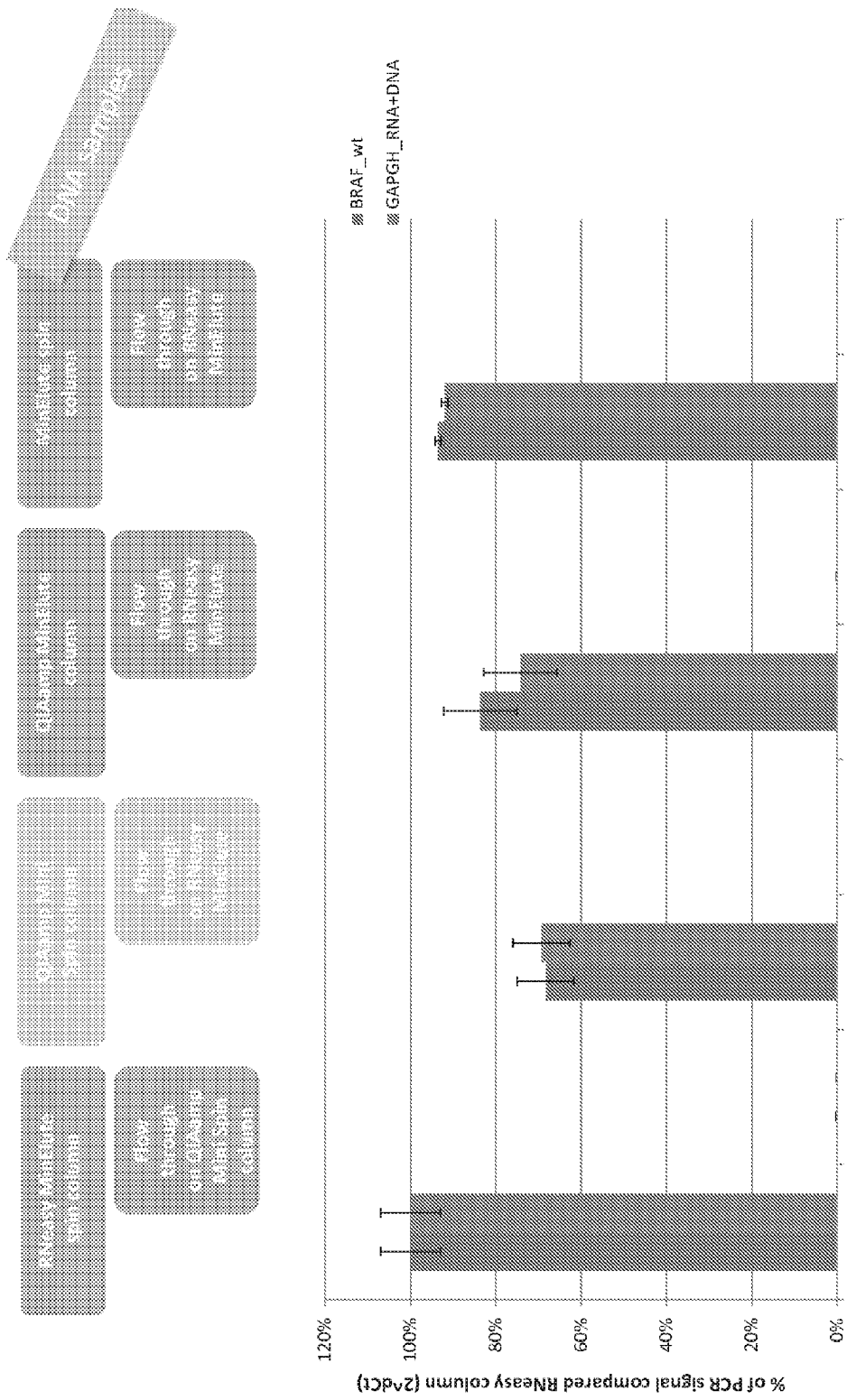

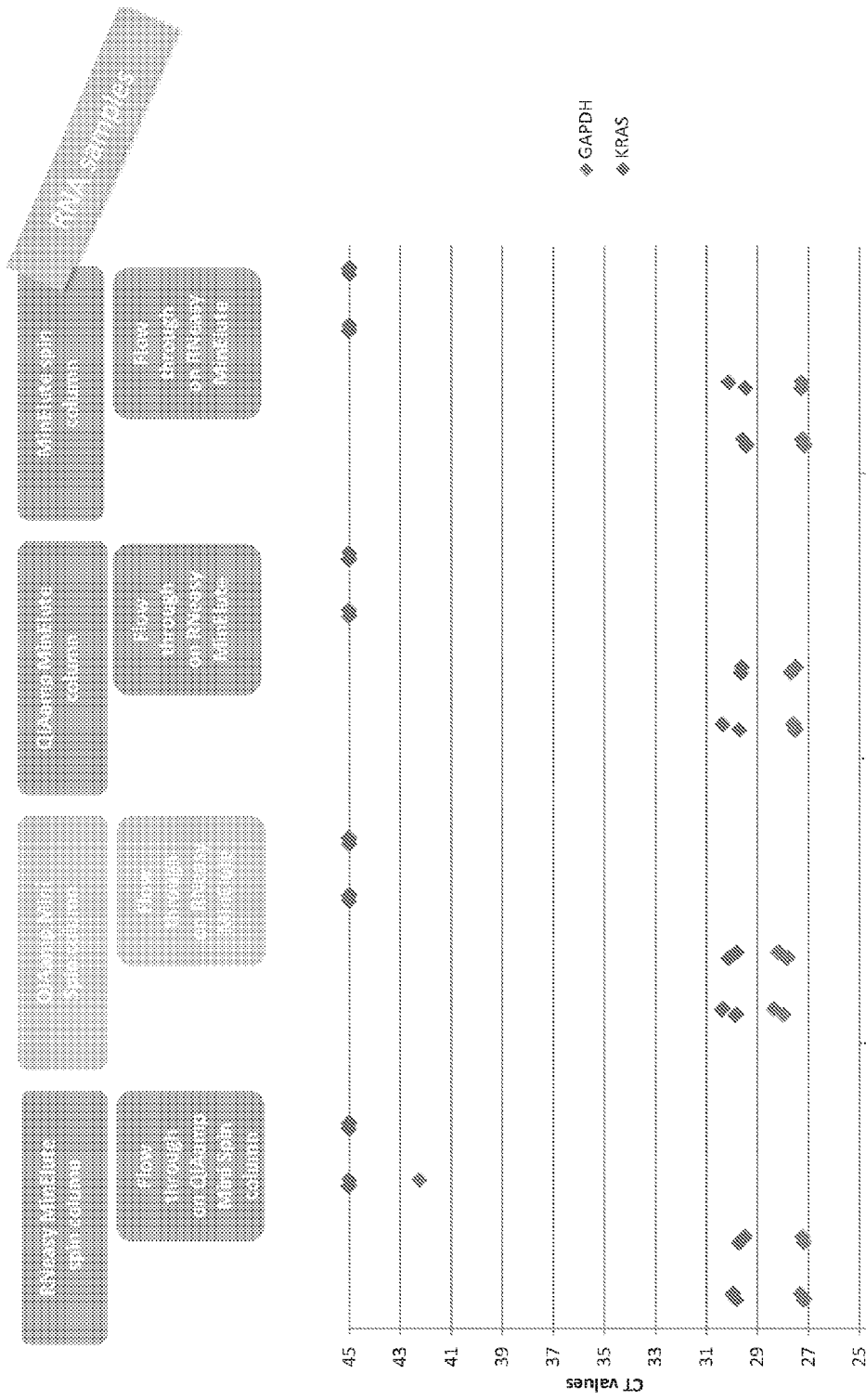

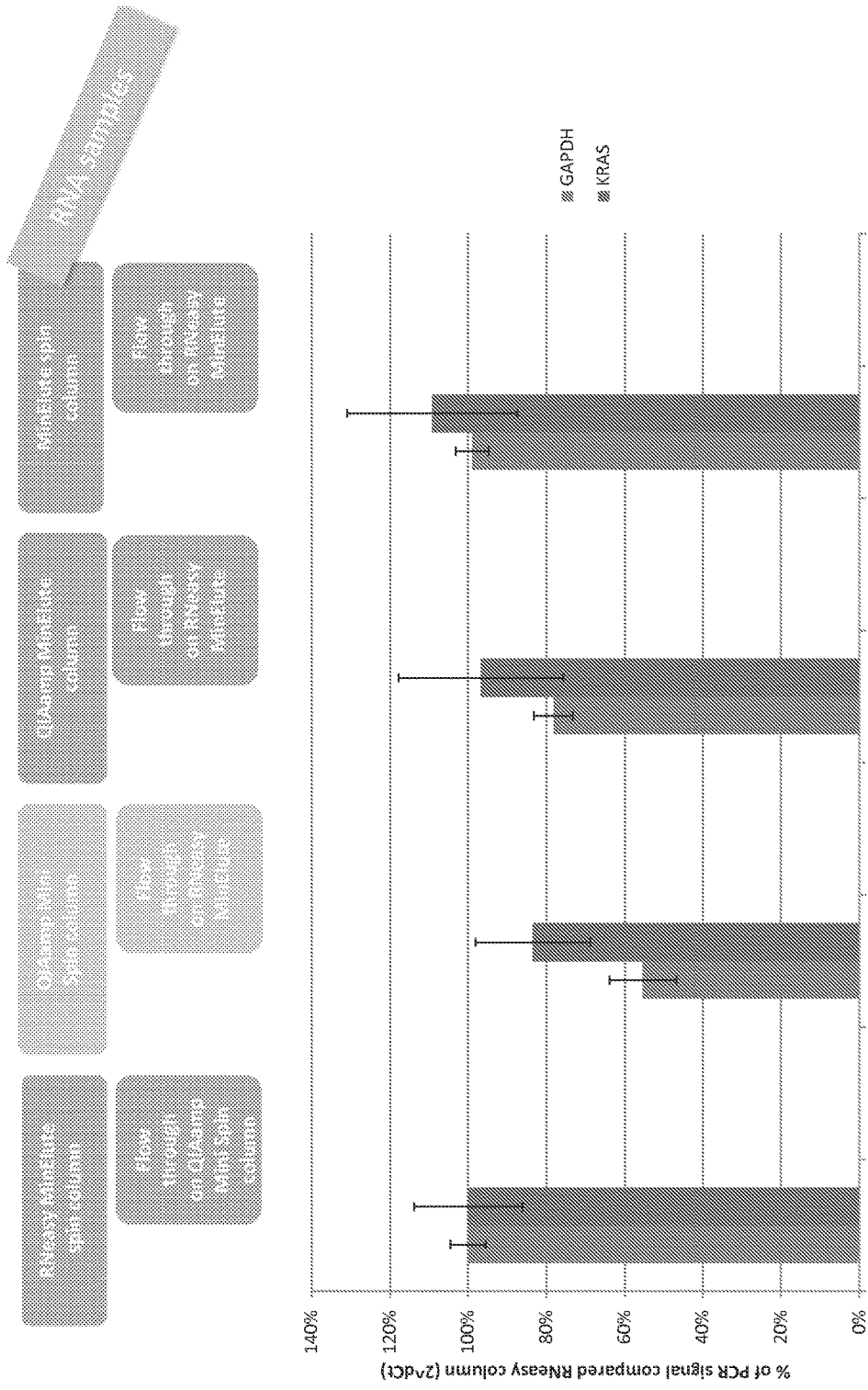

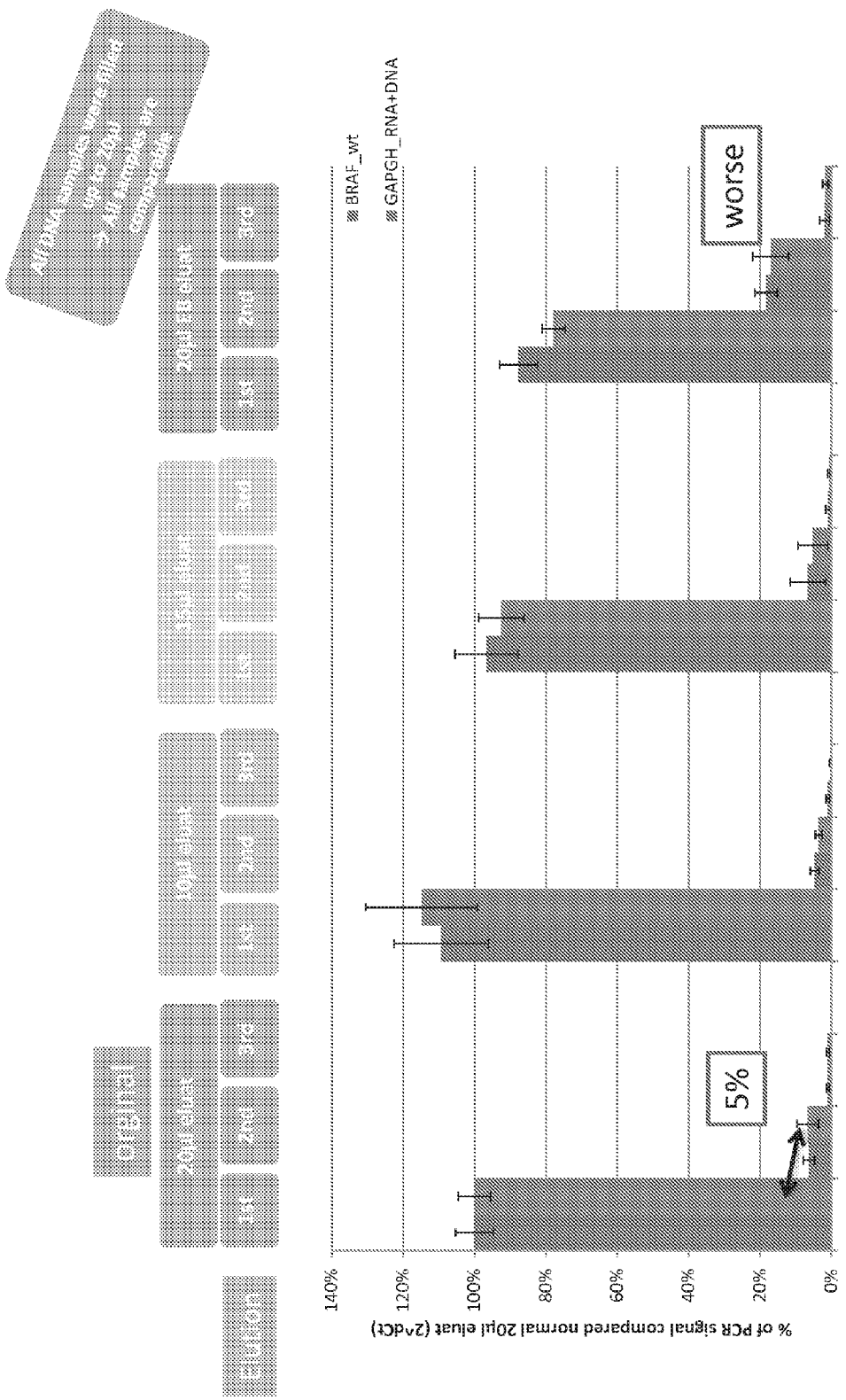

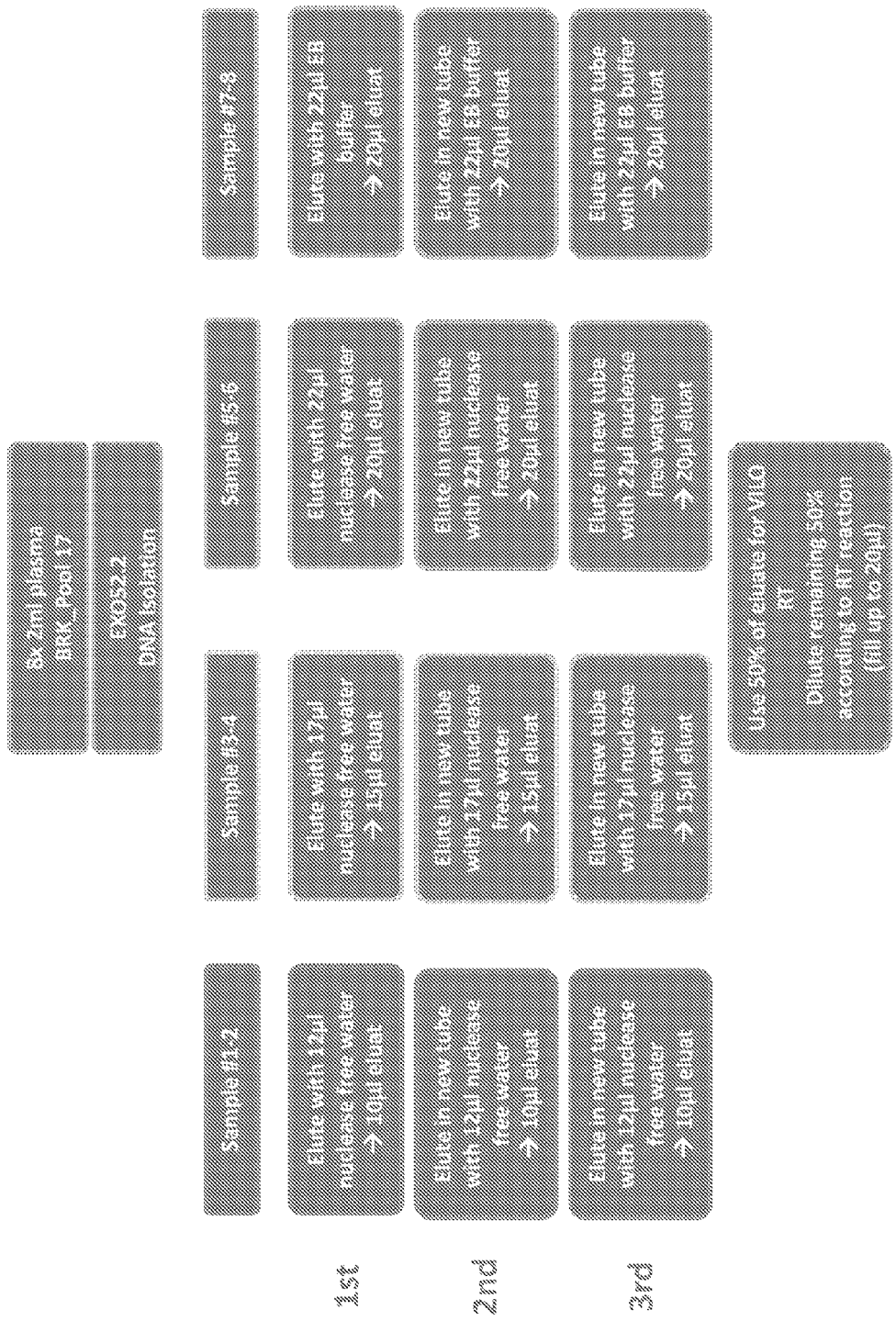

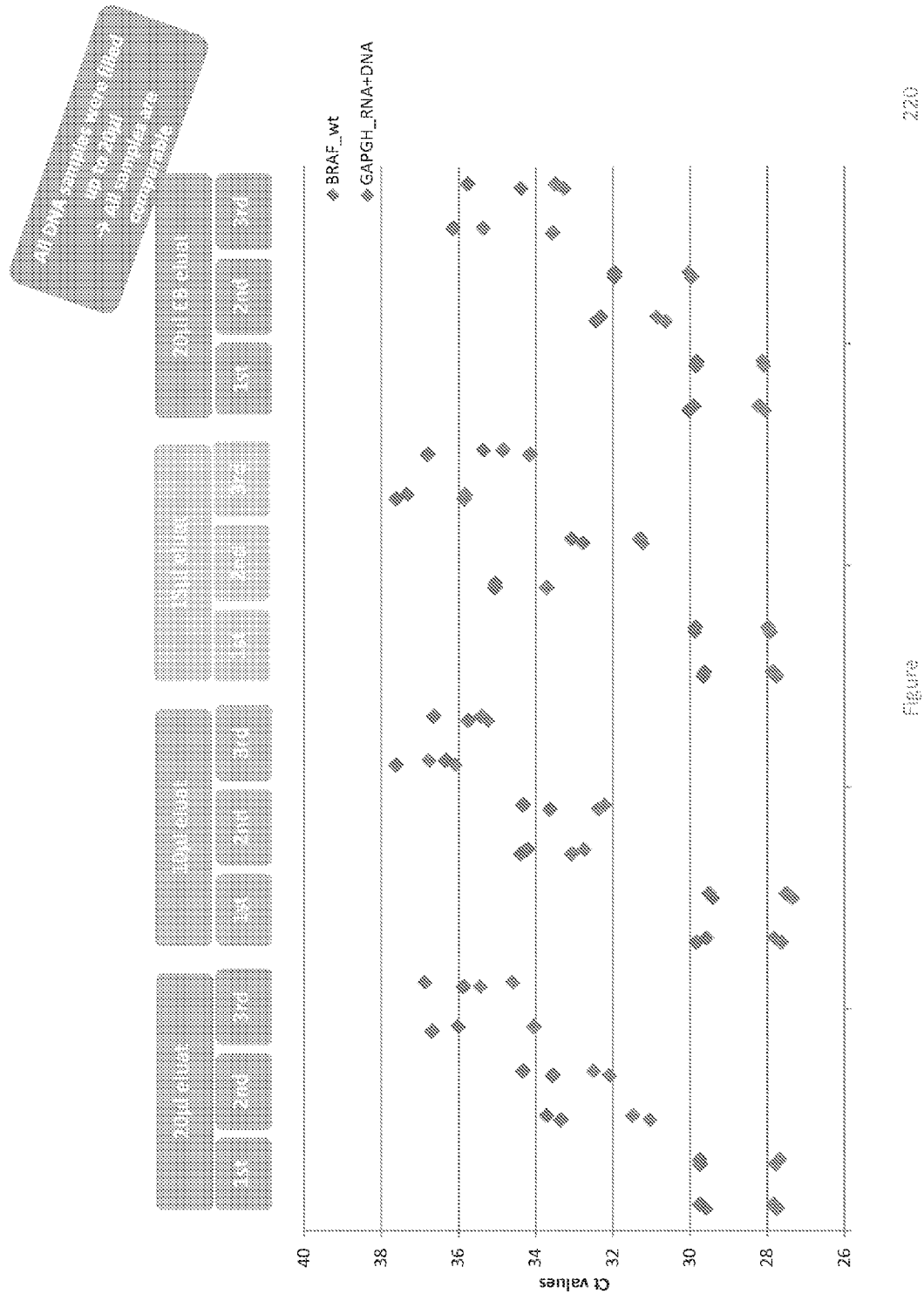

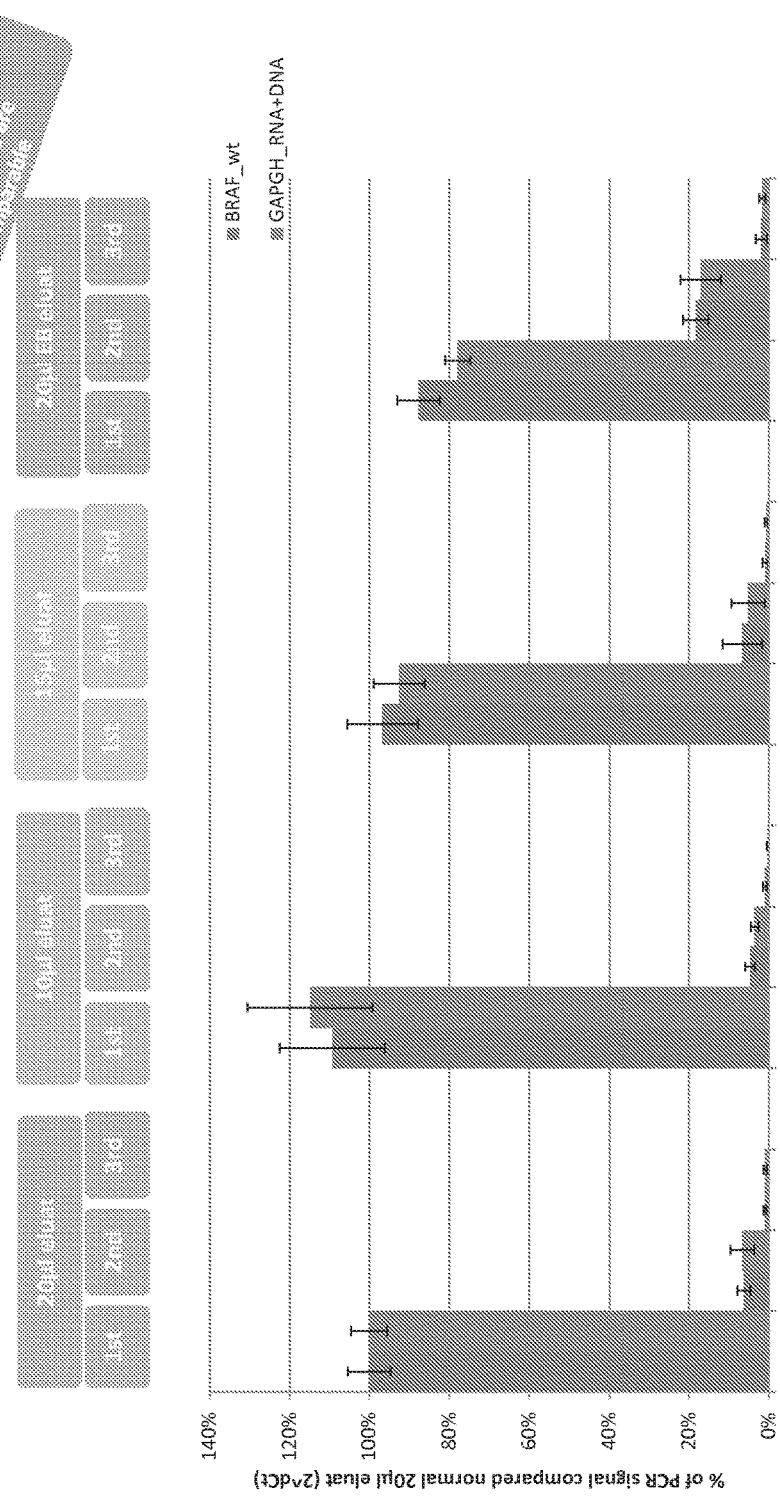

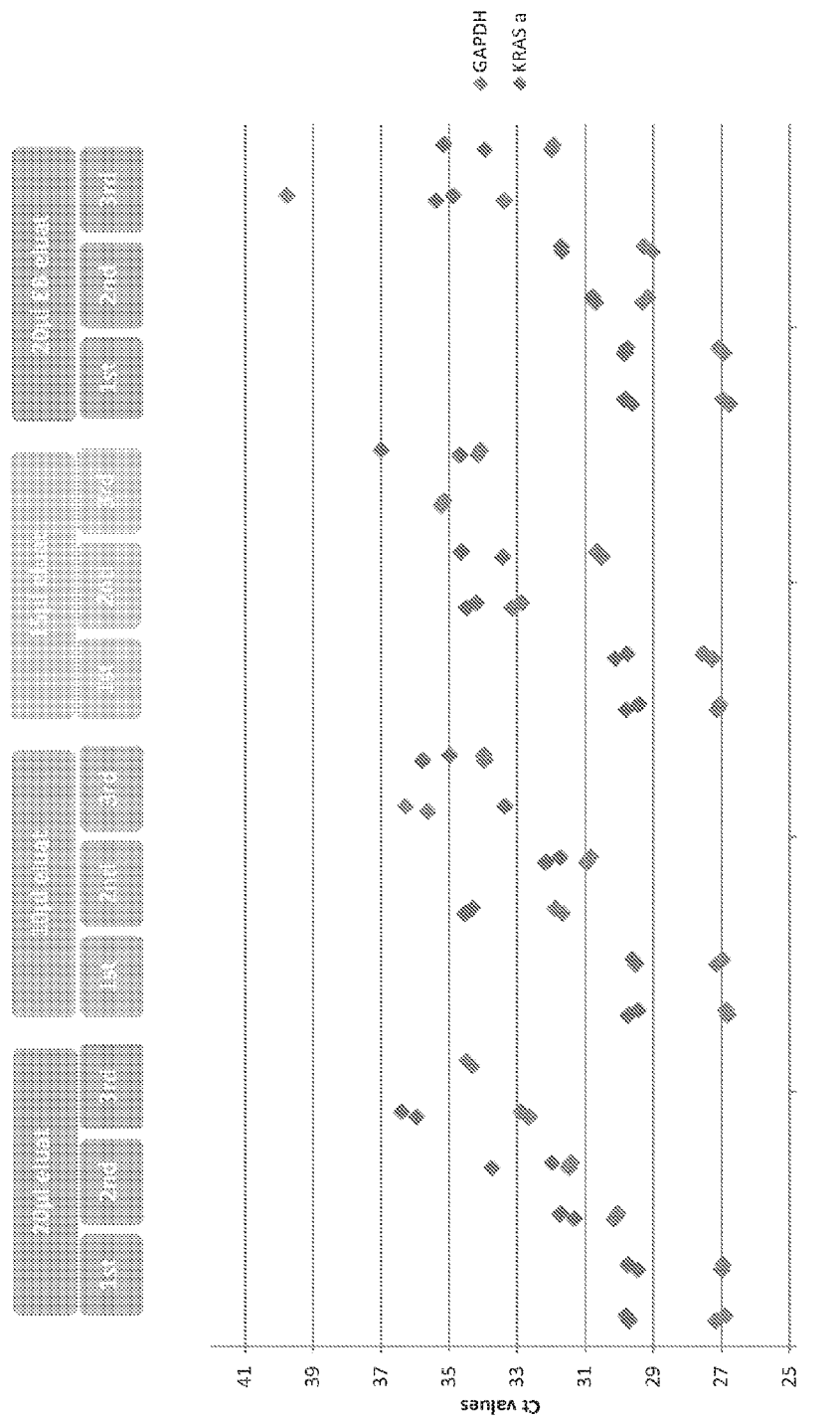

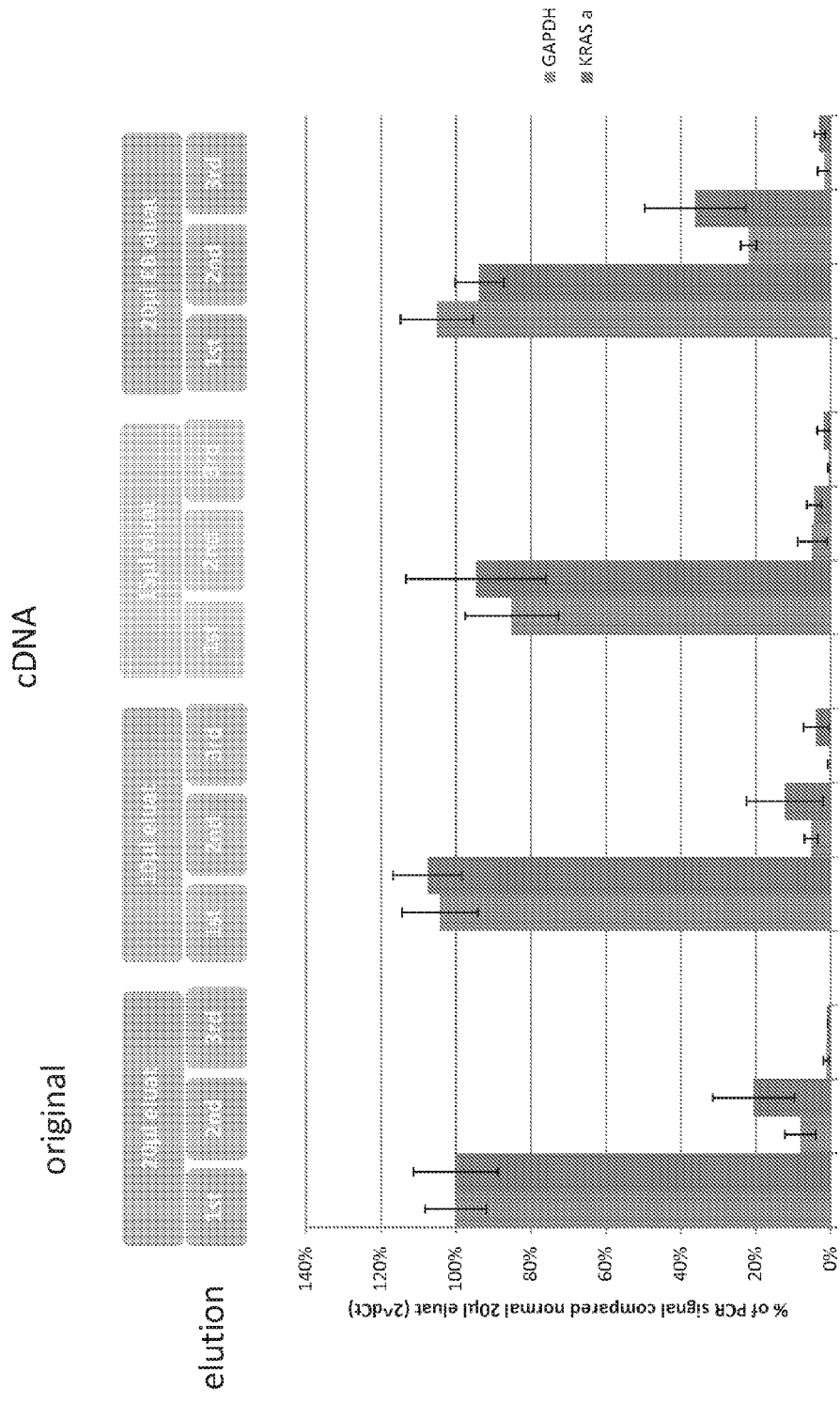

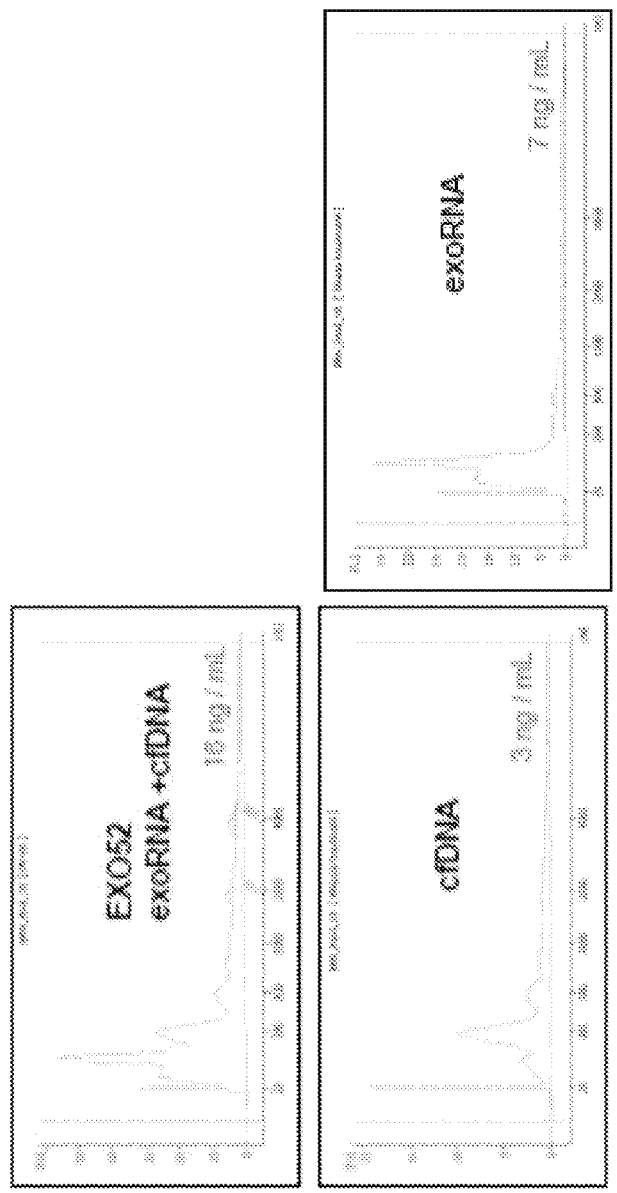

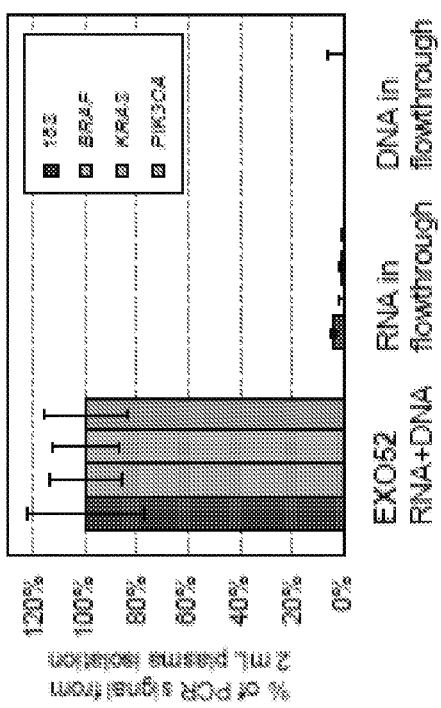

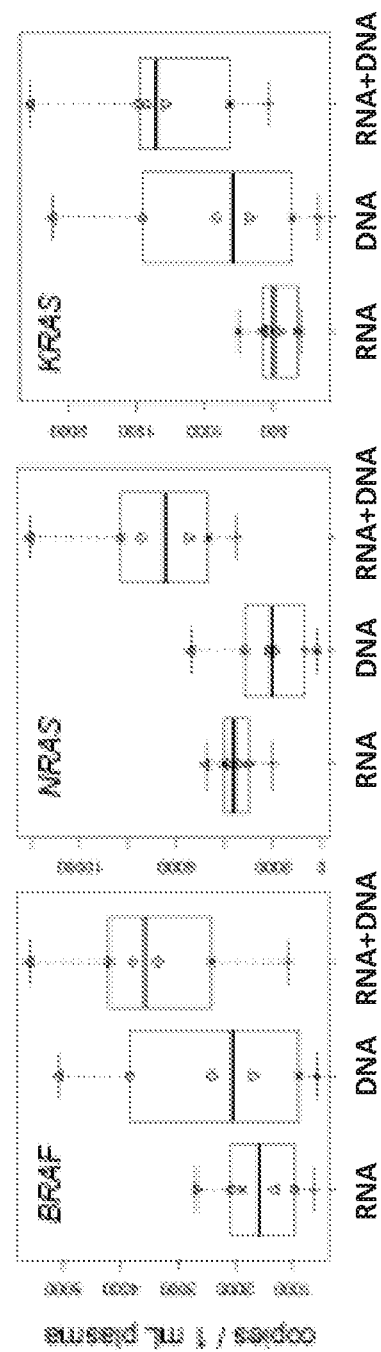

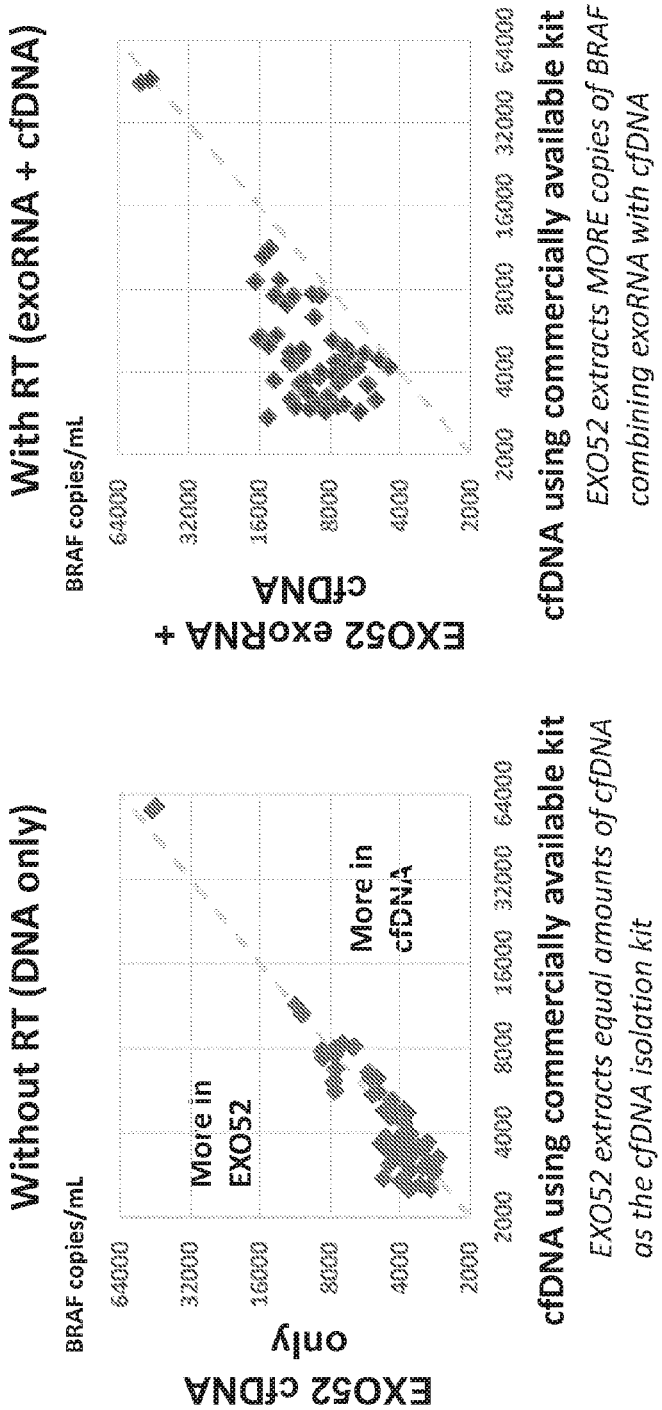

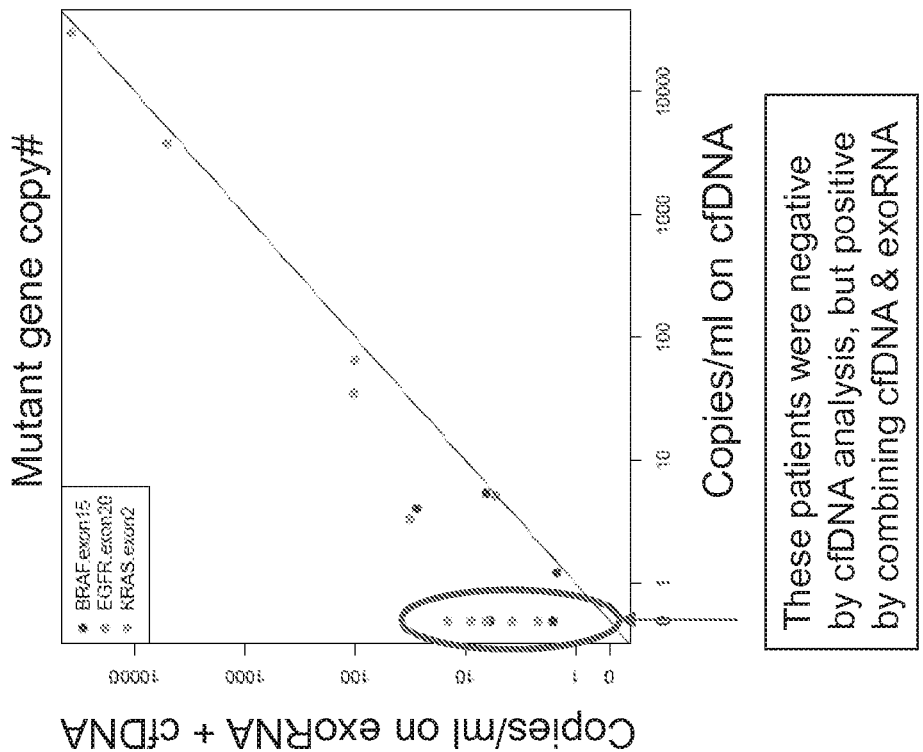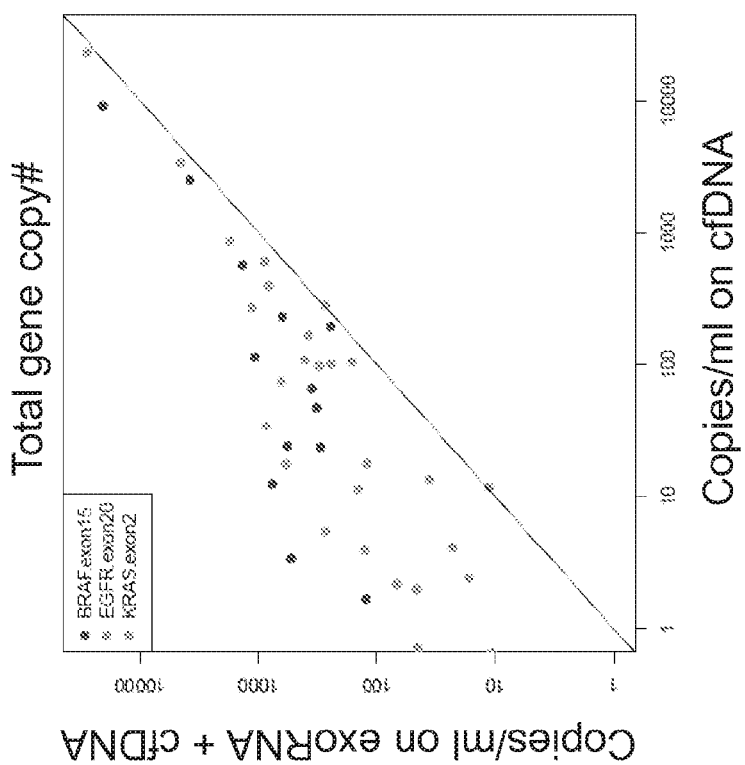
Figure 228

METHODS FOR ISOLATING MICROVESICLES AND EXTRACTING NUCLEIC ACIDS FROM BIOLOGICAL SAMPLES

RELATED APPLICATIONS

This application is a national stage application, filed under 35 U.S.C. § 371, of PCT Application No. PCT/US2015/039760, filed Jul. 9, 2015, which claims priority to and the benefit of U.S. Provisional Application No. 62/022,538, filed Jul. 9, 2014, U.S. Provisional Application No. 62/079,763, filed Nov. 14, 2014, and U.S. Provisional Application No. 62/166,890, filed May 27, 2015, the contents of each of which are hereby incorporated by reference in its entirety.

FIELD OF THE INVENTION

The invention provides novel methods and kits for isolating nucleic acids from biological samples, including cell-free DNA and/or cell-free DNA and nucleic acids including at least RNA from microvesicles, and for extracting nucleic acids from the microvesicles and/or from the biological samples.

BACKGROUND

Membrane vesicles that are shed by cells are referred collectively as microvesicles. Microvesicles from various cell sources have been extensively studied with respect to protein and lipid content. Recently, microvesicles have been found to also contain both DNA and RNA, including genomic DNA, cDNA, mitochondrial DNA, microRNA (miRNA), and messenger RNA (mRNA).

Due to the genetic and proteomic information contained in microvesicles shed by cells, current research is directed at utilizing microvesicles to gain further insight into the status of these cells, for example, disease state or predisposition for a disease. In addition, current research is also directed at utilizing cell-free DNA to gain further insight into the status of cells.

Accordingly, there is a need for methods of isolating cell-free DNA and for isolating microvesicles from biological samples and methods of extracting high quality nucleic acids for accurate diagnosis of medical conditions and diseases.

SUMMARY OF THE INVENTION

The present invention provides methods for isolation of cell-free DNA ("cfDNA," also known as circulating DNA) and/or for the combined isolation of cfDNA and nucleic acids including at least the RNA from microvesicles from a sample by capturing the DNA, DNA and RNA, and/or microvesicles to a surface, subsequently lysing the microvesicles to release the nucleic acids, particularly RNA, contained therein, and eluting the DNA and/or DNA and nucleic acids including at least RNA from the capture surface. Those of ordinary skill in the art will appreciate that the microvesicle fraction also includes DNA. Thus, lysis of the microvesicle fraction releases both RNA and DNA. Furthermore, the DNA isolated can be from any of a variety of sources including, but not limited to nucleosomes and other cell-free DNA sources.

Previous procedures used to isolate and extract nucleic acids from a sample, e.g., cfDNA and/or DNA and nucleic acids including at least RNA from the microvesicle fraction of a sample, relied on the use of ultracentrifugation, e.g., spinning at more than 10,000×g for 1-3 hrs, followed by removal of the supernatant, washing the pellet, lysing the pellet and purifying the nucleic acids, e.g., DNA and/or DNA and RNA on a column. These previous methods demonstrated several disadvantages such as being slow, tedious, subject to variability between batches, and not suited for scalability. The methods and kits for isolation and extraction provided herein overcome these disadvantages and provide a spin-based column for isolation and extraction that is fast, robust and easily scalable to large volumes.

The methods and kits isolate and extract nucleic acids, e.g., DNA and/or DNA and nucleic acids including at least RNA from a sample using the following general procedure, which is referred to herein as "EXO52." First, the nucleic acids in the sample, e.g., the DNA and/or the DNA and the microvesicle fraction, are bound to a capture surface such as a membrane filter, and the capture surface is washed. Then, a reagent is used to perform on-membrane lysis and release of the nucleic acids, e.g., DNA and/or DNA and RNA. Chloroform extraction is then performed using PLG tubes, followed by ethanol conditioning. The nucleic acids, e.g., DNA and/or DNA and RNA, are then bound to a silica column, washed and eluted.

The membranes used in the EXO52 methods and kits have large pores and are positively charged. In some embodiments, more than one membrane is used in the EXO52 methods and kits, for example, two or more membranes are used. In some embodiments, three membranes are used. The number of membranes used in the EXO52 methods and kits correlates with the total volume of sample that can be analyzed at one time. In some embodiments, about 1 ml of samples is processed for each layer of membrane used in the EXO52 methods and kits.

In some embodiments, the membrane is a positively charged membrane. In some embodiments, the capture surface is an anion exchanger. In some embodiments, the capture surface is an anion exchanger with quaternary amines. In some embodiments, the capture surface is a Q membrane, which is a positively charged membrane and is an anion exchanger with quaternary amines. For example, the Q membrane is functionalized with quaternary ammonium, $R-CH_2-N^+(CH_3)_3$. In some embodiments, the membrane has a pore size that is at least 3 µm.

Purification of the sample, including the microvesicle fraction, is performed using ion exchange techniques. In some embodiments, the ion exchange technique is a technique selected from those shown in the working examples provided herein.

In some embodiments, the agent used for on-membrane lysis is a phenol-based reagent. In some embodiments, the lysis reagent is a guanidinium-based reagent. In some embodiments, the lysis reagent is a high salt based buffer. In some embodiments, the lysis reagent is QIAzol. In some embodiments, the lysis reagent is a phenol-based lysis reagent, e.g., QIAzol, and it is used at a volume of about 700 ul.

In one aspect, the method for extracting nucleic acids from a biological sample comprises (a) providing a biological sample; (b) contacting the biological sample with a capture surface under conditions sufficient to retain the microvesicle fraction on or in the capture surface; (c) lysing the microvesicle fraction while the microvesicles are on or in the capture surface; and (d) extracting the nucleic acids from the microvesicle fraction. Alternatively, the method for extracting nucleic acids from the biological sample further comprises eluting the microvesicle fraction from the capture surface after step (b), collecting the eluted microvesicle fraction, and extracting the nucleic acids from the eluted microvesicle fraction. Optionally, the eluted microvesicle fraction can be concentrated by a spin concentrator to obtain a concentrated microvesicle fraction, and the nucleic acids are subsequently extracted from the concentrated microvesicle fraction.

In another aspect, the method for extracting nucleic acids from a biological sample comprises (a) providing a biological sample; (b) contacting the biological sample with a capture surface under conditions sufficient to retain the microvesicle fraction on or in the capture surface; and (c) eluting the microvesicle fraction while the microvesicles are on or in the capture surface. The eluted microvesicle fraction can then be processed for further analysis. Optionally, the eluted microvesicle fraction can be concentrated by a spin concentrator to obtain a concentrated microvesicle fraction. In some embodiments, the nucleic acids are subsequently extracted from the concentrated microvesicle fraction.

In some embodiments, the capture surface is a membrane. In one aspect, the membrane comprises regenerated cellulose. For example, the membrane has a pore size at least 1 μm, such as for example, in a range between 2-5 μm. In some embodiments, the membrane has a pore size in a range between 3-5 μm. In some embodiments, the membrane comprises polyethersulfone (PES).

In some embodiments, the membrane is charged. In some embodiments, the membrane is positively charged. In some embodiments, the membrane is negatively charged.

In some aspects, the membrane is functionalized. For example, the membrane is functionalized with quaternary ammonium R—$CH_2$—$N^+(CH_3)_3$.

In one embodiment, the capture surface comprises more than one membrane. In some embodiments, the capture surface comprises at least two membranes, wherein each membrane is adjacently next to the other membrane(s). In some embodiments, the capture surface comprises at least three membranes, wherein each of the three membranes is directly adjacent to one another. In some embodiments, the capture surface comprises at least four membranes, wherein each of the four membranes is directly adjacent to one another.

In some embodiments, the capture surface is a bead. For example, the bead is magnetic. Alternatively, the bead is non-magnetic. In yet another embodiment, the bead is functionalized with an affinity ligand.

In some embodiments, the capture surface is a slurry of polymer(s). In some embodiments, the slurry of polymer(s) is shaped into a bead.

In some embodiments, the biological sample is plasma. In some embodiments, the biological sample is serum. In some embodiments, the biological sample is urine. In some embodiments, the biological sample is cerebrospinal fluid. In some embodiments, the biological sample is cell culture supernatant.

In some aspects, the method described herein further comprises contacting the biological sample with a loading buffer. The loading buffer is in the range of pH 4-8. In one aspect, the loading buffer has a neutral pH.

The methods described herein provide for the extraction of nucleic acids from microvesicles. Preferably, the extracted nucleic acids are DNA and/or DNA and RNA. The extracted RNA may comprise messenger RNA, ribosomal RNA, transfer RNA, or small RNAs such as microRNAs, or any combination thereof.

Various nucleic acid sequencing techniques are used to detect and analyze nucleic acids such as cell free DNA and/or RNA extracted from the microvesicle fraction from biological samples. Analysis of nucleic acids such as cell free DNA and/or nucleic acids extracted from microvesicles for diagnostic purposes has wide-ranging implications due to the non-invasive nature in which microvesicles can be easily collected. Use of microvesicle analysis in place of invasive tissue biopsies will positively impact patient welfare, improve the ability to conduct longitudinal disease monitoring, and improve the ability to obtain expression profiles even when tissue cells are not easily accessible (e.g., in ovarian or brain cancer patients).

In some embodiments, the present invention is directed to compositions and methods for providing an in-process control for nucleic acid sequencing techniques, including, for example, next-generation sequencing (NGS) assays, to detect low-frequency sequence variants. These controls provide a number of technical advantages.

The biological sample is a bodily fluid. The bodily fluids can be fluids isolated from anywhere in the body of the subject, preferably a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. For example, the bodily fluid is urine, blood, serum, or cerebrospinal fluid.

In any of the foregoing methods, the nucleic acids are DNA and/or DNA and RNA. Examples of RNA include messenger RNAs, transfer RNAs, ribosomal RNAs, small RNAs (non-protein-coding RNAs, non-messenger RNAs), microRNAs, piRNAs, exRNAs, snRNAs and snoRNAs.

In any of the foregoing methods, the nucleic acids are isolated from or otherwise derived from a sample, including RNA isolated from the microvesicle fraction of a sample.

In any of the foregoing methods, the nucleic acids are cell-free nucleic acids, also referred to herein as circulating nucleic acids. In some embodiments, the cell-free nucleic acids are DNA or RNA.

Various aspects and embodiments of the invention will now be described in detail. It will be appreciated that modification of the details may be made without departing from the scope of the invention. Further, unless otherwise required by context, singular terms shall include pluralities and plural terms shall include the singular.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representations as to the contents of these documents are based on the information available to the applicants and do not constitute any admission as to the correctness of the dates or contents of these documents.

BRIEF DESCRIPTION OF THE FIGURES

FIG. 12 is two graphs showing the detection of different RNA targets after isolation and extraction by EXO70 or uCSC method. RNA was extracted and analyzed from the isolated microvesicle fraction (EXO70 or uCSC) and the flow-through or supernatant fraction after isolation (EXO70 flow or uCSC flow). (A) mRNA targets; (B) miRNA targets.

FIGS. 13-223 are a series of graphs and illustrations depicting the sensitivity and specificity of the EXO52 DNA and RNA isolation and extraction methods, along with comparisons to commercially available circulating nucleic acid isolation kits, referred to herein as commercially available CNA kits.

FIG. 13 is a schematic representation of studies designed to evaluate DNA extraction with and without PLG-tubes.

FIG. 27 is a graph depicting DNA isolation using RNeasy protocol (w/o PLG tube) and chloroform titration.

FIG. 28 is a schematic representation of studies designed to evaluate DNA isolation without PLG-tubes and with a chloroform titration.

FIGS. 29, 30, and 31 are a series of graphs depicting DNA isolation using RNeasy protocol (w/o PLG tube) and chloroform titration.

FIG. 32 is a graph depicting that adjusted chloroform addition co-isolates DNA and RNA.

FIG. 33 is a schematic representation of studies designed to evaluate DNA isolation without PLG-tubes and with a chloroform titration.

FIGS. 34, 35, 36, 37, 38, 39, 40, 41, 42, 43, and 44 are a series of graphs depicting DNA isolation using RNeasy protocol (w/o PLG tube) and chloroform titration.

FIG. 45 is a graph depicting the effect of pH changes in phase separation on DNA isolation.

FIG. 46 is a schematic representation of studies designed to evaluate DNA isolation from aqueous phase with a pH titration.

FIG. 47 is a schematic representation of the method of preparing pH conditioning solution.

FIG. 48 is a graph depicting Nala amplification curves for isolated RNA and DNA.

FIGS. 49, 50, 51, 52, 53, and 54 are a series of graphs depicting the effect of pH titration on DNA isolation from aqueous phase.

FIG. 55 is a graph depicting that chloroform addition is the predominant factor in determining the DNA content of the aqueous phase.

FIG. 56 is a graph depicting that RNA signal is not affected through the addition of DNA isolation.

FIG. 57 is a schematic representation of studies designed to evaluate DNA isolation from aqueous phase with a chloroform titration and with or without adding pH solution.

FIG. 58 is a schematic representation of the method of preparing pH conditioning solution.

FIGS. 59, 60, 61, 62, 63, 64, 65, 66, 67, and 68 are a series of graphs depicting the effect of chloroform titration with and without adding pH solution on DNA isolation from aqueous phase.

FIG. 69 is a graph depicting the effect of a 4° C. or a room temperature Qiazol spin step on RNA isolation using a commercially available kit.

FIG. 70 is a graph depicting the effect of a 4° C. or a room temperature Qiazol spin step on the methods of the disclosure.

FIGS. 71 and 72 are a schematic representation and an overview of studies designed to evaluate RNA isolation using a commercially available kit with either a 4° C. or a room temperature Qiazol spin step.

FIGS. 73, 74, and 75 are a series of graphs depicting the effect of a 4° C. or a room temperature Qiazol spin step on a commercially available kit.

FIGS. 76 and 77 are a schematic representation and an overview of studies designed to evaluate RNA isolation using the EXO52 method with either a 4° C. or a room temperature Qiazol spin step.

FIGS. 78 and 79 are a series of graphs depicting the effect of a 4° C. or a room temperature Qiazol spin step on the methods of the disclosure.

FIG. 81 is a schematic representation of studies designed to evaluate the effect of varying ethanol volumes between 1.5× to 2.6×.

FIGS. 81 and 82 are a series of graphs depicting the effect of varying ethanol volumes between 1.5× to 2.6× on DNA and RNA isolation.

FIG. 83 is a graph depicting the results of ProtK digestion at room temperature before the binding step.

FIG. 84 is a schematic representation of studies designed to evaluate ProtK digestion at room temperature before the binding step.

FIGS. 85 and 86 are a series of graphs depicting the results of ProtK digestion at room temperature before the binding step.

FIGS. 95, 96, and 97 are a series of graphs depicting the effect of varying the loading volume of plasma on DNA and RNA isolation.

FIG. 98 is a graph depicting that the flow-through does not have a breakthrough point up to 8 mL of plasma.

FIGS. 99 and 100 are a series of graphs depicting the effect of varying the loading volume of plasma on DNA and RNA isolation.

FIGS. 101, 102, 103, 104, 105, and 106 are a series of graphs depicting different binding capacity for exosomes and nucleosomes.

FIGS. 107 and 108 are a series of graphs depicting cell-free DNA (cfDNA) isolation using different isolation techniques including the methods of the disclosure and commercially available kits.

FIGS. 112, 113, 114, 115, 116, 117, 118, 119, 120, 121, 122, and 123 are a series of graphs depicting cfDNA isolation using different isolation techniques including the methods of the disclosure and commercially available kits.

FIGS. 124, 125, 126, 127, and 128 are a series of graphs and tables depicting a comparison of cfDNA copy number using different isolation techniques including methods of the disclosure and commercially available kits.

FIGS. 129, 130, and 131 are a schematic representation and overviews of studies designed to evaluate use of the AllPrep Micro kit for downstream analysis of isolated DNA and RNA.

FIGS. 132, 133, 134, 135, and 136 are a series of graphs depicting the use of the AllPrep Micro kit for downstream analysis of isolated DNA and RNA.

FIGS. 137 and 138 are a series of graphs depicting cell-free DNA (cfDNA) isolation using different isolation techniques including the methods of the disclosure and commercially available kits.

FIG. 139 is a schematic representation of studies designed to compare cfDNA isolated using methods of the disclosure and commercially available kits.

FIGS. 140, 141, 142, 143, 144, 145, and 146 are a series of graphs depicting cell-free DNA (cfDNA) isolation using different isolation techniques including the methods of the disclosure and commercially available kits.

FIGS. 147, 148, and 149 are schematic representations of studies designed to compare cfDNA isolated using methods of the disclosure and commercially available kits.

FIGS. 150, 151, 152, 153, 154, 155, 156, 157, 158, 159, 160, 161, 162, 163, 164, 165, 166, 167, 168, 169, and 170 are a series of graphs depicting cell-free DNA (cfDNA) isolation using different isolation techniques including the methods of the disclosure and commercially available kits.

FIG. 171 is series of graphs depicting that the methods of the disclosure consistently outperform the commercially available cNA kits.

FIGS. 172, 173, and 174 are schematic representations of studies designed to compare cfDNA isolated using methods of the disclosure and commercially available kits.

FIGS. 175, 176, 177, 178, 179, 180, 181, 182, 183, 184, 185, 186, 187, 188, 189, 190, 191, 192, 193, 194, 195, and 196 are a series of graphs depicting cell-free DNA (cfDNA) isolation using different isolation techniques including the methods of the disclosure and commercially available kits.

FIGS. 204, 205, and 206 are a series of graphs depicting the effect of multiple separate Qiazol elution steps on DNA and RNA isolation.

FIG. 207 is a graph depicting the effect of double RNeasy loading steps with ethanol precipitation on DNA and RNA isolation.

FIGS. 208 and 209 are a schematic representation and an overview of studies designed to evaluate DNA and RNA isolation using double RNeasy loading steps with ethanol precipitation.

FIGS. 210 and 211 are a series of graphs depicting the effect of double RNeasy loading steps with ethanol precipitation on DNA and RNA isolation.

FIG. 212 is a graph depicting the effect of different downstream columns on DNA and RNA isolation.

FIG. 213 is a schematic representation of studies designed to evaluate DNA and RNA isolation using different downstream columns.

FIGS. 214, 215, 216, and 217 are a series of graphs depicting the effect of different downstream columns on DNA and RNA isolation.

FIG. 219 is a schematic representation of studies designed to evaluate DNA and RNA isolation using multiple RNeasy elution steps.

FIGS. 220, 221, 222, and 223 are a series of graphs depicting the effect of multiple RNeasy elution steps on DNA and RNA isolation.

FIG. 224 is a series of graphs depicting the size distribution of nucleic acids in plasma. Complete nucleic acid isolation from 1 mL plasma was subjected to either RNase A digestion ("cfDNA"), DNase I digestion ("exoRNA"), or mock treatment ("EXO52"). After reaction cleanup, the size distribution of nucleic acids present in the isolation was measured by a Bioanalyzer Pico 6000 assay.

FIG. 225 is a graph depicting sequential isolation of nucleic acids from 2 ml of blood plasma. Blood plasma from a normal healthy donor was passed through an EXO52 column and the material left in the flow through was isolated using either a commercially available exoRNeasy kit (RNA) or a commercially available circulating nucleic acid kit (DNA). The overall yield is compared to EXO52 (RNA+DNA) using (RT)-qPCR against BRAF, KRAS and 18S genes as a function of delta CT. Error bars represent three replicate isolations.

FIG. 226 is a series of graphs depicting exoRNA and ciDNA both contribute substantially to the total nucleic acids harvested from blood plasma. 1 mL plasma from healthy donors was isolated using either the commercially available exoRNeasy kit (RNA) or an EXO52 isolation with a reverse transcription step (RNA+DNA) or without (DNA). Absolute quantification by RT-qPCR is presented as a box-plot and indicates the median copy number per mL plasma with individual donors plotted as shapes.

FIGS. 227 and 228 are a series of graphs depicting the ability of the EXO52 methods provided herein to capture total circulating nucleic acids. The EXO52 methods were compared to a commercially available circulating nucleic acid DNA isolation kit.

DETAILED DESCRIPTION OF THE INVENTION

Figure 1:
FIG. 1 is a schematic demonstrating one embodiment of the RNA and DNA isolation protocol for isolating a microvesicle fraction, releasing the microvesicle nucleic acids, and extracting RNA and DNA using two separate protocols.

The present invention provides methods of isolating cell-free DNA (cfDNA) and/or cfDNA and nucleic acids including at least RNA from microvesicles by capturing the DNA and the microvesicles to a surface, subsequently lysing the microvesicles to release the nucleic acids, particularly RNA, contained therein, and eluting the DNA and/or DNA and nucleic acids including at least RNA from the capture surface. Microvesicles are shed by eukaryotic cells, or budded off of the plasma membrane, to the exterior of the cell. These membrane vesicles are heterogeneous in size with diameters ranging from about 10 nm to about 5000 nm. All membrane vesicles shed by cells<0.8 µm in diameter are referred to herein collectively as "microvesicles." These microvesicles include microvesicles, microvesicle-like particles, prostasomes, dexosomes, texosomes, ectosomes, oncosomes, apoptotic bodies, retrovirus-like particles, and human endogenous retrovirus (HERV) particles. Small microvesicles (approximately 10 to 1000 nm, and more often 30 to 200 nm in diameter) that are released by exocytosis of intracellular multivesicular bodies are referred to in the art as "microvesicles."

Current methods of isolating DNA and/or DNA and nucleic acids including at least RNA from microvesicles include ultracentrifugation, ultrafiltration, e.g., using 100 kD filters, polymer precipitation techniques, and/or filtration based on size. However, there exists a need for alternative methods that are efficient and effective for isolating microvesicles and, optionally, extracting the nucleic acids contained therein, preferably microvesicle RNA, for use in a variety of applications, including diagnostic purposes.

The isolation and extraction methods and/or kits provided herein referred to as the EXO52 DNA and/or DNA and RNA isolation methods and/or kits use a spin-column based purification process using an affinity membrane that binds cell free DNA and/or microvesicles. The methods and kits of the disclosure allow for the capability to run large numbers of clinical samples in parallel, using volumes from 0.2 up to 4 mL on a single column. The cell-free DNA isolated using the EXO52 procedure is highly pure. The isolated RNA is highly pure, protected by a vesicle membrane until lysis, and intact vesicles can be eluted from the EXO52 membrane. The EXO52 procedure is able to deplete substantially all cell-free DNA from plasma input, and is equal to or better in DNA yield when compared to commercially available circulating DNA isolation kits. The EXO52 procedure is able to deplete substantially all mRNA from plasma input, and is equal or better in mRNA/miRNA yield when compared to ultracentrifugation or direct lysis. In contrast to commercially available kits and/or previous isolation methods, the EXO52 methods and/or kits enrich for the microvesicle bound fraction of miRNAs, and they are easily scalable to large amounts of input material. This ability to scale up enables research on interesting, low abundant transcripts. In comparison with other commercially available products on the market, the methods and kits of the disclosure provide unique capabilities that are demonstrated by the examples provided herein.

The EXO52 methods and kits isolate and extract nucleic acids, e.g., DNA and/or DNA and nucleic acids including at least RNA from a biological sample using the following the general procedure. First, the sample, including the cfDNA and the microvesicle fraction, is bound to a membrane filter, and the filter is washed. Then, a phenol-based reagent is used to perform on-membrane lysis and release of the nucleic acids, e.g., DNA and/or DNA and RNA. Chloroform extraction is then performed using PLG tubes, followed by ethanol conditioning. The nucleic acids, e.g., DNA and/or DNA and RNA, is then bound to a silica column, washed and then eluted. The extracted nucleic acids, e.g., DNA and/or DNA and RNA, can then be further analyzed, for example, using any of a variety of downstream assays.

In some embodiments, the method includes the following steps. The filter is contained in spin column. Prior to addition of the lysis reagent, the sample is bound to a membrane filter in a spin column, and the spin column is then spun for 1 min at approximately 500×g. The flow-through is then discarded, a buffer is added to the spin column, and the spin column is spun again for 5 min at approximately 5000×g to remove residual volume from the column. The flow-through is discarded after this second spin. The spin column is then contacted with the phenol-based lysis reagent and spun for 5 min at approximately 5000×g to collect the homogenate containing the lysed microvesicles and captured cfDNA. In some embodiments, the lysis buffer is a phenol-based lysis buffer. For example, the lysis buffer is QIAzol® lysis reagent (Qiagen). The homogenate is then subject to nucleic acid isolation and extraction. In some embodiments, a control for RNA isolation efficiency, such as, for example, Q-beta or any other control described herein, is spiked-in to the homogenate prior to nucleic acid isolation and extraction.

In some embodiments, the nucleic acid is isolated according to the following steps. After addition of the lysis reagent, chloroform is then added to the homogenate, and the solution is mixed vigorously for a brief time period. In some embodiments, 350 μl chloroform is added to the homogenate. The solution is then centrifuged for 5 min at 12,000×g at 4° C. The upper aqueous phase is then transferred to a new collection tube, and 2 volumes of 100% ethanol is added to the upper aqueous phase, and the solution is mixed. The solution can then be processed using any of a variety of art-recognized methods for isolating and/or extracting nucleic acids.

The isolated nucleic acids, e.g., DNA and/or DNA and RNA, can then be subject to further analysis using any of a variety of downstream assays. In some embodiments, the combined detection of DNA and RNA is used to increase the sensitivity for actionable mutations. There are multiple potential sources of detectable mutations in circulating nucleic acids. For example, living tumor cells are a potential source for RNA and DNA isolated from the microvesicle fraction of a sample, and dying tumor cells are potential sources for cell-free DNA sources such as, for example, apoptotic vesicle DNA and cell-free DNA from necrotic tumor cells. As mutated nucleic acids are relatively infrequent in circulation, the maximization of detection sensitivity becomes very important. Combined isolation of DNA and RNA delivers comprehensive clinical information to assess progression of disease and patient response to therapy. However, in contrast to the methods and kits provided herein, commercially available kits for detecting circulating nucleic acids are only able to isolate cfDNA from plasma, i.e., from dying cells. As shown in FIGS. 227-228, EXO52 captured all cfDNA, and EXO52 detected significantly more copies combining exoRNA and cfDNA vs. cfDNA alone. Those of ordinarily skill in the art will appreciate that more copies of a mutation or other biomarker leads to enhanced sensitivity and accuracy in identifying mutations and other biomarkers.

As used herein, the term "nucleic acids" refer to DNA and RNA. The nucleic acids can be single stranded or double stranded. In some instances, the nucleic acid is DNA. In some instances, the nucleic acid is RNA. RNA includes, but is not limited to, messenger RNA, transfer RNA, ribosomal RNA, non-coding RNAs, microRNAs, and HERV elements.

As used herein, the term "biological sample" refers to a sample that contains biological materials such as DNA, RNA and protein.

In some embodiments, the biological sample may suitably comprise a bodily fluid from a subject. The bodily fluids can be fluids isolated from anywhere in the body of the subject, such as, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and cell culture supernatant, and combinations thereof. Biological samples can also include fecal or cecal samples, or supernatants isolated therefrom.

In some embodiments, the biological sample may suitably comprise cell culture supernatant.

In some embodiments, the biological sample may suitably comprise a tissue sample from a subject. The tissue sample can be isolated from anywhere in the body of the subject.

A suitable sample volume of a bodily fluid is, for example, in the range of about 0.1 ml to about 30 ml fluid. The volume of fluid may depend on a few factors, e.g., the type of fluid used. For example, the volume of serum samples may be about 0.1 ml to about 4 ml, preferably about 0.2 ml to 4 ml. The volume of plasma samples may be about 0.1 ml to about 4 ml, preferably 0.5 ml to 4 ml. The volume of urine samples may be about 10 ml to about 30 ml, preferably about 20 ml.

While the examples provided herein used plasma samples, the skilled artisan will appreciate that these methods are applicable to a variety of biological samples.

The methods and kits of the disclosure are suitable for use with samples derived from a human subject. The methods and kits of the disclosure are suitable for use with samples derived from a human subject. In addition, the methods and kits of the disclosure are also suitable for use with samples derived from a human subject. The methods and kits of the disclosure are suitable for use with samples derived from a non-human subject such as, for example, a rodent, a non-human primate, a companion animal (e.g., cat, dog, horse), and/or a farm animal (e.g., chicken).

The term "subject" is intended to include all animals shown to or expected to have nucleic acid-containing particles. In particular embodiments, the subject is a mammal, a human or nonhuman primate, a dog, a cat, a horse, a cow, other farm animals, or a rodent (e.g. mice, rats, guinea pig. etc.). A human subject may be a normal human being without observable abnormalities, e.g., a disease. A human subject may be a human being with observable abnormalities, e.g., a disease. The observable abnormalities may be observed by the human being himself, or by a medical professional. The term "subject," "patient," and "individual" are used interchangeably herein.

While the working examples provided herein use a membrane as the capture surface, it should be understood that the format of the capturing surface, e.g., beads or a filter (also referred to herein as a membrane), does not affect the ability of the methods provided herein to efficiently capture microvesicles from a biological sample.

While the examples provided herein use chloroform during the extraction step, those of ordinary skill in the art will appreciate that any chemical that performs the same task as chloroform during nucleic acid extraction can be used in the methods provided herein. By way of non-limiting example, suitable chemicals for use in the extraction step include dichloromethane, toluene, hexane, MTBE, and ethyl acetate (EtOAc).

A wide range of surfaces are capable of capturing microvesicles according to the methods provided herein, but not all surfaces will capture microvesicles (some surfaces do not capture anything).

The present disclosure also describes a device for isolating and concentrating microvesicles from biological or clinical samples using disposable plastic parts and centrifuge equipment. For example, the device comprises a column comprising a capture surface (i.e., a membrane filter), a holder that secures the capture surface between the outer frit and an inner tube, and a collection tube. The outer frit comprises a large net structure to allow passing of liquid, and is preferably at one end of the column. The inner tube holds the capture surface in place, and preferably is slightly conus-shaped. The collection tube may be commercially available, i.e., 50 ml Falcon tube. The column is preferably suitable for spinning, i.e., the size is compatible with standard centrifuge and micro-centrifuge machines.

In embodiments where the capture surface is a membrane, the device for isolating the microvesicle fraction from a biological sample contains at least one membrane. In some embodiments, the device comprises one, two, three, four, five or six membranes. In some embodiments, the device comprises three membranes. In embodiments where the device comprises more than one membrane, the membranes are all directly adjacent to one another at one end of the column. In embodiments where the device comprises more than one membrane, the membranes are all identical to each other, i.e., are of the same charge and/or have the same functional group.

It should be noted that capture by filtering through a pore size smaller than the microvesicles is not the primary mechanism of capture by the methods provided herein. However, filter pore size is nevertheless very important, e.g. because mRNA gets stuck on a 20 nm filter and cannot be recovered, whereas microRNAs can easily be eluted off, and e.g. because the filter pore size is an important parameter in available surface capture area.

The methods provided herein use any of a variety of capture surfaces. In some embodiments, the capture surface is a membrane, also referred to herein as a filter or a membrane filter. In some embodiments, the capture surface is a commercially available membrane. In some embodiments, the capture surface is a charged commercially available membrane. In some embodiments, the capture surface is neutral. In some embodiments, the capture surface is selected from Mustang® Ion Exchange Membrane from PALL Corporation; Vivapure® Q membrane from Sartorius AG; Sartobind Q, or Vivapure® Q Maxi H; Sartobind® D from Sartorius AG, Sartobind (S) from Sartorius AG, Sartobind® Q from Sartorius AG, Sartobind® IDA from Sartorius AG, Sartobind® Aldehyde from Sartorius AG, Whatman® DE81 from Sigma, Fast Trap Virus Purification column from EMD Millipore; Thermo Scientific* Pierce Strong Cation and Anion Exchange Spin Columns.

In embodiments where the capture surface is charged, the capture surface can be a charged filter selected from the group consisting of 0.65 um positively charged Q PES vacuum filtration (Millipore), 3-5 um positively charged Q RC spin column filtration (Sartorius), 0.8 um positively charged Q PES homemade spin column filtration (Pall), 0.8 um positively charged Q PES syringe filtration (Pall), 0.8 um negatively charged S PES homemade spin column filtration (Pall), 0.8 um negatively charged S PES syringe filtration (Pall), and 50 nm negatively charged nylon syringe filtration (Sterlitech). Preferably, the charged filter is not housed in a syringe filtration apparatus, as Qiazol/RNA is harder to get out of the filter in these embodiments. Preferably, the charged filter is housed at one end of a column.

In embodiments where the capture surface is a membrane, the membrane can be made from a variety of suitable materials. In some embodiments, the membrane is polyethersulfone (PES) (e.g., from Millipore or PALL Corp.). In some embodiments, the membrane is regenerated cellulose (RC) (e.g., from Sartorius or Pierce).

In some embodiments, the capture surface is a positively charged membrane. In some embodiments, the capture surface is a Q membrane, which is a positively charged membrane and is an anion exchanger with quaternary amines. For example, the Q membrane is functionalized with quaternary ammonium, R—CH$_2$—N$^+$(CH$_3$)$_3$. In some embodiments, the capture surface is a negatively charged membrane. In some embodiments, the capture surface is an S membrane, which is a negatively charged membrane and is a cation exchanger with sulfonic acid groups. For example, the S membrane is functionalized with sulfonic acid, R—CH$_2$—SO$_3^-$. In some embodiments, the capture surface is a D membrane, which is a weak basic anion exchanger with diethylamine groups, R—CH$_2$—NH$^+$(C$_2$H$_5$)$_2$. In some embodiments, the capture surface is a metal chelate membrane. For example, the membrane is an IDA membrane, functionalized with minodiacetic acid —N(CH$_2$COOH$^-$)$_2$. In some embodiments, the capture surface is a microporous membrane, functionalized with aldehyde groups, —CHO. In other embodiments, the membrane is a weak basic anion exchanger, with diethylaminoethyl (DEAE) cellulose. Not all charged membranes are suitable for use in the methods provided herein, e.g., RNA isolated using Sartorius Vivapure S membrane spin column showed RT-qPCR inhibition and, thus, unsuitable for PCR related downstream assay.

In embodiments where the capture surface is charged, microvesicles can be isolated with a positively charged filter.

In embodiments where the capture surface is charged, the pH during microvesicle capture is a pH≤7. In some embodiments, the pH is greater than 4 and less than or equal to 8.

In embodiments where the capture surface is a positively charged Q filter, the buffer system includes a wash buffer comprising 250 mM Bis Tris Propane, pH 6.5-7.0. In embodiments where the capture surface is a positively charged Q filter, the lysis buffer is Qiazol. In embodiments where the capture surface is a positively charged Q filter, the lysis buffer is present at one volume. In embodiments where the capture surface is a positively charged Q filter, the lysis buffer is present at more than one volume.

Depending on the membrane material, the pore sizes of the membrane range from 3 µm to 20 nm.

The surface charge of the capture surface can be positive, negative or neutral. In some embodiments, the capture surface is a positively charged bead or beads.

The methods provided herein include a lysis reagent. In some embodiments, the agent used for on-membrane lysis is a phenol-based reagent. In some embodiments, the lysis reagent is a guanidinium-based reagent. In some embodiments, the lysis reagent is a high salt based buffer. In some embodiments, the lysis reagent is QIAzol.

The methods provided herein include a variety of buffers including loading and wash buffers. Loading and wash buffers can be of high or low ionic strength. The salt concentration, e.g., NaCl concentration, can be from 0 to 2.4M. The buffers can include a variety of components. In some embodiments, the buffers include one or more of the following components: Tris, Bis-Tris, Bis-Tris-Propane, Imidazole, Citrate, Methyl Malonic Acid, Acetic Acid, Ethanolamine, Diethanolamine, Triethanolamine (TEA) and Sodium phosphate. In the methods provided herein, the pH of loading and wash buffers is important. Filters tend to clog when plasma samples at set to pH≤5.5 before loading (the plasma will not spin through the column at all), and at higher pH microvesicle RNA recovery is lower due to instability of the microvesicles. At neutral pH, the RNA recovery from microvesicles is optimal. In some embodiments, the buffer used is at 1× concentration, 2× concentration, 3× concentration, or 4× concentration. For example, the loading or binding buffer is at 2× concentration while the wash buffer is at 1× concentration.

In some embodiments, the methods include one or more wash steps, for example, after contacting the biological sample with the capture surface. In some embodiments, detergents are added to the wash buffer to facilitate removing the non-specific binding (i.e., contaminants, cell debris, and circulating protein complexes or nucleic acids), to obtain a more pure microvesicle fraction. Detergents suitable for use include, but are not limited to, sodium dodecyl sulfate (SDS), Tween-20, Tween-80, Triton X-100, Nonidet P-40 (NP-40), Brij-35, Brij-58, octyl glucoside, octyl thioglucoside, CHAPS or CHAPSO.

In some embodiments, the capture surface, e.g., membrane, is housed within a device used for centrifugation; e.g.

spin columns, or for vacuum system e.g. vacuum filter holders, or for filtration with pressure e.g. syringe filters. In a preferred embodiment, the capture surface is housed in a spin column or vacuum system.

The isolation of microvesicles from a biological sample prior to extraction of nucleic acids is advantageous for the following reasons: 1) extracting nucleic acids from microvesicles provides the opportunity to selectively analyze disease or tumor-specific nucleic acids obtained by isolating disease or tumor-specific microvesicles apart from other microvesicles within the fluid sample; 2) nucleic acid-containing microvesicles produce significantly higher yields of nucleic acid species with higher integrity as compared to the yield/integrity obtained by extracting nucleic acids directly from the fluid sample without first isolating microvesicles; 3) scalability, e.g., to detect nucleic acids expressed at low levels, the sensitivity can be increased by concentrating microvesicles from a larger volume of sample using the methods described herein; 4) more pure or higher quality/integrity of extracted nucleic acids in that proteins, lipids, cell debris, cells and other potential contaminants and PCR inhibitors that are naturally found within biological samples are excluded before the nucleic acid extraction step; and 5) more choices in nucleic acid extraction methods can be utilized as isolated microvesicle fractions can be of a smaller volume than that of the starting sample volume, making it possible to extract nucleic acids from these fractions or pellets using small volume column filters.

Several methods of isolating microvesicles from a biological sample have been described in the art. For example, a method of differential centrifugation is described in a paper by Raposo et al. (Raposo et al., 1996), a paper by Skog et. al. (Skog et al., 2008) and a paper by Nilsson et. al. (Nilsson et al., 2009). Methods of ion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et al. (Miranda et al., 2010). Further, microvesicles may be identified and isolated from bodily fluid of a subject by a microfluidic device (Chen et al., 2010). In research and development, as well as commercial applications of nucleic acid biomarkers, it is desirable to extract high quality nucleic acids from biological samples in a consistent, reliable, and practical manner.

An object of the present invention is therefore to provide a method for quick and easy isolation of nucleic acid-containing particles from biological samples such as body fluids and extraction of high quality nucleic acids from the isolated particles. The method of the invention may be suitable for adaptation and incorporation into a compact device or instrument for use in a laboratory or clinical setting, or in the field.

In some embodiments, the sample is not pre-processed prior to isolation and extraction of nucleic acids, e.g., DNA and/or DNA and RNA, from the biological sample.

In some embodiments, the sample is subjected to a pre-processing step prior to isolation, purification or enrichment of the microvesicles is performed to remove large unwanted particles, cells and/or cell debris and other contaminants present in the biological sample. The pre-processing steps may be achieved through one or more centrifugation steps (e.g., differential centrifugation) or one or more filtration steps (e.g., ultrafiltration), or a combination thereof. Where more than one centrifugation pre-processing steps are performed, the biological sample may be centrifuged first at the lower speed and then at the higher speed. If desired, further suitable centrifugation pre-processing steps may be carried out. Alternatively or in addition to the one or more centrifugation pre-processing steps, the biological sample may be filtered. For example, a biological sample may be first centrifuged at 20,000 g for 1 hour to remove large unwanted particles; the sample can then be filtered, for example, through a 0.8 µm filter.

In some embodiments, the sample is pre-filtered to exclude particles larger than 0.8 µm. In some embodiments, the sample includes an additive such as EDTA, sodium citrate, and/or citrate-phosphate-dextrose. Preferably, the sample does not contain heparin, as heparin can negatively impact RT-qPCR and other nucleic acid analysis. In some embodiments, the sample is mixed with a buffer prior to purification and/or nucleic acid isolation and/or extraction. In some embodiments, the buffer is XBP buffer.

In some embodiments, one or more centrifugation steps are performed before or after contacting the biological sample with the capture surface to separate microvesicles and concentrate the microvesicles isolated from the biological fraction. For example, the sample is centrifuged at 20,000 g for 1 hour at 4° C. To remove large unwanted particles, cells, and/or cell debris, the samples may be centrifuged at a low speed of about 100-500 g, preferably about 250-300 g. Alternatively or in addition, the samples may be centrifuged at a higher speed. Suitable centrifugation speeds are up to about 200,000 g; for example from about 2,000 g to less than about 200,000 g. Speeds of above about 15,000 g and less than about 200,000 g or above about 15,000 g and less than about 100,000 g or above about 15,000 g and less than about 50,000 g are preferred. Speeds of from about 18,000 g to about 40,000 g or about 30,000 g; and from about 18,000 g to about 25,000 g are more preferred. Particularly preferred is a centrifugation speed of about 20,000 g. Generally, suitable times for centrifugation are from about 5 minutes to about 2 hours, for example, from about 10 minutes to about 1.5 hours, or more preferably from about 15 minutes to about 1 hour. A time of about 0.5 hours may be preferred. It is sometimes preferred to subject the biological sample to centrifugation at about 20,000 g for about 0.5 hours. However the above speeds and times can suitably be used in any combination (e.g., from about 18,000 g to about 25,000 g, or from about 30,000 g to about 40,000 g for about 10 minutes to about 1.5 hours, or for about 15 minutes to about 1 hour, or for about 0.5 hours, and so on). The centrifugation step or steps may be carried out at below-ambient temperatures, for example at about 0-10° C., preferably about 1-5° C., e.g., about 3° C. or about 4° C.

In some embodiments, one or more filtration steps are performed before or after contacting the biological sample with the capture surface. A filter having a size in the range about 0.1 to about 1.0 µm may be employed, preferably about 0.8 µm or 0.22 µm. The filtration may also be performed with successive filtrations using filters with decreasing porosity.

In some embodiments, one or more concentration steps are performed, in order to reduce the volumes of sample to be treated during the chromatography stages, before or after contacting the biological sample with the capture surface. Concentration may be through centrifugation of the sample at high speeds, e.g. between 10,000 and 100,000 g, to cause the sedimentation of the microvesicles. This may consist of a series of differential centrifugations. The microvesicles in the pellet obtained may be reconstituted with a smaller volume and in a suitable buffer for the subsequent steps of the process. The concentration step may also be performed by ultrafiltration. In fact, this ultrafiltration both concentrates the biological sample and performs an additional purification of the microvesicle fraction. In another embodiment, the filtration is an ultrafiltration, preferably a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibers (Amicon, Millipore, Sartorius, Pall, GF, Sepracor). Within the scope of the invention, the use of membranes with a cut-off threshold below 1000 kDa, preferably between 100 kDa and 1000 kDa, or even more preferably between 100 kDa and 600 kDa, is advantageous.

In some embodiments, one or more size-exclusion chromatography steps or gel permeation chromatography steps are performed before or after contacting the biological sample with the capture surface. To perform the gel permeation chromatography step, a support selected from silica, acrylamide, agarose, dextran, ethylene glycol-methacrylate co-polymer or mixtures thereof, e.g., agarose-dextran mixtures, are preferably used. For example, such supports include, but are not limited to: SUPERDEX® 200HR (Pharmacia), TSK G6000 (TosoHaas) or SEPHACRYL® S (Pharmacia).

In some embodiments, one or more affinity chromatography steps are performed before or after contacting the biological sample with the capture surface. Some microvesicles can also be characterized by certain surface molecules. Because microvesicles form from budding of the cell plasma membrane, these microvesicles often share many of the same surface molecules found on the cells they originated from. As used herein, "surface molecules" refers collectively to antigens, proteins, lipids, carbohydrates, and markers found on the surface or in or on the membrane of the microvesicle. These surface molecules can include, for example, receptors, tumor-associated antigens, membrane protein modifications (e.g., glycosylated structures). For example, microvesicles that bud from tumor cells often display tumor-associated antigens on their cell surface. As such, affinity chromatography or affinity exclusion chromatography can also be utilized in combination with the methods provided herein to isolate, identify, and or enrich for specific populations of microvesicles from a specific donor cell type (Al-Nedawi et al., 2008; Taylor and Gercel-Taylor, 2008). For example, tumor (malignant or non-malignant) microvesicles carry tumor-associated surface antigens and may be detected, isolated and/or enriched via these specific tumor-associated surface antigens. In one example, the surface antigen is epithelial cell adhesion molecule (EpCAM), which is specific to microvesicles from carcinomas of long, colorectal, breast, prostate, head and neck, and hepatic origin, but not of hematological cell origin (Balzar et al., 1999; Went et al., 2004). Additionally, tumor-specific microvesicles can also be characterized by the lack of certain surface markers, such as CD80 and CD86. In these cases, microvesicles with these markers may be excluded for further analysis of tumor specific markers, e.g., by affinity exclusion chromatography. Affinity chromatography can be accomplished, for example, by using different supports, resins, beads, antibodies, aptamers, aptamer analogs, molecularly imprinted polymers, or other molecules known in the art that specifically target desired surface molecules on microvesicles.

Optionally, control particles may be added to the sample prior to microvesicle isolation or nucleic acid extraction to serve as an internal control to evaluate the efficiency or quality of microvesicle purification and/or nucleic acid extraction. The methods described herein provide for the efficient isolation and the control particles along with the microvesicle fraction. These control particles include Q-beta bacteriophage, virus particles, or any other particle that contains control nucleic acids (e.g., at least one control target gene) that may be naturally occurring or engineered by recombinant DNA techniques. In some embodiments, the quantity of control particles is known before the addition to the sample. The control target gene can be quantified using real-time PCR analysis. Quantification of a control target gene can be used to determine the efficiency or quality of the microvesicle purification or nucleic acid extraction processes.

Preferably, the control particle is a Q-beta bacteriophage, referred to herein as "Q-beta particle." The Q-beta particle used in the methods described herein may be a naturally-occurring virus particle or may be a recombinant or engineered virus, in which at least one component of the virus particle (e.g., a portion of the genome or coat protein) is synthesized by recombinant DNA or molecular biology techniques known in the art. Q-beta is a member of the leviviridae family, characterized by a linear, single-stranded RNA genome that consists of 3 genes encoding four viral proteins: a coat protein, a maturation protein, a lysis protein, and RNA replicase. Due to its similar size to average microvesicles, Q-beta can be easily purified from a biological sample using the same purification methods used to isolate microvesicles, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. After addition of the Q-beta particles to the biological sample, the nucleic acids from the Q-beta particle are extracted along with the nucleic acids from the biological sample using the extraction methods described herein. Detection of the Q-beta control target gene can be determined by RT-PCR analysis, for example, simultaneously with the biomarker(s) of interest. A standard curve of at least 2, 3, or 4 known concentrations in 10-fold dilution of a control target gene can be used to determine copy number. The copy number detected and the quantity of Q-beta particle added can be compared to determine the quality of the isolation and/or extraction process.

In a preferred embodiment, the Q-beta particles are added to the urine sample prior to nucleic extraction. For example, the Q-beta particles are added to the urine sample prior to ultrafiltration and/or after the pre-filtration step.

In some embodiments, 50, 100, 150, 200, 250, 300, 350, 400, 450, 500, 1,000 or 5,000 copies of Q-beta particles added to a bodily fluid sample. In a preferred embodiment, 100 copies of Q-beta particles are added to a bodily fluid sample. The copy number of Q-beta particles can be calculated based on the ability of the Q-beta bacteriophage to infect target cells. Thus, the copy number of Q-beta particles is correlated to the colony forming units of the Q-beta bacteriophage.

Nucleic Acid Extraction

The present invention is directed towards the use of a capture surface for the improved isolation, purification, or enrichment of microvesicles. The methods disclosed herein provide a highly enriched microvesicle fraction for extraction of high quality nucleic acids from said microvesicles. The nucleic acid extractions obtained by the methods described herein may be useful for various applications in which high quality nucleic acid extractions are required or preferred, such as for use in the diagnosis, prognosis, or monitoring of diseases or medical conditions.

Recent studies reveal that nucleic acids within microvesicles have a role as biomarkers. For example, WO 2009/100029 describes, among other things, the use of nucleic acids extracted from microvesicles in GBM patient serum for medical diagnosis, prognosis and therapy evaluation. WO 2009/100029 also describes the use of nucleic acids extracted from microvesicles in human urine for the same purposes. The use of nucleic acids extracted from microvesicles is considered to potentially circumvent the need for biopsies, highlighting the enormous diagnostic potential of microvesicle biology (Skog et al., 2008).

The quality or purity of the isolated microvesicles can directly affect the quality of the extracted microvesicle nucleic acids, which then directly affects the efficiency and sensitivity of biomarker assays for disease diagnosis, prognosis, and/or monitoring. Given the importance of accurate and sensitive diagnostic tests in the clinical field, methods for isolating highly enriched microvesicle fractions from biological samples are needed. To address this need, the present invention provides methods for isolating microvesicles from biological sample for the extraction of high quality nucleic acids from a biological sample. As shown herein, highly enriched microvesicle fractions are isolated from biological samples by methods described herein, and wherein high quality nucleic acids subsequently extracted from the highly enriched microvesicle fractions. These high quality extracted nucleic acids are useful for measuring or assessing the presence or absence of biomarkers for aiding in the diagnosis, prognosis, and/or monitoring of diseases or other medical conditions.

As used herein, the term "high quality" in reference to nucleic acid extraction means an extraction in which one is able to detect 18S and 28S rRNA, preferably in a ratio of approximately 1:1 to approximately 1:2; and more preferably, approximately 1:2. Ideally, high quality nucleic acid extractions obtained by the methods described herein will also have an RNA integrity number of greater than or equal to 5 for a low protein biological sample (e.g., urine), or greater than or equal to 3 for a high protein biological sample (e.g., serum), and a nucleic acid yield of greater than or equal to 50 pg/ml from a 20 ml low protein biological sample or a 1 ml high protein biological sample.

High quality RNA extractions are desirable because RNA degradation can adversely affect downstream assessment of the extracted RNA, such as in gene expression and mRNA analysis, as well as in analysis of non-coding RNA such as small RNA and microRNA. The new methods described herein enable one to extract high quality nucleic acids from microvesicles isolated from a biological sample so that an accurate analysis of nucleic acids within the microvesicles can be performed.

Following the isolation of microvesicles from a biological sample, nucleic acid may be extracted from the isolated or enriched microvesicle fraction. To achieve this, in some embodiments, the microvesicles may first be lysed. The lysis of microvesicles and extraction of nucleic acids may be achieved with various methods known in the art. In some embodiments, the nucleic acid extraction may be achieved using phenol:chloroform according to standard procedures and techniques known in the art. Such methods may also utilize a nucleic acid-binding column to capture the nucleic acids contained within the microvesicles. Once bound, the nucleic acids can then be eluted using a buffer or solution suitable to disrupt the interaction between the nucleic acids and the binding column, thereby successfully eluting the nucleic acids.

In some embodiments, the nucleic acid extraction methods also include the step of removing or mitigating adverse factors that prevent high quality nucleic acid extraction from a biological sample. Such adverse factors are heterogeneous in that different biological samples may contain various species of adverse factors. In some biological samples, factors such as excessive DNA may affect the quality of nucleic acid extractions from such samples. In other samples, factors such as excessive endogenous RNase may affect the quality of nucleic acid extractions from such samples. Many agents and methods may be used to remove these adverse factors. These methods and agents are referred to collectively herein as an "extraction enhancement operations." In some instances, the extraction enhancement operation may involve the addition of nucleic acid extraction enhancement agents to the biological sample. To remove adverse factors such as endogenous RNases, such extraction enhancement agents as defined herein may include, but are not limited to, an RNase inhibitor such as Superase-In (commercially available from Ambion Inc.) or RNaseINplus (commercially available from Promega Corp.), or other agents that function in a similar fashion; a protease (which may function as an RNase inhibitor); DNase; a reducing agent; a decoy substrate such as a synthetic RNA and/or carrier RNA; a soluble receptor that can bind RNase; a small interfering RNA (siRNA); an RNA binding molecule, such as an anti-RNA antibody, a basic protein or a chaperone protein; an RNase denaturing substance, such as a high osmolarity solution, a detergent, or a combination thereof.

For example, the extraction enhancement operation may include the addition of an RNase inhibitor to the biological sample, and/or to the isolated microvesicle fraction, prior to extracting nucleic acid; preferably the RNase inhibitor has a concentration of greater than 0.027 AU (I X) for a sample equal to or more than 1 µl in volume; alternatively, greater than or equal to 0.135 AU (5×) for a sample equal to or more than 1 µl; alternatively, greater than or equal to 0.27 AU (10×) for a sample equal to or more than 1 µl; alternatively, greater than or equal to 0.675 AU (25×) for a sample equal to or more than 1 µl; and alternatively, greater than or equal to 1.35 AU (50×) for a sample equal to or more than 1 µl; wherein the I X concentration refers to an enzymatic condition wherein 0.027 AU or more RNase inhibitor is used to treat microvesicles isolated from 1 µl or more bodily fluid, the 5× concentration refers to an enzymatic condition wherein 0.135 AU or more RNase inhibitor is used to treat microvesicles isolated from 1 µl or more bodily fluid, the 10× protease concentration refers lo an enzymatic condition wherein 0.27 AU or more RNase inhibitor is used to treat particles isolated from 1 µl or more bodily fluid, the 25× concentration refers to an enzymatic condition wherein 0.675 AU or more RNase inhibitor is used to treat microvesicles isolated from 1 µl or more bodily fluid, and the 50× protease concentration refers to an enzymatic condition wherein 1.35 AU or more RNase inhibitor is used to treat particles isolated from 1 µl or more bodily fluid. Preferably, the RNase inhibitor is a protease, in which case, 1 AU is the protease activity that releases folin-positive amino acids and peptides corresponding to 1 µmol tyrosine per minute.

These enhancement agents may exert their functions in various ways, e.g., through inhibiting RNase activity (e.g., RNase inhibitors), through a ubiquitous degradation of proteins (e.g., proteases), or through a chaperone protein (e.g., a RNA-binding protein) that binds and protects RNAs. In all instances, such extraction enhancement agents remove or at least mitigate some or all of the adverse factors in the biological sample or associated with the isolated particles that would otherwise prevent or interfere with the high quality extraction of nucleic acids from the isolated particles.

In some embodiments, the quantification of 18S and 28S rRNAs extracted can be used determine the quality of the nucleic acid extraction.

Detection of Nucleic Acid Biomarkers

In some embodiments, the extracted nucleic acid comprises DNA and/or DNA and RNA. In embodiments where the extracted nucleic acid comprises DNA and RNA, the RNA is preferably reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first of reverse transcription to convert RNA into cDNA and a second step of quantifying the amount of cDNA using quantitative PCR. As demonstrated in the examples that follow, the RNAs extracted from nucleic acid-containing particles using the methods disclosed herein include many species of transcripts including, but not limited to, ribosomal 18S and 28S rRNA, microRNAs, transfer RNAs, transcripts that are associated with diseases or medical conditions, and biomarkers that are important for diagnosis, prognosis and monitoring of medical conditions.

For example, RT-PCR analysis determines a Ct (cycle threshold) value for each reaction. In RT-PCR, a positive reaction is detected by accumulation of a fluorescence signal. The Ct value is defined as the number of cycles required for the fluorescent signal to cross the threshold (i.e., exceeds background level). Ct levels are inversely proportional to the amount of target nucleic acid, or control nucleic acid, in the sample (i.e., the lower the Ct level, the greater the amount of control nucleic acid in the sample).

In another embodiment, the copy number of the control nucleic acid can be measured using any of a variety of art-recognized techniques, including, but not limited to, RT-PCR. Copy number of the control nucleic acid can be determined using methods known in the art, such as by generating and utilizing a calibration, or standard curve.

In some embodiments, one or more biomarkers can be one or a collection of genetic aberrations, which is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

The analysis of nucleic acids present in the isolated particles is quantitative and/or qualitative. For quantitative analysis, the amounts (expression levels), either relative or absolute, of specific nucleic acids of interest within the isolated particles are measured with methods known in the art (described below). For qualitative analysis, the species of specific nucleic acids of interest within the isolated microvesicles, whether wild type or variants, are identified with methods known in the art.

The present invention also includes various uses of the new methods of isolating microvesicles from a biological sample for high quality nucleic acid extraction from a for (i) aiding in the diagnosis of a subject, (ii) monitoring the progress or reoccurrence of a disease or other medical condition in a subject, or (iii) aiding in the evaluation of treatment efficacy for a subject undergoing or contemplating treatment for a disease or other medical condition; wherein the presence or absence of one or more biomarkers in the nucleic acid extraction obtained from the method is determined, and the one or more biomarkers are associated with the diagnosis, progress or reoccurrence, or treatment efficacy, respectively, of a disease or other medical condition.

Kits for Isolating Microvesicles From a Biological Sample

One aspect of the present invention is further directed to kits for use in the methods disclosed herein. The kit comprises a capture surface apparatus sufficient to separate microvesicles from a biological sample from unwanted particles, debris, and small molecules that are also present in the biological sample. The present invention also optionally includes instructions for using the foregoing reagents in the isolation and optional subsequent nucleic acid extraction process.

EXAMPLES

While the examples provided herein use a variety of membranes and devices used for centrifugation and/or filtration purposes, it is to be understood that these methods can be used with any capture surface and/or housing device that allows for the efficient capture of microvesicles and release of the nucleic acids, particularly, RNA, contained therein.

Example 1: EXO52 Isolation of DNA, as Well as Co-Isolation of RNA and DNA

This example demonstrates the ability of the EXO52 method to isolate all DNA from a plasma sample. It should be noted that in some of the Figures presented herein, various terminology has been used to identify precursor methods to the isolation methods referred to herein as EXO52. For example, some Figures include terms such as old EXO52, EXO52.1, and variations thereof. These earlier versions are provided solely as a comparison and to demonstrate the superior isolation achieved using the EXO52 methods of the disclosure. The use of the term EXO52.2 is the EXO52 method where the RNA and DNA extraction is performed in a single tube.

Figure 2:
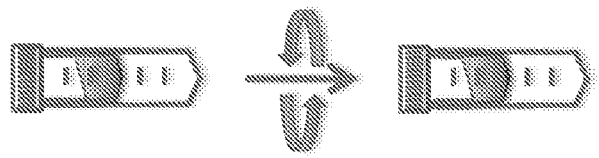
FIG. 2 is a schematic demonstrating another embodiment of the RNA and DNA isolation protocol for isolating a microvesicle fraction, releasing the microvesicle nucleic acids, and extracting RNA and DNA using a single protocol.
Figure 3:
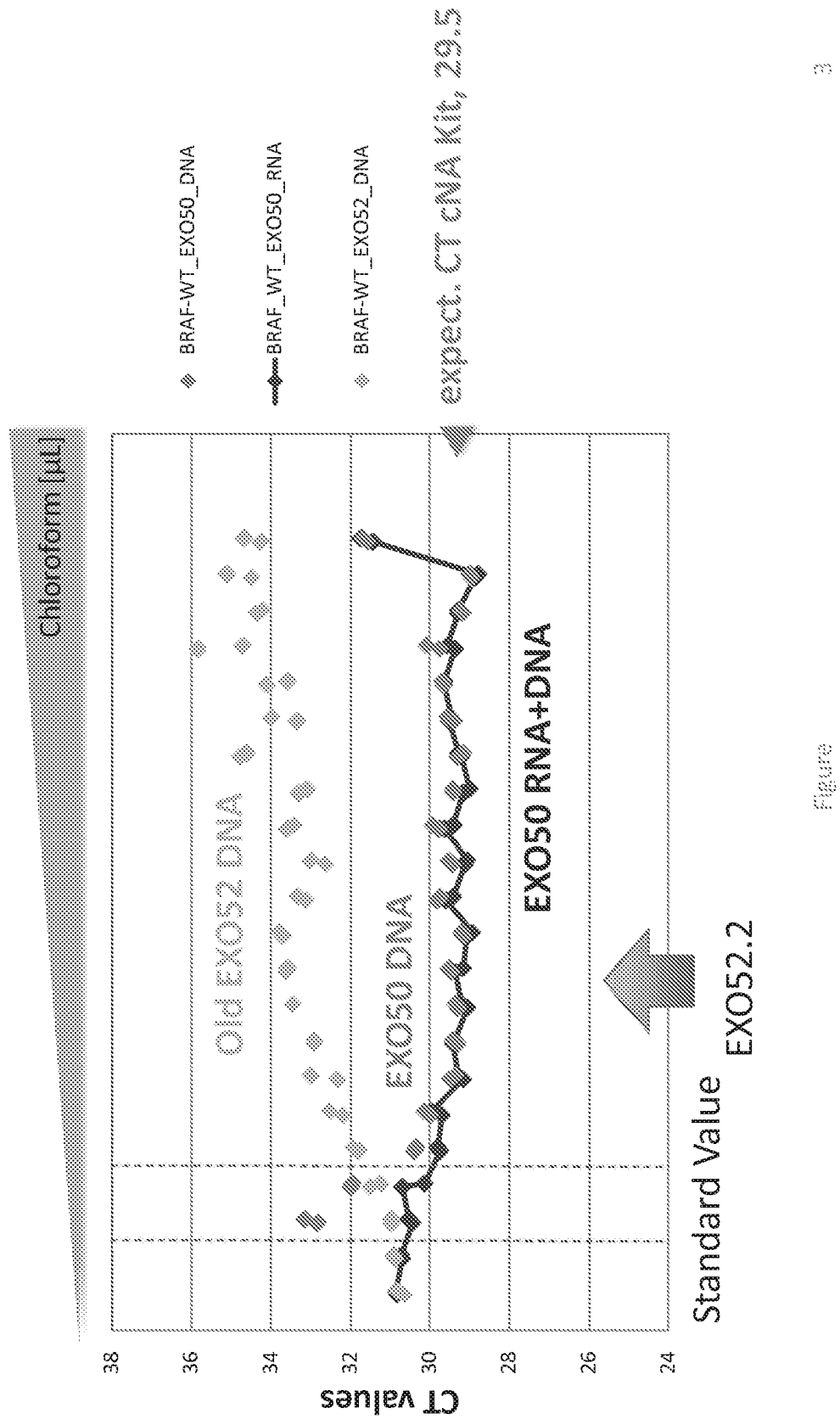
FIG. 3 is a graph showing the effect of chloroform concentration in phase separation for isolating microvesicle RNA and DNA in a single extraction, as demonstrated by detection of wild-type BRAF RNA and DNA.
Figure 4:
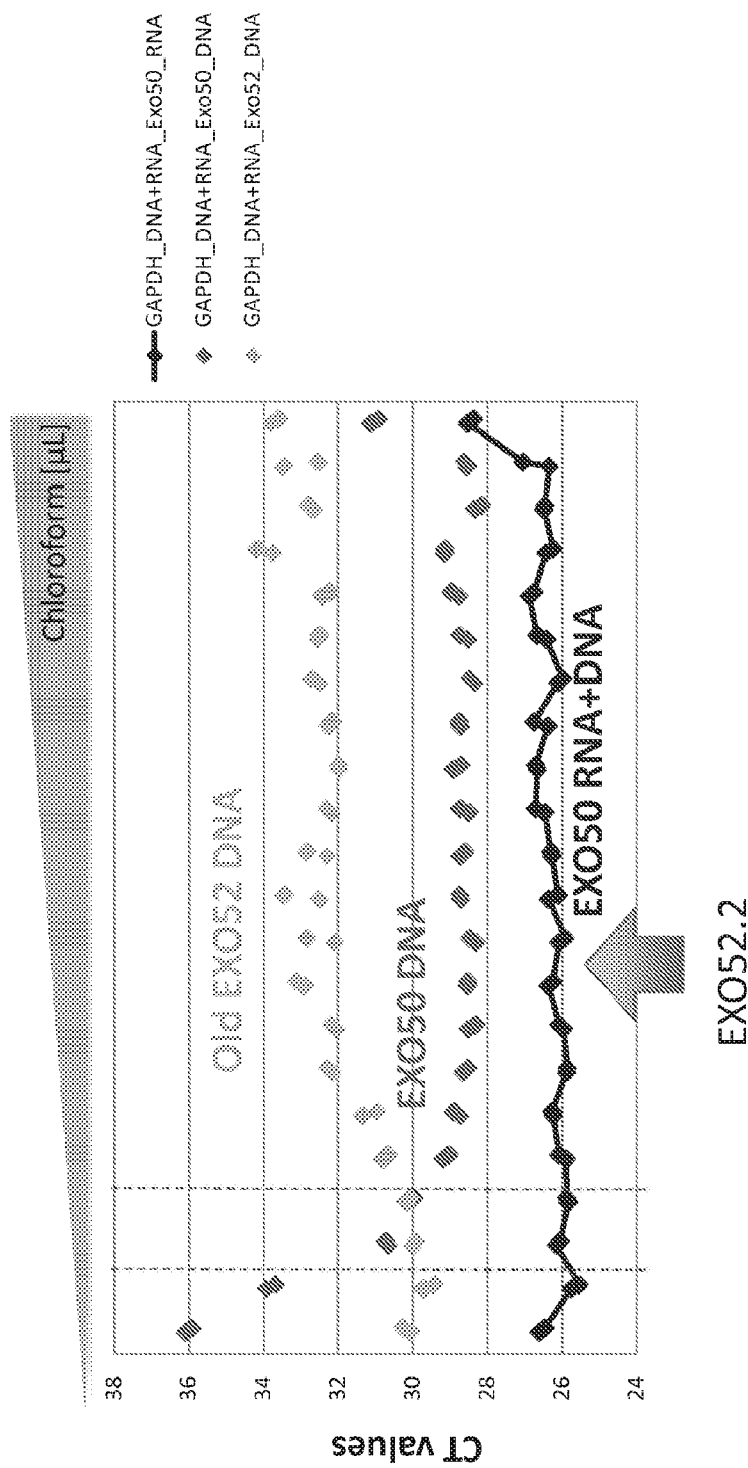
FIG. 4 is a graph showing the effect of chloroform concentration in phase separation for isolating microvesicle RNA and DNA in a single extraction, as demonstrated by detection of GAPDH RNA and DNA.
Figure 5:
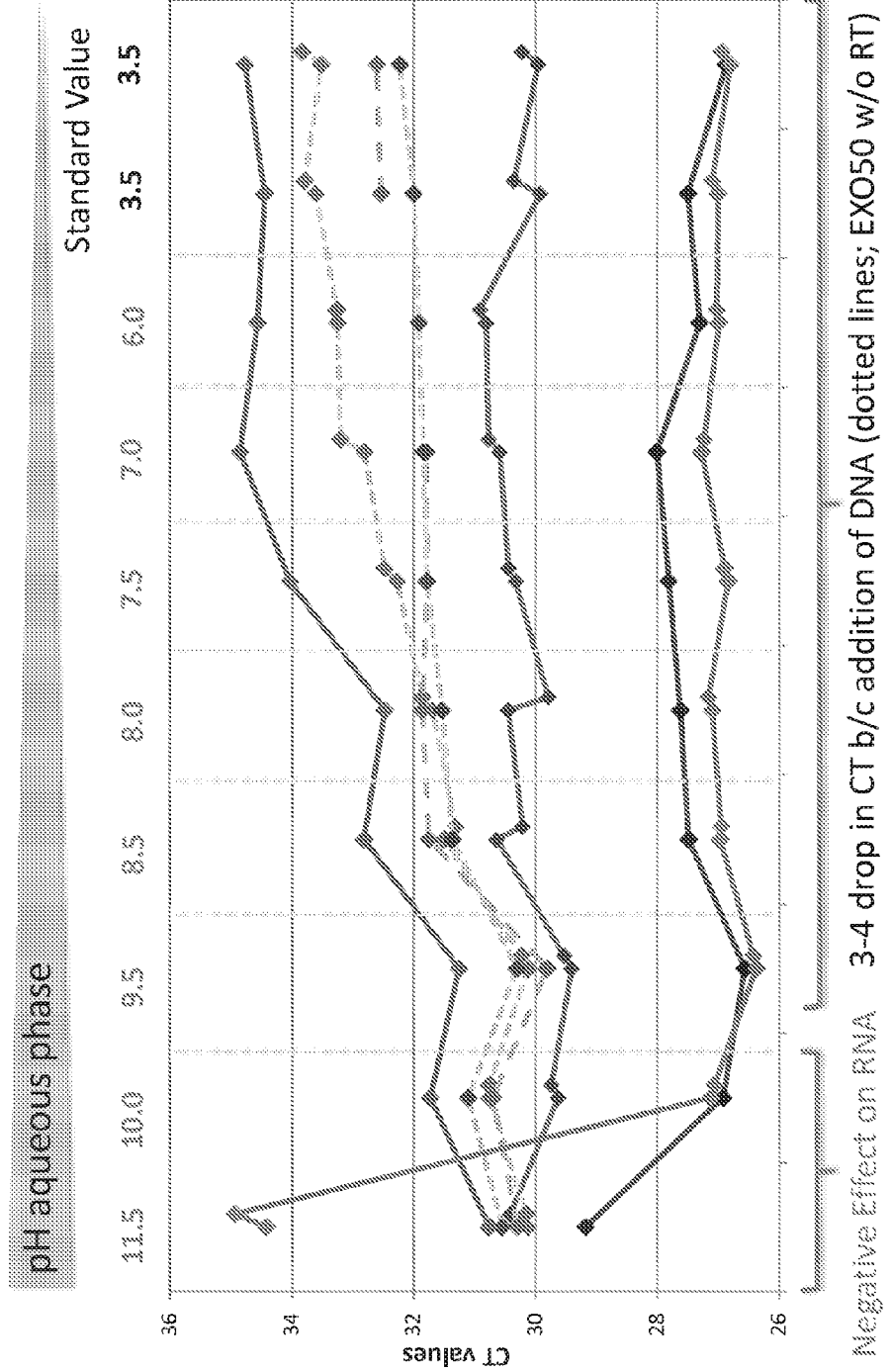
FIG. 5 is a graph showing that the adjustment of pH in phase separation influences the DNA extraction and detection.
Figure 6:
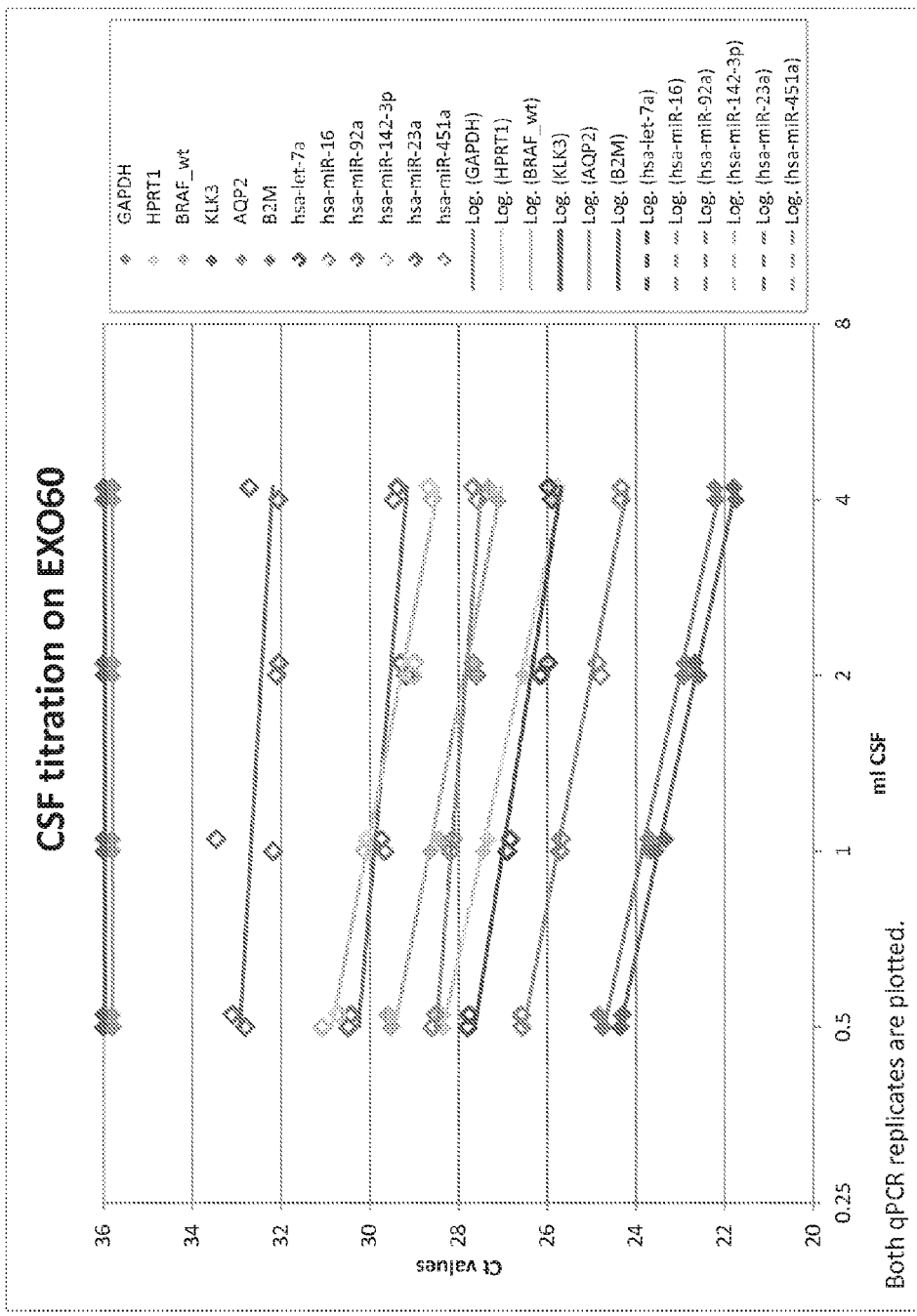
FIG. 6 is a graph showing the effect of titration of sample volume of cerebrospinal fluid (CSF) on microvesicle RNA extraction and detection.
Figure 7:
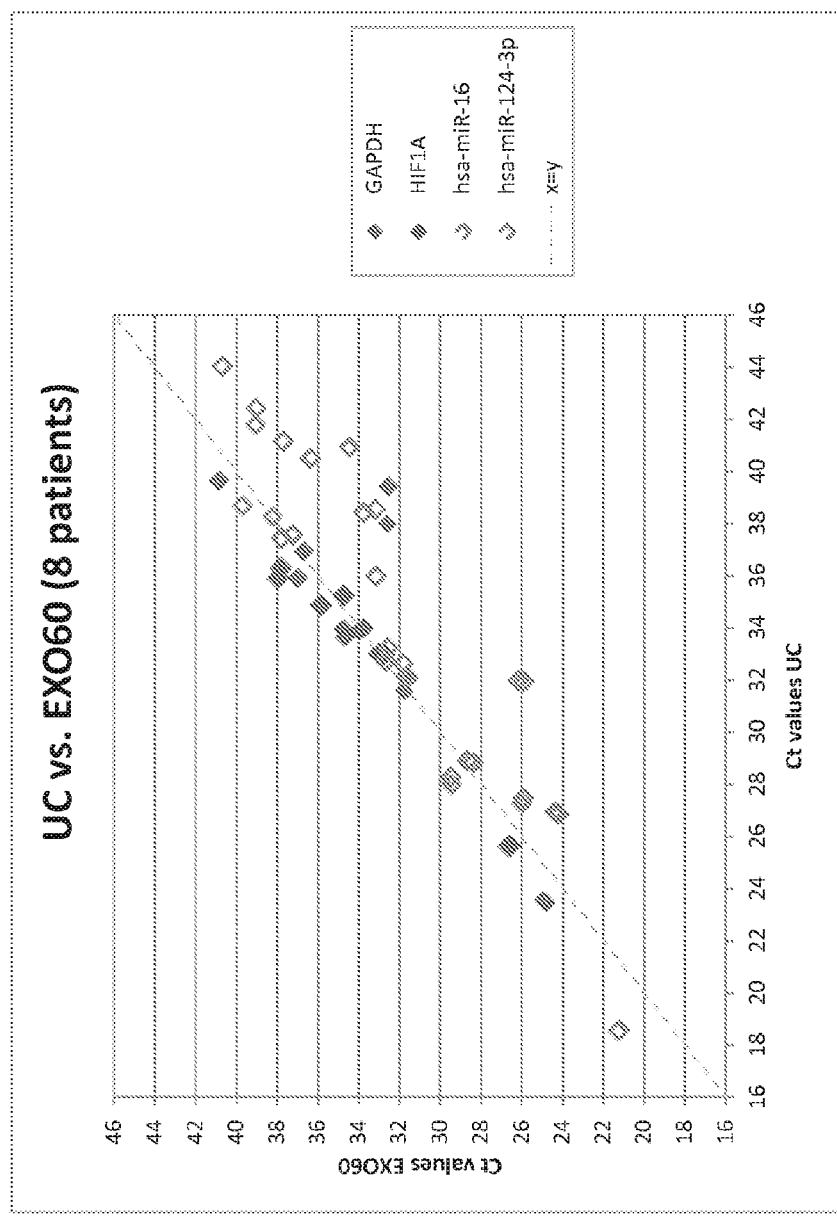
FIG. 7 is a graph showing the comparison of detection of microvesicle RNA targets from ultracentrifugation and EXO60 isolation methods.
Figure 8:
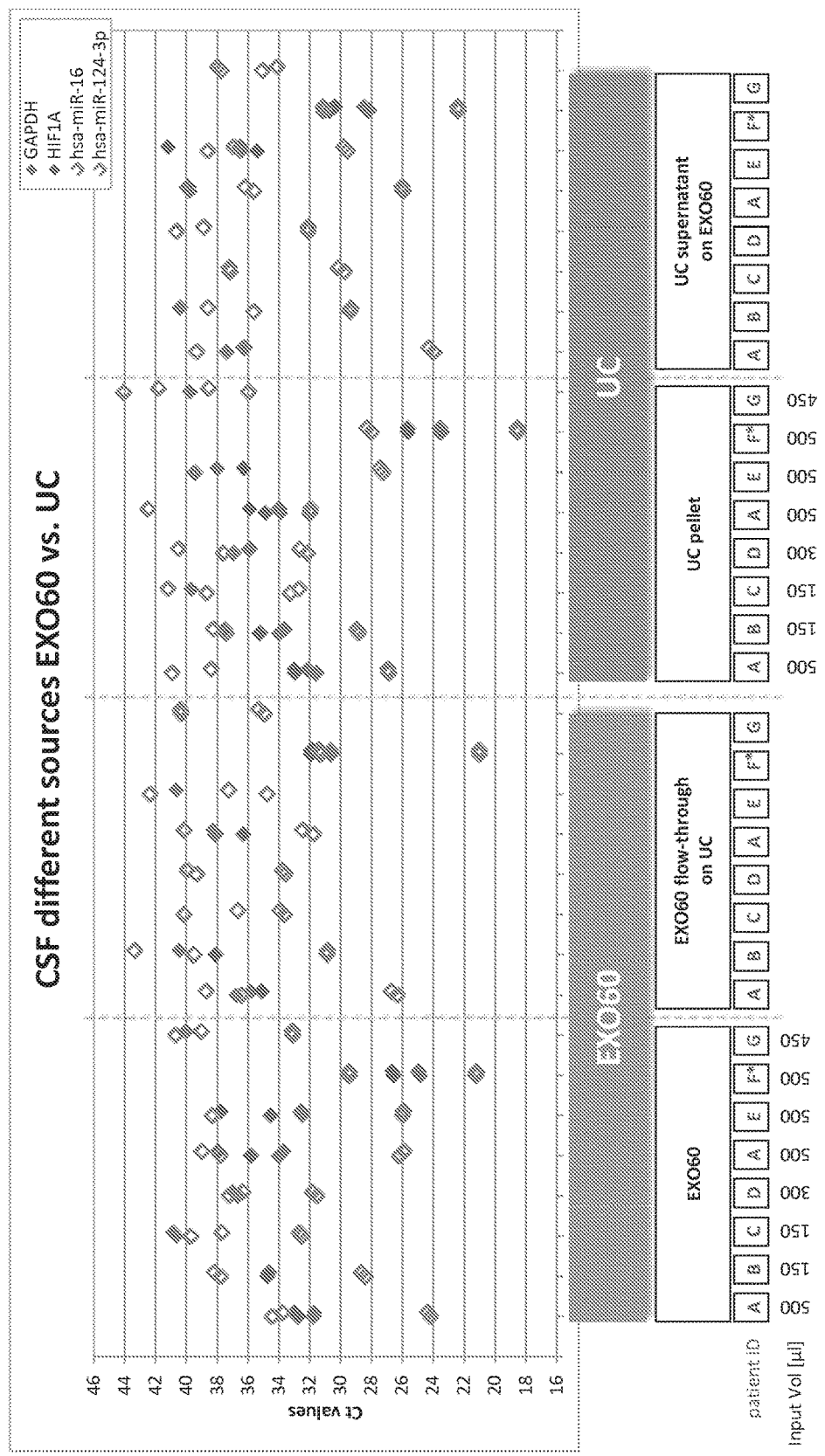
FIG. 8 is a graph showing the comparison of detection of microvesicle RNA targets from ultracentrifugation and EXO60 isolation methods for different patient CSF samples. Patient samples are designated by patient ID. Varying sample volumes were utilized. (*) indicates post-mortem sample.
Figure 9:
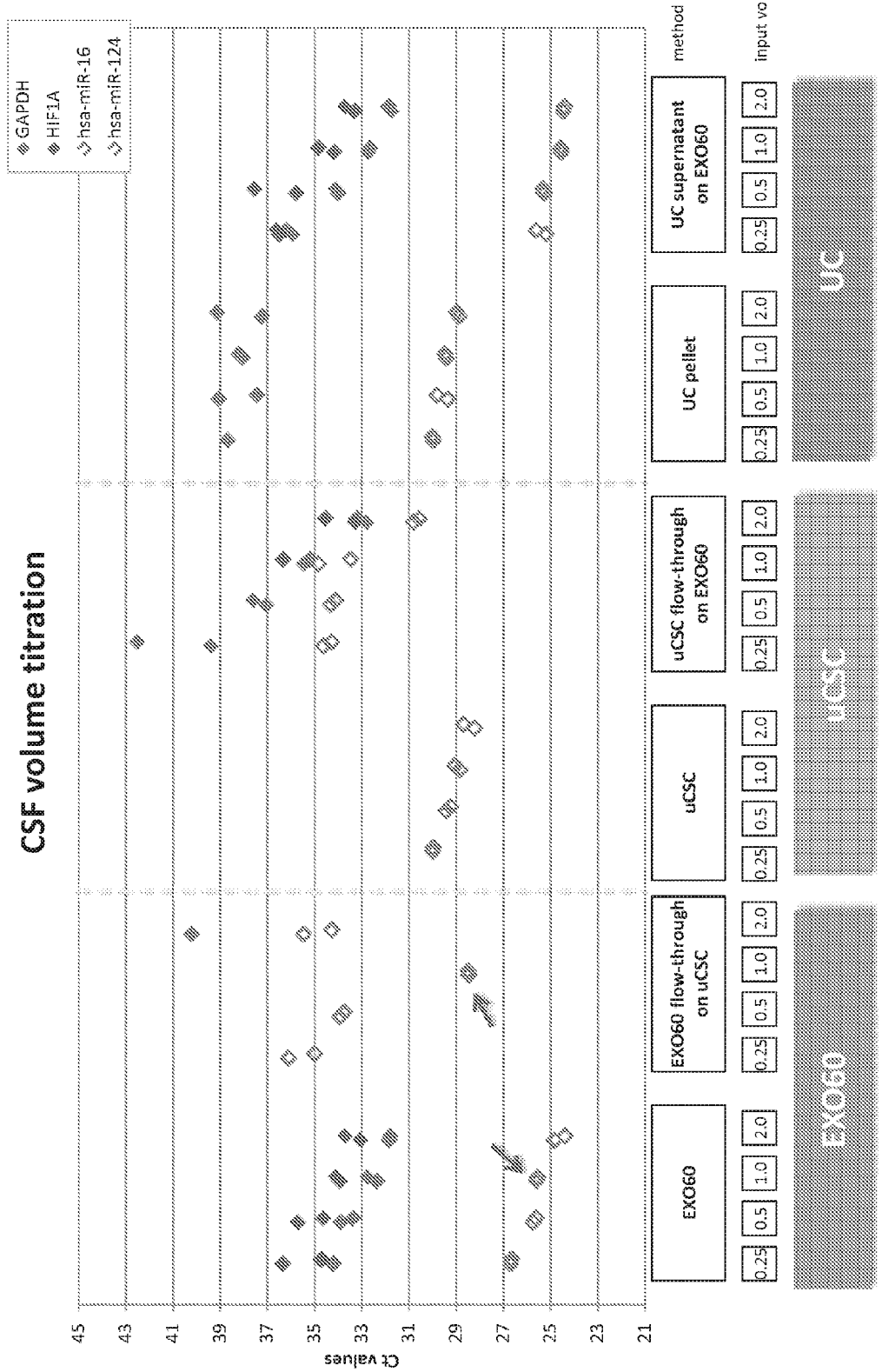
FIG. 9 is a graph showing the effect of CSF sample volume (0.25 ml, 0.5 ml, 1.0 ml and 2.0 ml) on different microvesicle RNA isolation and extraction methods. UC (ultracentrifugation), uCSC (urine filtration method), and EXO60.
Figure 10:
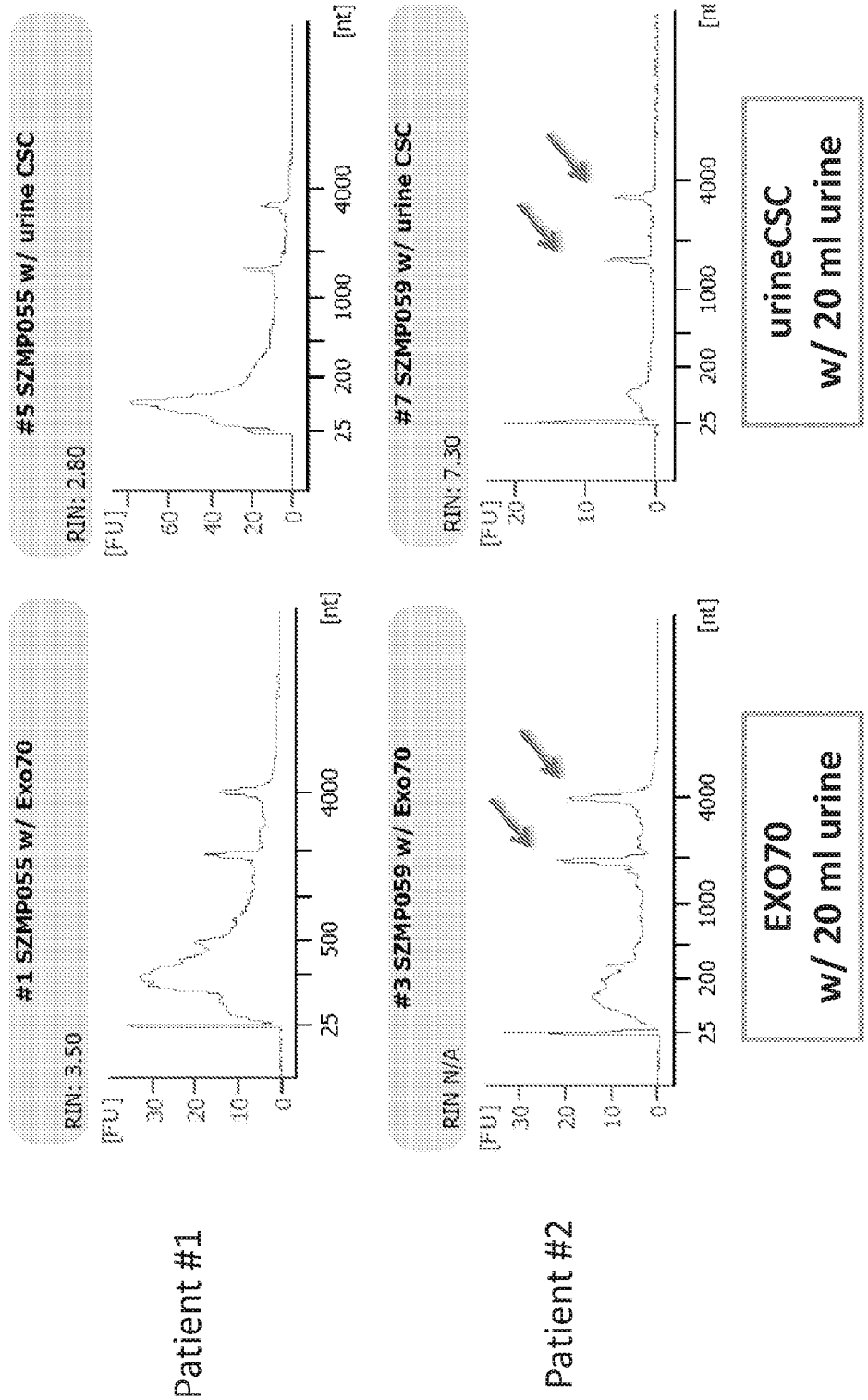
FIG. 10 is a series of bioanalyzer plots depicting the RNA profiles from extraction from 2 different urine samples using the EXO70 protocol compared to the urine circulating stem cell (uCSC) method.
Figure 11:
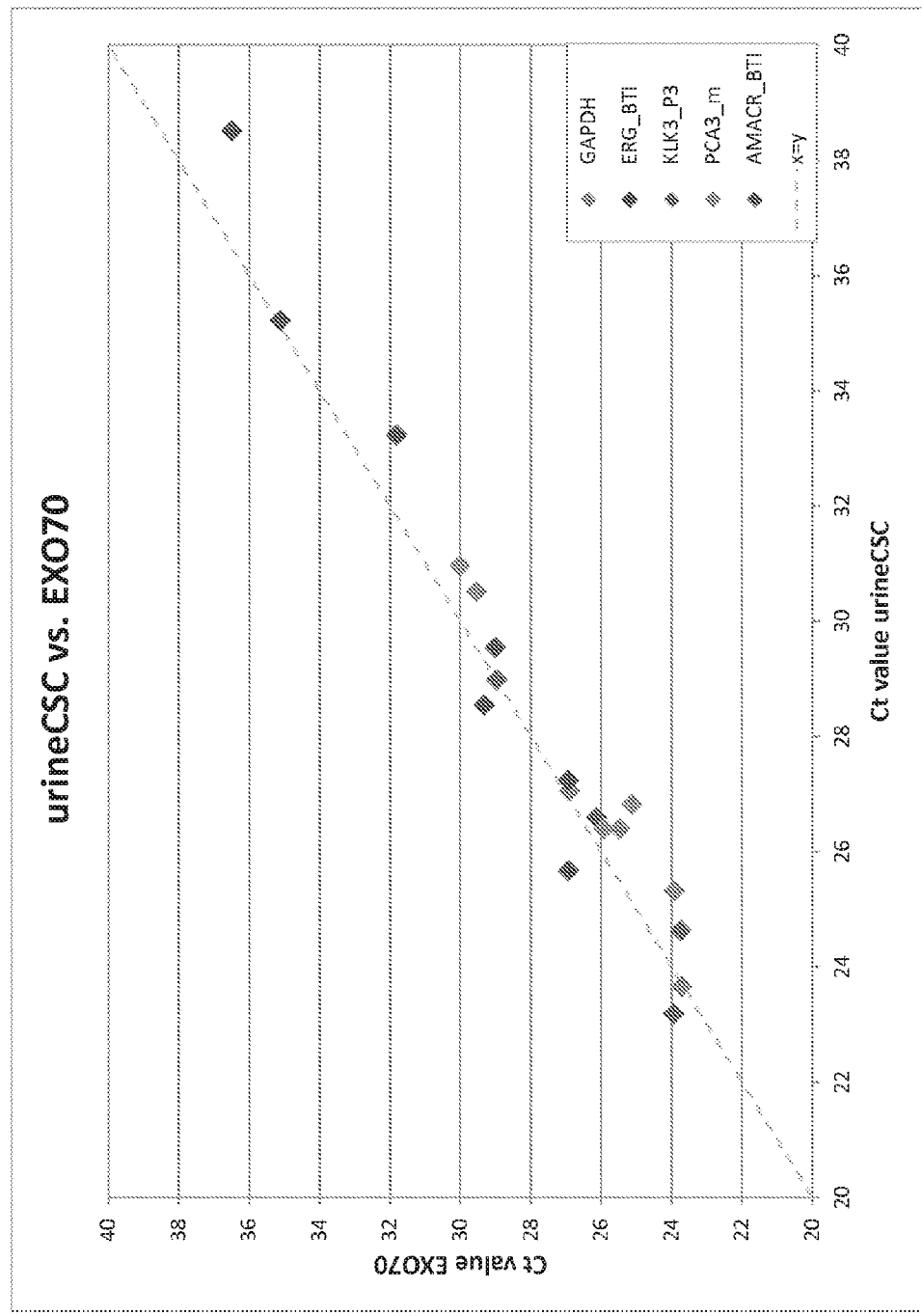
FIG. 11 is a graph showing the correlation between RNA detection after isolation and extraction by EXO70 compared to the urineCSC method.

The EXO52 column can also be used to isolate all DNA from a plasma sample. Two methods for utilizing the EXO52 column for DNA isolation in addition to RNA are depicted in FIG. 1 and FIG. 2. Specifically, the difference between the two processes is that the RNA and DNA extraction is combined in one tube in EXO52, for ease in usability, streamlining of the protocol, and increased reproducibility. FIG. 3 shows a gain of 1.5 Cts in EXO50 RNA+DNA (EXO52). EXO50 is a method for isolating RNA from microvesicles in a biological sample such as, for example, plasma. This method is described in PCT Publication No. WO2014/107571. FIG. 4 shows that increasing the amount of chloroform during phase separation adds the DNA back to the aqueous phase, such that the DNA is co-isolated with the normal EXO50 procedure. Further optimization of pH levels during phase separation also adds the DNA to the prep, as shown in FIG. 5.

Thus, the methods of the disclosure can be used to isolate all DNA from plasma samples. The DNA is recovered from the lower, hydrophobic phase of the QIAzol lysis after phase separation. The methods of the disclosure (e.g., two tubes or a single tube as in EXO52), separate RNA and DNA at similar levels for the same sample volume, and the RNA and DNA can be separated from each other. These methods of the disclosure capture the same or more mRNA and much more miRNA than a commercially available isolation kit, e.g., Qiagen.

EXO52 can also be used for co-purification of RNA and DNA. As used herein, EXO52 refers to the following protocol, unless otherwise specified.

Sample Preparation: The EXO52 procedure can be used to isolate RNA and DNA from exosomes and other microvesicles using 0.2-4 mL of plasma or serum. It is recommended to only use pre-filtered plasma or serum, excluding particles larger than 0.8 µm. The list of compatible plasma tubes includes plasma with the additives EDTA, sodium citrate, and citrate-phosphate-dextrose. Plasma containing heparin can inhibit RT-qPCR.

The sample, alone or diluted with a binding buffer, is then loaded onto the EXO52 spin column and spun for 1 min at 500×g. Discard the flow-through and place the column back into the same collection tube. Wash buffer is then added and the EXO52 column is spun for 5 min at 5000×g to remove residual volume from the column. Note: After centrifugation, the EXO52 spin column is removed from the collection tube so that the column does not contact the flow-through. The spin column is then transferred to a fresh collection tube, and 700 µL Qiazol is added to the membrane. Then, the spin column is spun for 5 min at 5000×g to collect the homogenate containing the lysed exosomes. The homogenate is then transferred to a PLG tube.

Then, 350 µl chloroform is added to the tube containing the homogenate and shaken vigorously for 15 s. The tube containing the homogenate is then kept at room temperature for 2-3 min, followed by centrifugation for 5 min at 12,000×g at 4° C. After centrifugation, the centrifuge is heated up to room temperature (15-25° C.) if the same centrifuge will be used for the next centrifugation steps.

The upper aqueous phase is transferred to a new collection tube, avoiding transfer of any interphase material. 2 volumes of 100% ethanol are then added and mixed thoroughly by pipetting up and down several times and without the use of a centrifuge. 700 µl of the sample, including any precipitate that may have formed, is then pipeted up to into an RNeasy MinElute spin column in a 2 ml collection tube (Cat. #1026497), followed by centrifugation at ≥8000×g (≥10,000 rpm) for 15 s at room temperature (15-25° C.). The flow-through is discarded. These steps are repeated with the remaining of the sample, and the flow-through is discarded.

EXO52 is useful for isolating and detecting DNA from biological samples. Vesicle RNA is thought to be derived from living cells in e.g. the diseased tissue. Cell-free DNA cfDNA) is thought to be derived from dying cells e.g. necrotic cells in the disease tissue. Thus, cfDNA is useful as an indicator of therapeutic response, while the RNA is an indicator of resistance mutations on the rise.

EXO52 is useful for detection of rare mutations in blood, as EXO52 provides a sufficiently sensitive method that can be applied on nucleic acids of sufficient amount. The amount of actual DNA and RNA molecules in biofluids is very limited, and EXO52 provides an isolation method that extracts all molecules of the blood that are relevant for mutation detection in a volume small enough for effective downstream processing and/or analysis.

Figure 13:
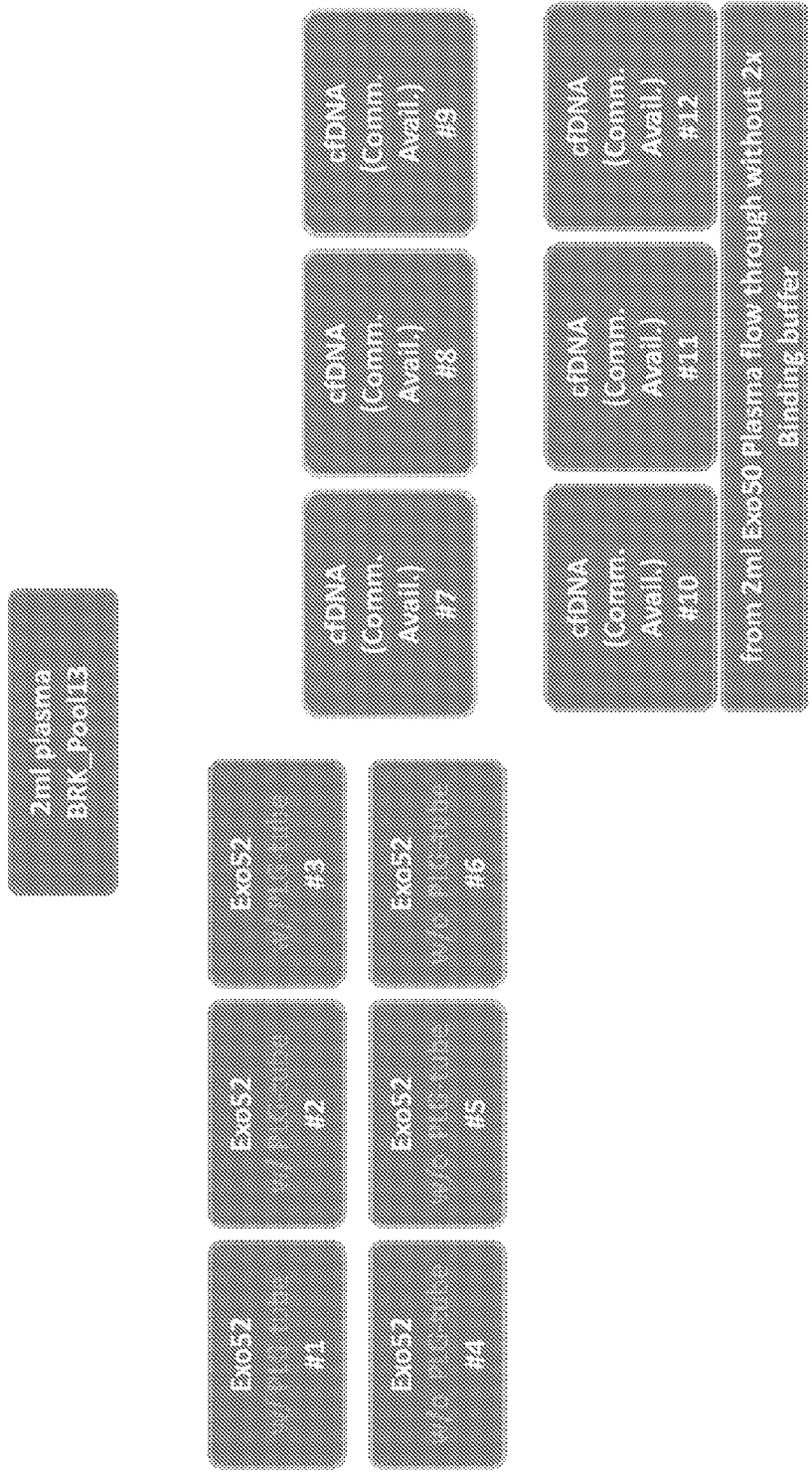
Figure 14:
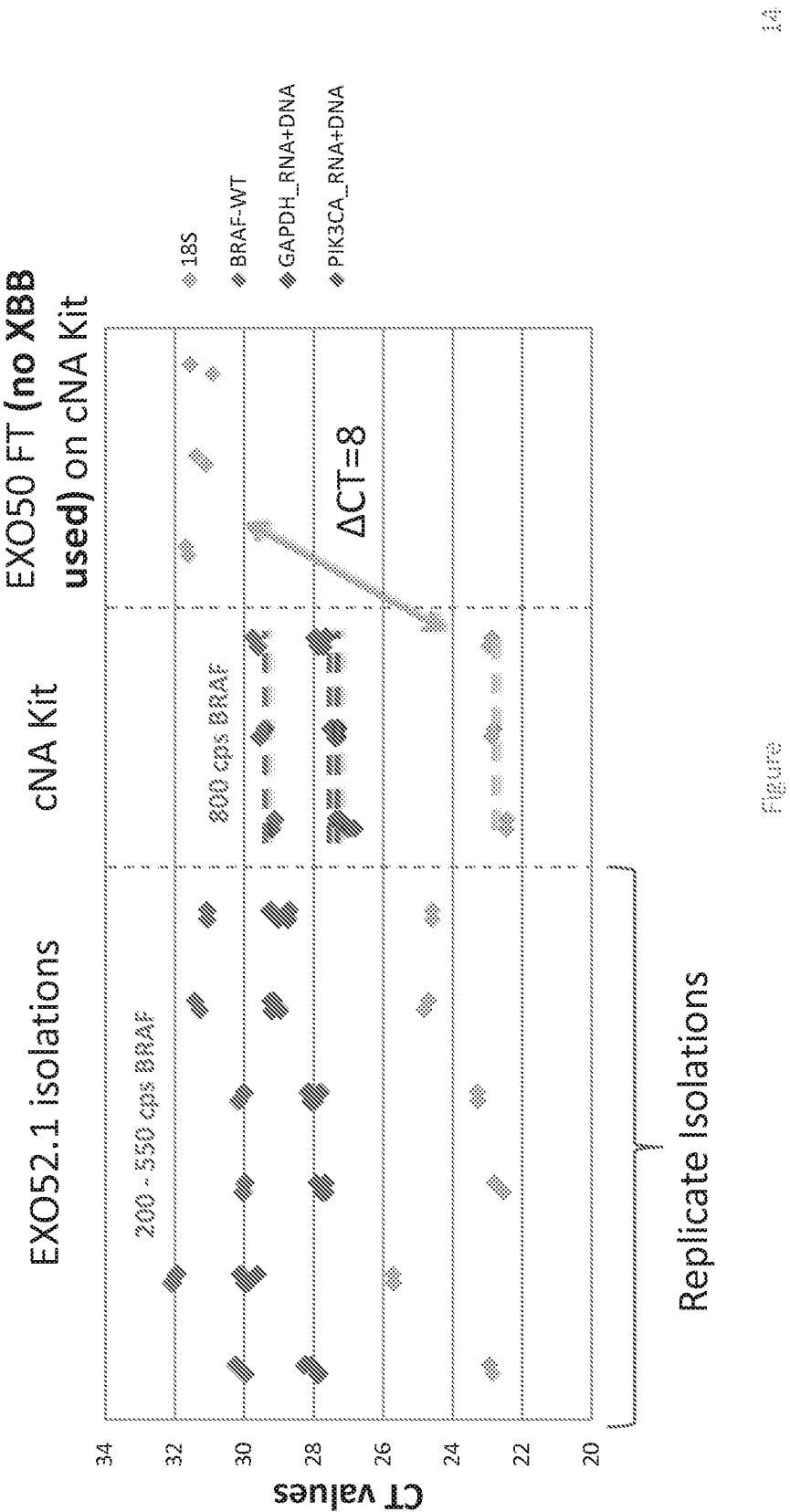
FIGS. 14, 15, 16, and 17 are a series of graphs depicting DNA extraction with and without PLG-tubes using an initial method of DNA/RNA isolation (EXO52.1) and commercially available kits.
Figure 15:
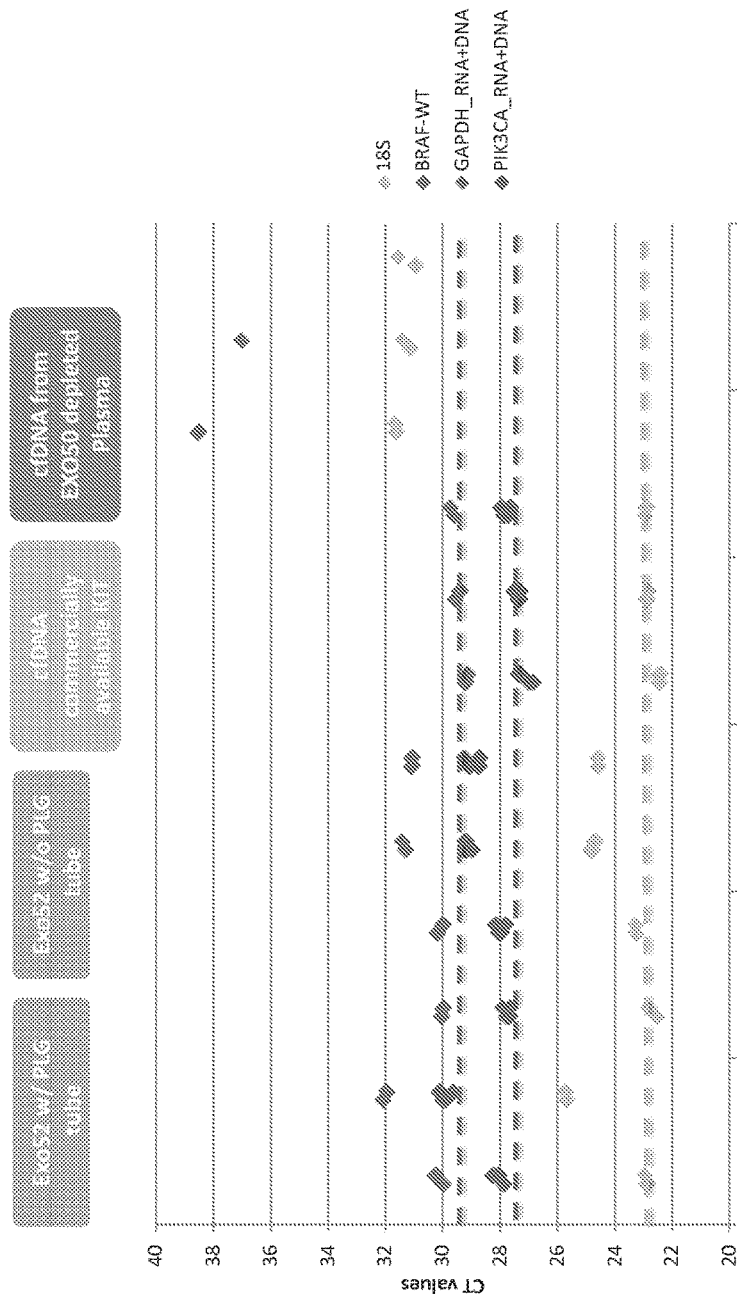
Figure 16:
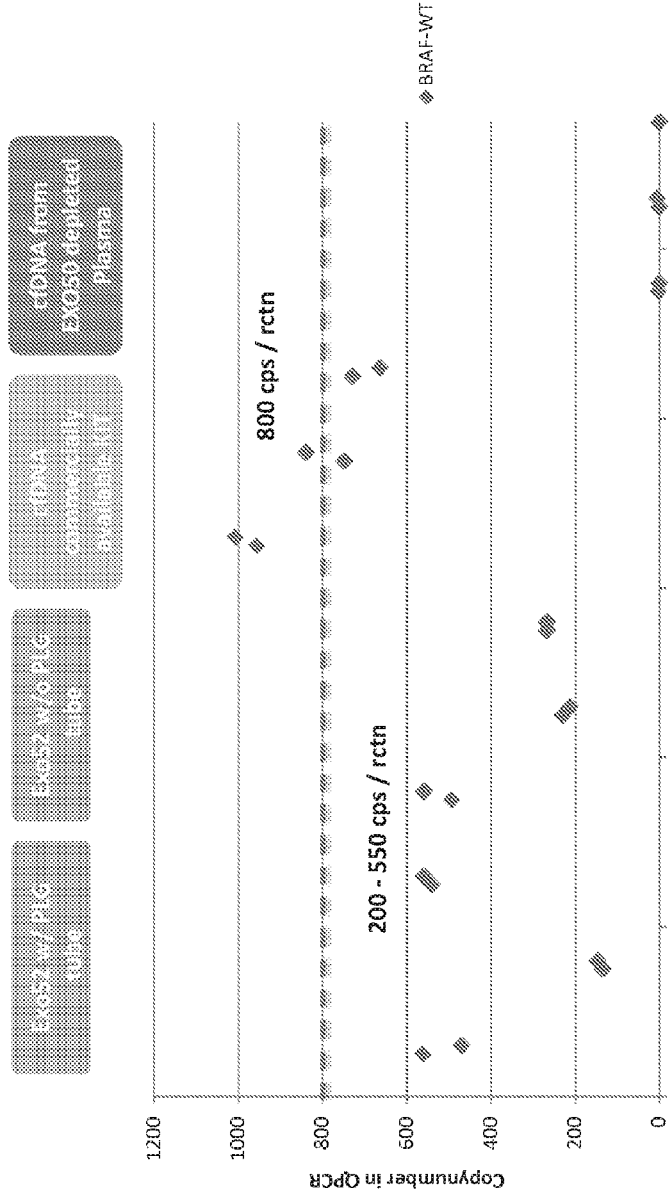
Figure 17:
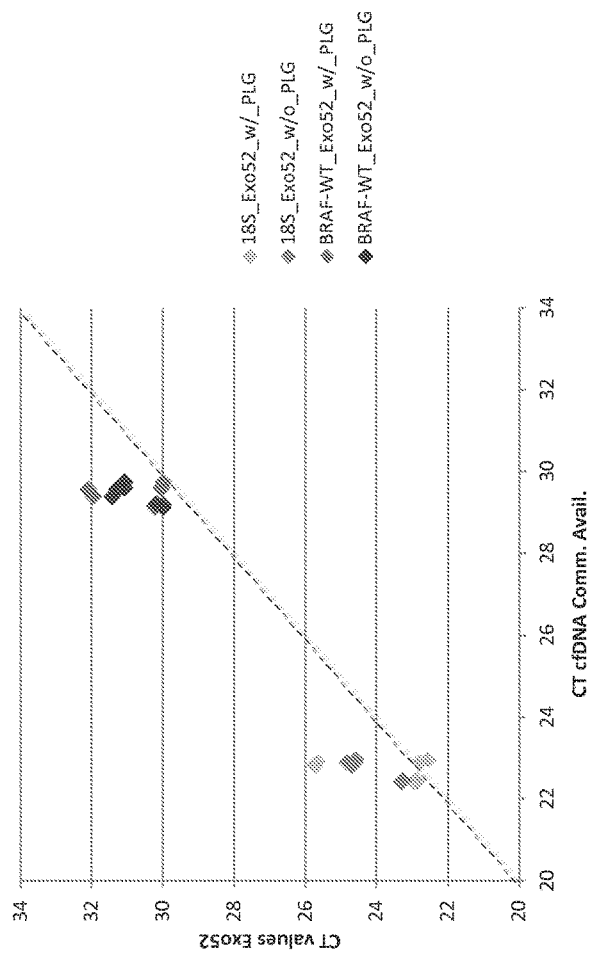
Figure 18:
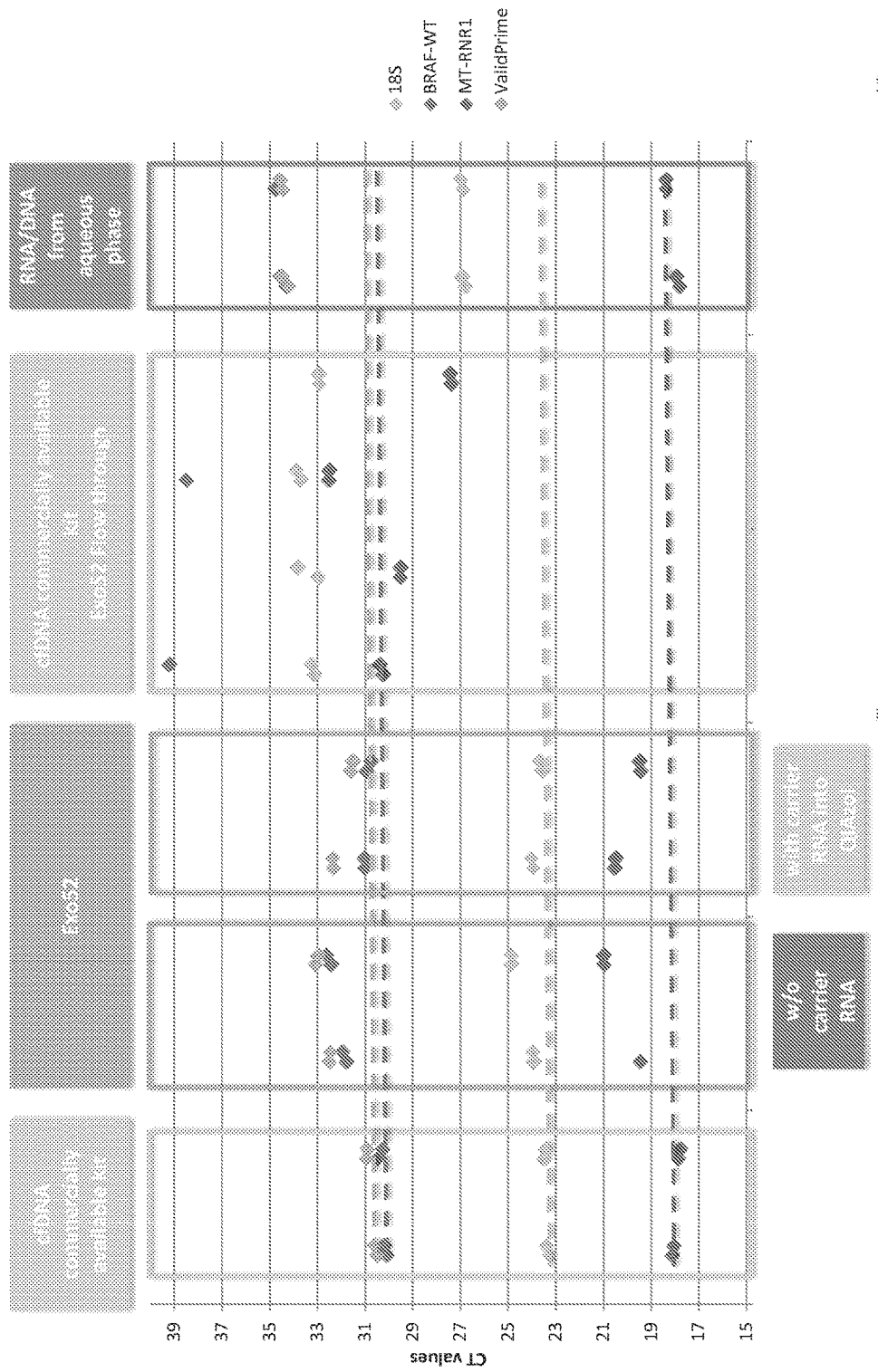
FIGS. 18 and 19 are a series of graphs depicting DNA extraction using methods of the disclosure versus a commercially available circulating nucleic acid extraction kit.
Figure 19:
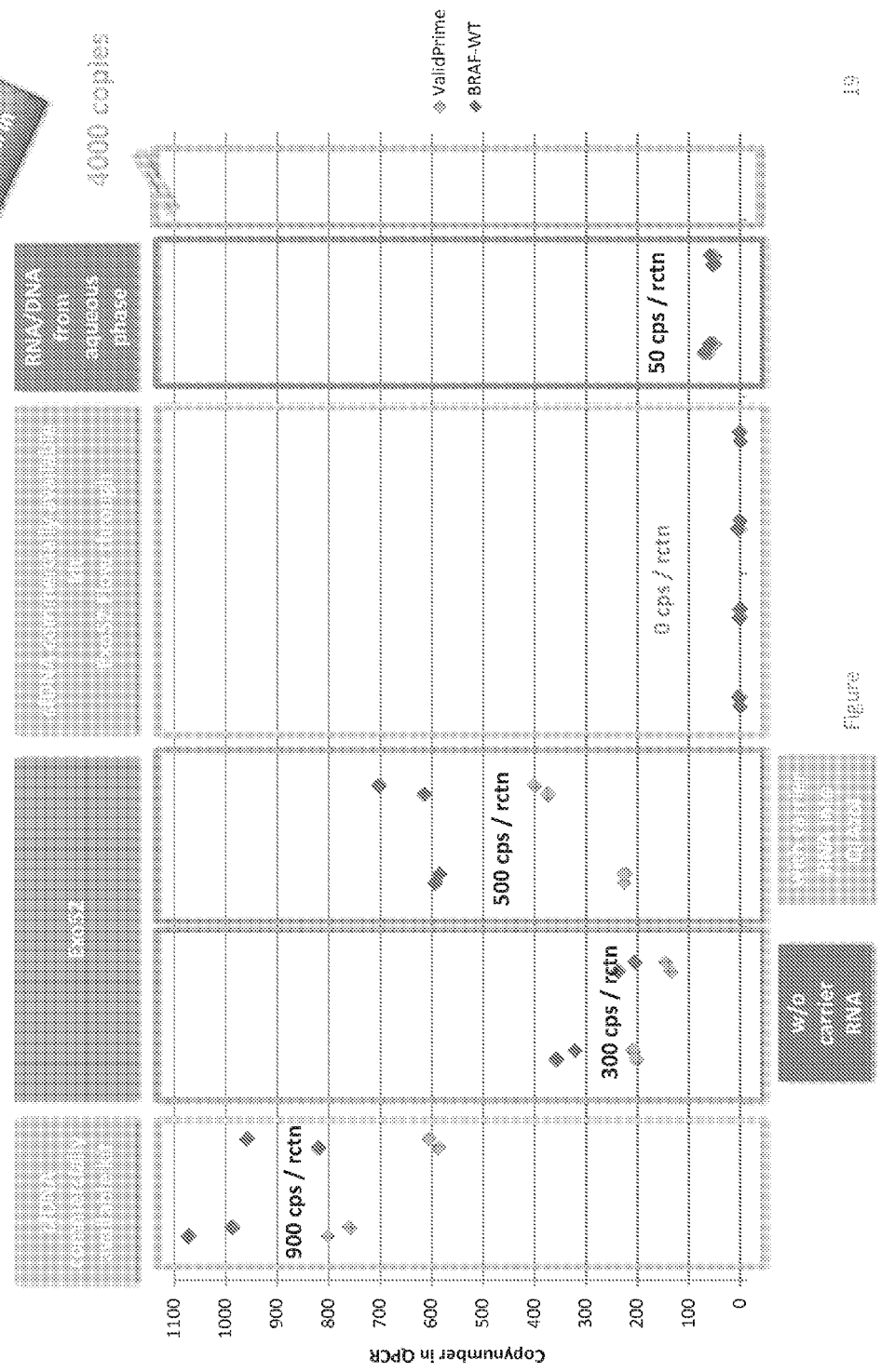
Figure 20:
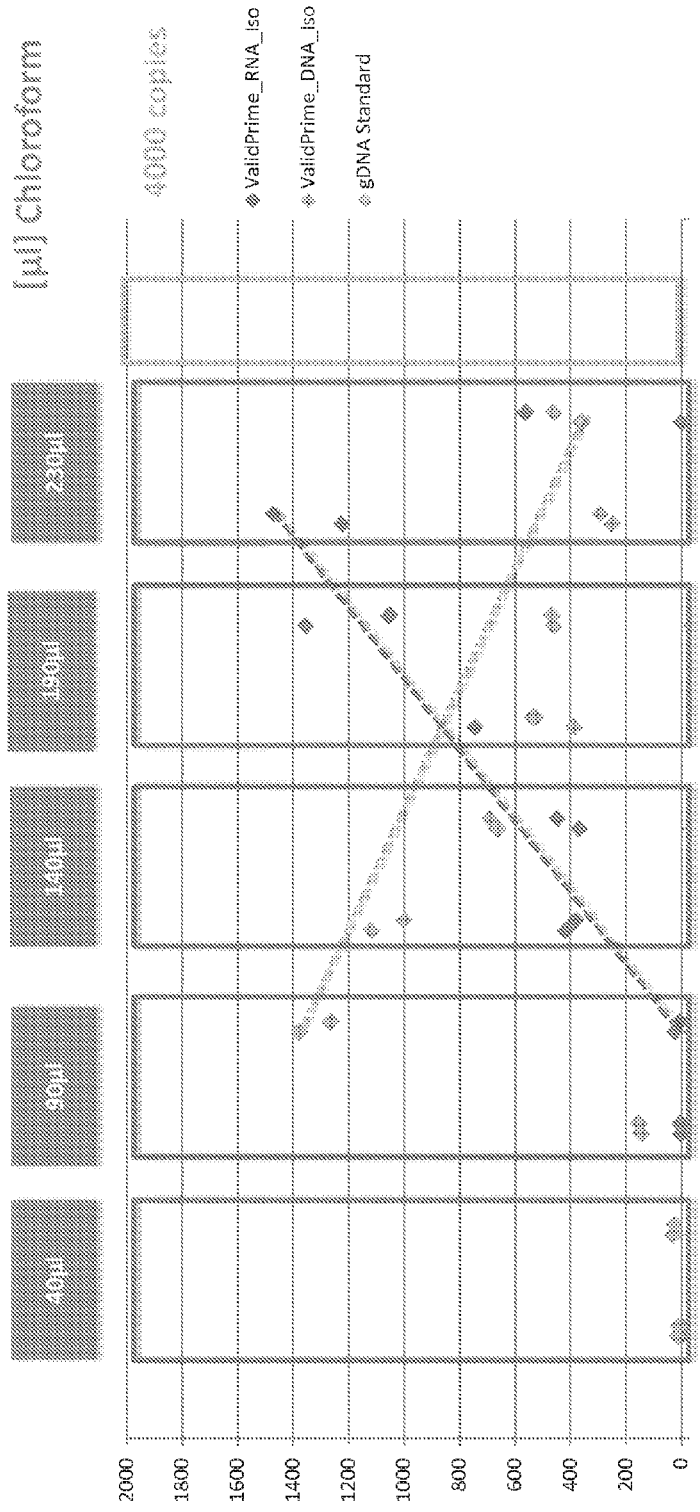
FIG. 20 is a graph depicting the effect of chloroform titration on RNA and DNA isolation of phenol phase.
Figure 21:
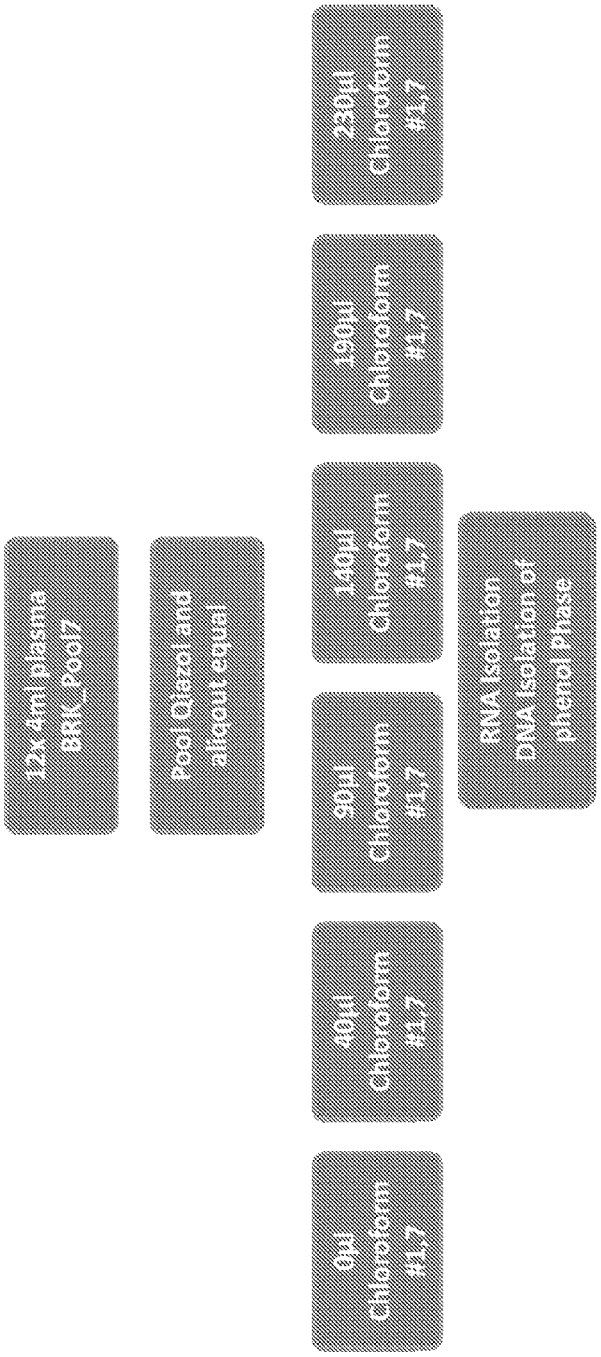
FIG. 21 is a schematic representation of studies designed to evaluate the effect of chloroform titration on RNA isolation and DNA isolation of phenol phase in PLG-tubes.
Figure 22:
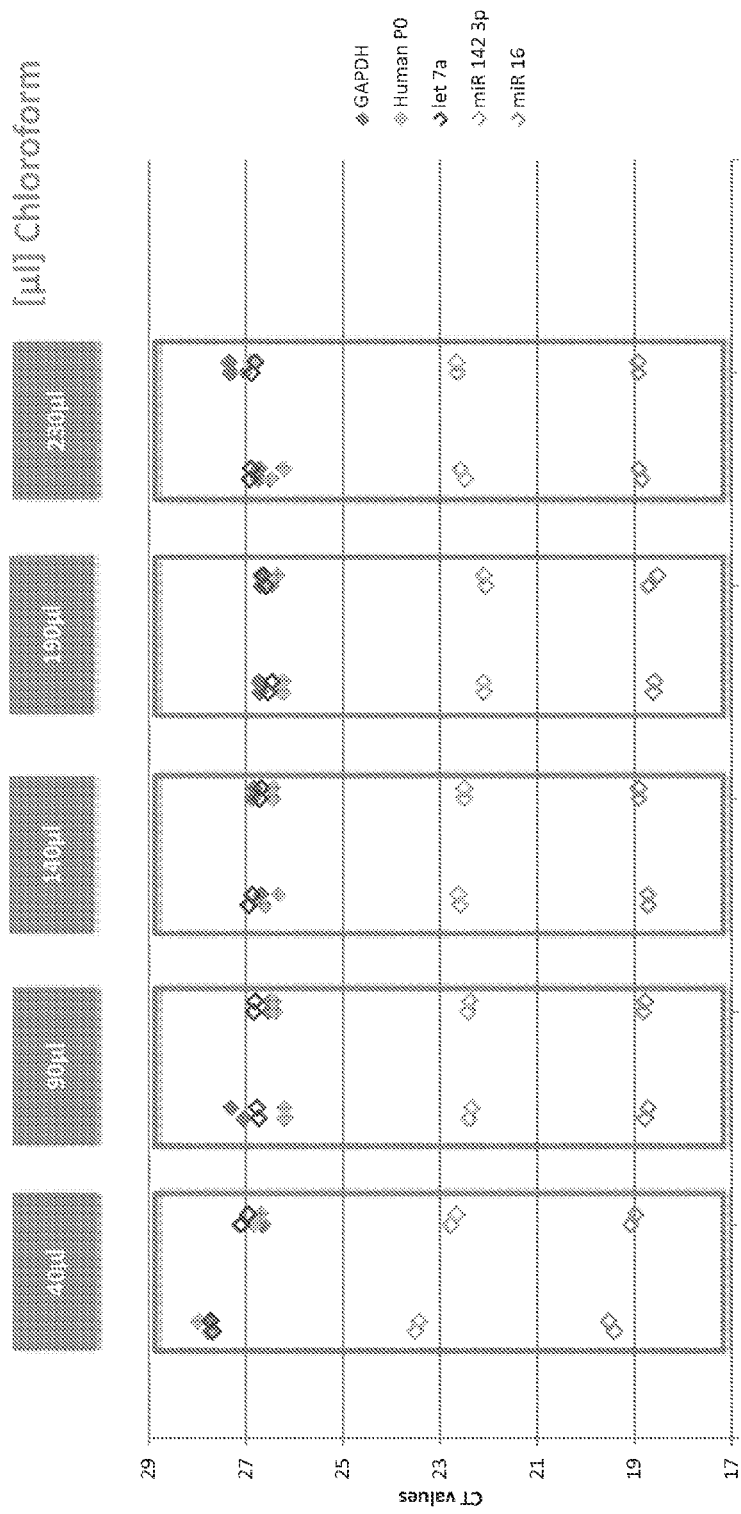
FIGS. 22, 23, 24, 25, and 26 are a series of graphs depicting the effects of chloroform titration on RNA isolation (FIG. 22), RNA and DNA isolation (FIGS. 23, 24), and DNA isolation (FIGS. 25, 26).
Figure 23:
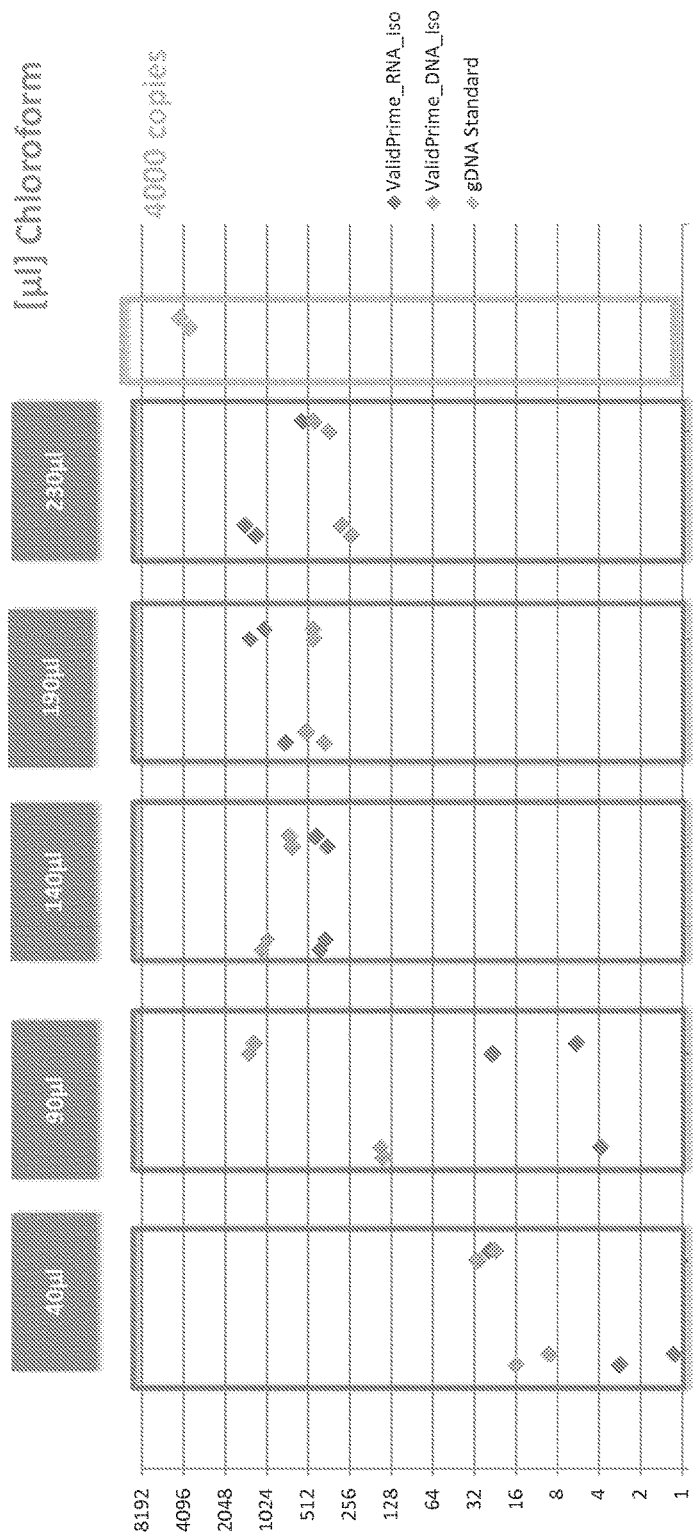
Figure 24:
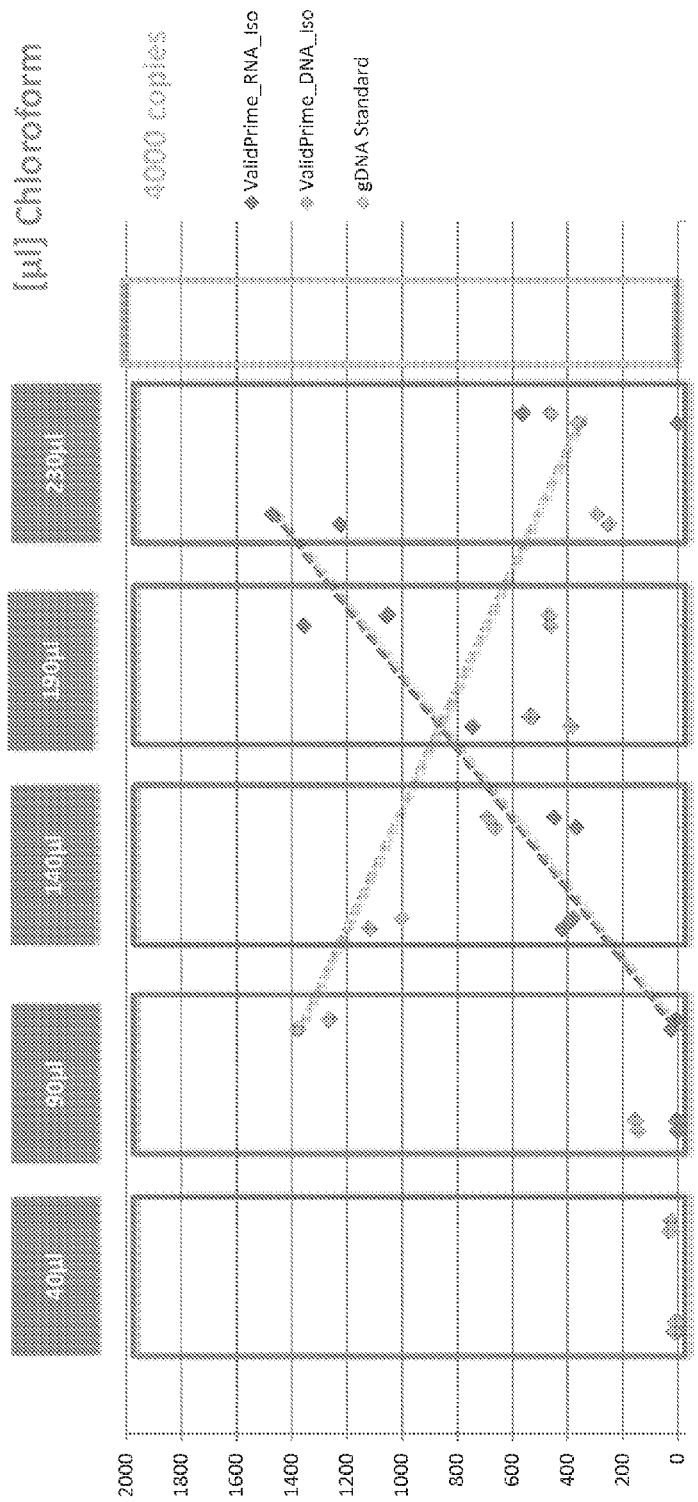
Figure 25:
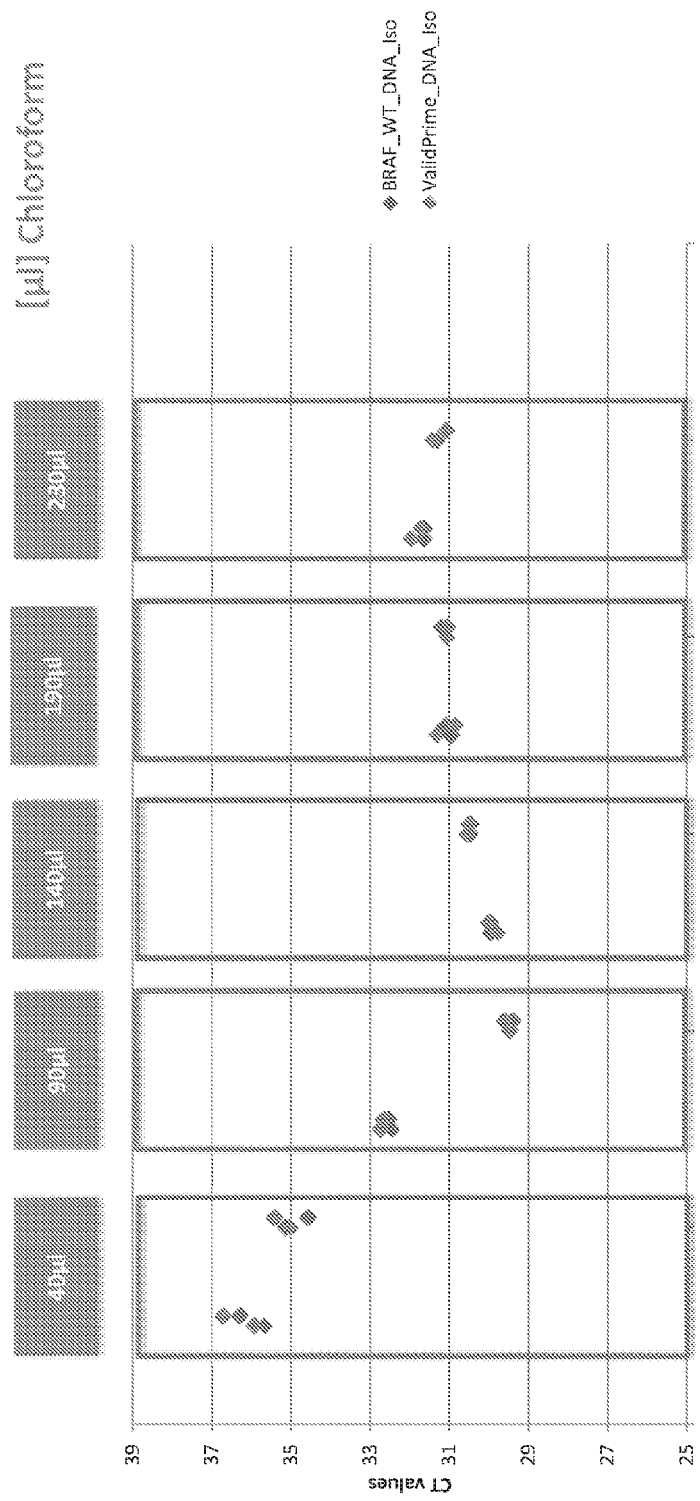
Figure 26:
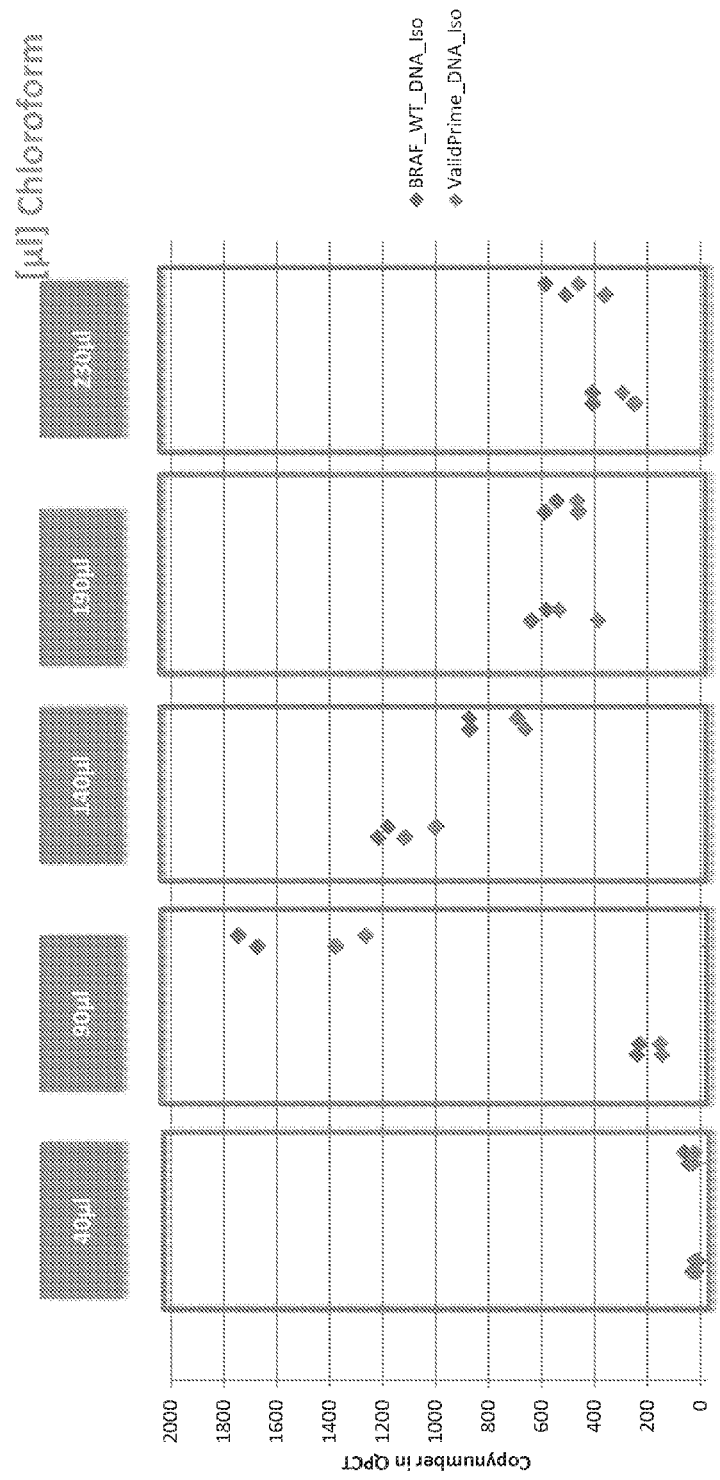
Figure 87:
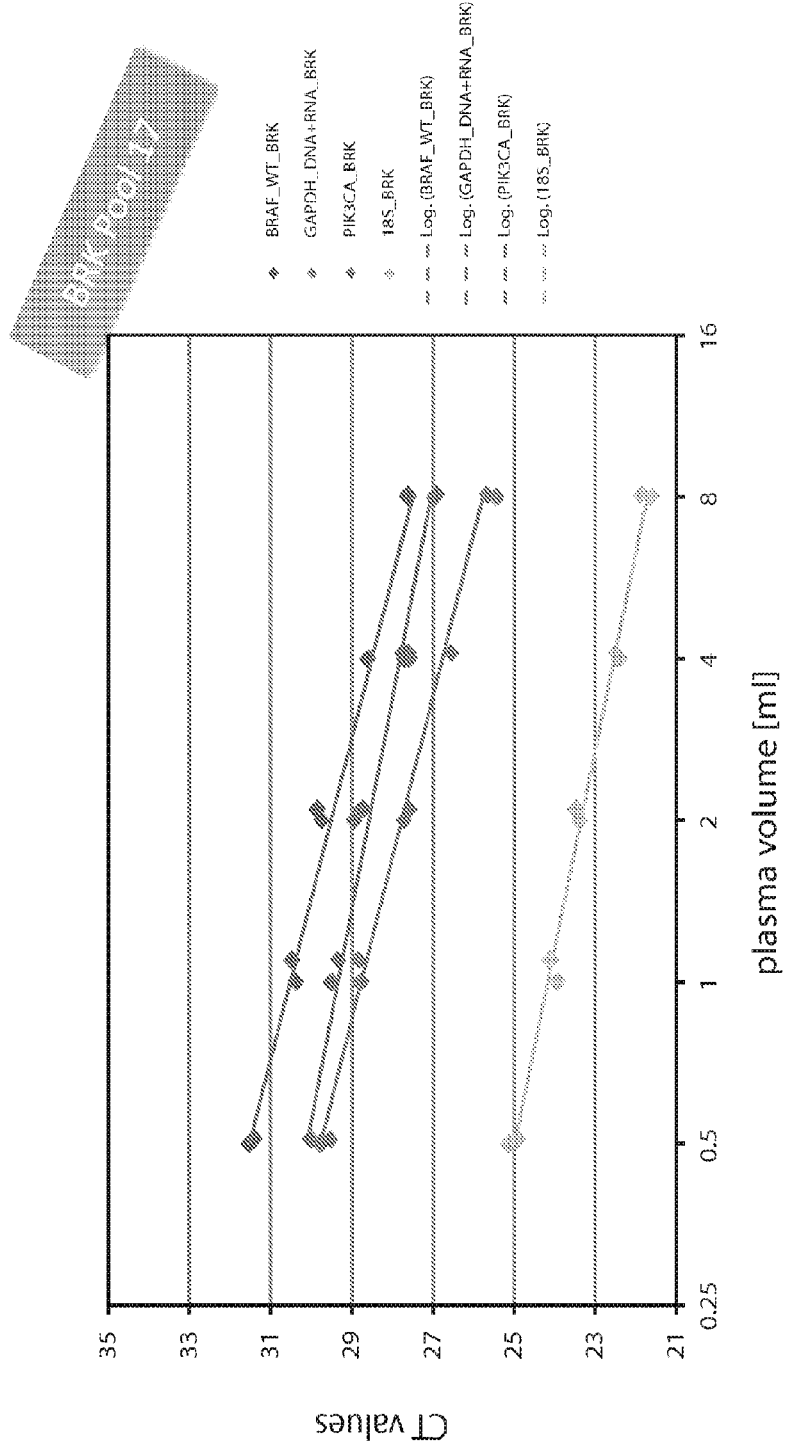
FIG. 87 is a graph depicting that the loading capacity is over 8 mL of plasma.
Figure 88:
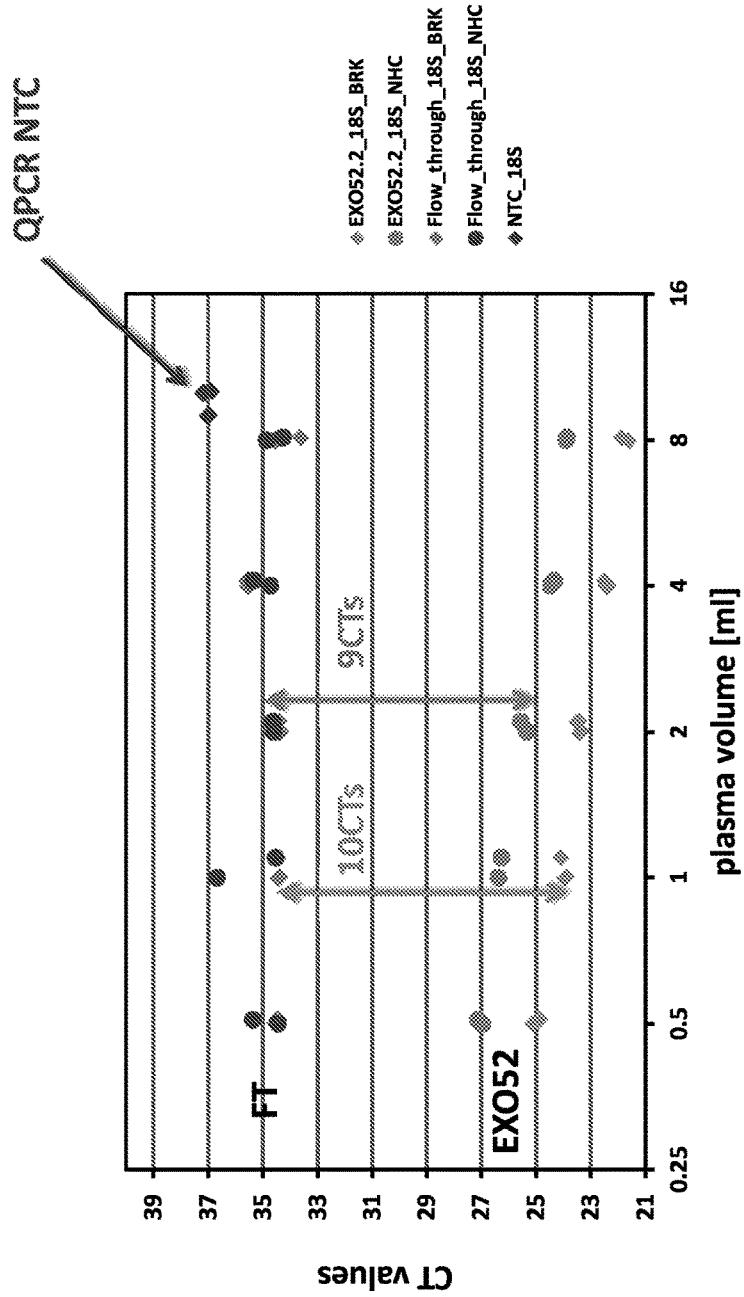
FIG. 88 is a graph depicting that the flow-through does not have a breakthrough point up to 8 mL of plasma.
Figure 89:
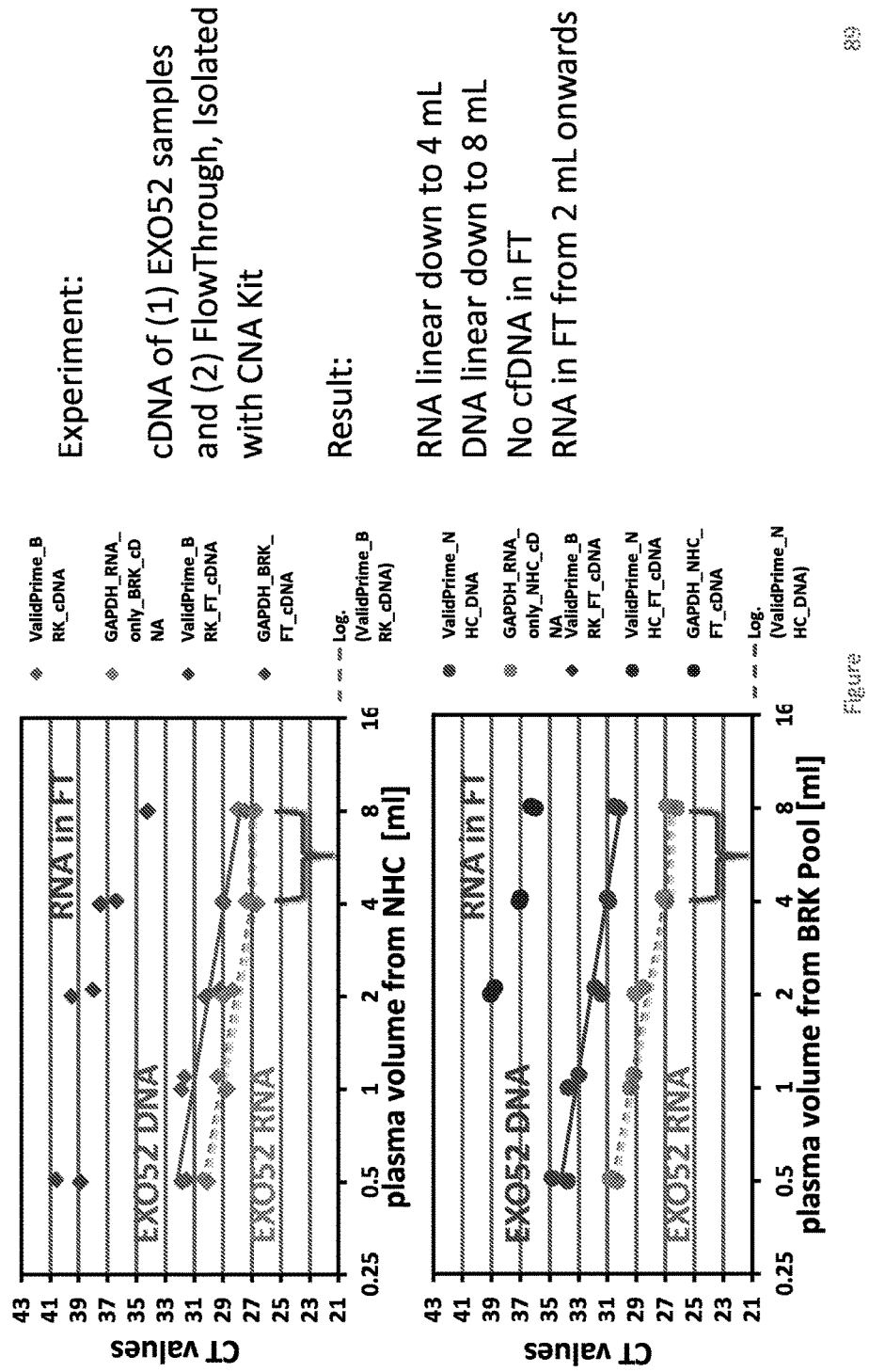
FIG. 89 is a graph depicting different binding capacity for exosomes and nucleosomes.
Figure 90:
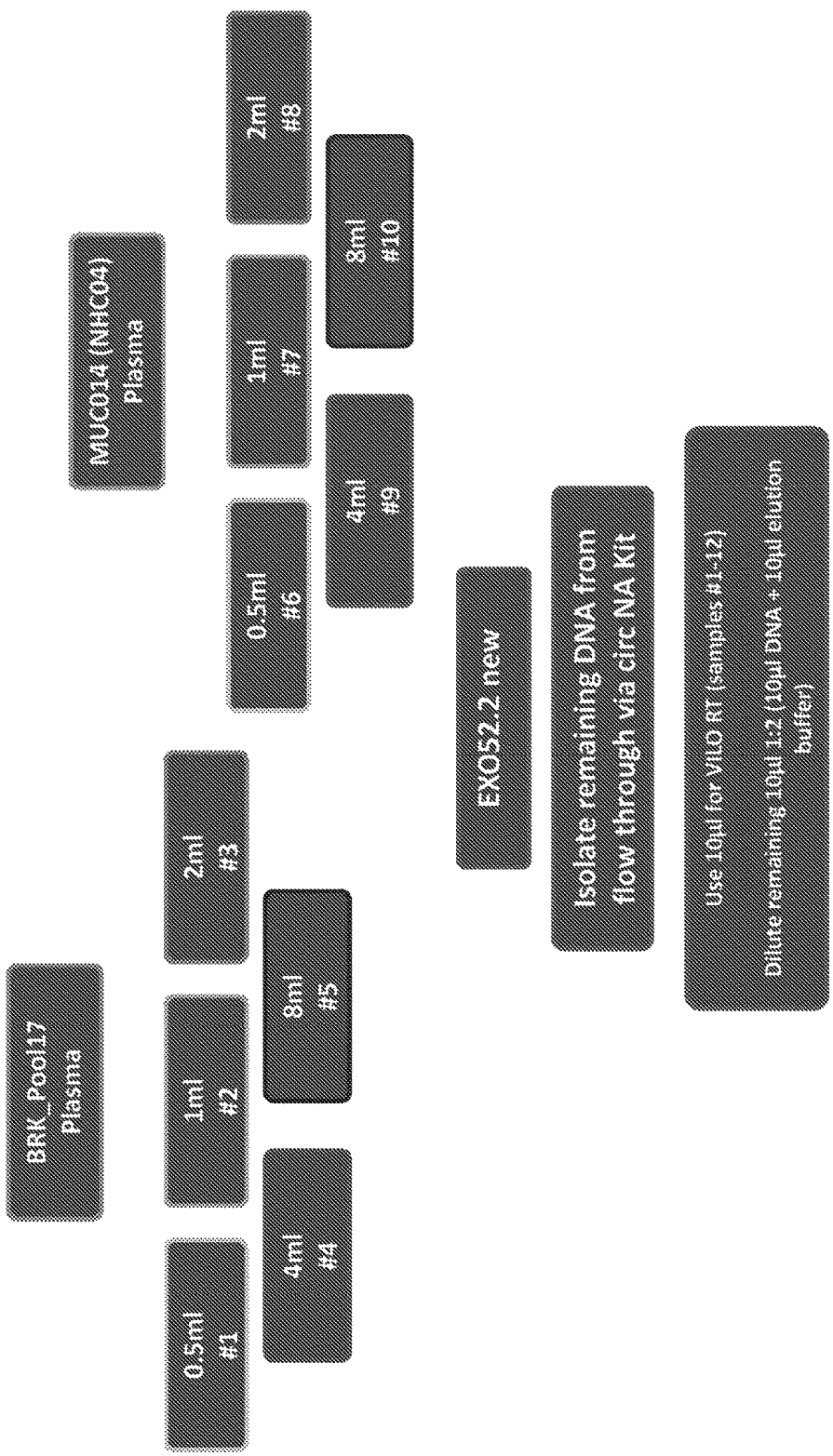
FIG. 90 is a schematic representation of studies designed to evaluate the loading capacity.
Figure 91:
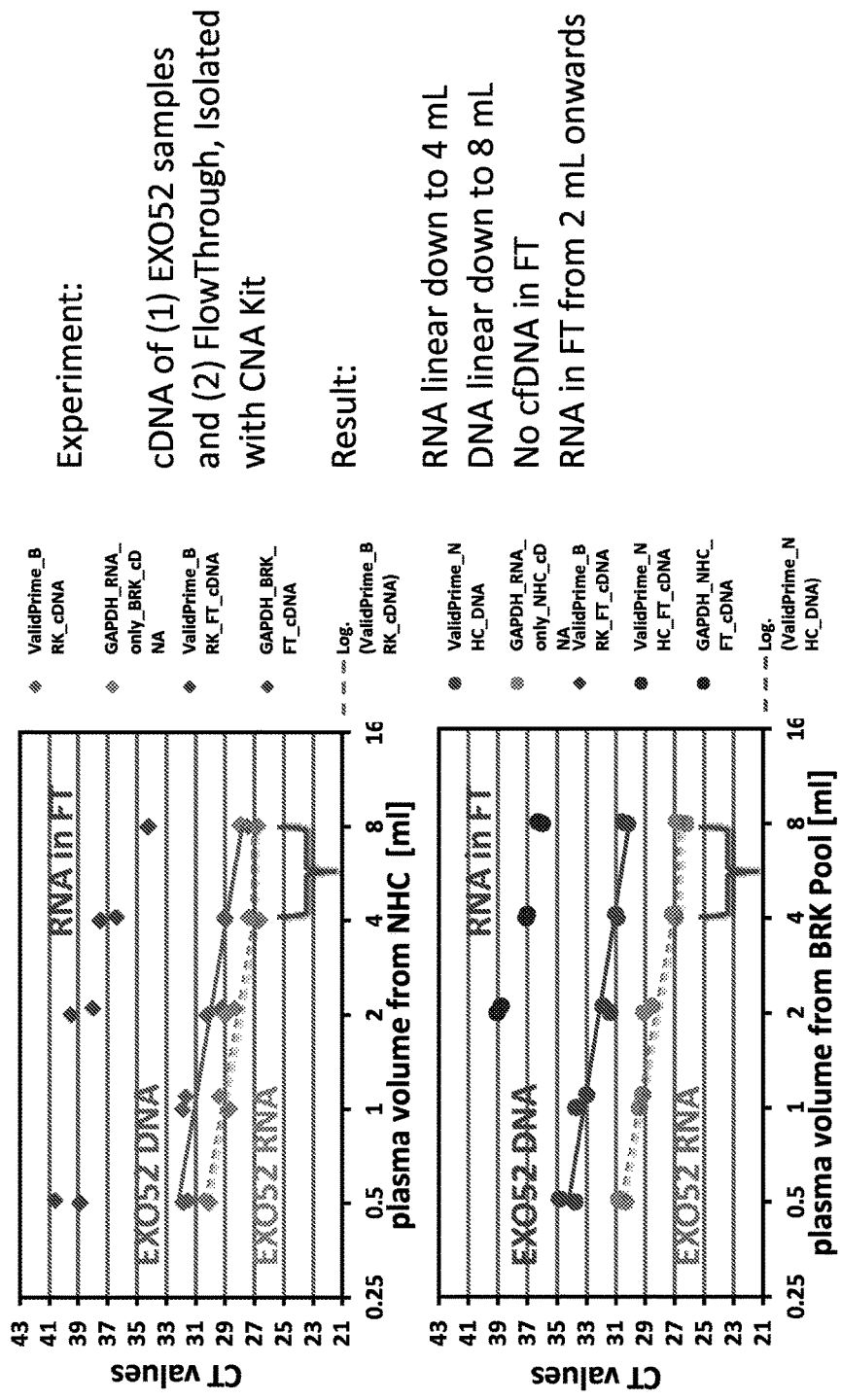
FIG. 91 is a graph depicting different binding capacity for exosomes and nucleosomes.
Figure 92:
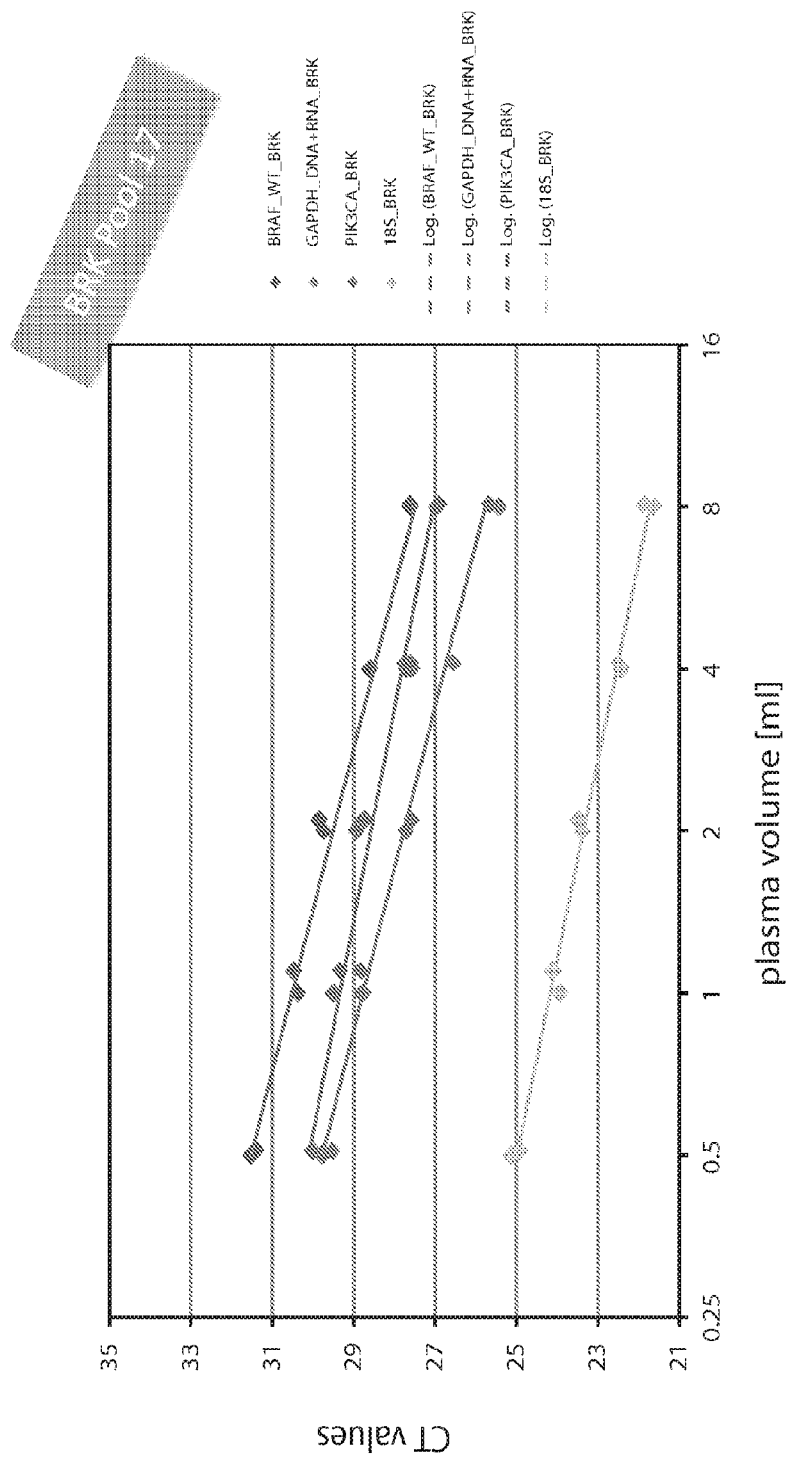
FIGS. 92 and 93 are a series of graphs depicting that the loading capacity is over 8 mL of plasma.
Figure 93:
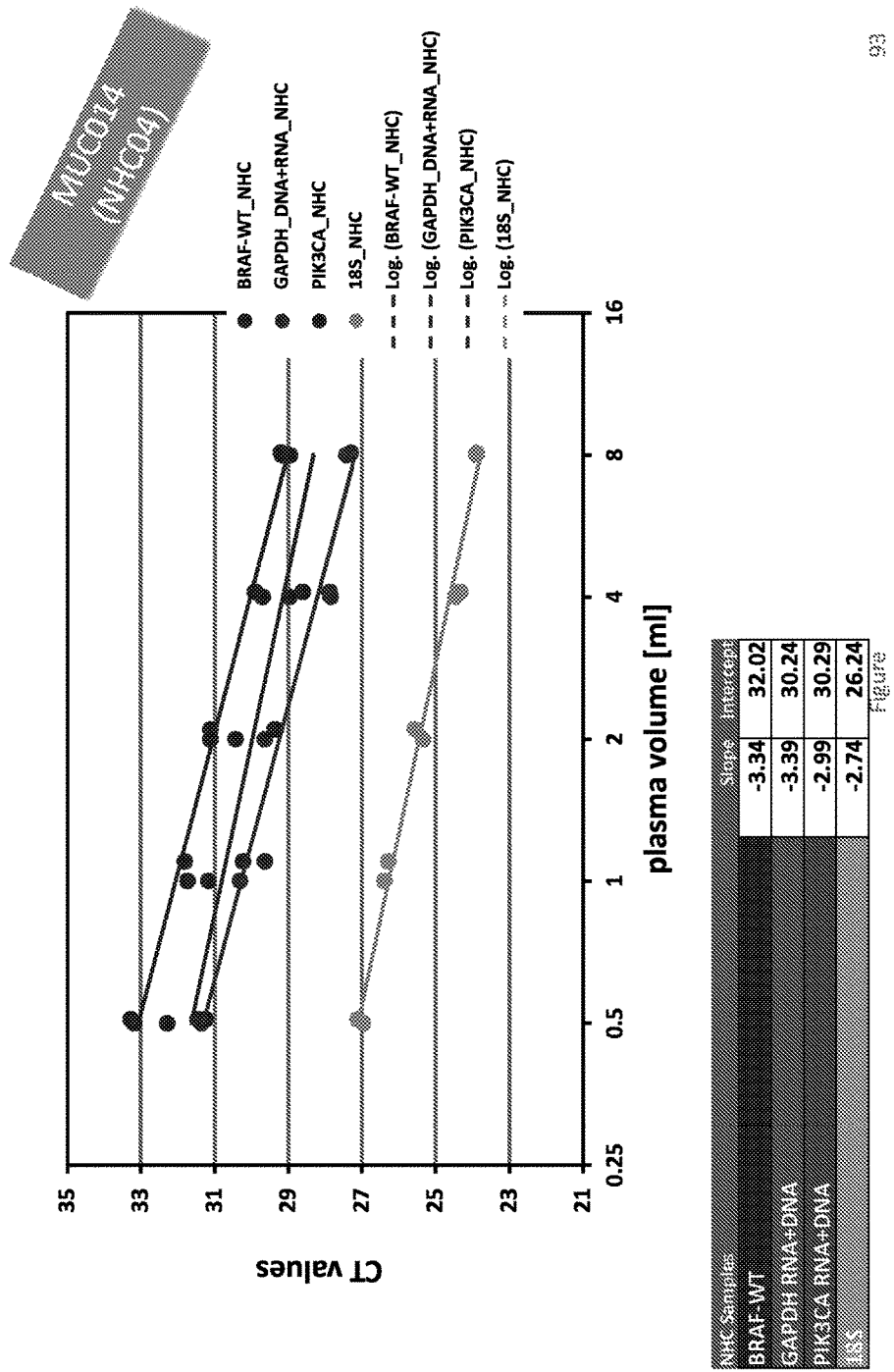
Figure 94:
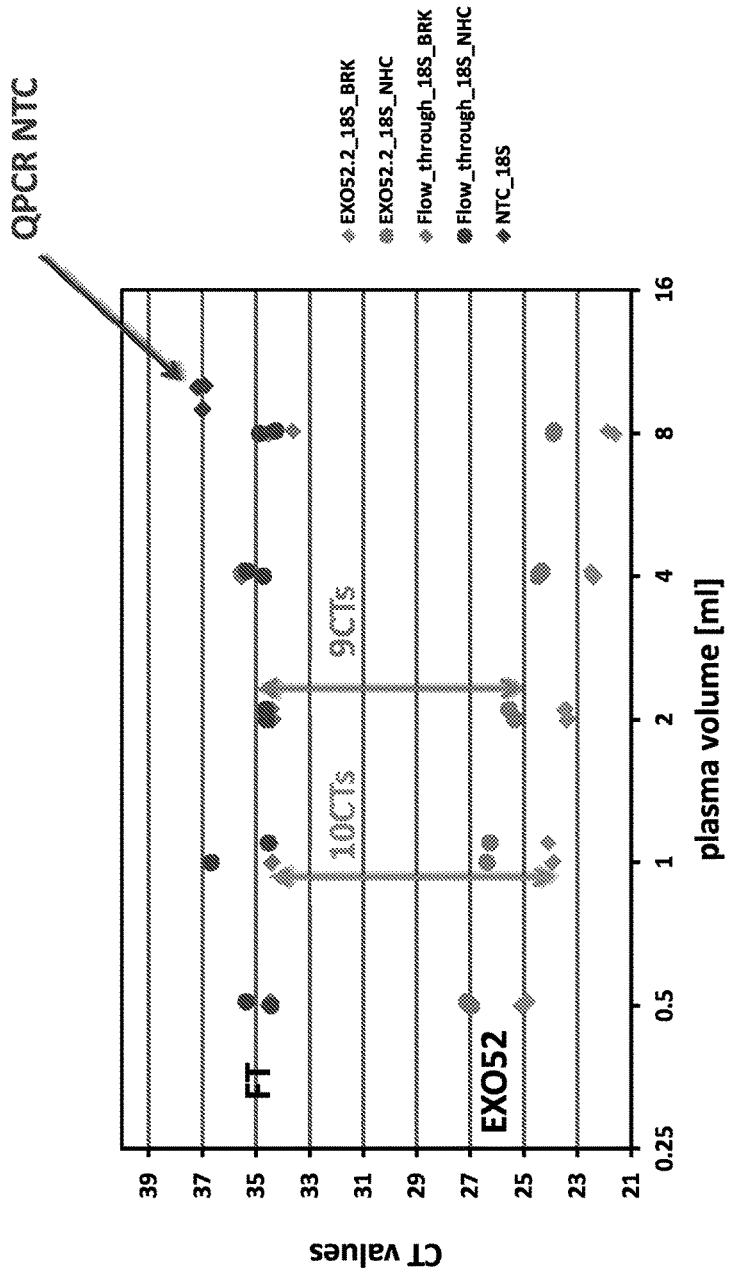
FIG. 94 is a graph depicting that the flow-through does not have a breakthrough point up to 8 mL of plasma.
Figure 95:
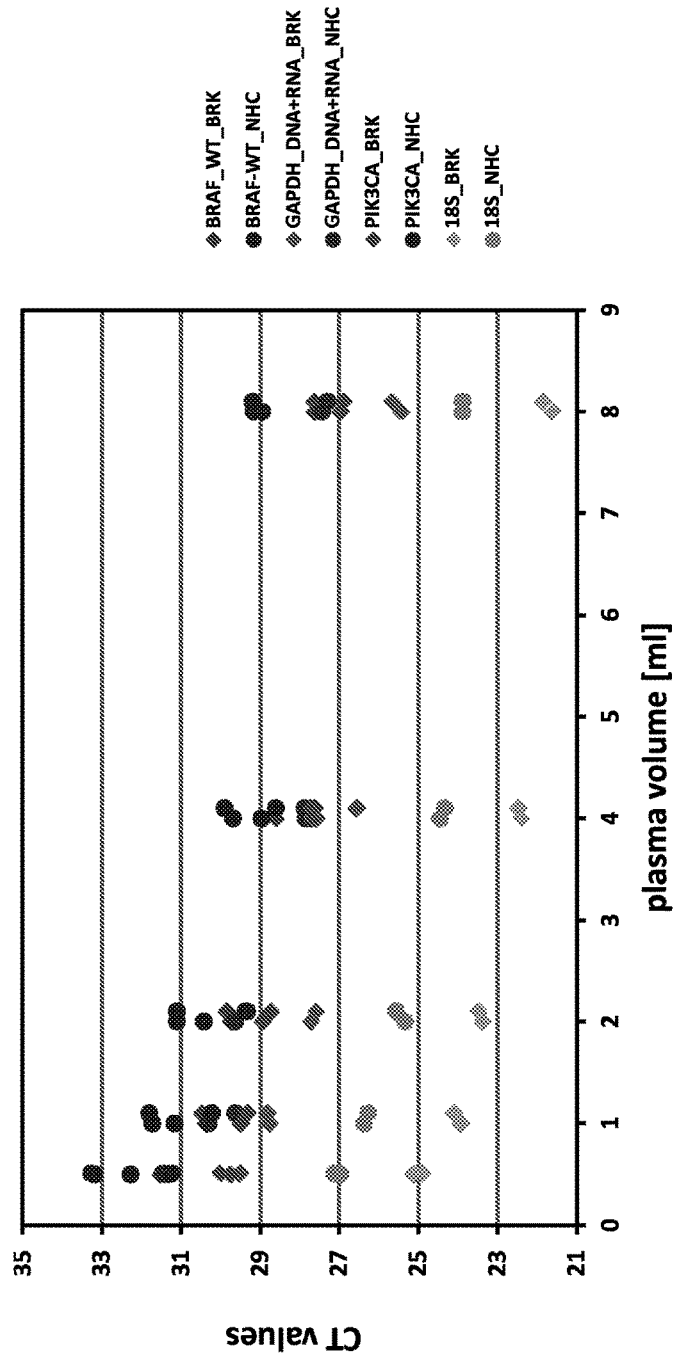
Figure 96:
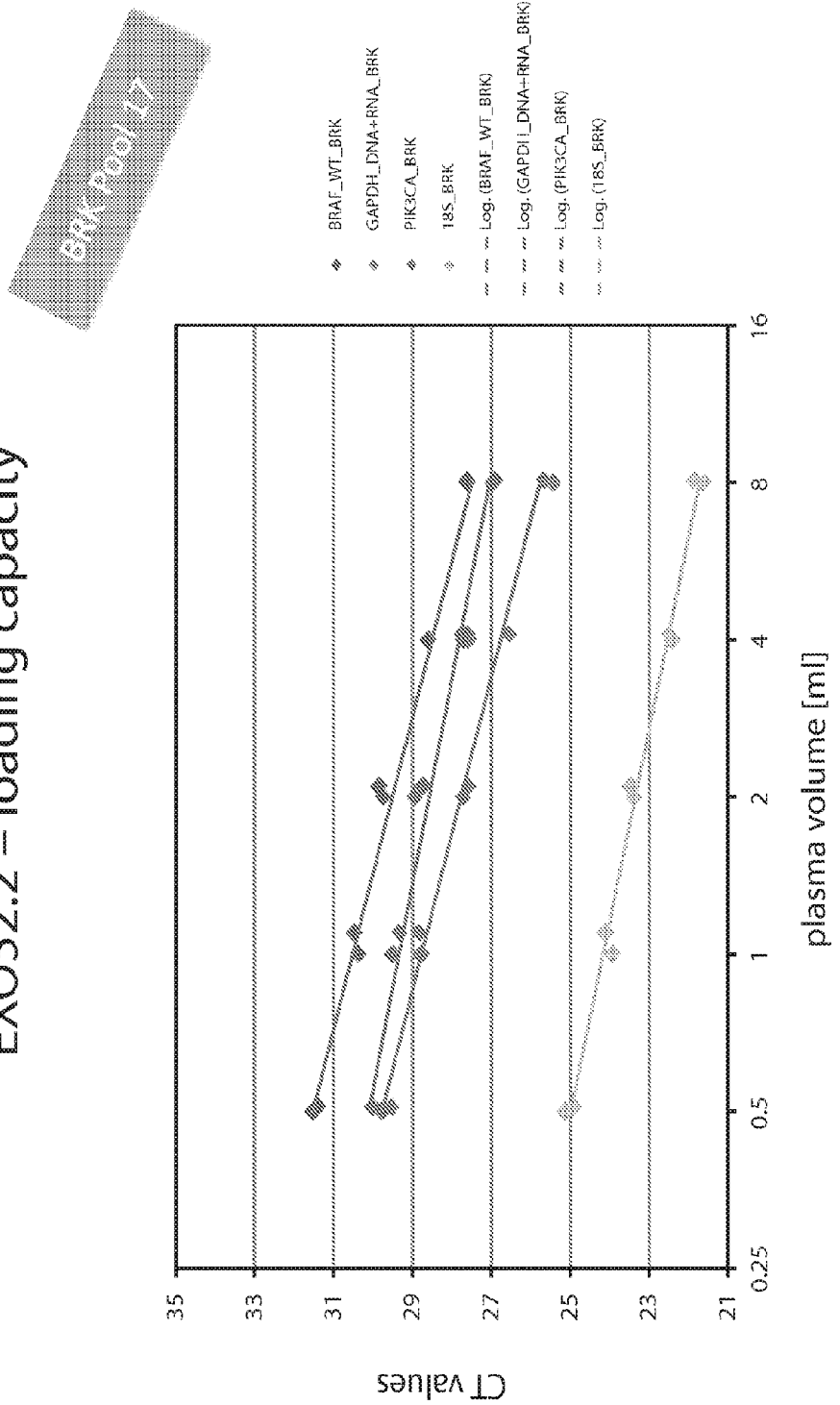
Figure 108:
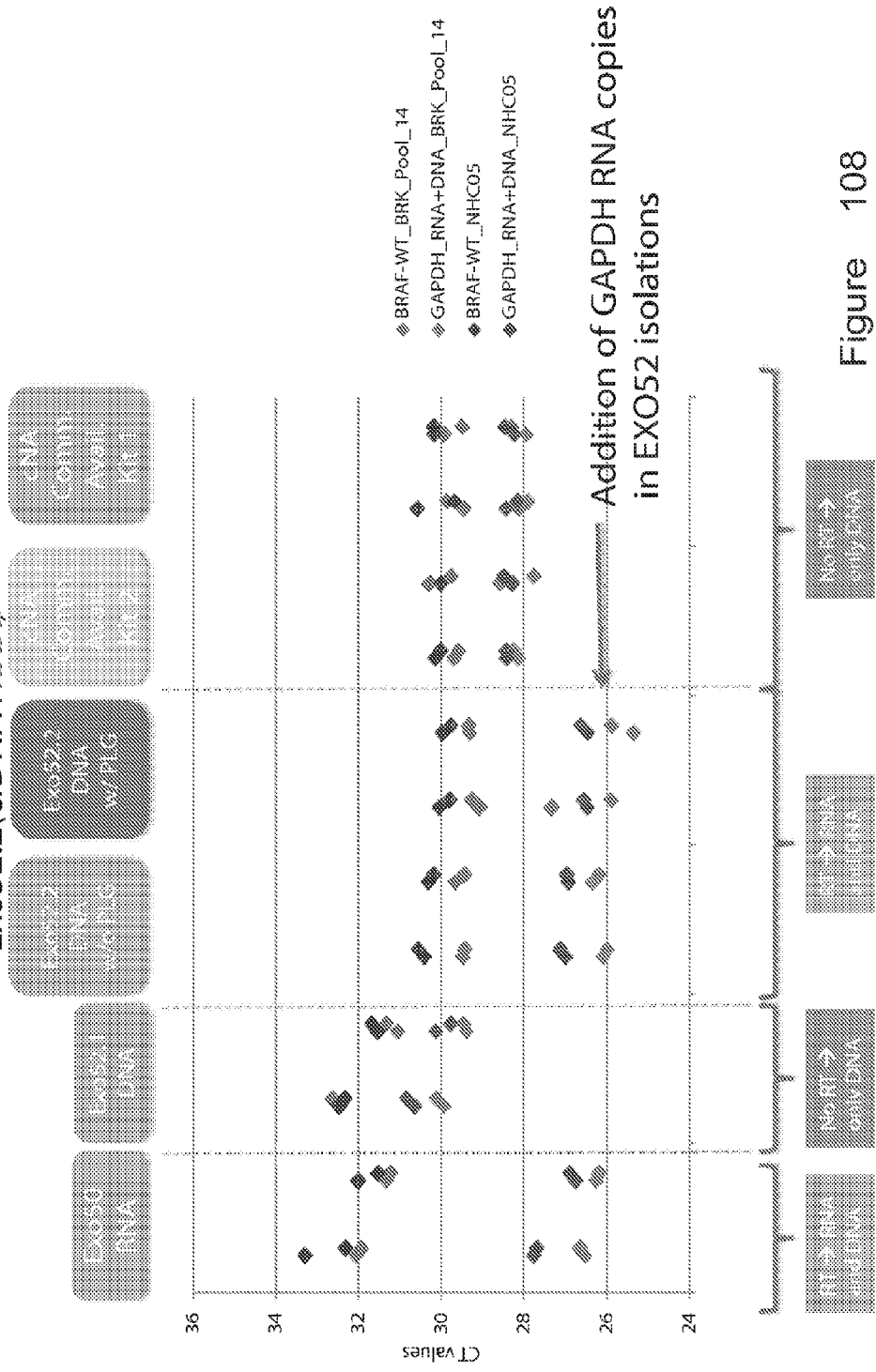
Figure 109:
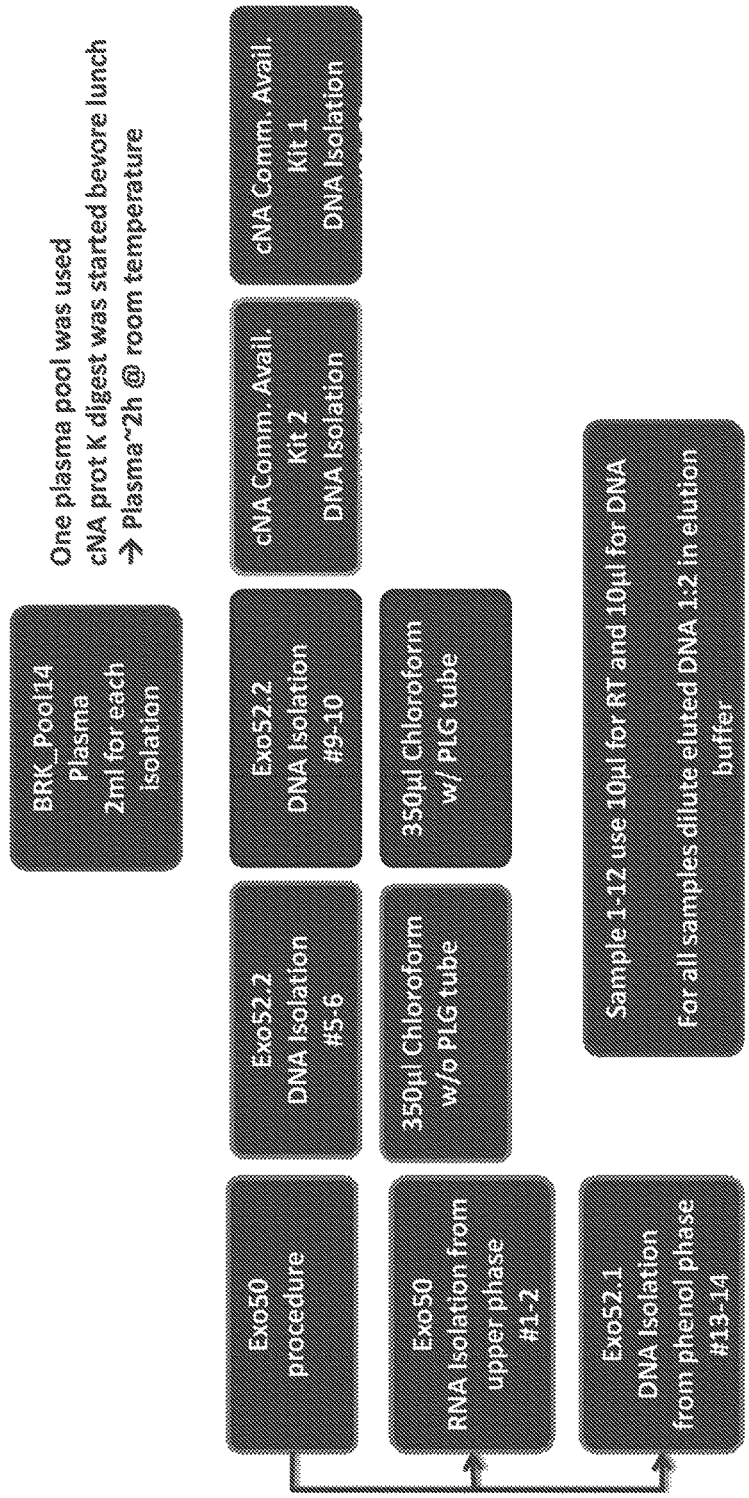
FIG. 109 is a schematic representation of studies designed to compare cfDNA isolating using methods of the disclosure with commercially available kits.
Figure 110:
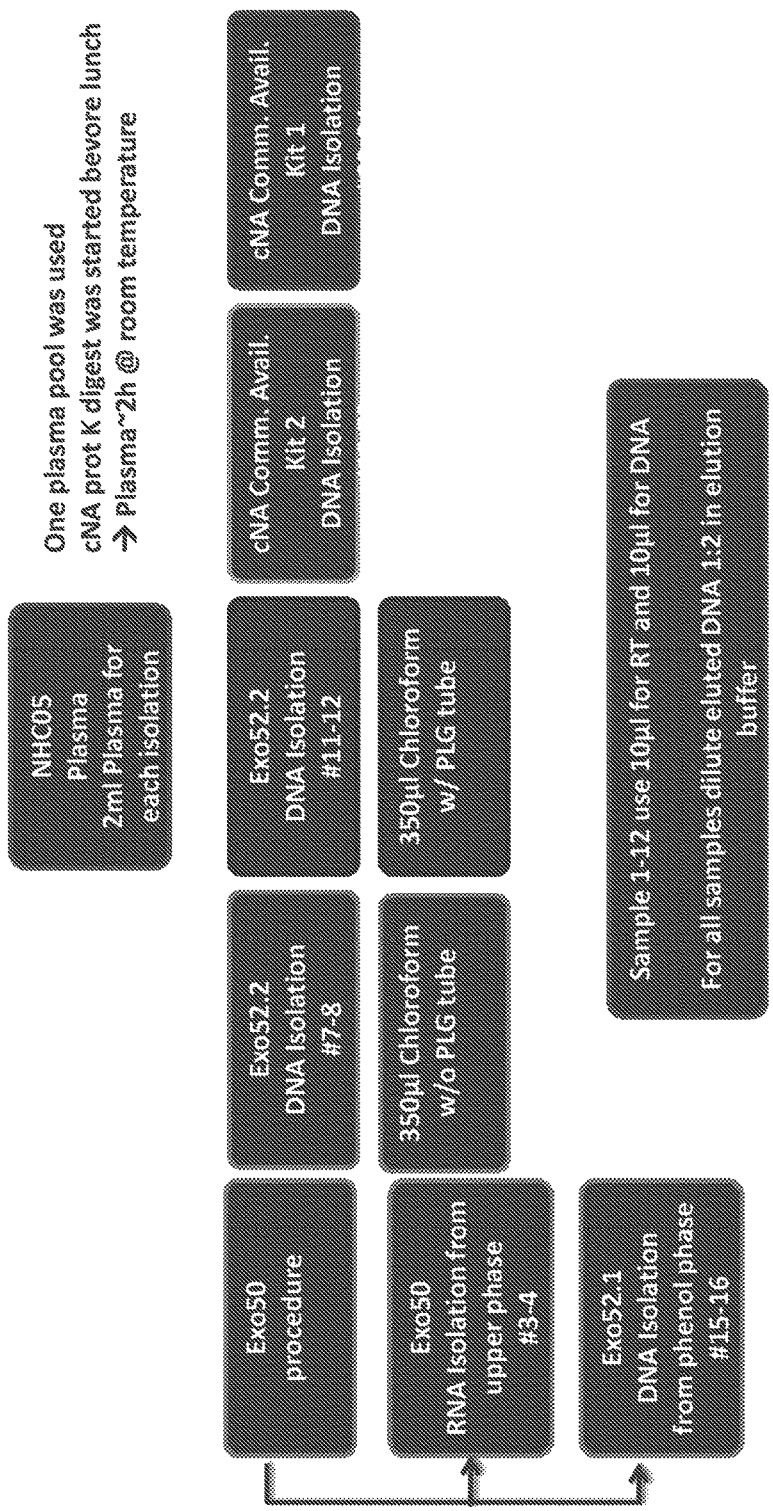
FIGS. 110 and 111 are a schematic representation and an overview of studies designed to compare cfDNA isolation using different isolation techniques including methods of the disclosure and commercially available kits.
Figure 111:
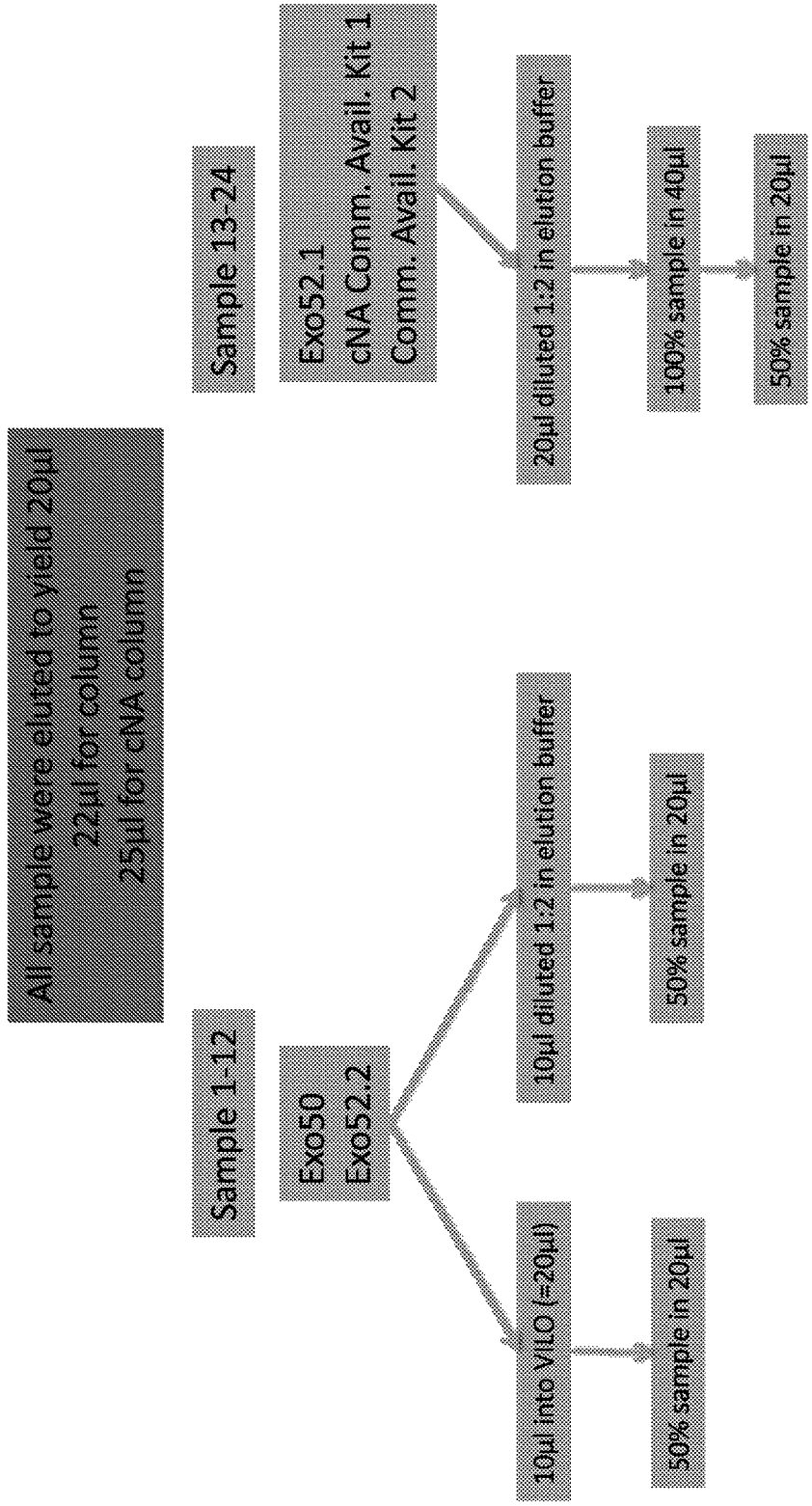
Figure 112:
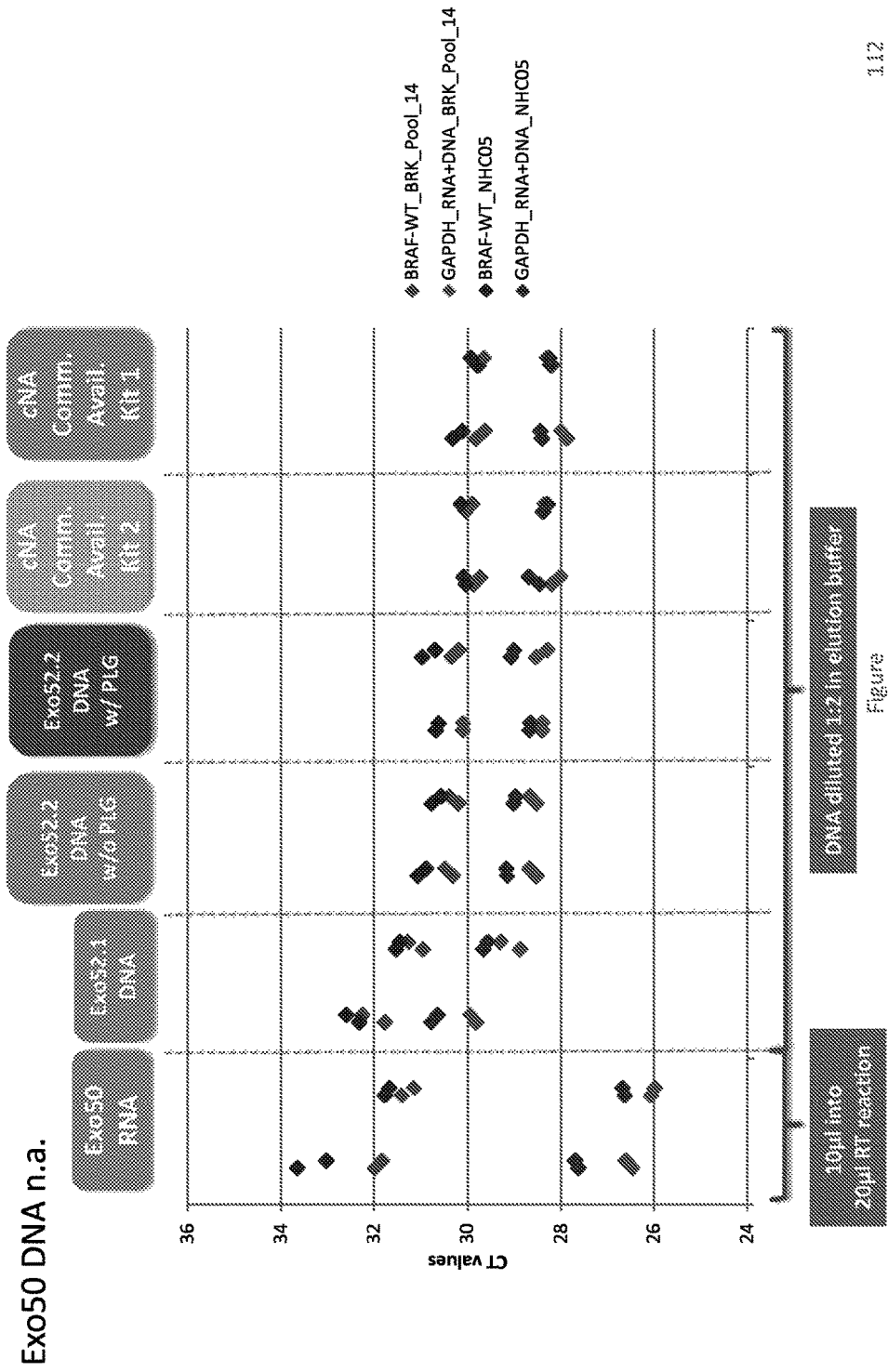
Figure 113:
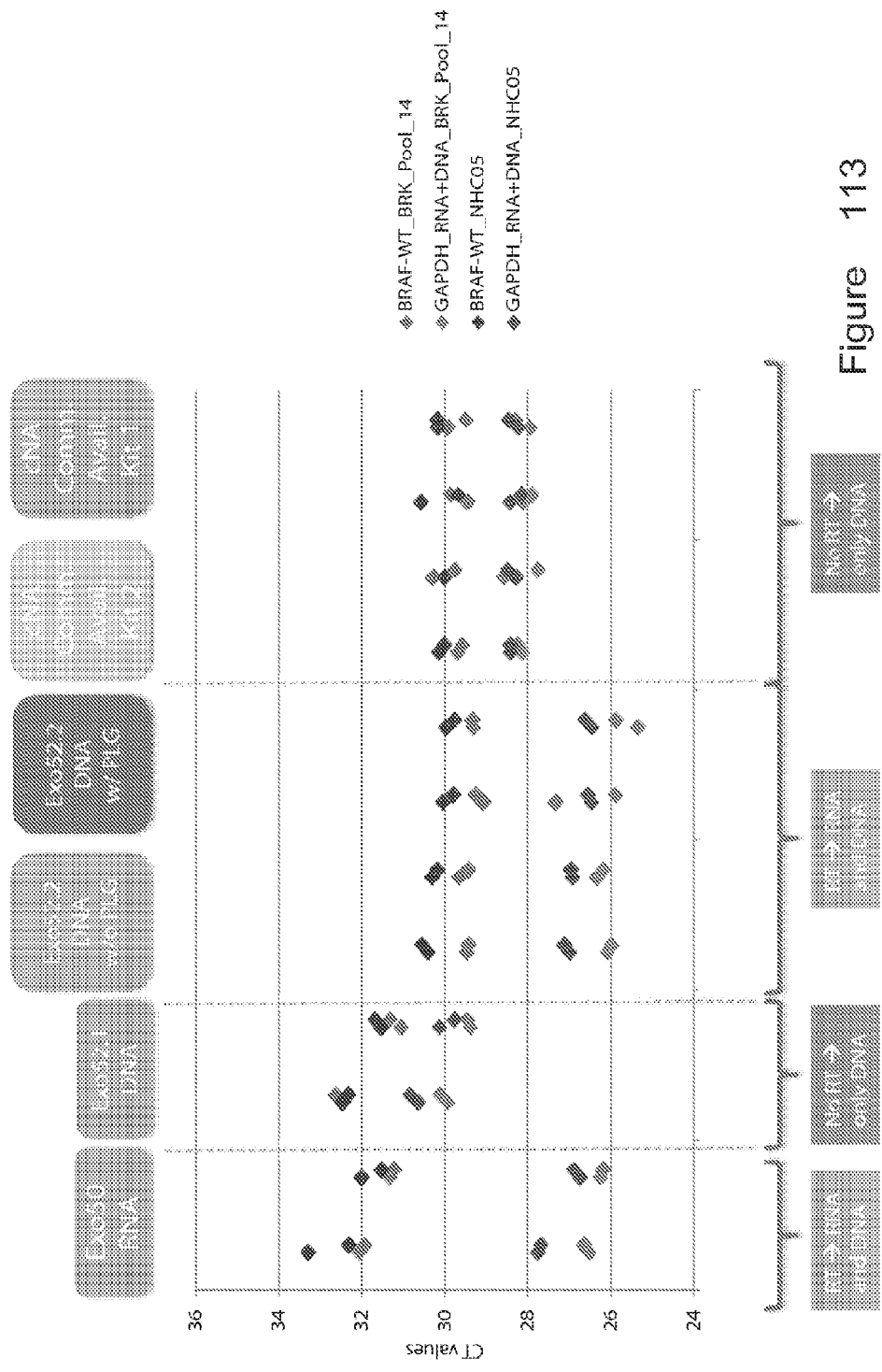
Figure 119:
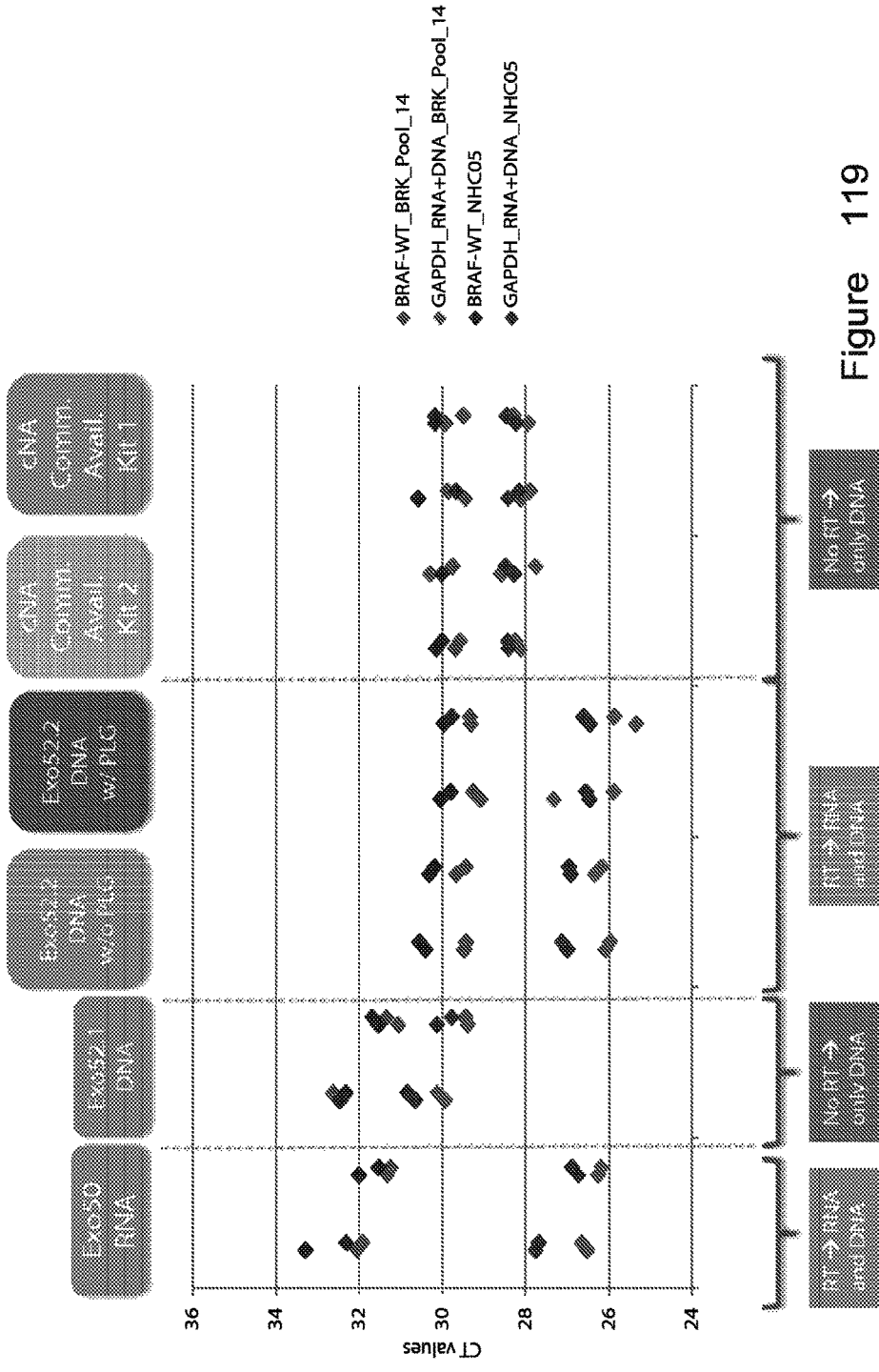
Figure 120:
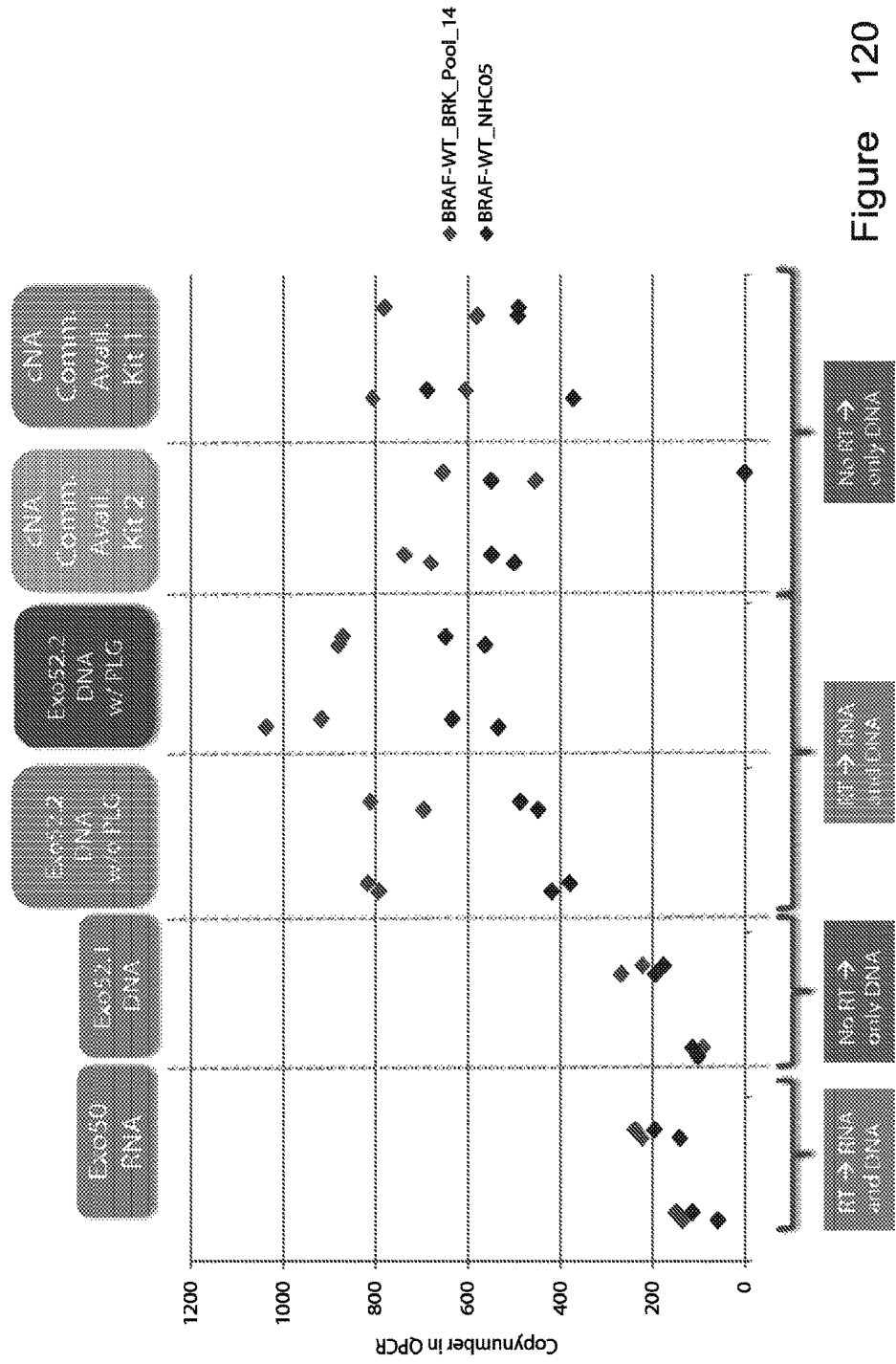
Figure 121:
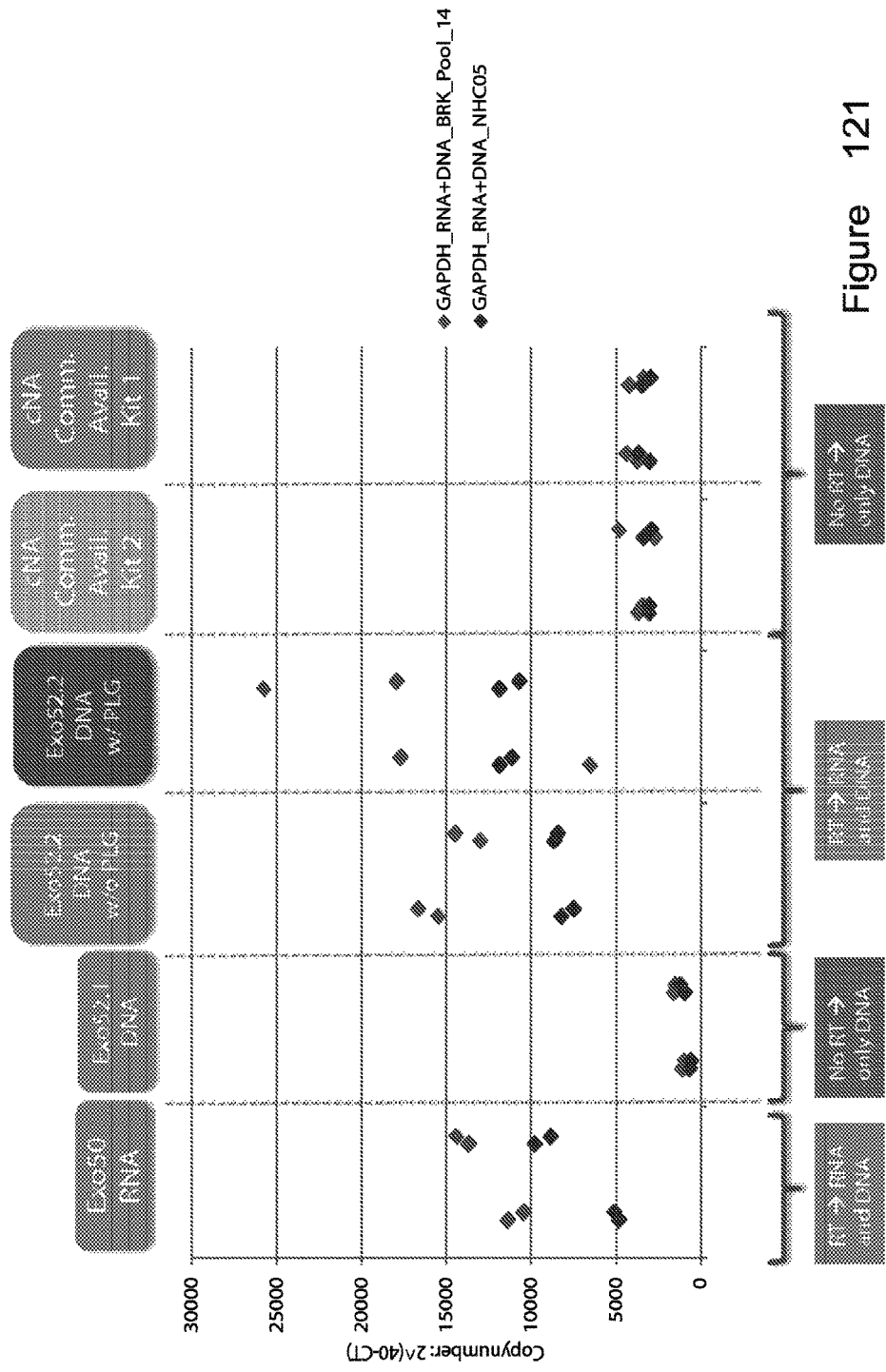
Figure 152:
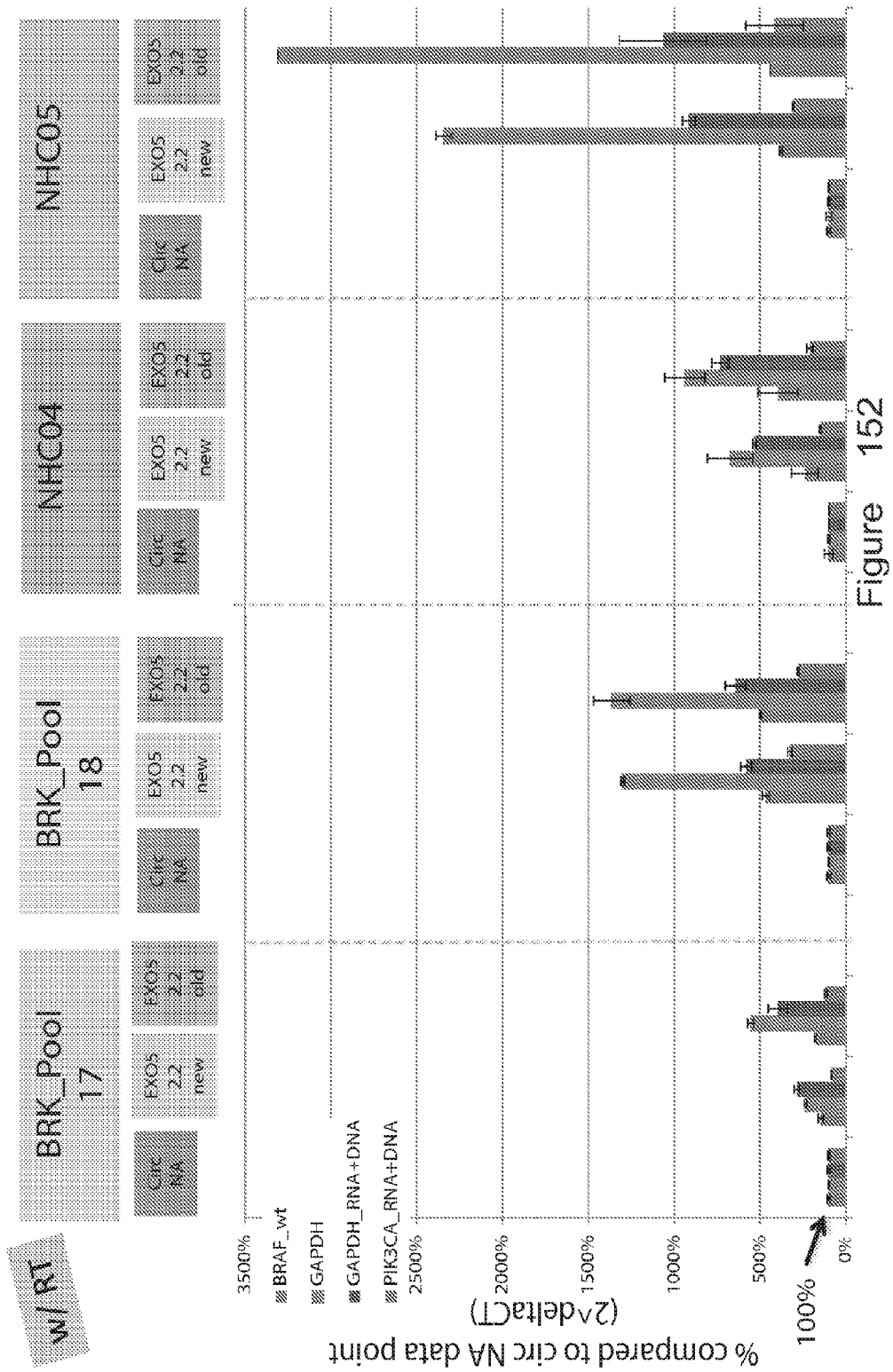
Figure 177:
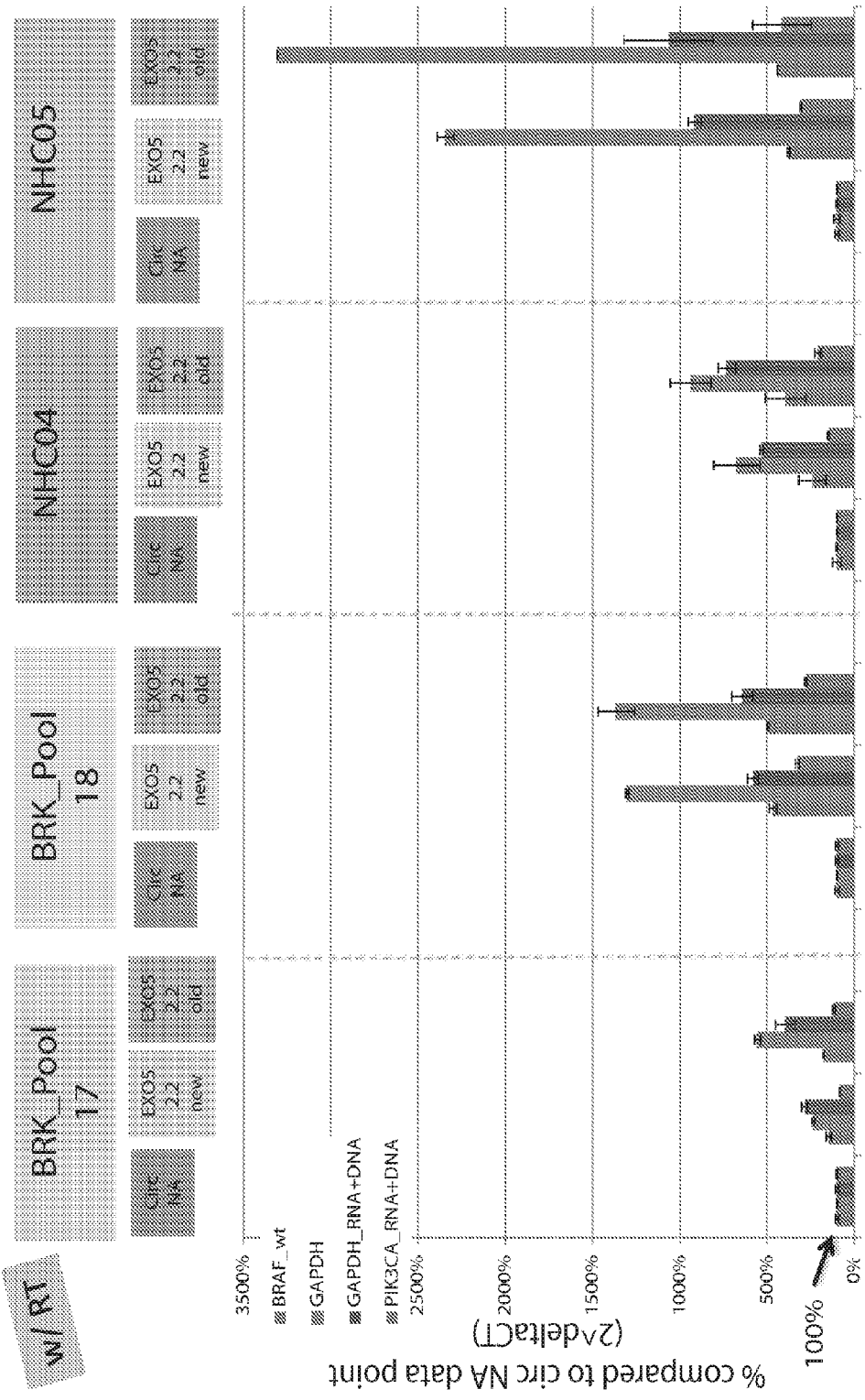
Figure 178:
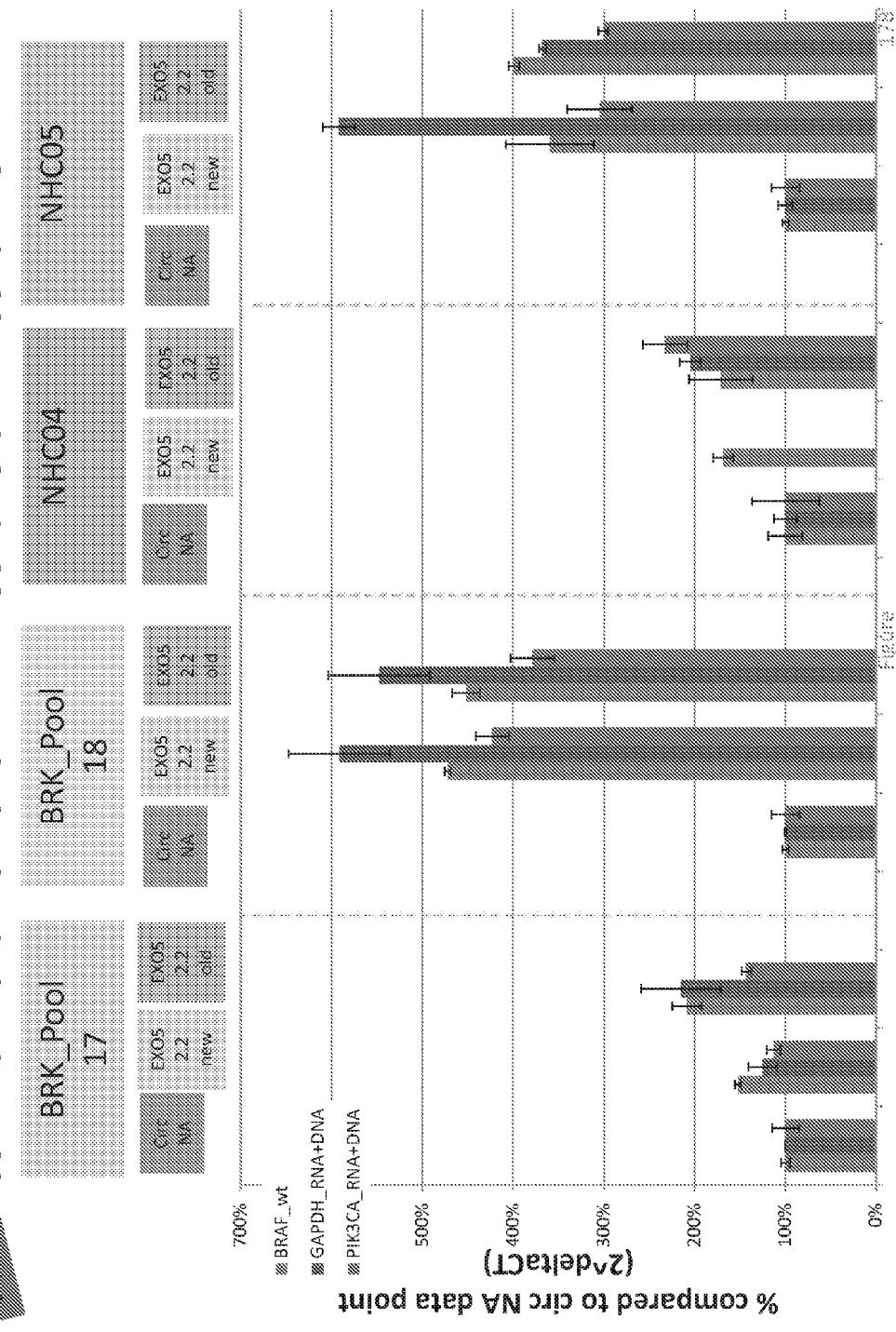
Figure 179:
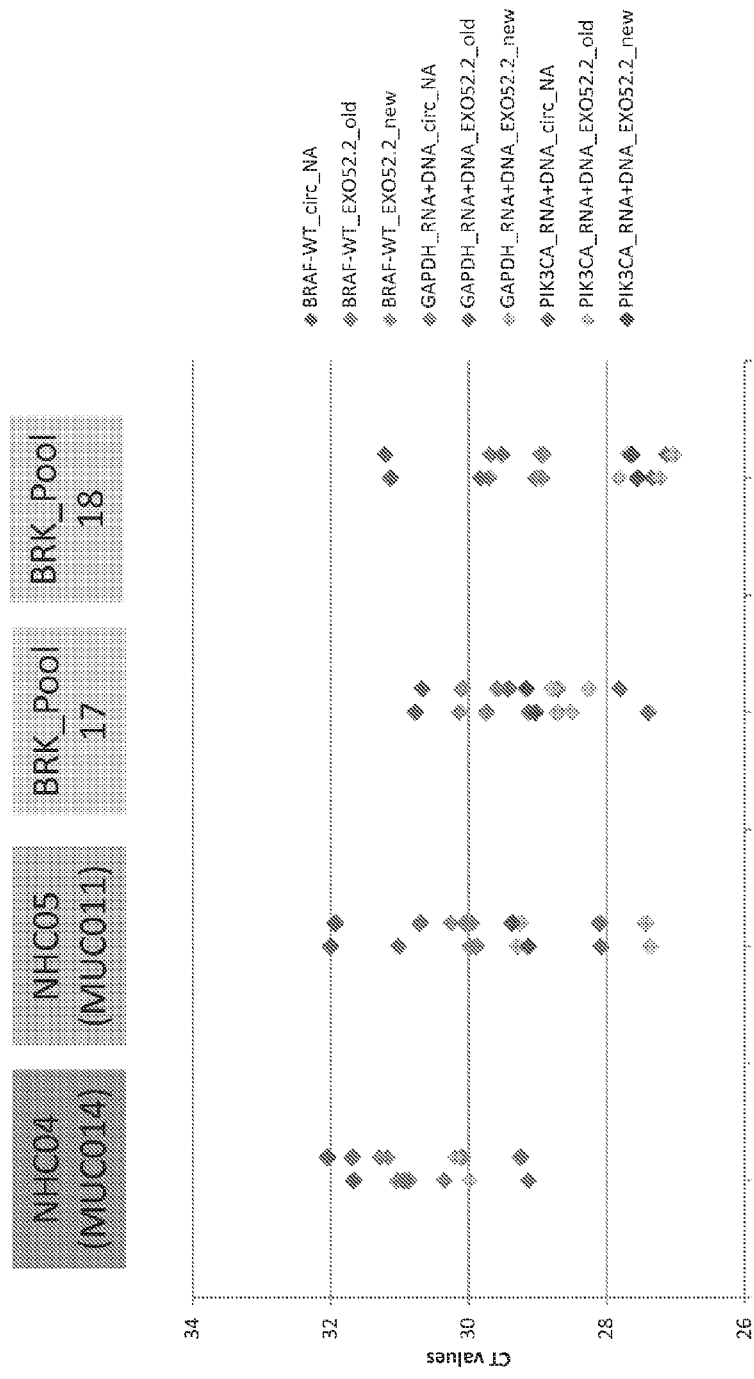
Figure 180:
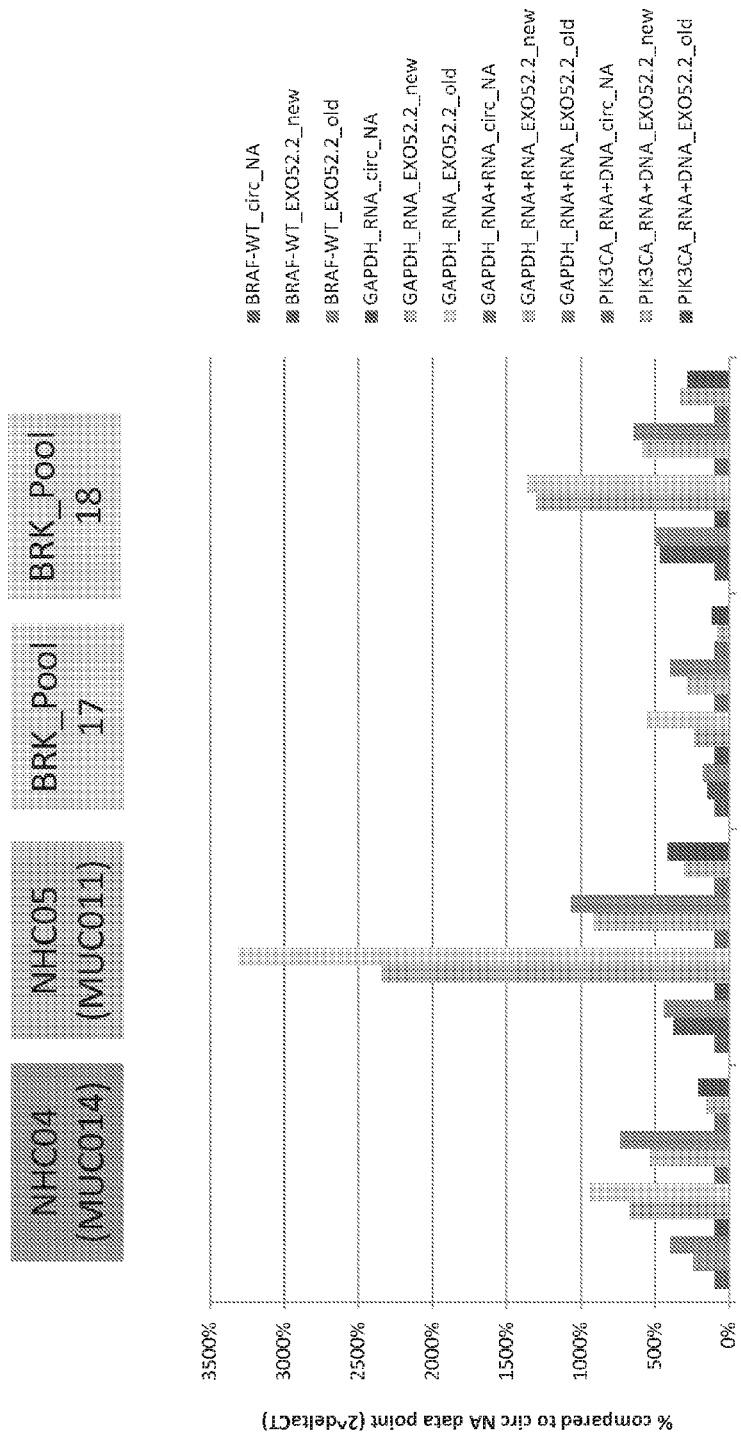
Figure 181:
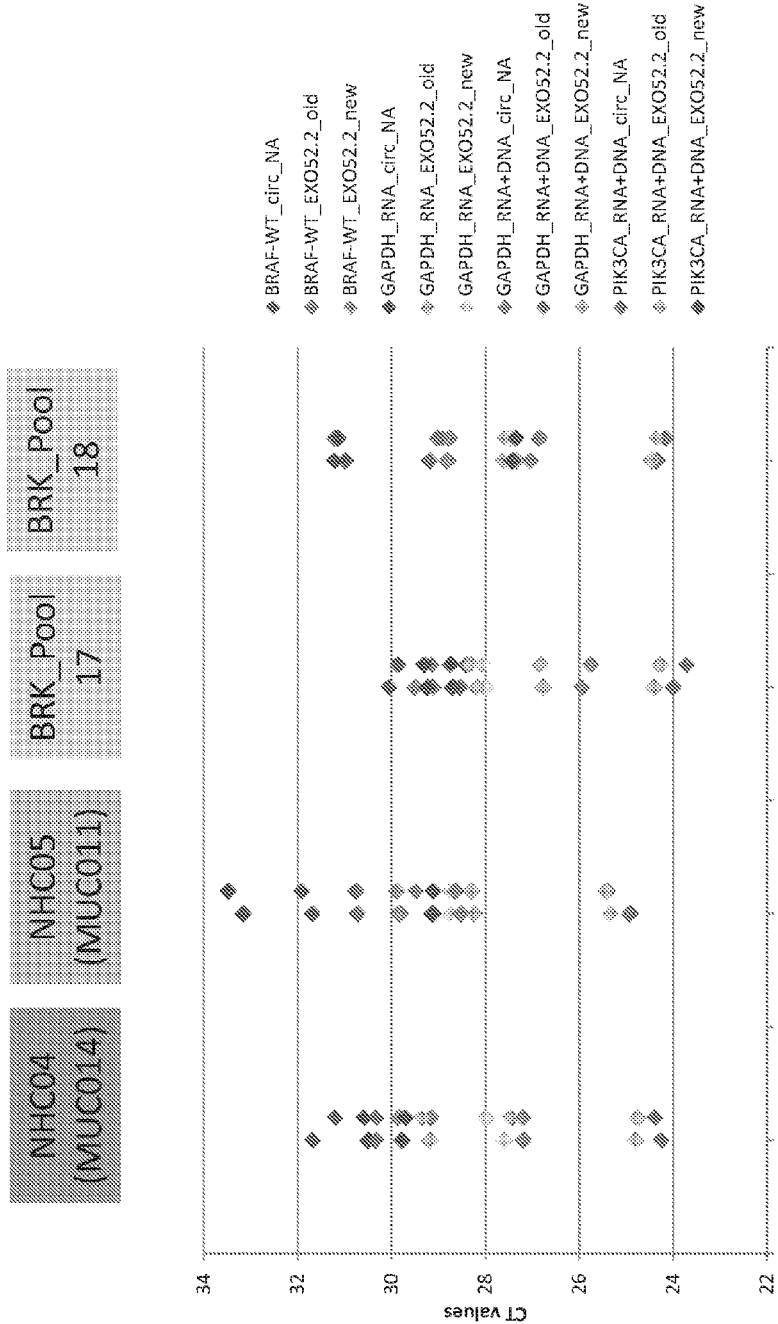
Figure 182:
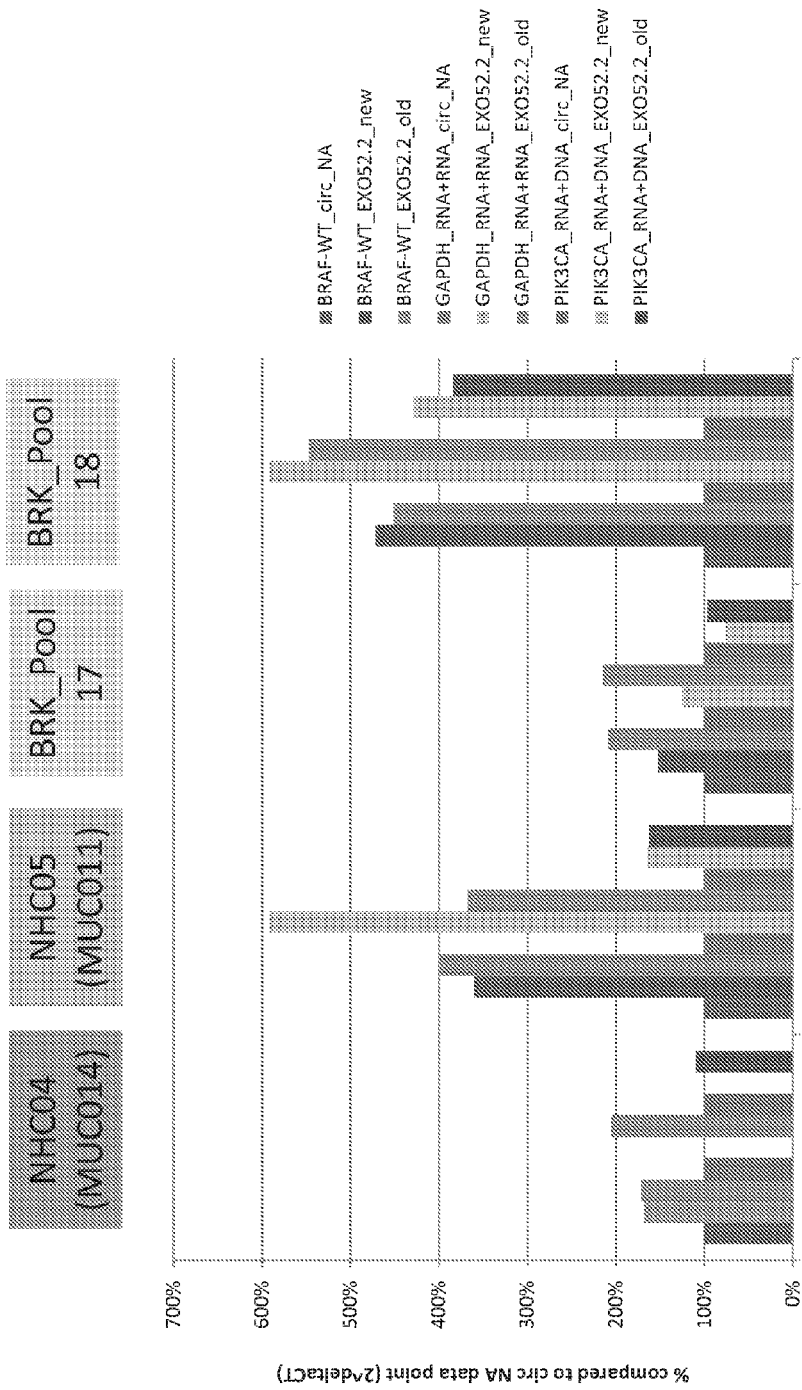
Figure 183:
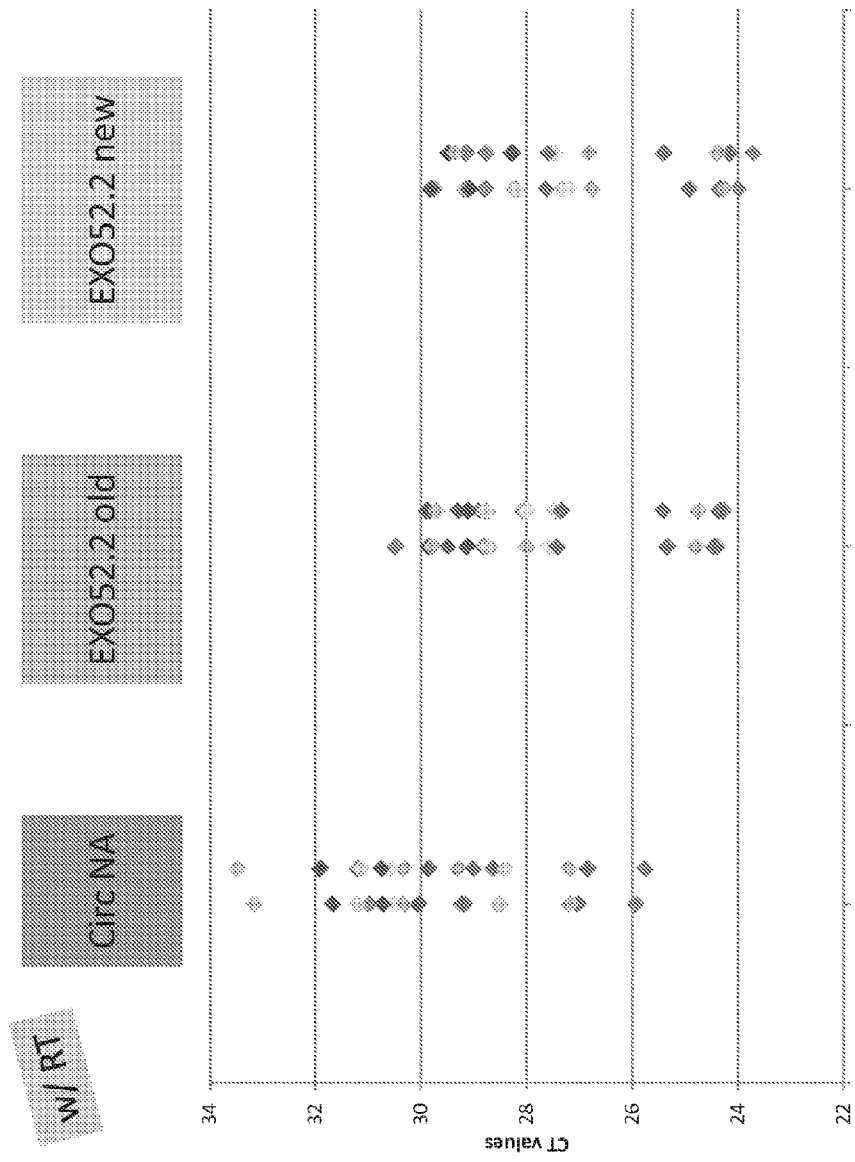
Figure 184:
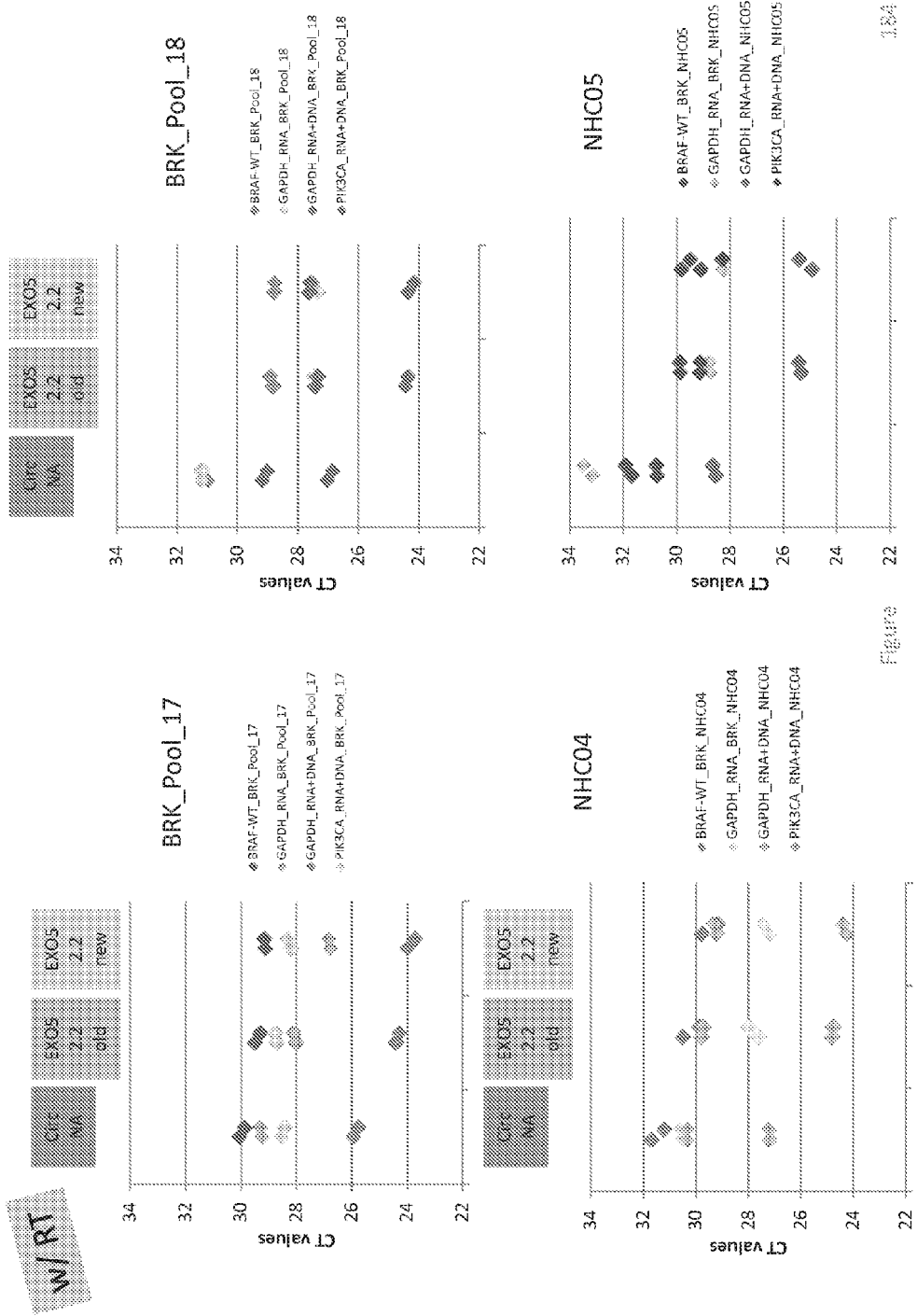
Figure 185:
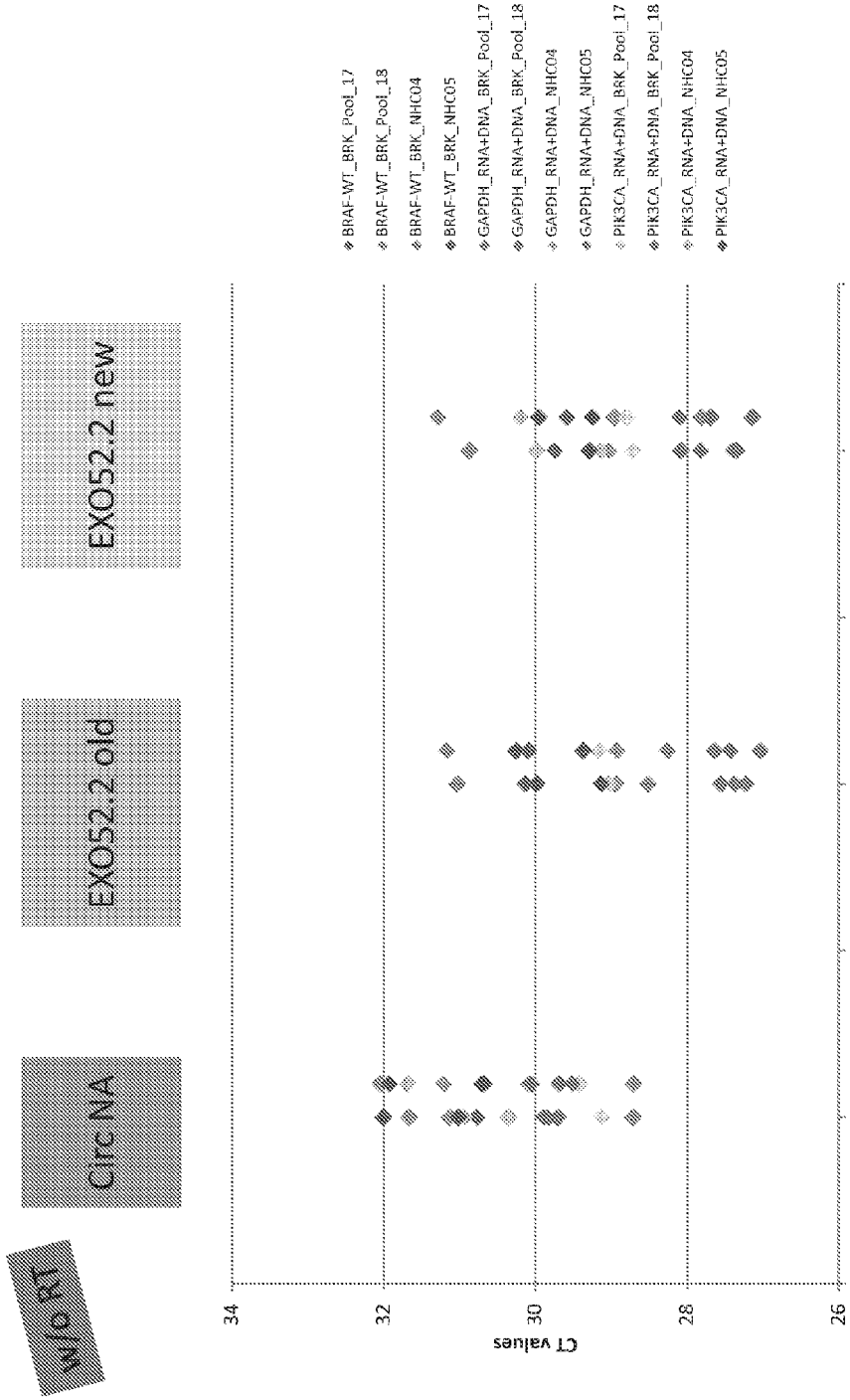
Figure 186:
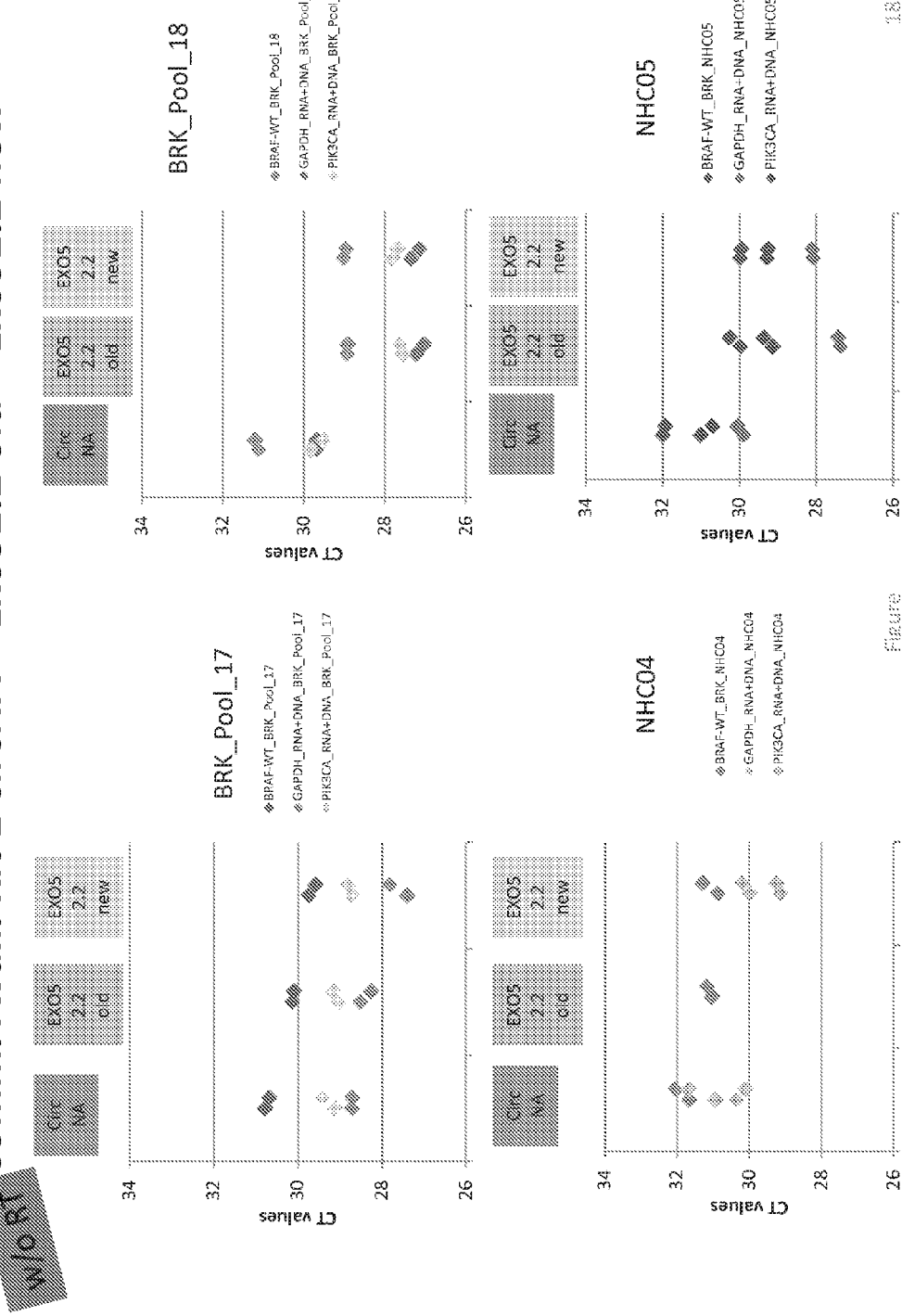
Figure 187:
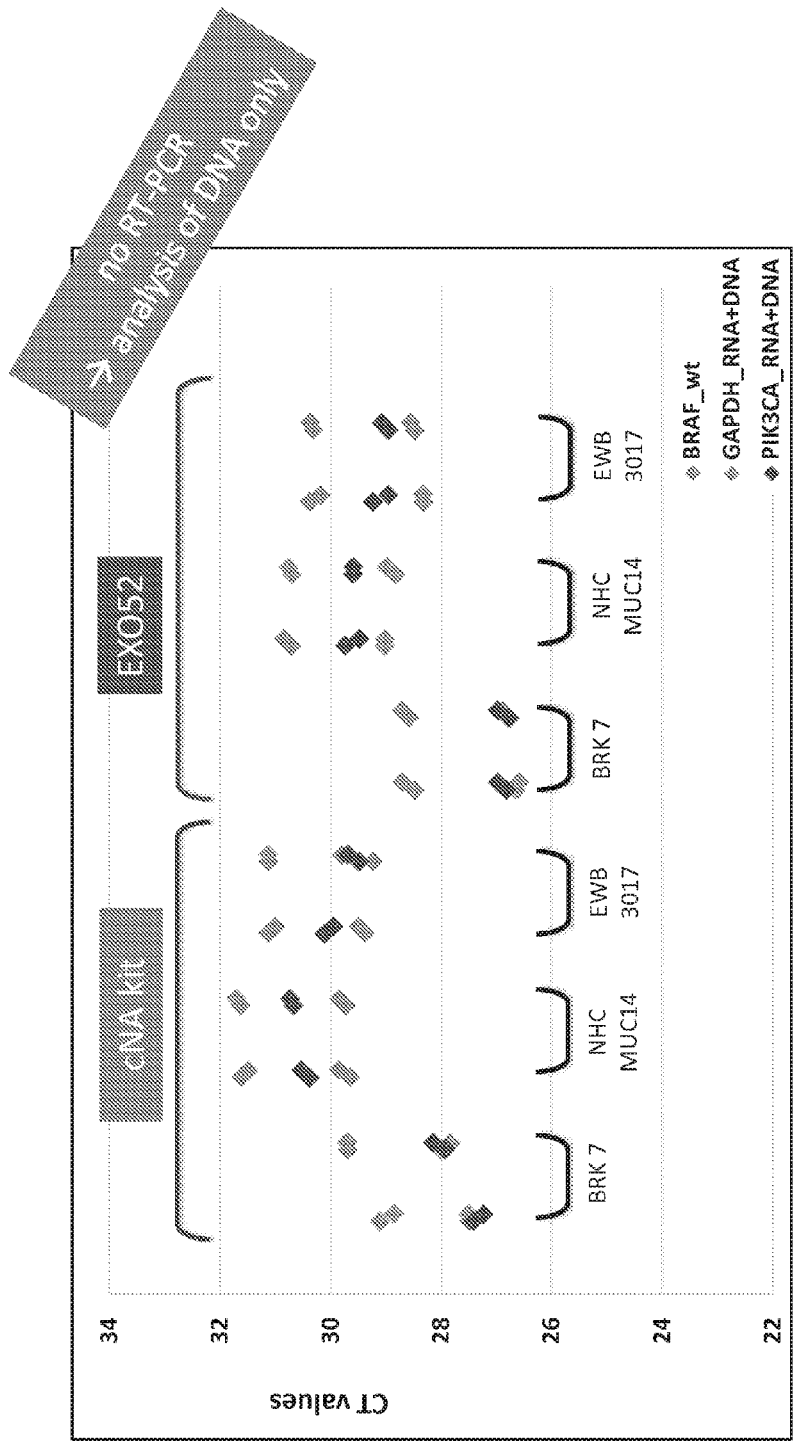
Figure 188:
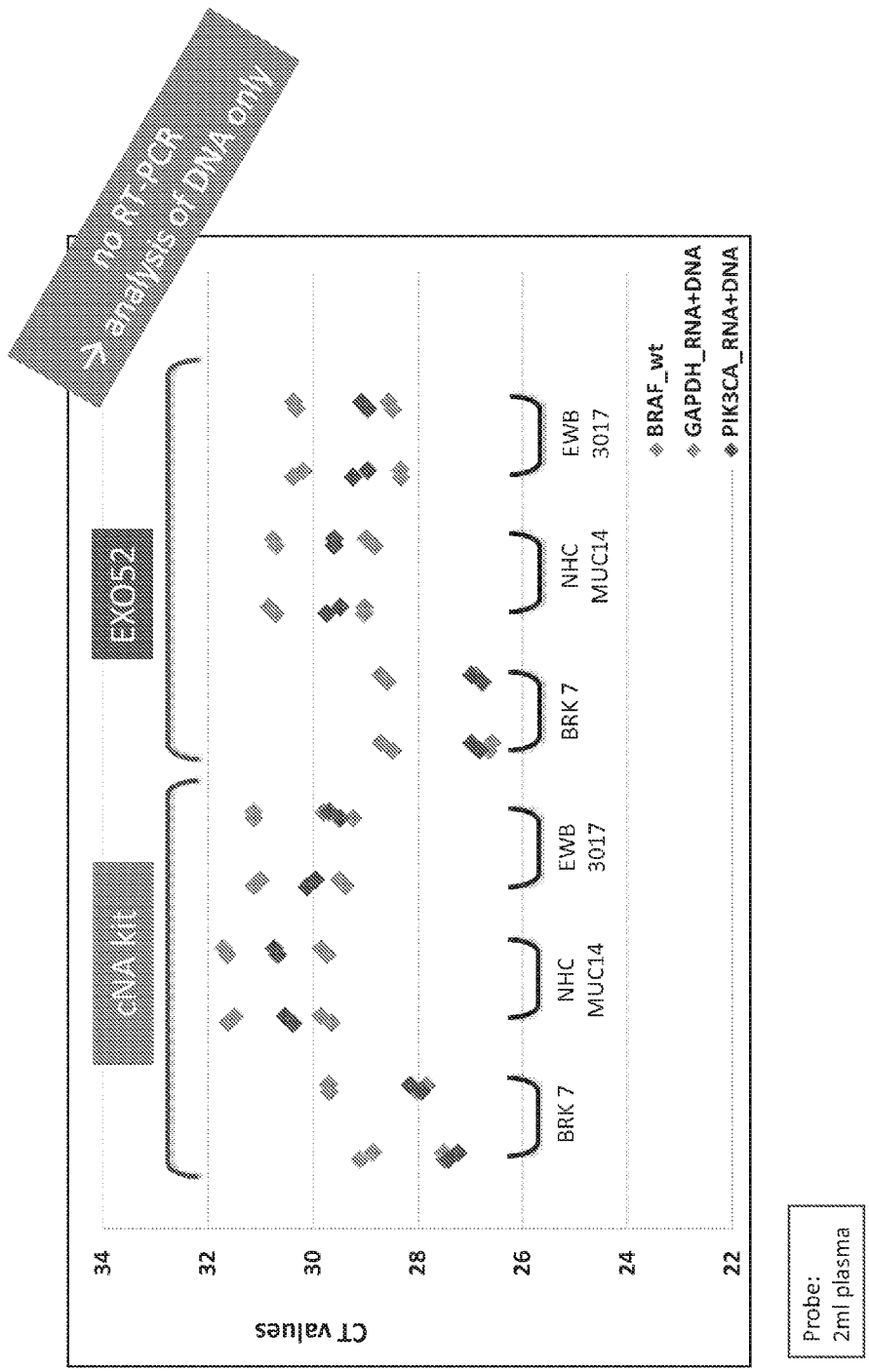
Figure 189:
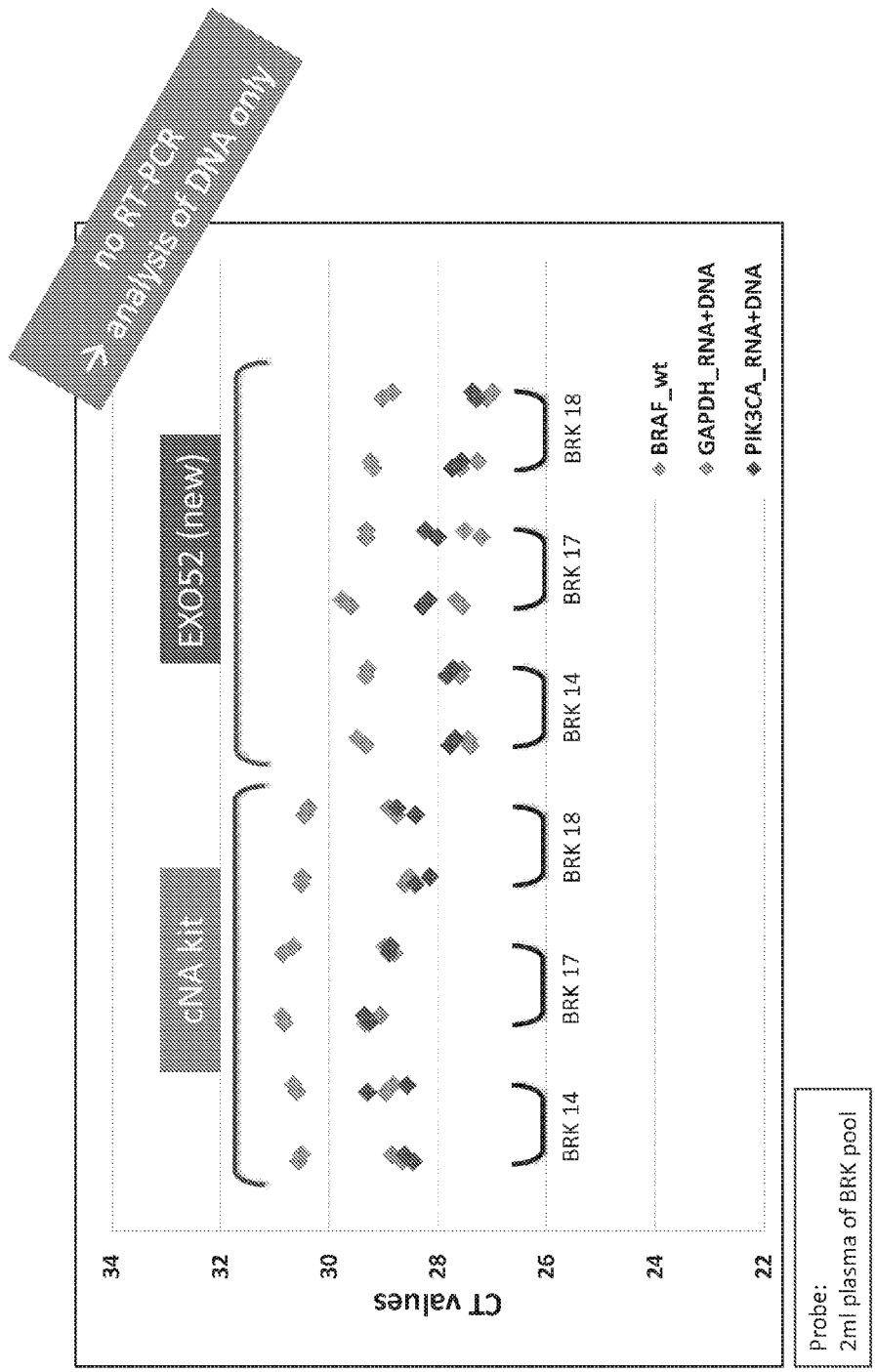
Figure 190:
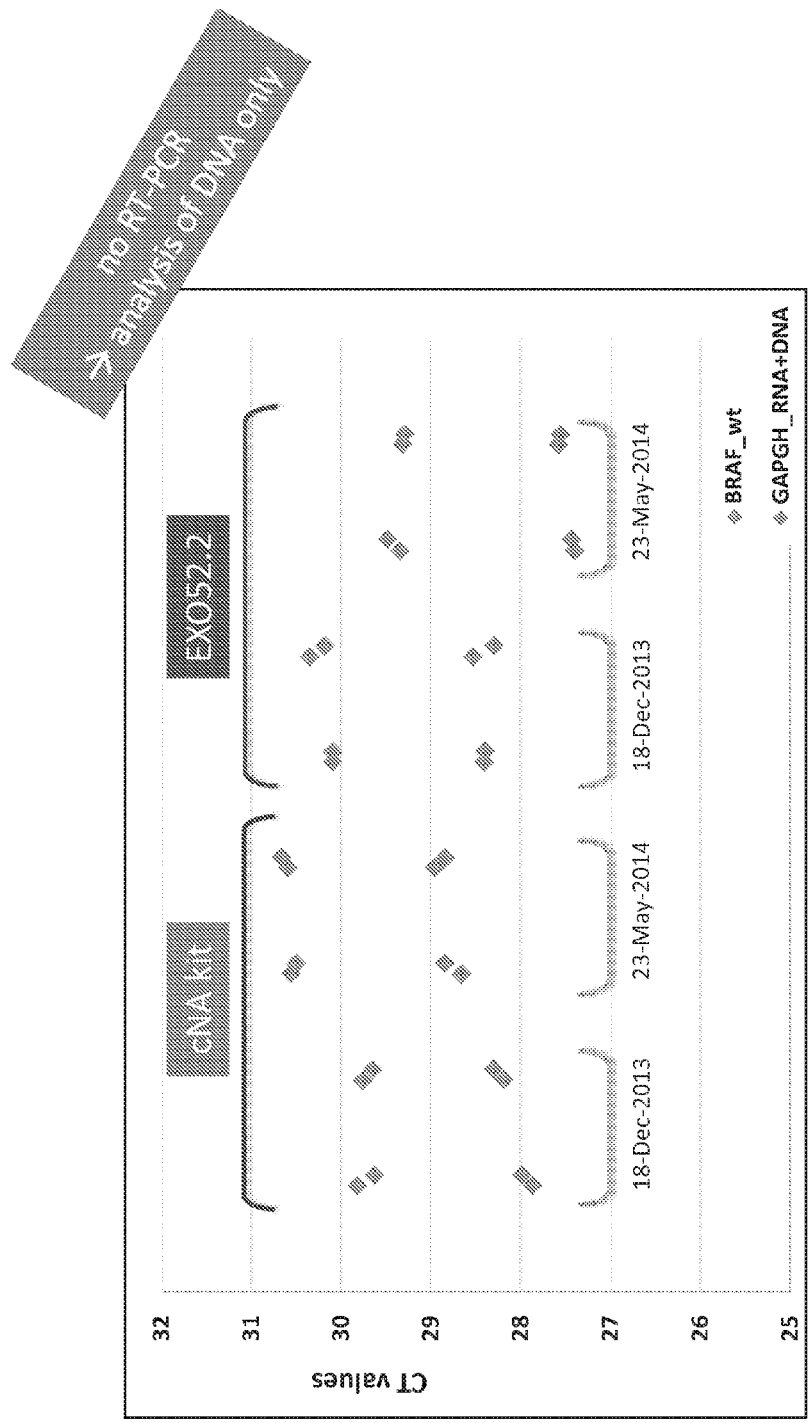
Figure 191:
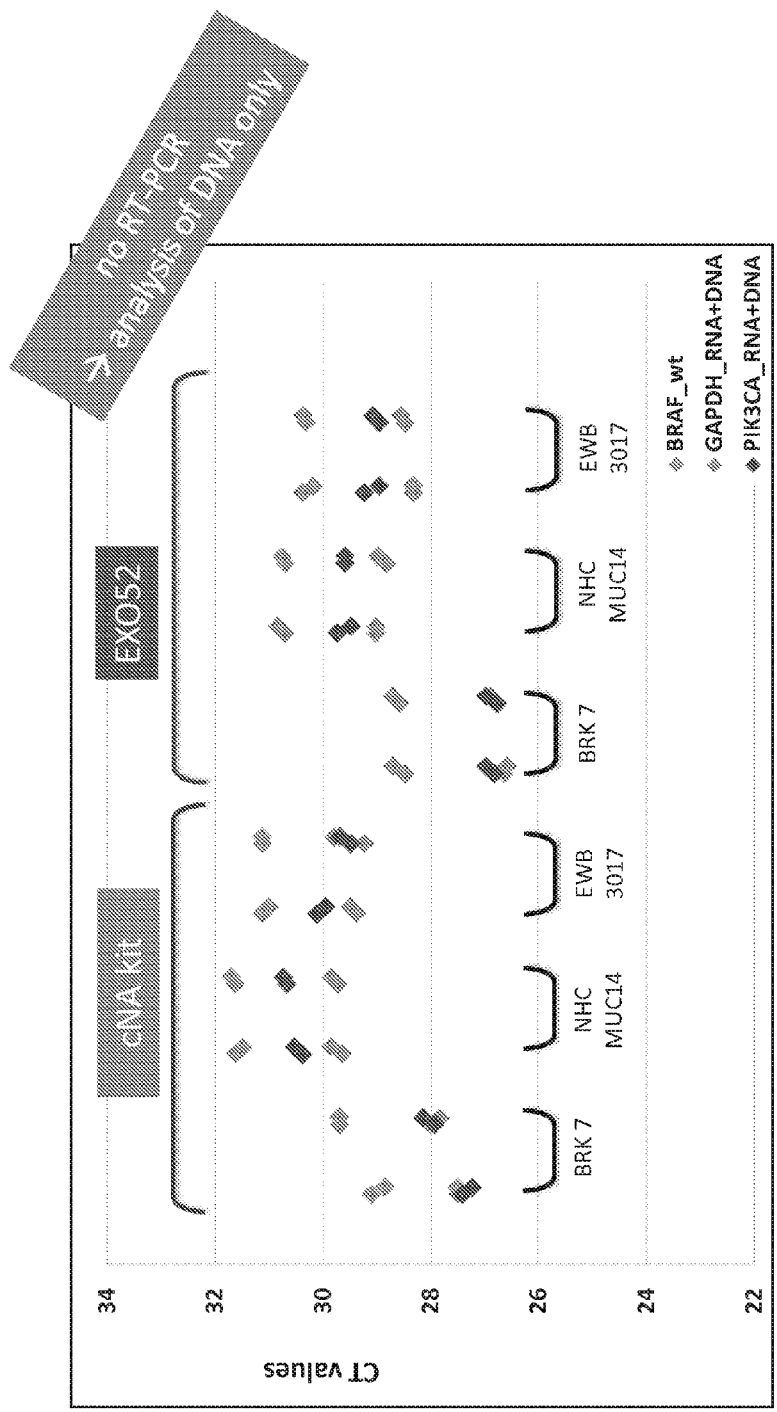
Figure 192:
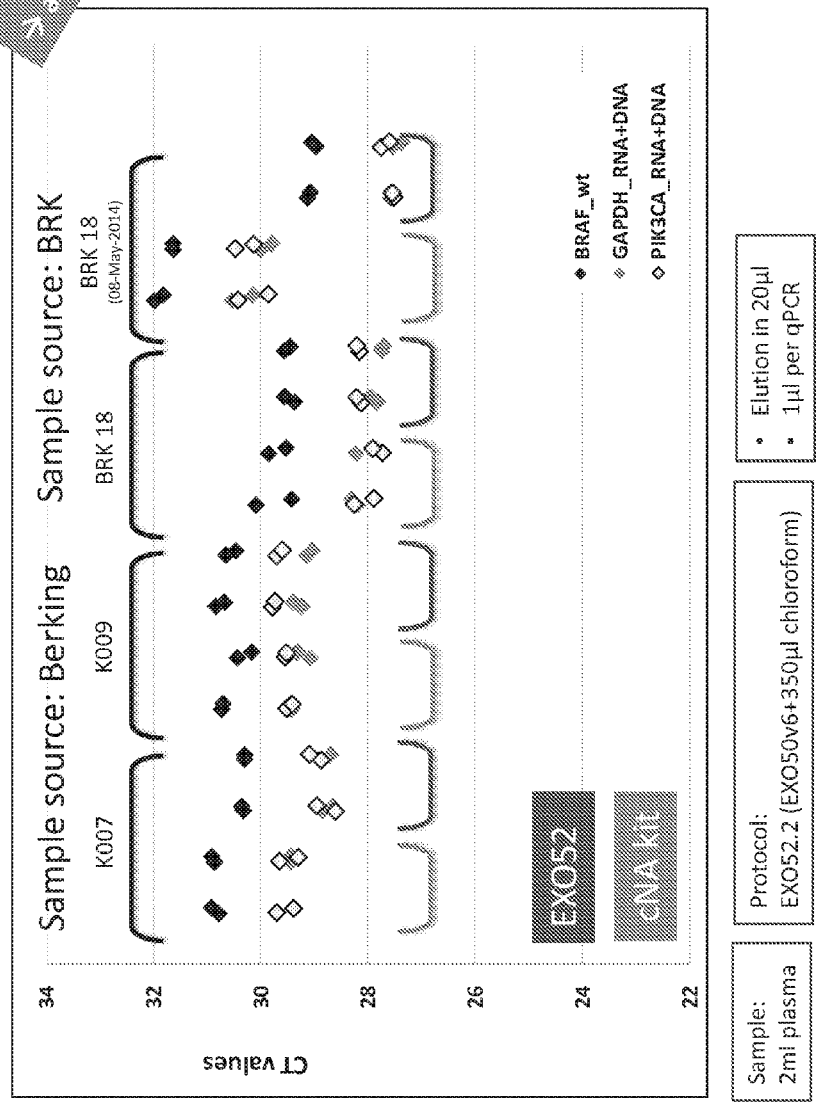
Figure 193:
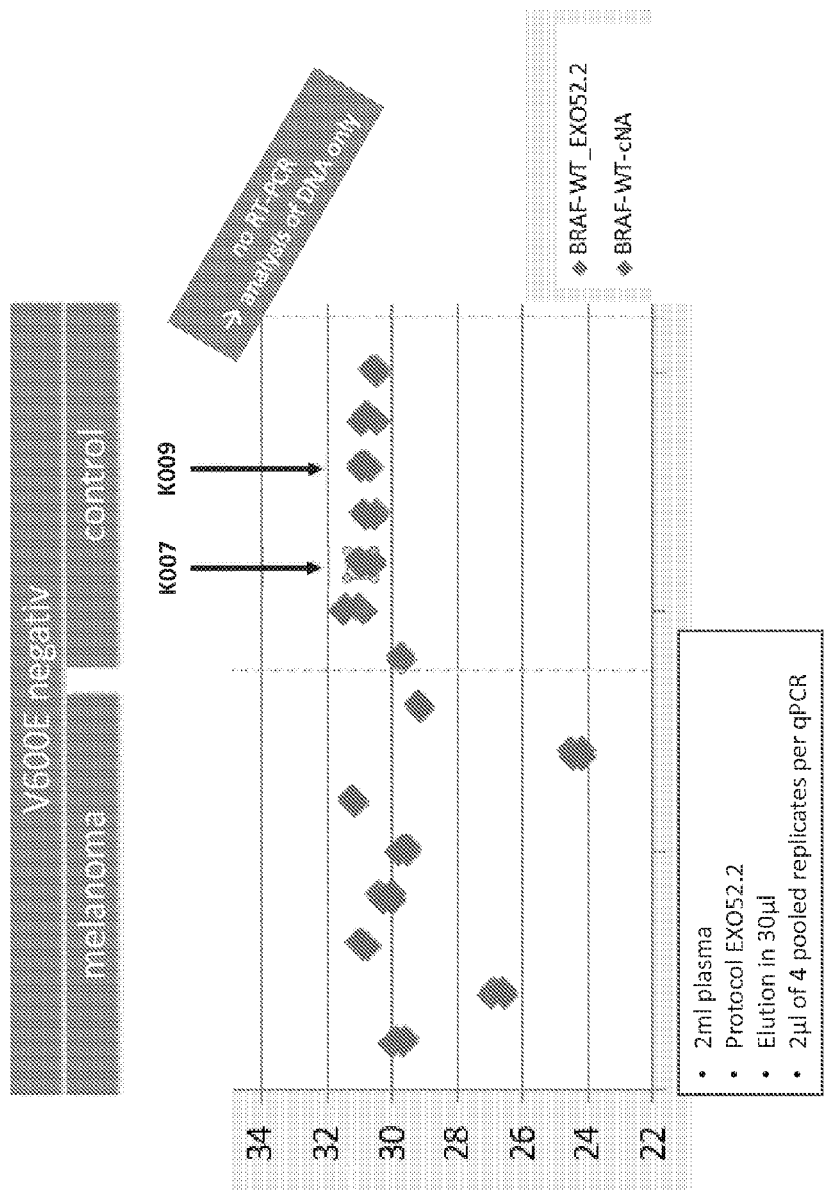
Figure 194:
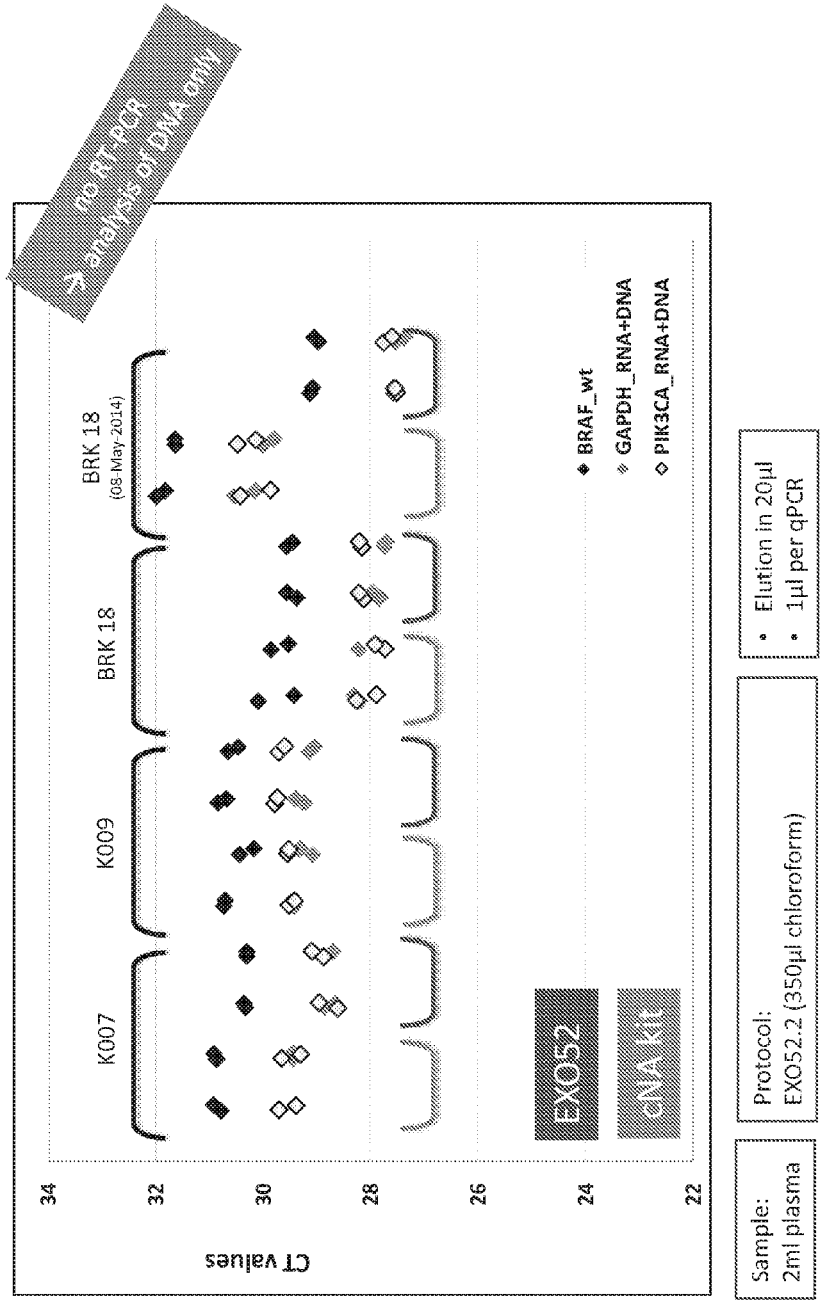
Figure 195:
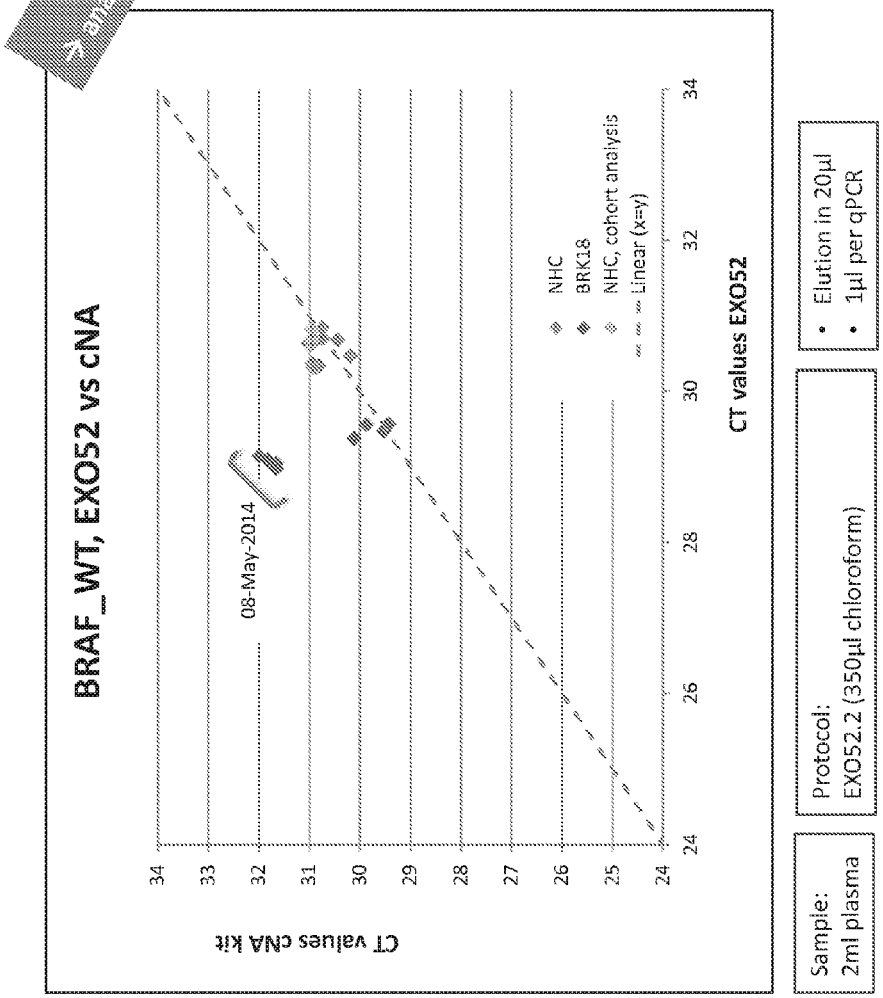
Figure 196:
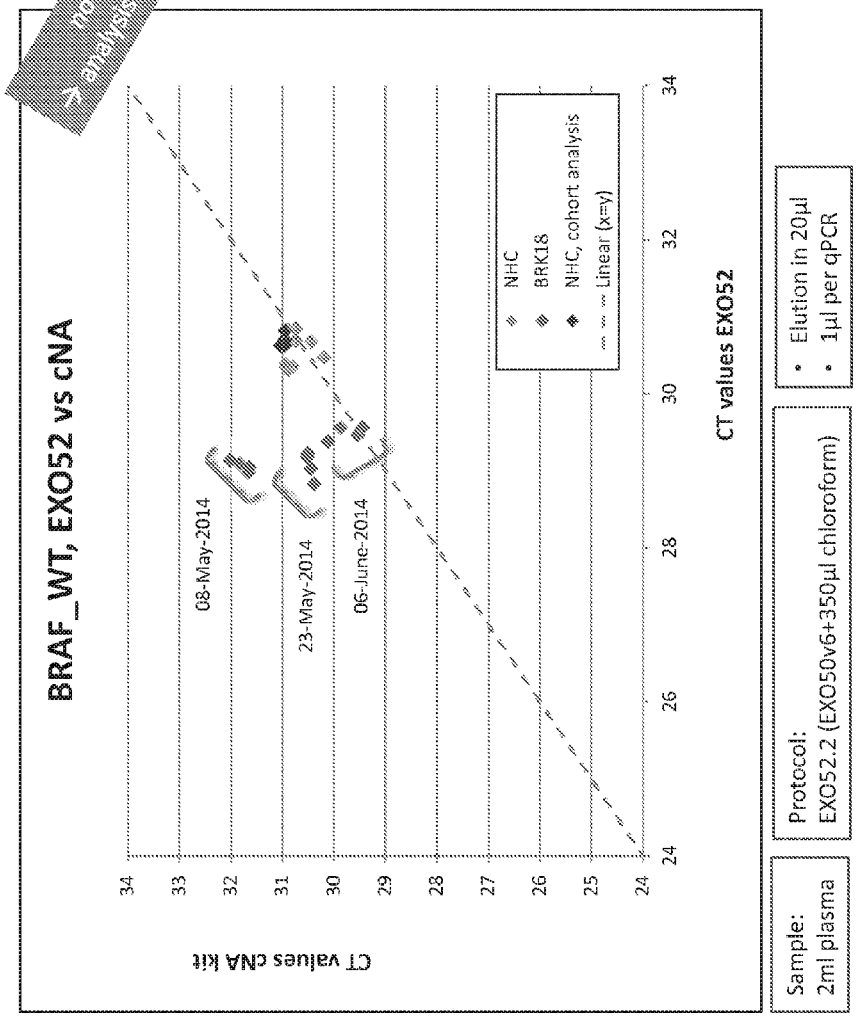
Figure 197:
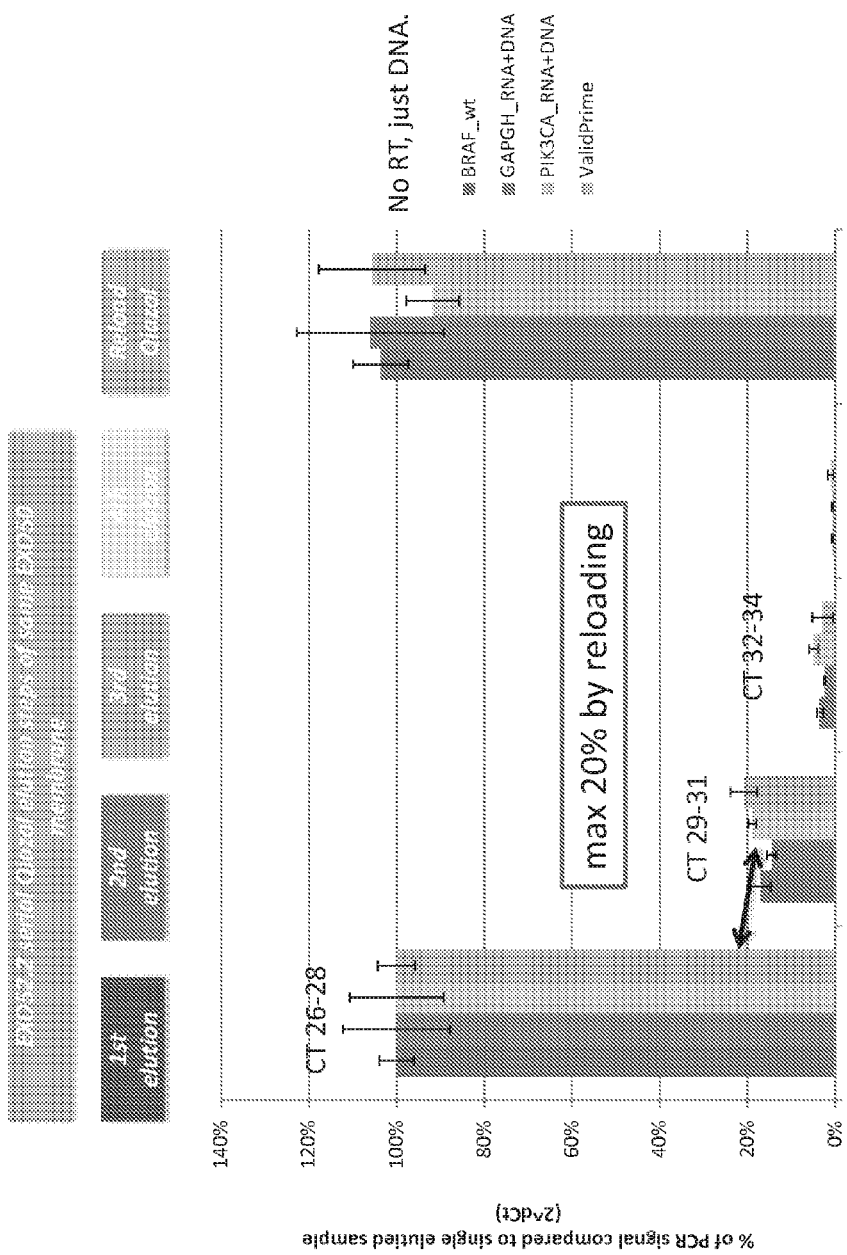
FIG. 197 is a graph depicting the effect of multiple separate Qiazol elution steps on DNA and RNA isolation.
Figure 198:
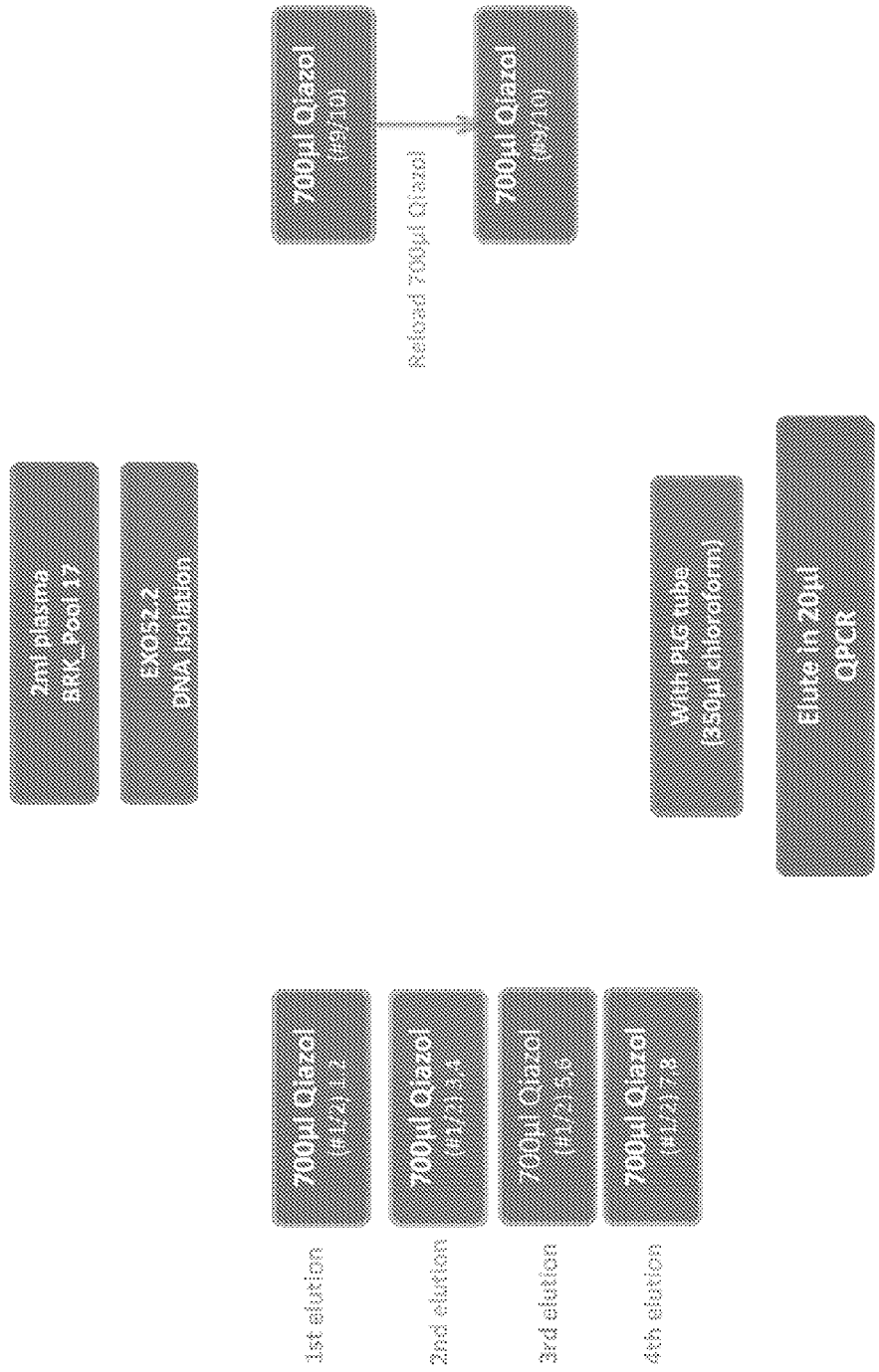
FIG. 198 is a schematic representation of studies designed to evaluate DNA and RNA isolation using multiple Qiazol elution steps.
Figure 199:
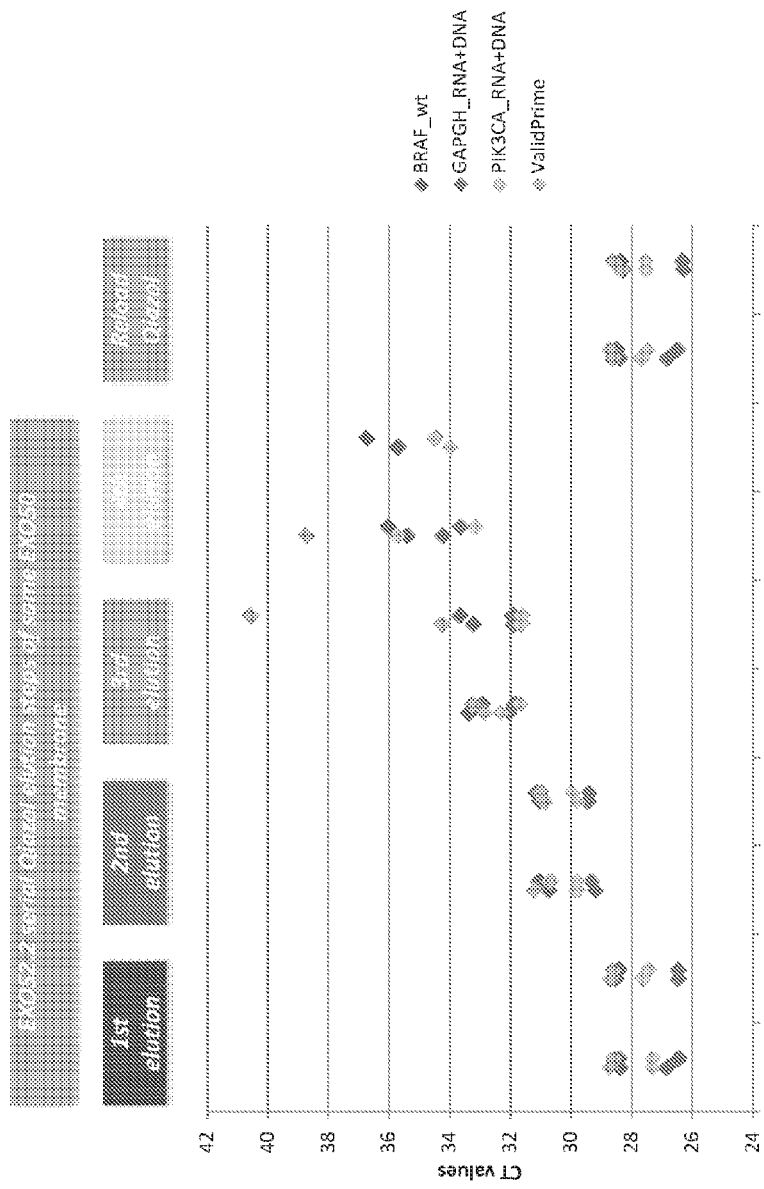
FIGS. 199, 200, 201, and 202 are a series of graphs depicting the effect of multiple separate Qiazol elution steps on DNA and RNA isolation.
Figure 200:
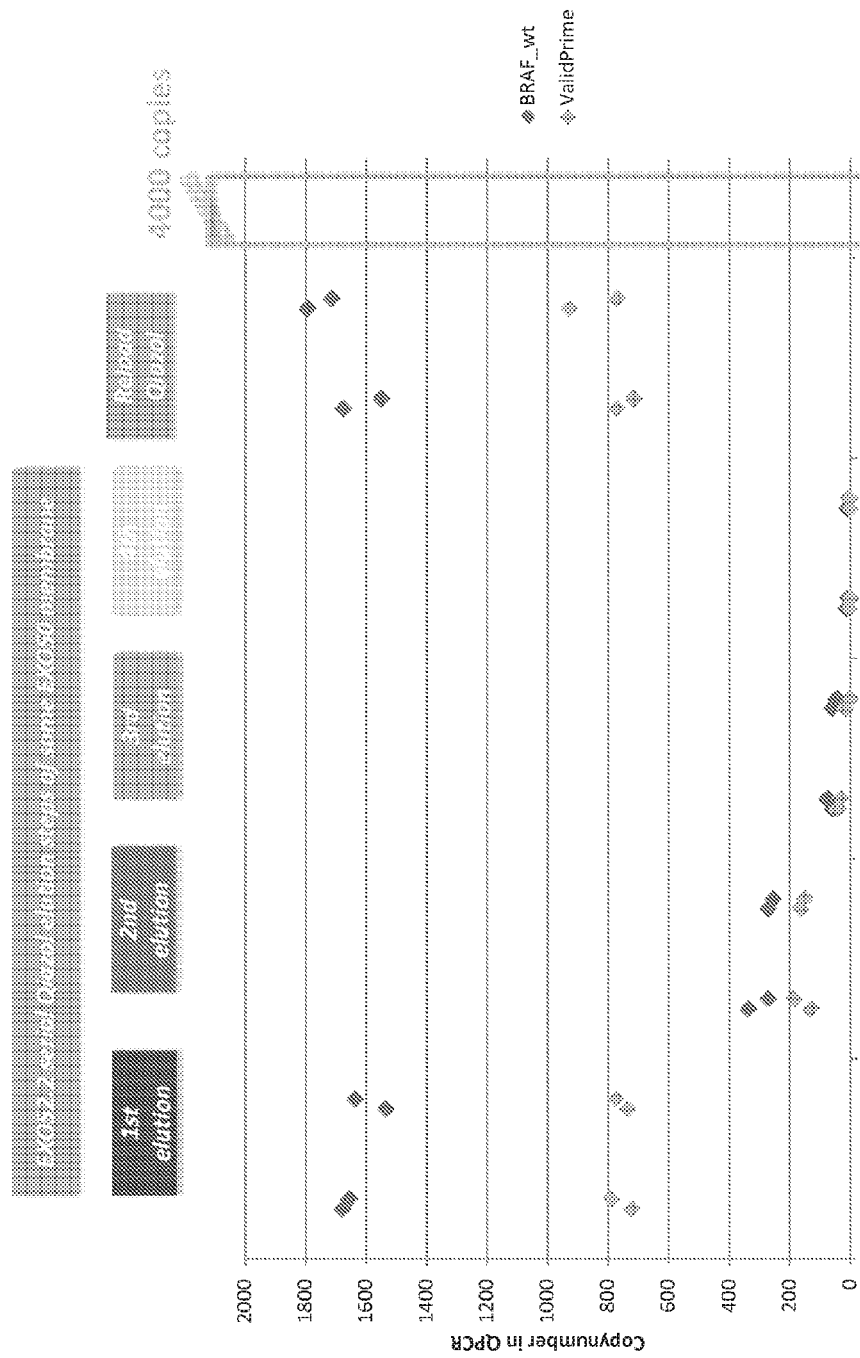
Figure 201:
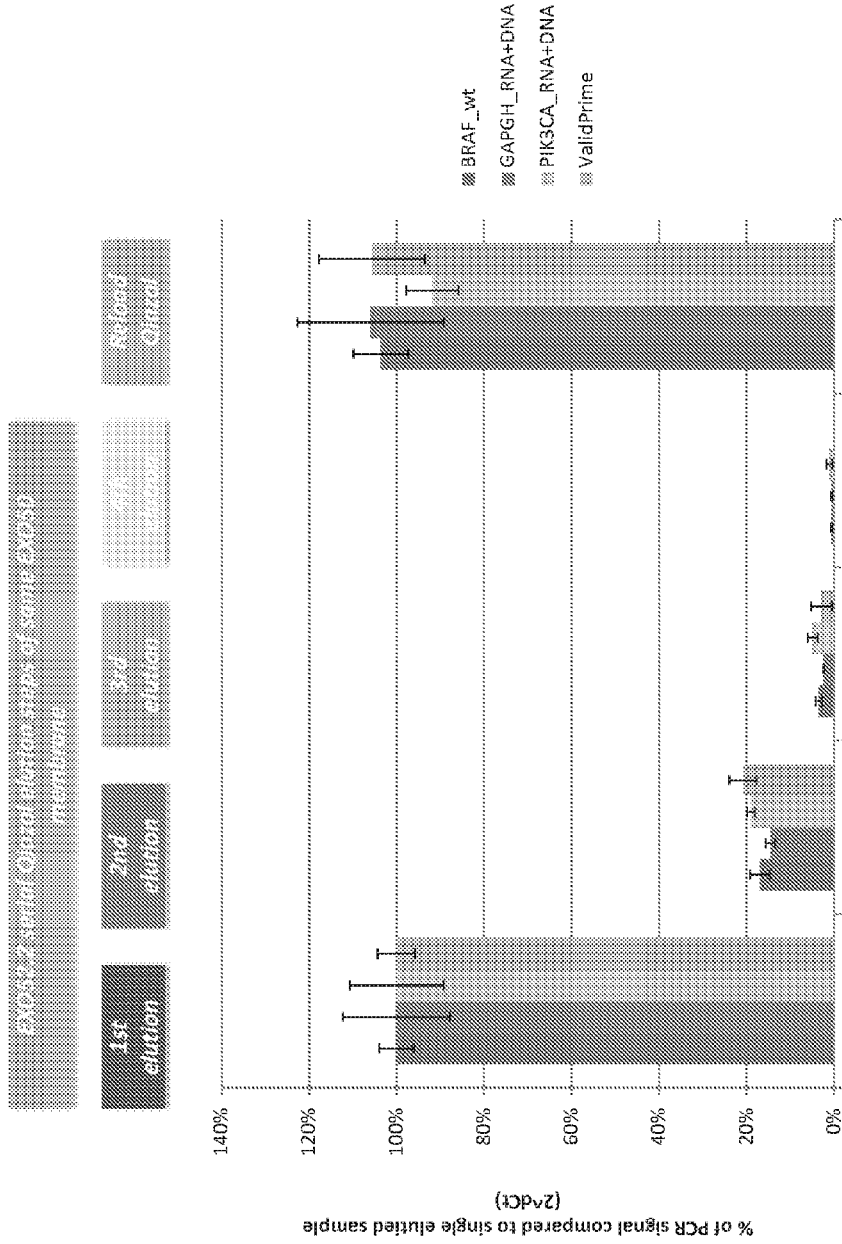
Figure 202:
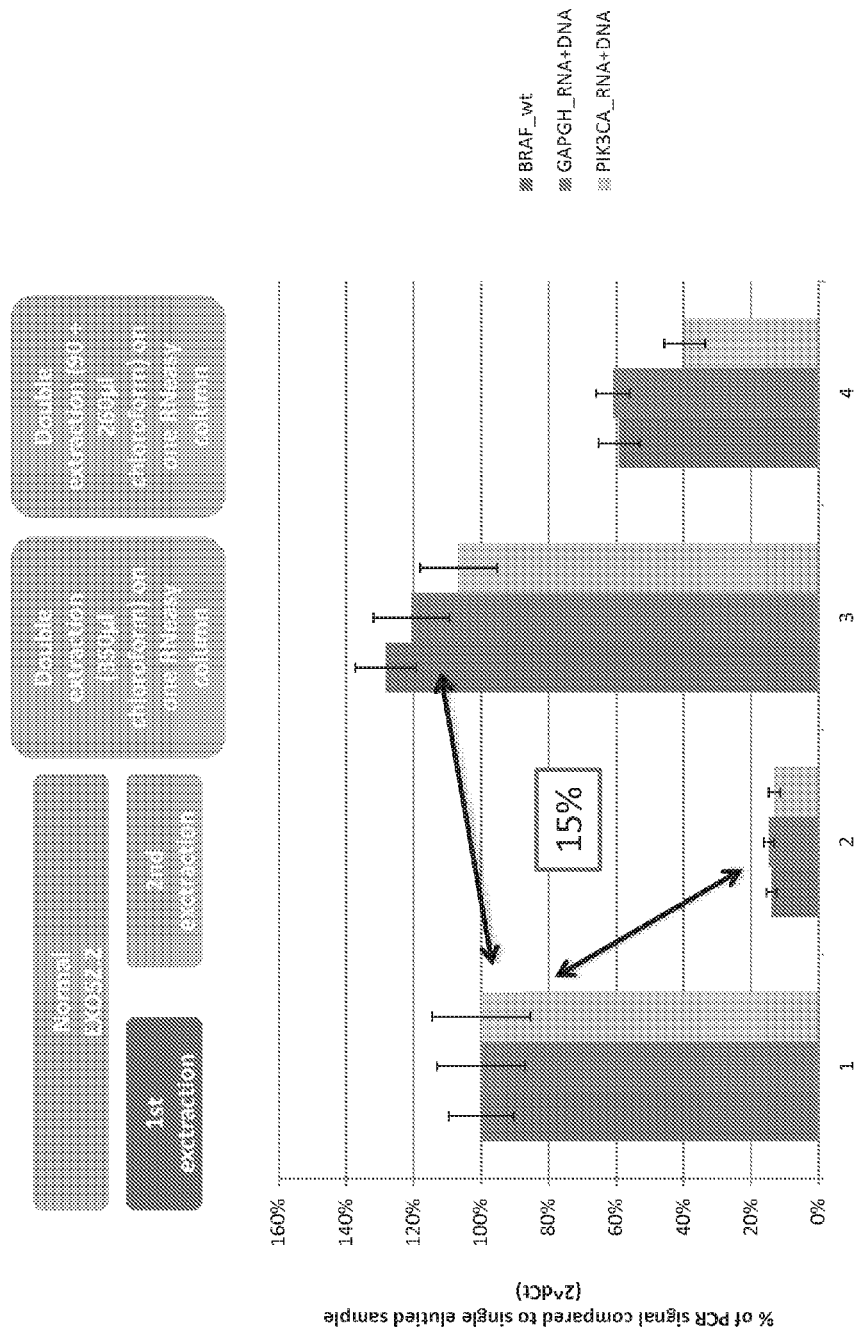
Figure 203:
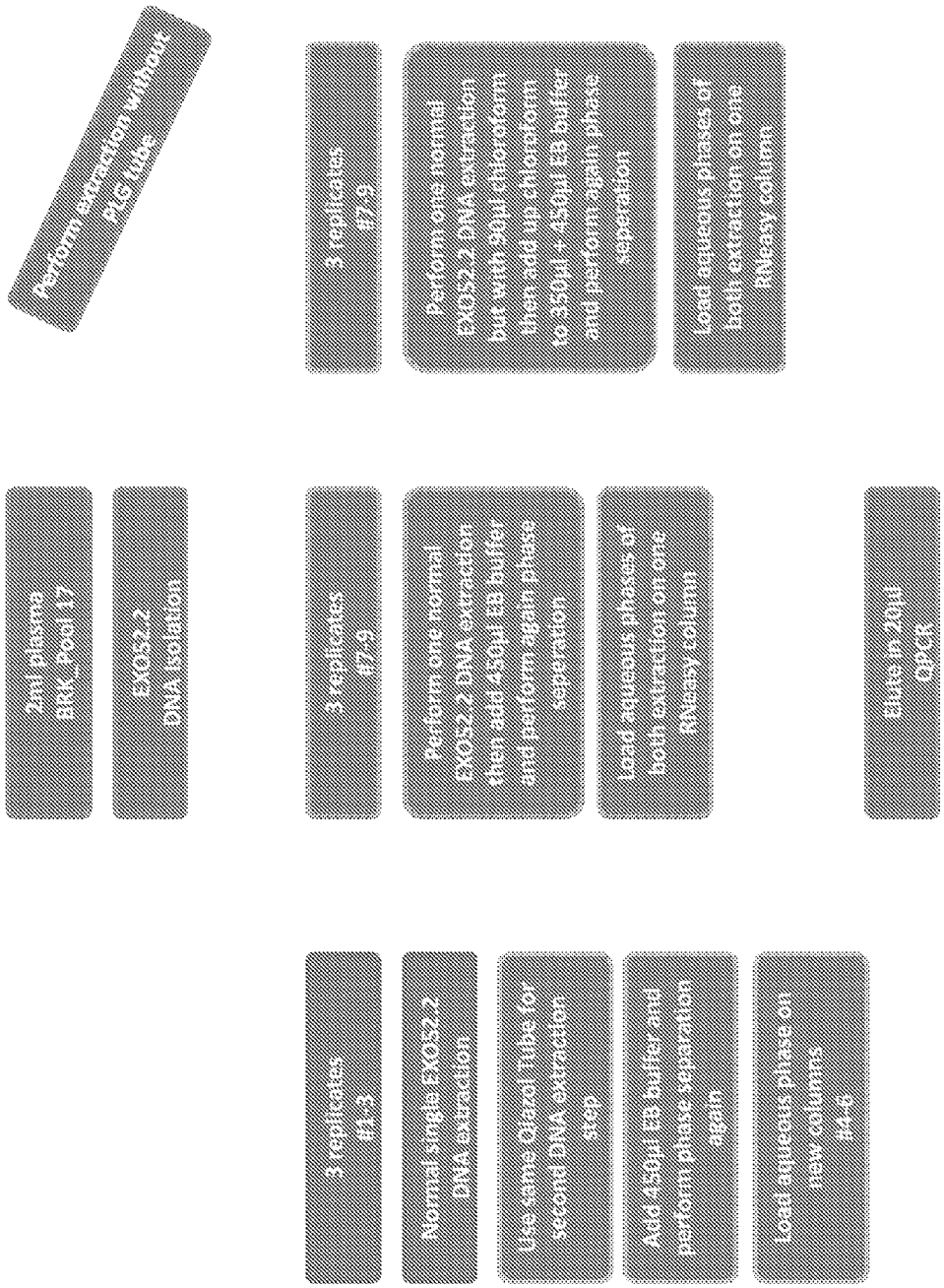
FIG. 203 is a schematic representation of studies designed to evaluate DNA and RNA isolation using multiple Qiazol elution steps.
Figure 204:
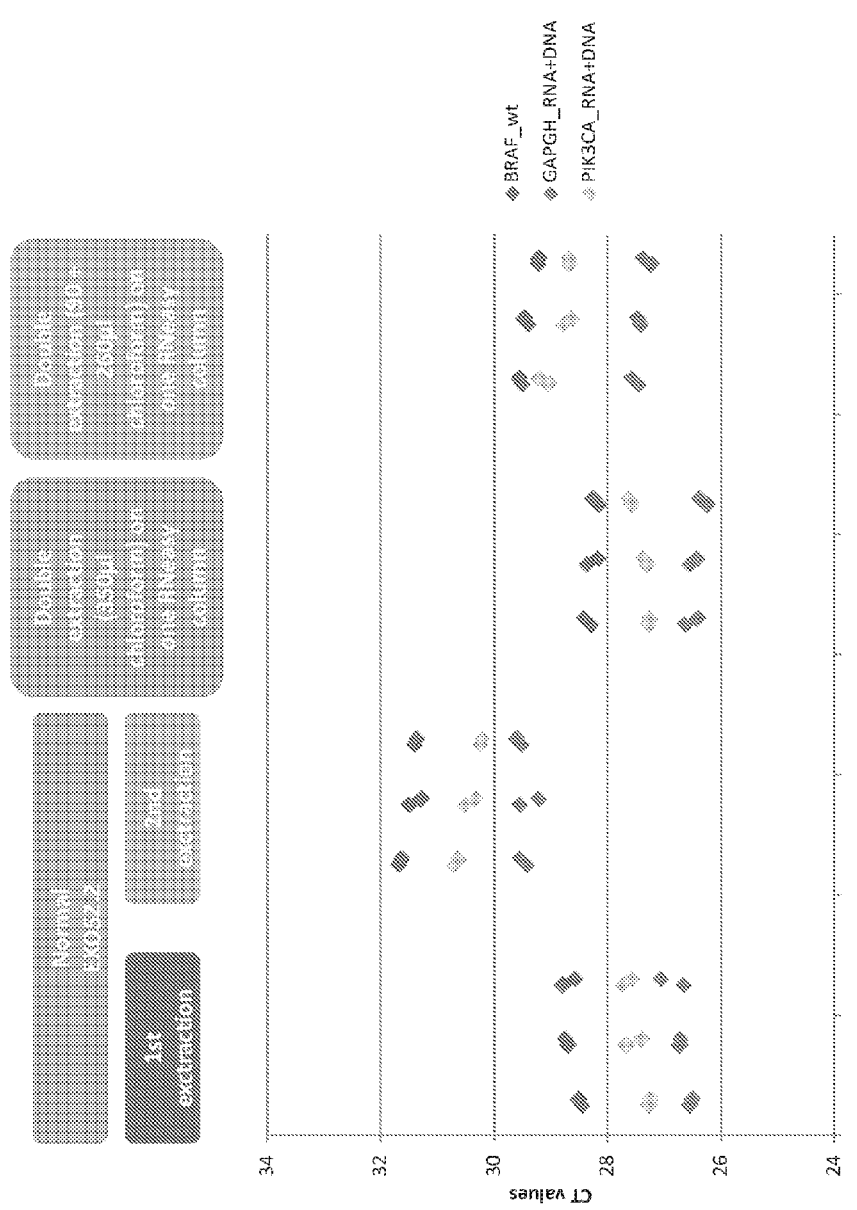

FIGS. 13-223 (referred to in only this example as "the Figures") demonstrate the specificity and sensitivity of the EXO52 methods.

Studies have shown that the EXO50/52 column binds all DNA in plasma, but the procedure to get the DNA out of the phenol phase does not produce satisfactory results, as the isolation procedure is very variable. The methods provided herein allow for reproducible and efficient isolation and/or extraction of DNA from the membrane of the EXO50/52 column.

Two out of three replicates of Exo52 isolation with PLG tube show almost the same CT values as a commercially available cfDNA KIT. One out of three replicates of EXO52 isolation without PLG tube show almost same CT values as cfDNA KIT. Depleted Plasma (Exo50 flow through of plasma without 2× Binding buffer) do not contain a lot of DNA (18S~9CT difference to normal isolation). Almost all almost all DNA bound to the Exo50 column.

As shown in the Figures, adding chloroform to the EXO52 method allowed for the co-isolation of both RNA and DNA, and adding chloroform did not harm the detection or isolation of RNA.

With regard to RNA isolation, it was determined that adding more chloroform did not influence RNA isolation if using RNA specific assays. DNA specific assays will result in lower CTs when adding more chloroform because DNA is in aqueous phase.

With regard to DNA isolation, CTs for DNA detecting assays increased in aqueous phase isolation with adding more chloroform and decreased in EXO52 phenol phase DNA isolation.

EXO50 isolation from phenol phase resulted in lowest CT values (=highest DNA yield). 90 µl chloroform resulted in best DNA yield from phenol phase.

Also without the PLG tube, the chloroform ratio at which no DNA contamination was observed was approximately 0.13×.

As shown in the Figures, 350 µL of chloroform was sufficient to add all DNA from the EXO52 column to the aqueous phase during PC extraction. Higher chloroform amounts may interfere with RNA isolation.

As shown in the Figures, DNA yield increased in aqueous phase with adding more chloroform, whereas DNA yield decreased in phenol phase (EXO52 DNA Isolation). DNA isolation from aqueous phase yield more DNA compared to EXO52 DNA Isolation from phenol phase. Little DNA appeared to stay in phenol phase or in remaining aqueous phase after removing upper phase, as it is difficult to remove whole phase w/o using PLG tube. DNA yield is similar in RT reaction (10 µl EXO50 eluate in final 20 µl RT Mix) and 1:2 diluted EXO50 eluate. DNA did not seem to react with reverse transcription mix.

Studies were repeating using an RNA only GAPDH assay to see if the RNA only GAPDH assay was affected by increasing chloroform addition. RNA was not affected with increasing chloroform addition. Studies were also run using a GAPDH_RNA_DNA assay, which showed no replacement of RNA signal by the DNA (~2CTs difference).

The BRAF assay showed a 2× increase in signal in the EXO50 RNA fraction by having DNA present in the aqueous phase. The GAPDH assay did not show a clear additive effect of DNA in the EXO50 RNA fraction since the added copies were minute in comparison to the RNA copies. With this clear difference between RNA and DNA copies, no replacement of RNA signal can be shown.

Studies were run to determine the effect, if any, of pH changes in phase separation. Adjustment of pH provides an alternative tool for adding DNA to the aqueous phase. It was found that too high of a pH interfered with RNA isolation.

High pH seemed to trouble BA. For example, BA profile from 10N NaOH sample showed the highest DNA peak but very low FU ([FU]=2 compared to [FU]=40). High pH seemed to trouble RT reaction. An increase of the aqueous phase pH resulted in lower CT values in Exo50 DNA Isolation whereas EXO52 DNA isolation resulted in higher values, but there was higher DNA amount left in phenol phase compared to chloroform titration.

Decreasing pH was able to remove DNA from the EXO52 phenol phase and enrich in the aqueous phase. DNA was not harmed in the RT. RNA was harmed at highest pH. BA was affected at the three highest pH steps.

As shown in the Figures, chloroform addition was the predominant factor in determining the DNA content of the aqueous phase. A positive effect of high pH was seen only at low chloroform levels. The RNA signal was not affected through addition of DNA into the aqueous phase.

As shown in the Figures, there was no additive effect of pH solution to DNA copy number, and also no shift in needed chloroform amount was necessary to bring DNA in aqueous phase. Samples even resulted in lower copy numbers compared to samples processed without pH solution. Only samples which were processed with 90 µl resulted in higher copy numbers. pH solution and higher chloroform amount did not affect RNA Isolation (mRNA). During whole titration, samples which were processed with pH solution resulted in little lower copy numbers (except 90 µl chloroform samples) compared to samples processed without pH solution.

As shown in the Figures, a QIAzol spin at room temperature increased the percentage of DNA material in the aqueous phase. This was not the case when using higher amounts of chloroform in the EXO52 procedure.

A Qiazol centrifugation step caused DNA contamination in aqueous phase, but only in samples without PLG tube. PLG-Tube samples with centrifugation step at room temperature also showed a little more DNA, but copy number were under LOQ=32 Copies. Temperature for centrifugation step did not influence mRNA and miRNA isolation.

A Qiazol spin at room temperature did not add up DNA to normal EXO52 DNA isolation. There was no difference in CT values referred to the spin temperature. Temperature for centrifugation step did not influence mRNA and miRNA isolation.

As shown in the Figures, the binding and elution of DNA from EXO52 to the RNeasy spin column did not depend on ethanol concentration in the range from 1.5× volume to 2.6× volume.

As shown in the Figures, the performance of EXO52 was not increased when higher ethanol concentration was used. CT values of all three assays remained constant during whole ethanol titration. Ethanol concentration in the pre-conditioning step of the RNA isolation did not influence the recovery of cfDNA.

As shown in the Figures, a proteinase K (ProtK) digestion of a plasma sample led specifically to loss of signal from RNA, but ProtK treatment did not influence DNA yield, as the same CT was obtained for all samples.

As shown in the Figures, the DNA loading capacity of EXO52 was not reached at 8 ml plasma since the yield of DNA was still linearly increasing and there was no detectable DNA in the flow-through. This is in contrast to the linear loading capacity of vesicles, which is reached at 4 mL. No cfDNA was detected in the flow through (FT) but RNA was seen to accumulate from 2 mL on. The sample output is linear for DNA, but not for RNA. RNA has a different saturation point than DNA. Adding a PLG tub to the procedure was found to increase the yield slightly. EXO52 method added RNA copies, when compared to commercially available CNA kits.

In some embodiments, the methods use an extraction buffer only based on guanidinium thiocyanate to extract RNA and DNA from the EXO52 column.

As shown in the Figures for RNA Isolation, 1 out of 2 replicates of RLT+ high DTT 56° C. resulted in expected CT values. Variation between replicates may have been caused by clogging RNeasy membrane after adding loading mixture. BA profile showed very low RNA concentration for left on column data point for RLT+ high DTT 56° C. but only one RNA isolation resulted in expected CT values.

As shown in the Figures for DNA Isolation, AllPrep DNA column resulted in very high copy number for DNA detecting assays. Also left on column data point showed very high CT values. DNA seemed to be lost by AllPrep DNA spin column caused by a high cut off (15-30 kb). The size of cfDNA is typically in the range of 35 bp-10 kb.

The Figures also demonstrate isolation of microRNAs using various DNA or DNA/RNA isolation procedures. The EXO52 isolated more mRNA and much more miRNAs than the commercially available CNA kit, and EXO52 and the CNA kit isolated the same amount of DNA. The EXO52 method seemed to isolate all DNA from plasma.

As shown in the Figures, EXO52 consistently outperforms the commercially available circulating nucleic acids (CAN) kit. EXO52 has better yield than CNA Kit on three different plasma pools, different CNA reagent lots, different operators and different sample sources.

The EXO52 methods were used to analyze cfDNA in samples from a melanoma cohort. The results obtained using the EXO52 methods were compared with the results obtained using a commercially available CNA kit. The intra-assay variation (based on different time points of isolation of the same plasma sample) of the CNA kit was higher than that observed using the EXO52 methods. As shown in the figures, the performance of the EXO52 methods is equal or better to those obtained using the commercially available kit.

As shown in the Figures, there was approximately 15% DNA left in organic phase after phase separation with 350 µl chloroform. Double extraction increased DNA yield by about 15% points. Phase separation with 90 µl chloroform (RNA) followed by second extraction with additional 260 µl (sum: 350 µl chloroform) only resulted in about 50% DNA yield as compared to normal EXO52 DNA extraction. Reloading of conditioned EXO52 material onto the same column did not improve yield.

Example 2. Development of a One-Step Isolation Platform for Exosomal RNA and Cell-Free DNA from Cancer Plasma Circulating nucleic acids in the bloodstream of cancer patients are of great interest to medical research because of their potential to yield information on the patient's disease status and treatment options without requiring a tissue biopsy. Any diagnostic test that seeks to utilize Biofluids for mutation analysis needs a platform that can maximize the capture of tumor derived mutations in circulation. Blood plasma contains at least two cell-free sources of nucleic acids: circulating cell-free DNA (cfDNA), generated from apoptotic or necrotic cells, and RNA enclosed in extracellular vesicles including exosomes (exoRNA), which are actively secreted by cells in the body. Since the total amount of nucleic acids in Biofluids is very limited and tumor mutations are reflected on both RNA and DNA, a method was devised to co-isolate all exoRNA and cfDNA out of blood plasma samples into a volume small enough for effective downstream processing by RT-qPCR and targeted re-sequencing by NGS.

FIGS. 224-226 illustrate the studies presented herein which demonstrate the following: (i) Blood plasma contains cell-free RNA in addition to cell-free DNA; (ii) EXO52 is a fast, reproducible and convenient procedure to co-isolate all exoRNA and cfDNA from high volumes of Biofluids; and (iii) Using both, exoRNA and cfDNA typically doubles the molecules available for rare mutant detection by qPCR and NGS.

FIGS. 227 and 228 are a series of graphs depicting the ability of the EXO52 methods provided herein to capture total circulating nucleic acids. The EXO52 methods were compared to a commercially available circulating nucleic acid DNA isolation kit. As shown in FIGS. 227-228, EXO52 captured all cfDNA, and EXO52 detected significantly more copies combining exoRNA and cfDNA vs. cfDNA alone. FIG. 228 also demonstrates that patients were identified as negative for a biomarker based solely on cfDNA analysis, but with the combined DNA and RNA analysis, these patients were identified as positive for the biomarker. Those of ordinarily skill in the art will appreciate that more copies of a mutation or other biomarker leads to enhanced sensitivity and accuracy in identifying mutations and other biomarkers.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A method for extracting cell-free DNA and microvesicular RNA from a biological sample comprising:
   (a) contacting the biological sample with a capture surface under conditions sufficient to retain cell-free DNA and microvesicles from the biological sample on or in the capture surface, wherein the capture surface comprises one or more beads that are positively charged and functionalized with quaternary ammonium;
   (b) contacting the capture surface with a phenol-based lysis reagent while cell-free DNA and the microvesicles are on or in the capture surface, thereby releasing the cell-free DNA and microvesicular RNA from the sample and producing a homogenate;
   (c) extracting the cell-free DNA, the microvesicular RNA, or both the cell-free DNA and microvesicular RNA from the homogenate.

2. The method of claim 1, wherein the one or more beads are an anion exchanger functionalized with quaternary ammonium.

3. The method of claim 1, wherein the biological sample is plasma or serum.

4. The method of claim 3, wherein the biological sample is between 0.2 to 4 mL.

5. The method of claim 1, wherein the biological sample is urine, cerebrospinal fluid or cell culture supernatant.

6. The method of claim 1, wherein step (a) further comprises processing the biological sample by filtering the biological sample.

7. The method of claim 6, wherein the filtration is performed using a 0.8 µm filter.

8. The method of claim 1, wherein step (a) further comprises a centrifugation step after contacting the biological sample with the capture surface.

9. The method of claim 1, wherein step (a) further comprises washing the capture surface after contacting the biological sample with the capture surface.

10. The method of claim 1, wherein step (b) further comprises a centrifugation step after contacting the capture surface with the phenol-based lysis reagent.

11. The method of claim 1, wherein step (c) further comprises adding a control to the homogenate prior to extraction.

12. The method of claim 1, wherein the method further comprises step (d) ethanol conditioning of the extraction from step (c); step (e) binding of the ethanol-conditioned extraction to a silica column; and step (f) eluting the extraction from the silica column.

13. The method of claim 1, wherein the phenol-based lysis reagent comprises phenol and guanidinium.

* * * * *

UNITED STATES PATENT AND TRADEMARK OFFICE
CERTIFICATE OF CORRECTION

PATENT NO. : 10,465,183 B2
APPLICATION NO. : 15/325021
DATED : November 5, 2019
INVENTOR(S) : Johan Karl Olov Skog et al.

Page 1 of 1

It is certified that error appears in the above-identified patent and that said Letters Patent is hereby corrected as shown below:

In the Claims

At Column 28, Claim number 1, Line number 18:
"sample and producing a homogenate;"
Should read:
-- sample and producing a homogenate; and --

Signed and Sealed this
Seventh Day of January, 2020

Andrei Iancu
*Director of the United States Patent and Trademark Office*